US012498384B2

(12) United States Patent
Wallach et al.

(10) Patent No.: US 12,498,384 B2
(45) Date of Patent: *Dec. 16, 2025

(54) BIOMARKERS AND METHODS FOR EVALUATION AND TREATMENT OF EPILEPTIC VS NON-EPILEPTIC SEIZURES / NO SEIZURES / PSYCHOGENIC NON-EPILEPTIC SEIZURES

(71) Applicant: COGNIZANCE BIOMARKERS, INC., Miami, FL (US)

(72) Inventors: Todd Wallach, Overland Park, KS (US); John Gledhill, Overland Park, KS (US); Richard St. Clair, Overland Park, KS (US); Elizabeth Brand, Overland Park, KS (US)

(73) Assignee: COGNIZANCE BIOMARKERS, INC., Miami, FL (US)

( * ) Notice: Subject to any disclaimer, the term of this patent is extended or adjusted under 35 U.S.C. 154(b) by 1100 days.

This patent is subject to a terminal disclaimer.

(21) Appl. No.: 17/058,502

(22) PCT Filed: May 29, 2019

(86) PCT No.: PCT/US2019/034381

§ 371 (c)(1),
(2) Date: Nov. 24, 2020

(87) PCT Pub. No.: WO2019/232037

PCT Pub. Date: Dec. 5, 2019

(65) Prior Publication Data

US 2021/0199672 A1 Jul. 1, 2021

Related U.S. Application Data

(60) Provisional application No. 62/826,088, filed on Mar. 29, 2019, provisional application No. 62/767,762,
(Continued)

(51) Int. Cl.
*G01N 33/68* (2006.01)
*A61K 45/06* (2006.01)
(Continued)

(52) U.S. Cl.
CPC ......... *G01N 33/6896* (2013.01); *A61K 45/06* (2013.01); *G01N 33/563* (2013.01);
(Continued)

(58) Field of Classification Search
None
See application file for complete search history.

(56) References Cited

U.S. PATENT DOCUMENTS

| | | | | |
|---|---|---|---|---|
| 6,346,270 B1 * | 2/2002 | Shivanand | A61K 9/0004 424/464 |
| 2013/0331329 A1 * | 12/2013 | Pollard | A61K 38/1709 514/17.7 |
| 2017/0326330 A1 * | 11/2017 | Bulaj | G16H 40/63 |

FOREIGN PATENT DOCUMENTS

| | | |
|---|---|---|
| WO | 2012116264 A1 | 8/2012 |
| WO | 2014202098 A1 | 12/2014 |

(Continued)

OTHER PUBLICATIONS

Luo, Jing, et al. "Concentration of soluble adhesion molecules in cerebrospinal fluid and serum of epilepsy patients." Journal of Molecular Neuroscience 54 (2014): 767-773. (Year: 2014).*

(Continued)

*Primary Examiner* — Bao-Thuy L Nguyen
*Assistant Examiner* — Chau N.B. Tran
(74) *Attorney, Agent, or Firm* — Viksnins Harris Padys Malen LLP

(57) ABSTRACT

Epileptic seizures, NES, NS, PNES or NEE are difficult to diagnose and are often difficult to distinguish from several conditions with similar presentations, and therefore, diag-
(Continued)

nosis of seizures is often a long, expensive, and unreliable process. This invention provides biomarkers for identifying and monitoring seizures and epilepsy, ES, NES, NS, PNES or NEE assays for measuring and assessing biomarker concentration, predictive models based on biomarkers and computational systems for diagnosing, monitoring and predicting therapeutic efficacy associated with seizures and epilepsy, ES, NES, NS, PNES or NEE in all clinical and healthcare settings. Diagnostic and treatment methods, systems, kits, and predictive models provided herein, provide quantitative and/or qualitative assessment in order to allow patients to proceed immediately to diagnostic and/or treatment protocols, and assess therapeutic treatment effectiveness.

5 Claims, 65 Drawing Sheets

Related U.S. Application Data filed on Nov. 15, 2018, provisional application No. 62/679,298, filed on Jun. 1, 2018, provisional application No. 62/677,452, filed on May 29, 2018.

(51) Int. Cl.
*G01N 33/563* (2006.01)
*G16H 50/20* (2018.01)

(52) U.S. Cl.
CPC ......... *G16H 50/20* (2018.01); *G01N 2496/00* (2013.01); *G01N 2800/2857* (2013.01); *G01N 2800/52* (2013.01)

(56) References Cited

FOREIGN PATENT DOCUMENTS

WO 2017120166 A1 7/2017
WO WO-2018213437 A1 * 11/2018 .............. A61P 25/08

OTHER PUBLICATIONS

Rana, Amna, and Alberto E. Musto. "The role of inflammation in the development of epilepsy." Journal of neuroinflammation 15 (2018): 1-12. (Year: 2018).*

Goldenberg et al. (Overview of Drugs Used For Epilepsy and Seizures, P&T, vol. 35 No. 7, Jul. 2010) (Year: 2010).*

Health Fairview (Four things you should know about responsive neurostimulation for epilepsy, 2017) (Year: 2017).*

Stacey et al. (Technology Insight: neuroengineering and epilepsy-designing devices for seizure control, Nat Clin Pract Neurol. Feb. 26, 2008;4(4):190-201). (Year: 2008).*

Chen et al. (Multiplex analyte assays to characterize different dementias: brain inflammatory cytokines in poststroke and other dementias, Neurobiology of Aging 38 (2016) 56e67) (Year: 2016).*

Brigo, F , et al., "Postictal serum creatine kinase for the differential diagnosis of epileptic seizures and psychogenic non-epileptic seizures: a systematic review", J Neurol 262, 251-257 (2015).

Chang, C , et al., "Clinical significance of serological biomarkers and neuropsychological performances in patients with temporal lobe epilepsy", BMC Neurology 12 (15), 10 pages (2012).

Ehsan, T , et al., "Sensitivity and Specificity of Paired Capillary Prolactin Measurement in Diagnosis of Seizures", J Epilepsy 9, 101-105 (1996).

Pollard, J , et al., "Predictive Blood Test for Seizures post hoc Assessment of Plasma Biomarkers", AES Annual Meeting, Abstract No. 3.089, 3 pages (Nov. 22, 2016).

International Search Report mailed Aug. 27, 2019 for International Patent Application No. PCT/US2019/034381.

Written Opinion mailed Aug. 27, 2019 for International Patent Application No. PCT/US2019/034381.

Sundararajan et al. "Biomarkers in the diagnosis and study of psychogenic nonepileptic seizures: A systematic review," Seizure, Dec. 31, 2015 (Dec. 31, 2015), vol. 35, pp. 11-22 (entire document).

Gupta, M. "Review of somatic symptoms in post-traumatic stress disorder," Int Rev Psychiatry, Feb. 6, 2013 (Feb. 6, 2013), vol. 25, Iss. 1, pp. 86-99 (entire document).

Man-Sheng, Chen , "Comparative Analysis on Variation of Cardiac Muscle Enzymes in Children with Non-convulsive Epilepsy or Psychogenic Non-epileptic Seizure,", Practical Preventive Medicine 18(7), 1294-1296 (2011). [English Abstract].

Peng, Xi , "Gelsolin in Cerebrospinal Fluid as a Potential Biomarker of Epilepsy", Neurochem Res 36, 2250-2258 (2011).

Wang, W. , et al., "Role of a Neural Cell Adhesion Molecule Found in Cerebrospinal Fluid as a Potential Biomarker for Epilepsy", Neurochem Res. 37, 819-825 (2012).

Wang, R. , et al., "Serum matrix metalloproteinase-2: A potential biomarker for diagnosis of epilepsy", Epilepsy Research 122, 114-119 (2016).

Yu, W. , et al., "Time-Dependent Decrease of Clusterin as a Potential Cerebrospinal Fluid Biomarker for Drug-Resistant Epilepsy", J Mol Neurosci 54, 1-9 (2014).

Gledhill, J, et al., "Predictive Blood Test for Psychogenic Nonepileptic Seizures: Post hoc Assessment of Plasma Biomarkers and Risk Factors", AES Abstracts, abstract 3.094, https://aesnet.org/abstractslisting/predictive-blood-test-for-psychogenic-nonepileptic-seizures--post-hoc-assessment-of-plasma-biomarkers-and-risk-factors, Nov. 5, 2018 (Nov. 5, 2018).

Teocchi, L. , et al., "Apoptosis through Death Receptors in Temporal Lobe Epilepsy-Associated Hippocampal Sclerosis", Mediators of Inflammation 2016, 1-12 (2016).

Zhao, X. , et al., "Noninflammatory Changes of Microglia Are Sufficient to Cause Epilepsy", Cell Rep. 22(8), 2080-2093 (2018).

Javali, M , et al., "Role of Biomarkers in Differentiating New-onset Seizures from Psychogenic Nonepileptic Seizures", J Neurosci Rural Pract 8, 581-584 (2017).

Yamamoto, A , et al., "Evidence of tumor necrosis factor receptor 1 signaling in human temporal lobe epilepsy", Experimental Neurology 202, 410-420 (2006).

* cited by examiner

Epileptic Seizures (ES)

- Seizures in patients whose brains demonstrate a pathologic and enduring tendency to have recurrent seizures[1]
- Patients who have experienced at least two unprovoked seizures at least 24 hours apart
- Patients who have experienced a single unprovoked seizure and are as likely to experience additional seizures (for example, patients who have experienced a single seizure subsequent to a remote brain insult, like a stroke)
- Diagnosis of an unresolved epilepsy syndrome

Non-Epileptic Seizures (NES)

- Seizures that are secondary to a transient factor
- Transient factor acting on an otherwise normal brain to temporarily lower the seizure threshold
- Examples include seizures in the context of fever or alcohol withdrawal[1]

No Seizures (NS)

- No seizure-like events, or events that mimic seizures
- Explained by specific medical and psychological conditions
- Examples include TIA, vertigo, panic attacks, and conversion disorder/psychogenic spells

FIG. 1

| | True Positive | True Negative | |
|---|---|---|---|
| Predicted Positive | 29 | 1 | PPV 96.6= % |
| Predicted Negative | 3 | 8 | NPV 72.7= % |
| | Sensitivity = 90.6% | Specificity 88.8= % | |

FIG. 8C

| | **True Positive** | **True Negative** | |
|---|---|---|---|
| **Predicted Positive** | 21 | 1 | PPV = 95% |
| **Predicted Negative** | 10 | 8 | NPV = 44% |
| | Sensitivity = 68% | Specificity = 89% | |

FIG. 9C

| | True Positive | True Negative | |
|---|---|---|---|
| Predicted Positive | 27 | 0 | PPV = % |
| Predicted Negative | 4 | 9 | NPV = % |
| | Sensitivity = 87% | Specificity = 100% | |

FIG. 10C

| | True Positive | True Negative | |
|---|---|---|---|
| Predicted Positive | 29 | 3 | PPV 90.6= % |
| Predicted Negative | 2 | 6 | NPV 75.0= % |
| | Sensitivity 93.5= % | Specificity 66.6= % | |

FIG. 11C

| | True Positive | True Negative | |
|---|---|---|---|
| Predicted Positive | 29 | 0 | PPV 100= % |
| Predicted Negative | 2 | 9 | NPV 81.8= % |
| | Sensitivity 93.5= % | Specificity 100= % | |

FIG. 12C

OLS Regression Results

| | | | |
|---|---|---|---|
| Dep. Variable: | freq reduction | R-squared: | 0.418 |
| Model: | OLS | Adj. R-squared: | 0.355 |
| Method: | Least Squares | F-statistic: | 6.637 |
| Date: | Thu, 21 Mar 2019 | Prob (F-statistic): | 0.000394 |
| Time: | 15:30:54 | Log-Likelihood: | -41.279 |
| No. Observations: | 42 | AIC: | 92.56 |
| Df Residuals: | 37 | BIC: | 101.2 |
| Df Model: | 4 | | |
| Covariance Type: | nonrobust | | |

| | coef | std err | t | P>\|t\| | [95.0% Conf. | Int.] |
|---|---|---|---|---|---|---|
| const | -0.0820 | 0.487 | -0.168 | 0.867 | -1.069 | 0.906 |
| GM-CSF | 0.5257 | 0.245 | 2.143 | 0.039 | 0.029 | 1.023 |
| IL-17A | 0.8183 | 0.219 | 3.737 | 0.001 | 0.375 | 1.262 |
| TNF-a | -1.7103 | 0.392 | -4.359 | 0.000 | -2.505 | -0.915 |
| VEGF-A | 0.4152 | 0.166 | 2.501 | 0.017 | 0.079 | 0.752 |

| | | | |
|---|---|---|---|
| Omnibus: | 16.686 | Durbin-Watson: | 1.837 |
| Prob(Omnibus): | 0.000 | Jarque-Bera (JB): | 21.088 |
| Skew: | -1.277 | Prob(JB): | 2.64e-05 |
| Kurtosis: | 5.352 | Cond. No. | 12.6 |

FIG. 25B

BIOMARKERS AND METHODS FOR EVALUATION AND TREATMENT OF EPILEPTIC VS NON-EPILEPTIC SEIZURES / NO SEIZURES / PSYCHOGENIC NON-EPILEPTIC SEIZURES

CROSS-REFERENCE TO RELATED APPLICATIONS

This application is a U.S. National Stage Patent Application of International Patent Application No. PCT/US2019/034381 filed May 29, 2019, which claims the benefit of U.S. Provisional Patent Applications Nos. 62/677,452, filed May 29, 2018, 62/679,298, filed Jun. 1, 2018, 62/767,762, filed Nov. 15, 2018, and 62/826,088, filed Mar. 29, 2019, which are all incorporated by reference herein in their entireties.

FIELD OF THE INVENTION

The present inventions are generally directed to biomarkers associated with inflammation, seizures and seizure mimics, and indicate methods of characterizing biological conditions by scoring quantitative data sets derived from a subject sample, as well as various other embodiments, as described herein.

BACKGROUND OF THE INVENTION

Epileptic Seizures (ES) and epilepsy, non-epileptic seizures (NES), no seizures (NS), psychogenic non-epileptic seizures (PNES) or non-epileptic events (NEE) are very common neurological and/or other disorders that are associated with health complications, significant morbidity, health care cost, and even mortality. Epilepsy is the fourth most common neurological disorder behind migraine, stroke, and Alzheimer's. Epilepsy is a common neurological affliction affecting over 2.3 million patients in the US and 65 million patients worldwide, with significant financial burden. Current estimates are that epilepsy affects approximately 1% of the world population. The prevalence of total active cases currently being treated for epilepsy is 17.8 million, with India (7.5 million), China (4.9 million), and the US (2.3 million) leading other countries. The financial burden of epilepsy, ES, NES, NS, PNES or NEE care is substantial with a major expense contributed by tests required for appropriate diagnosis. Estimates are that epilepsy and seizures in the U.S. incurs an estimated annual cost of $17.6 billion in direct and indirect costs. A major limitation in providing care for patients with seizures—ES, NES, NS, PNES or NEE—is the lack of a diagnostic blood test to identify clinical events as truly Epileptic Seizures as opposed to other disorder such as transient ischemic attacks, fainting, sleep disorders, and psychogenic events, including NES, NS, PNES or NEE.

Epilepsy defined by spontaneous and recurrent seizures, resulting from abnormal electrical activity in the brain that are not caused by a specifically known medical condition, is a highly prevalent public health problem. Also known as "seizure disorder," epilepsy is not diagnosed until after the patient has had two epileptic seizures not caused by a known medical condition. In 70% of new cases, no cause is apparent. Approximately, 30-50% of people who have had a single, unprovoked seizure will develop recurrent seizures (epilepsy). One-third of people with epilepsy live with uncontrolled seizures because no available treatment works for them.

SUMMARY OF THE INVENTION

In an embodiment, the invention "EvoScore™" includes a blood based diagnostic test that effectively screens plasma from patients to identify measurable changes in select proteins following suspected seizures—either ES, NES, NS, PNES or NEE. Multiple proteins linked to inflammatory processes are used to generate, a predictive algorithm with associated score (EvoScore Predictive Models™) that can be translated into a diagnostic test for the determination of seizures—whether ES, NES, NS, PNES or NEE. The algorithms, which combine protein levels has demonstrated, with strong diagnostic performance, predictions of both phasic and tonic changes (acute and chronic) in patients with seizures and epilepsy—both ruling out patients and ruling in patients with epileptic seizures (ES) and epilepsy vs NES, NS, PNES or NEE, with the ability to monitor patients over time and over the course of treatment. EvoScore can be used in all clinical and healthcare settings, including direct use by a patient. The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy, ES, NES, NS, PNES or NEE patients, drug controlled epilepsy, patients and drug refractory patients. It is important to note that epilepsy patients may experience a NES, NS, PNES or NEE of the course of their lifetimes, and it is important to distinguish between the events for future treatment. The test score and biomarkers can be analyzed and compared across patients, patient groups, other indications and normal controls, and across an individual patient over time for personalized medicine.

In some embodiments, the disclosure provides for methods of leveraging one or more biomarker concentrations, and combined into a diagnostic algorithm that can predict changes in patient epileptic seizure burden or frequency over a time period as a result of additional intervention or no intervention. In some embodiments, the disclosure provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In an embodiment, the invention includes a method for diagnosing epilepsy and/or a seizure, ES, NES, NS, PNES or NEE in a mammalian subject. In some embodiments, the method may include the step of contacting a blood plasma or blood serum sample obtained from the mammalian subject with a diagnostic reagent that can measure or detect the expression of one biomarker. In some embodiments, the method may include the step of contacting said blood plasma or blood serum sample obtained from the mammalian subject with a diagnostic reagent that can measure or detect the expression level of one biomarker and developing a diagnostic algorithm. In some embodiments, the method may include the step of contacting a blood plasma or blood serum sample obtained from the mammalian subject with a diagnostic reagent that can measure or detect the expression of two biomarkers. In some embodiments, the method may include the step of contacting said blood plasma or blood serum sample obtained from the mammalian subject with a diagnostic reagent that can measure or detect the expression level of two biomarkers and developing a diagnostic algorithm. In some embodiments, the method may include the step of contacting a blood plasma or blood serum sample obtained from the mammalian subject with a diagnostic reagent that can measure or detect the expression of three biomarkers. In some embodiments, the method may include the step of contacting said blood plasma or blood serum sample obtained from the mammalian subject with a diagnostic reagent that can measure or detect the expression level of three biomarkers and developing a diagnostic algorithm. In some embodiments, the method may include the step of contacting a blood plasma or blood serum sample obtained from the mammalian subject with a diagnostic reagent that can measure or detect the expression of three or more biomarkers. In some embodiments, the method may include the step of contacting said blood plasma or blood serum sample obtained from the mammalian subject with a diagnostic reagent that can measure or detect the expression level of three or more biomarkers and developing a diagnostic algorithm. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the subject is a human subject.

In one embodiment, the invention includes a method for treating epilepsy, ES, NES, NS, PNES or NEE in a patient, the method including: (a) contacting a blood sample obtained from said patient with an antibody targeting IL-16; (b) measuring the concentration of IL-16 in said sample; (c) comparing the concentration of IL-16 in said sample to the concentration of IL-16 in a control; (d) wherein said patient has epilepsy, ES, NES, NS, PNES or NEE when the concentrations of IL-16 is altered in said sample relative to control; and (e) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient, the method including: (a) contacting a blood sample obtained from said patient with an antibody targeting ICAM-1; (b) measuring the concentration of ICAM-1 in said sample; (c) comparing the concentration of ICAM-1 in said sample to the concentration of ICAM-1 in a control; (d) wherein said patient has epilepsy, ES, NES, NS, PNES or NEE when the concentrations of ICAM-1 is altered in said sample relative to control; and (e) treating said patient for epilepsy, ES, NES, NS, PNES or NEE. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient, the method including: (a) contacting a blood sample obtained from said patient with an antibody targeting MIP-1β; (b) measuring the concentration of MIP-1β in said sample; (c) comparing the concentration of ICAM-1 in said sample to the concentration of MIP-1β in a control; (d) wherein said patient has epilepsy, ES, NES, NS, PNES or NEE when the concentrations of MIP-1β is altered in said sample relative to control; and (e) treating said patient for epilepsy, ES, NES, NS, PNES or NEE. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient, the method including: (a) contacting a blood sample obtained from said patient with an antibody targeting TRAIL; (b) measuring the concentration of TRAIL in said sample; (c) comparing the concentration of TRAIL in said sample to the concentration of TRAIL in a control; (d) wherein said patient has epilepsy, ES, NES, NS, PNES or NEE when the concentrations of TRAIL is altered in said sample relative to control; and (e) treating said patient for epilepsy, ES, NES, NS, PNES or NEE. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient, the method including: (a) contacting a blood sample obtained from said patient with an antibody targeting TARC; (b) contacting said sample with an antibody targeting IL16; (c) measuring the concentration of TARC in said sample; (d) measuring the concentration of IL-16 in said sample; (e) comparing the concentration of TARC in said sample to the concentration of TARC in a control; (f) comparing the concentration of IL-16 in said sample to the concentration of IL-16 in a control; (g) wherein said patient has epilepsy, ES, NES, NS, PNES or NEE when the concentrations of TARC and IL-16 is altered in said sample relative to control; and (h) treating said patient for epilepsy, ES, NES, NS, PNES or NEE. In some embodiments, the patient has suffered one or more seizures, ES, NES, NS, PNES or NEE. In some embodiments, the patient has suffered one seizure. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient comprising targeting one of the biomarkers selected from Table 2, the method including: (a) contacting a blood sample obtained from said patient with an antibody targeting biomarker 1; (b) measuring the concentration of biomarker 1 in said sample; (c) comparing the concentration of biomarker 1 in said sample to the concentration of biomarker 1 in a control; (d) wherein said patient has epilepsy, ES, NES, NS, PNES or NEE when the concentration of biomarker 1 is altered in said sample relative to control; and (h) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient comprising targeting two biomarkers selected from Table 2, the method including: (a) contacting a blood sample obtained from said patient with an antibody targeting biomarker 1; (b) contacting said sample with an antibody targeting biomarker 2; (c) measuring the concentration of biomarker 1 in said sample; (d) measuring the concentration of biomarker 2 in said sample; (e) comparing the concentration of biomarker 1 in said sample to the concentration of biomarker 1 in a control; (f) comparing the concentration of biomarker 2 in said sample to the concentration of biomarker 2 in a control; (g) wherein said patient has epilepsy, ES, NES, NS, PNES or NEE when the concentrations of biomarker 1 and biomarker 2 is altered in said sample relative to control; and (h) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient comprising targeting three biomarkers selected from Table 2, the method including: (a) contacting a blood sample obtained from said patient with an antibody targeting biomarker 1; (b) contacting said sample with an antibody targeting biomarker 2; (c) contacting said sample with an antibody targeting biomarker 3; (d) measuring the concentration of biomarker 1 in said sample; (e) measuring the concentration of biomarker 2 in said sample; (f) measuring the concentration of biomarker 3 in said sample; (g) comparing the concentration of biomarker 1 in said sample to the concentration of biomarker 1 in a control; (h) comparing the concentration of biomarker 2 in said sample to the concentration of biomarker 2 in a control; (i) comparing the concentration of biomarker 3 in said sample to the concentration of biomarker 3 in a control; (j) wherein said patient has epilepsy, ES, NES, NS, PNES or NEE when the concentrations of biomarker 1, biomarker 2 and biomarker 3 is altered in said sample relative to control; and (k) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient comprising targeting three or more biomarkers selected from Table 2, the method including: (a) contacting a blood sample obtained from said patient with an antibody targeting biomarkers; (b) measuring the concentration of biomarkers in said sample; (c) comparing the concentration of biomarkers in said sample to the concentration of biomarkers in a control; (d) wherein said patient has epilepsy, ES, NES, NS, PNES or NEE when the concentrations of biomarkers are altered in said sample relative to control; and (e) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method for treating epilepsy, ES, NES, NS, PNES or NEE in a patient comprising targeting three biomarkers selected from Table 2, the method including: (a) contacting a blood sample obtained from said patient with an antibody targeting TARC; (b) contacting said sample with an antibody targeting IL-16; (c) contacting said sample with an antibody targeting biomarker TNF-alpha; (d) measuring the concentration of TARC in said sample; (e) measuring the concentration of IL-16 in said sample; (f) measuring the concentration of TNF-alpha in said sample; (g) comparing the concentration of TARC in said sample to the concentration of TARC in a control; (h) comparing the concentration of IL-16 in said sample to the concentration of IL-16 in a control; (i) comparing the concentration of TNF-alpha in said sample to the concentration of TNF-alpha in a control; (j) wherein said patient has epilepsy, ES, NES, NS, PNES or NEE when the concentrations of TARC, IL-16 and TNF-alpha is altered in said sample relative to control; and (k) treating said patient for epilepsy, ES, NES, NS, PNES or NEE. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method of treating epilepsy, ES, NES, NS, PNES or NEE in a patient in need of epilepsy, ES, NES, NS, PNES or NEE treatment, the method comprising: contacting one or more blood samples obtained from the patient with one or more antibodies targeting one or more biomarkers selected from Table 2; measuring the concentrations of the one or more biomarkers in the one or more blood samples; comparing the concentrations of the one or more biomarkers in the one or more blood samples to the concentration of the one or more biomarkers in one or more controls; and treating the patient for epilepsy, ES, NES, NS, PNES or NEE; wherein the patient is in need of epilepsy, ES, NES, NS, PNES or NEE treatment when the concentrations of the one or more biomarkers are altered in the one or more blood samples relative to the one or more controls. In some embodiments, the one or more biomarkers are selected from the group consisting of one biomarker, two biomarkers, and three biomarkers. In some embodiments, the one or more biomarkers are selected from the ICAM-1, MIP-1β, TRAIL, TARC, and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures, ES, NES, NS, PNES or NEE. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method of predicting whether a subject will have a seizure, ES, NES, NS, PNES or NEE, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is predicted to have a seizure when the concentrations of the one or more biomarkers are altered in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has already suffered one or more seizures, NES, NS, PNES or NEE. In some embodiments, the subject has already suffered one seizure, NES, NS, PNES or NEE. In some embodiments, the subject has already suffered two seizures, NES, NS, PNES or NEE. In some embodiments, the subject is a human subject.

In one embodiment, the invention includes a method of predicting whether a subject needs treatment including a therapeutic agent effective to treat seizures, ES, NES, NS, PNES or NEE, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is predicted to need treatment including a therapeutic agent effective to treat epileptic seizures when the concentrations of the one or more biomarkers are altered in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures, ES, NES, NS, PNES or NEE. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, a therapeutic agent effective to treat epileptic seizures includes one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials.

In one embodiment, the invention includes a method of selecting a therapeutic agent effective to treat epileptic seizures, ES, NES, NS, PNES or NEE in a subject, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the ratio(s) of the concentrations of the one or more biomarkers from the one or more blood samples relative to the one or more controls is predictive of the effectiveness of a specific therapeutic agent. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures, ES, NES, NS, PNES or NEE. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, a therapeutic agent effective to treat epileptic seizures, ES, NES, NS, PNES or NEE, includes one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials.

In one embodiment, the invention includes a method of adjusting the dose of a therapeutic agent effective to treat epileptic seizures, ES, NES, NS, PNES or NEE in a subject, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the ratio(s) of the concentrations of the one or more biomarkers from the one or more blood samples relative to the one or more controls is predictive of a need to adjust the dose of the therapeutic agent. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures, ES, NES, NS, PNES or NEE. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, a therapeutic agent effective to treat epileptic seizures, NES, NS, PNES or NEE includes one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials.

In some embodiments, a method of treating epilepsy, ES, NES, NS, PNES or NEE in a patient includes administering to the patient one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method of treating epilepsy, ES, NES, NS, PNES or NEE in a patient likely to benefit from epilepsy, ES, NES, NS, PNES or NEE treatment, the method including administering to the patient one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the likelihood of beneficial epilepsy, ES, NES, NS, PNES or NEE treatment is determined by a serum based analytical method including the steps of: contacting one or more blood samples obtained from the patient with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is likely to benefit from epilepsy, ES, NES, NS, PNES or NEE treatment when the concentrations of the one or more biomarkers are altered in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a method of treating epilepsy, ES, NES, NS, PNES or NEE in a patient having an altered blood level of one or more biomarkers selected from Table 2, the method including administering to the patient one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the altered blood level of the one or more biomarkers is determined by a serum based analytical method including the steps of: contacting one or more blood samples obtained from the patient with one or more antibodies targeting the one or more biomarkers; measuring the concentrations of the one or more biomarkers in the one or more blood samples; and comparing the concentrations of the one or more biomarkers in the one or more blood samples to the concentration of the one or more biomarkers in one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In some embodiments, the invention provides for methods of leveraging one or more biomarker concentrations, and combined into a diagnostic algorithm that can predict changes in patient epileptic seizure burden or frequency over a time period as a result of additional intervention or no intervention. This includes a method of treating epilepsy, ES, NES, NS, PNES or NEE in a patient having an altered blood level of one or more biomarkers selected from Table 2, the method including administering to the patient one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the altered blood level of the one or more biomarkers is determined by a serum based analytical method including the steps of: contacting one or more blood samples obtained from the patient with one or more antibodies targeting the one or more biomarkers; measuring the concentrations of the one or more biomarkers in the one or more blood samples; and comparing the concentrations of the one or more biomarkers in the one or more blood samples to the concentration of the one or more biomarkers in one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective. This includes a method of treating epilepsy, ES, NES, NS, PNES or NEE in a patient having an altered blood level of one or more biomarkers selected from Table 2, the method including administering to the patient one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the altered blood level of the one or more biomarkers is determined by a serum based analytical method including the steps of: contacting one or more blood samples obtained from the patient with one or more antibodies targeting the one or more biomarkers; measuring the concentrations of the one or more biomarkers in the one or more blood samples; and comparing the concentrations of the one or more biomarkers in the one or more blood samples to the concentration of the one or more biomarkers in one or more controls. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure, ES, NES, NS, PNES or NEE. In some embodiments, the patient has suffered two seizures, ES, NES, NS, PNES or NEE. In some embodiments, the patient is a human subject.

In one embodiment, the invention includes a system for determining a likelihood that a subject will be responsive to a treatment regimen that includes administering to the subject an epilepsy, ES, NES, NS, PNES or NEE therapeutic agent, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy, ES, NES, NS, PNES or NEE to the subject or to a practitioner charged with caring for the subject. In some embodiments, altered concentrations of the one or more biomarkers in the one or more blood samples compared to the concentration of the one or more biomarkers in the one or more controls indicate a positive likelihood that the subject will be responsive to the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In one embodiment, the invention includes a system for predicting a likelihood that a subject will have a seizure, ES, NES, NS, PNES or NEE, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions to the subject or to a practitioner charged with caring for the subject that the subject is likely to have a seizure. In some embodiments, altered concentrations of the one or more biomarkers in the one or more blood samples compared to the concentration of the one or more biomarkers in the one or more controls indicate that the subject will have a seizure. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In one embodiment, the invention includes a system for determining a likelihood that a subject needs a treatment regimen that includes administering to the subject an epilepsy, ES, NES, NS, PNES or NEE therapeutic agent, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy, ES, NES, NS, PNES or NEE to the subject or to a practitioner charged with caring for the subject. In some embodiments, altered concentrations of the one or more biomarkers in the one or more blood samples compared to the concentration of the one or more biomarkers in the one or more controls indicate that the subject needs the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In one embodiment, the invention includes a system for selecting a specific therapeutic agent for a treatment regimen in a subject, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for selecting a specific therapeutic agent to the subject or to a practitioner charged with caring for the subject. In some embodiments, altered concentrations of the one or more biomarkers in the one or more blood samples compared to the concentration of the one or more biomarkers in the one or more controls indicate that the subject needs a specific therapeutic agent. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from the TRAIL, ICAM-1, MCP-2, TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In one embodiment, the invention includes a system for adjusting the dosage of a therapeutic agent for a treatment regimen in a subject, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for adjusting dosage of the therapeutic agent to the subject or to a practitioner charged with caring for the subject. In some embodiments, altered concentrations of the one or more biomarkers in the one or more blood samples compared to the concentration of the one or more biomarkers in the one or more controls indicate that the dosage of the therapeutic agent needs to be adjusted. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, eslicarbazepine acetate, ethosuxemide, ezogabine, felbamate, divalproex, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure, ES, NES, NS, PNES or NEE. In some embodiments, the subject has suffered two seizures, ES, NES, NS, PNES or NEE. In some embodiments, the subject is a human subject. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In one embodiment, the invention includes a non-transitory computer readable storage medium for determining a likelihood that a subject will be responsive to a treatment regimen that includes administering to the subject an epilepsy, ES, NES, NS, PNES or NEE therapeutic agent, the non-transitory computer readable storage medium storing one or more programs for execution by one or more processors of a computer system, the one or more computer programs including instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy, ES, NES, NS, PNES or NEE to the subject or to a practitioner charged with caring for the subject. In some embodiments, altered concentrations of the one or more biomarkers in the one or more blood samples compared to the concentration of the one or more biomarkers in the one or more controls indicate a positive likelihood that the subject will be responsive to the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, ICAM-1, MIP-1β, TRAIL and TNF-alpha. In some embodiments, the one or more biomarkers are selected from TRAIL, ICAM-1, MCP-2, and TNF-R1. In some embodiments, the one or more biomarkers are selected from MIP-5, IL-7, and M-CSF. In some embodiments, the one or more biomarkers are selected from IL-16, TARC, TNF-alpha, MCP-1 and VCAM-1. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure. In some embodiments, the subject has suffered two seizures. In some embodiments, the subject is a human subject. The invention also includes non-transitory computer readable storage mediums for determining likelihoods as described herein, as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the invention provides for methods of leveraging one or more biomarker concentrations, and combined into a diagnostic algorithm that can predict changes in patient epileptic seizure burden or frequency over a time period as a result of additional intervention or no intervention. In some embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective.

In some embodiments, the method may include the step of contacting said blood plasma or blood serum sample obtained from the mammalian subject with a diagnostic reagent that can measure or detect the expression level of IL-16. In some embodiments, the method may include the step of comparing the concentrations of IL-16 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TARC. In some embodiments, the method may include the step of comparing the concentrations of TARC to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TRAIL. In some embodiments, the method may include the step of comparing the concentrations of TRAIL to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-4. In some embodiments, the method may include the step of comparing the concentrations of MCP-4 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of IL-7. In some embodiments, the method may include the step of comparing the concentrations of IL-7 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of P-Cadherin. In some embodiments, the method may include the step of comparing the concentrations of P-Cadherin to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of Osteoactivin. In some embodiments, the method may include the step of comparing the concentrations of Osteoactivin to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of ICAM-1. In some embodiments, the method may include the step of comparing the concentrations of ICAM-1 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MMP-3. In some embodiments, the method may include the step of comparing the concentrations of MMP-3 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of M-CSF. In some embodiments, the method may include the step of comparing the concentrations of M-CSF to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-2. In some embodiments, the method may include the step of comparing the concentrations of MCP-2 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of GM-CSF. In some embodiments, the method may include the step of comparing the concentrations of GM-CSF to normal control concentrations. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-1. In some embodiments, the method may include the step of comparing the concentrations of MCP-1 to normal control concentrations. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of VCAM-1. In some embodiments, the method may include the step of comparing the concentrations of VCAM-1 to normal control concentrations. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MIP-1β. In some embodiments, the method may include the step of comparing the concentrations of MIP-1β to normal control concentrations. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TNF-α. In some embodiments, the method may include the step of comparing the concentrations of TNF-α to normal control concentrations. In some embodiments, the method may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of IL-8. In some embodiments, the method may include the step of comparing the concentrations of IL-8 to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of SAA. In some embodiments, the method may include the step of comparing the concentrations of SAA to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of other markers defined herein. In some embodiments, the method may include the step of comparing the concentrations of other markers defined herein to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of CRP. In some embodiments, the method may include the step of comparing the concentrations of CRP to normal control concentrations. In some embodiments, the method may include the step of diagnosing epilepsy, ES, NES, NS, PNES or NEE in the mammalian subject. In some embodiments, it may be combined with one or more biomarkers as defined herein, and may be incorporated into a diagnostic algorithm. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In an embodiment, the invention includes a method for diagnosing epilepsy, ES, NES, NS, PNES or NEE and/or a seizure in a mammalian subject that may include the step of contacting a blood plasma or blood serum sample obtained from the mammalian subject with a diagnostic reagent that can measure or detect the expression level of TARC. In some embodiments, the method may include the step of contacting said blood plasma or blood serum sample obtained from the mammalian subject with a diagnostic reagent that can measure or detect the expression level of IL-16. In some embodiments, the method may include the step of comparing the concentrations of TARC and IL-16 to normal control concentrations. In some embodiments, the method may include the step of comparing concentration ratios of TARC and IL-16 to normal control concentration ratios. In some embodiments, the measurements can be performed in multiple locations, including but not limited to, direct by the patient, at the point of care, in a physician's office or performed in a laboratory, which may include the step of diagnosing epilepsy, ES, NES, NS, PNES or NEE in the mammalian subject. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the mammalian subject is a human subject.

In an embodiment, the invention includes a kit for generating quantitative data for a patient. In some embodiments, the kit may include a diagnostic reagent that can measure an expression level of IL-16 in a blood plasma or blood serum sample taken from the patient. In some embodiments, the kit may include a diagnostic reagent that can measure an expression level of TARC in the blood plasma or blood serum sample taken from the patient. In some embodiments, the kit may include a diagnostic reagent that can measure an expression level of TNF-α in the blood plasma or blood serum sample taken from the patient. In some embodiments, the kit may include an analysis unit for comparison of the expression levels of IL-16, TARC, and TNF-α to expression levels of normal controls. In some embodiments, the kit may include an analysis unit for comparison of the expression levels of IL-16, TARC, and TNF-α and any one or more biomarkers contained and defined herein, including but not limited to IL-1B, IL-2, IL-6, IL-8, IL-10, IL-12p70, IFN-γ, IL-13, IL-4, IL-17A, GM-CSF, IL-12/IL-23p40, IL-15, IL-1α, IL-5, IL-7, TNF-β, VEGF-A, MCP-1/CCL2, Eotaxin, Eotaxin-3, IP-10, MCP-4, MDC, MIP-1α, MIP-1β, sICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL such as to expression levels of normal controls. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the patient is a human subject.

In an embodiment, the invention includes a system for scoring a sample, said system comparing expression levels of one or more biomarkers to determine epilepsy, ES, NES, NS, PNES or NEE from normal controls. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the patient is a human subject.

In an embodiment, the invention includes a computer having software, with said software comparing expression levels of one or more biomarkers to determine epilepsy, ES, NES, NS, PNES or NEE from normal controls. The method may also include administering a therapy for seizure and or epilepsy, ES, NES, NS, PNES or NEE to the patient. Measurements can be performed in multiple locations, including but not limited to, direct by the patient, at the point of care, in a physician's office or performed in a laboratory. In some embodiments, the patient is a human subject.

In an embodiment, the invention includes a method of treating a seizure disorder in a patient with altered blood plasma or blood serum expression levels of one or more biomarkers, a product of or a ratio of a combination thereof, relative to a normal control, the method including administering a therapy for epilepsy, ES, NES, NS, PNES or NEE to the patient. Measurements can be performed in multiple locations, including but not limited to, direct by the patient, at the point of care, in a physician's office or performed in a laboratory.

In an embodiments, the invention provides for methods of leveraging one or more biomarker concentrations, and combined into a diagnostic algorithm that can predict changes in patient epileptic seizure burden or frequency over a time period as a result of additional intervention or no intervention. Measurements can be performed in multiple locations, including but not limited to, direct by the patient, at the point of care, in a physician's office or performed in a laboratory.

In an embodiments, the invention provides for methods of leveraging one or more biomarker concentrations, and combined into a diagnostic algorithm that can predict changes in patient epileptic seizure burden or frequency over a time period as a result of additional intervention or no intervention to determine if current or new treatment is effective. Measurements can be performed in multiple locations, including but not limited to, direct by the patient, at the point of care, in a physician's office or performed in a laboratory.

The disclosure provides a method of diagnosing ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-γ, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient has ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a diagnosis class, including, but not limited to, ES, NES, NS, PNES, NEE, non-ES, non-NES, non-NS, non-PNES, and/or non-NEE.

The disclosure also provides a method of differentially and/or comparatively diagnosing between ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is positively diagnosed with having one of ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a differentially and/or comparatively diagnosis class, including, but not limited to, ES, NES, NS, PNES, and/or NEE.

The disclosure also provides a method of differentially and/or comparatively diagnosing between ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-γ, IL-1a, IL-1B, IL-2, IL-4, IL-5, IL-7, IL-6, IL-13, IL-12XIL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is positively diagnosed with not having one or more of ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a differentially and/or comparatively diagnosis class, including, but not limited to, non-ES, non-NES, non-NS, non-PNES, and/or non-NEE.

The disclosure also provides a method of diagnosing epilepsy, ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1β, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient has epilepsy, ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a differentially and/or comparatively diagnosis class, including, but not limited to, epilepsy, ES, NES, NS, PNES, NEE, non-epilepsy, non-ES, non-NES, non-NS, non-PNES, and/or non-NEE.

The disclosure also provides a method of differentially and/or comparatively diagnosing between epilepsy, ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is positively diagnosed with having one of epilepsy, ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a differentially and/or comparatively diagnosis class, including, but not limited to, epilepsy, ES, NES, NS, PNES, and/or NEE.

The disclosure also provides a method of differentially and/or comparatively diagnosing between epilepsy, ES, NES, NS, PNES, or NEE in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is positively diagnosed with not having one or more of epilepsy, ES, NES, NS, PNES, or NEE when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with a differentially and/or comparatively diagnosis class, including, but not limited to, non-epilepsy, non-ES, non-NES, non-NS, non-PNES, and/or non-NEE.

The disclosure also provides a method of evaluating, monitoring, and/or predicting patient epileptic seizure burden and/or frequency in a patient, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12XIL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is predicted to have one or more seizures, or no seizures, within a period of time, when the concentrations of the one or more biomarkers are altered in the one or more biological samples relative to the one or more control samples. In some embodiments, the period of time is selected from one hour, two hours, three hours, four hours, five hours, six hours, seven hours, eight hours, nine hours, ten hours, eleven hours, twelve hours, eighteen hours, twenty-four hours, one day, two days, three days, four days, five days, six days, seven days, one week, two weeks, three weeks, four weeks, one month, two months, three months, four months, five months, six months, nine months, and one year. In some embodiments, the seizure burden and/or frequency of the patient is predicted to increase. In some embodiments, the seizure burden and/or frequency of the patient is predicted to decrease. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with seizure burden and/or frequency predicted to increase. In some embodiments, a trained model output value allows classification of the patient with seizure burden and/or frequency predicted to decrease.

The disclosure also provides a method of determining, monitoring, and/or predicting the likelihood of a patient to respond to epilepsy, ES, NES, NS, PNES, or NEE treatment, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is likely to respond to epilepsy, ES, NES, NS, PNES, or NEE treatment when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel.

In some embodiments, a trained model output value allows classification of the patient with likelihood to respond to epilepsy, ES, NES, NS, PNES, or NEE treatment.

The disclosure also provides a method of determining, monitoring, and/or predicting the likelihood of a patient to respond to epilepsy, ES, NES, NS, PNES, or NEE treatment, the method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12XIL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is unlikely to respond to epilepsy, ES, NES, NS, PNES, or NEE treatment when the concentrations of the one or more biomarkers are altered in the one or more biological samples relative to the one or more control samples. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with likelihood not to respond to epilepsy, ES, NES, NS, PNES, or NEE treatment.

In some embodiments of a method described herein, the patient has a co-occurring inflammation associated disease. In some embodiments, the associated disease is selected from, without limitation, Crohn's disease, encephalitis, Sturge-Weber syndrome, celiac disease, type 2 diabetes, migraine, rheumatoid arthritis, and one or more unspecified autoimmune diseases. In some embodiments of a method described herein, the patient has under medication. In some embodiments, medication includes NSAID use.

The disclosure also provides a method of treating epilepsy, ES, NES, NS, PNES, or NEE in a patient, the method comprising: (a) selecting a patient for epilepsy, ES, NES, NS, PNES, or NEE treatment; and (b) treating the patient for epilepsy, ES, NES, NS, PNES, or NEE; wherein the patient is selected for epilepsy, ES, NES, NS, PNES, or NEE treatment according to any method described herein.

In some embodiments of a method described herein, an altered biomarker concentration is independently selected for each biomarker from an increased concentration and a decreased concentration. In some embodiments of a method described herein, a biological sample is independently for each biomarker a blood sample. In some embodiments of a method described herein, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1β and osteoactivin. In some embodiments of a method described herein, the one or more biomarkers are IL-16, ICAM-1, and TRAIL. In some embodiments of a method described herein, the one or more biomarkers are IL-16, ICAM-1, TRAIL, and MIP-1β. In some embodiments of a method described herein, the one or more biomarkers are TRAIL, ICAM-1, MCP-2, and TNF-R1. In some embodiments of a method described herein, the one or more biomarkers are IL-10, MCP-4, MMP-3, and TNF-α. In some embodiments of a method described herein, the patient has suffered one or more seizures. In some embodiments of a method described herein, the patient has suffered one seizure, two seizures, or more than two seizures. In some embodiments of a method described herein, the patient has not suffered any seizures.

In some embodiments of a method described herein, treating the patient for epilepsy, ES, NES, NS, PNES, or NEE comprises administering to the patient one or more therapeutic agents selected from parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, this may be for drugs and therapeutic agents and methods currently in development and or in clinical trials. In some embodiments of a method described herein, treating the patient for epilepsy, ES, NES, NS, PNES, or NEE comprises one or more of psychotherapy, cognitive therapy, behavioral therapy, and standard medical care.

The disclosure also provides a method of treating epilepsy, ES, NES, NS, PNES, or NEE in a patient likely to benefit from treatment for epilepsy, ES, NES, NS, PNES, or NEE, the method comprising administering to the patient one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. The disclosure also provides a method of treating epilepsy, ES, NES, NS, PNES, or NEE in a patient likely to benefit from treatment for epilepsy, ES, NES, NS, PNES, or NEE, the method comprising administering to the patient one or more of psychotherapy, cognitive therapy, behavioral therapy, and standard medical care. In some embodiments, the likelihood of beneficial treatment for epilepsy, ES, NES, NS, PNES, or NEE is determined by a serum based analytical method comprising: (a) contacting one or more biological samples obtained from the patient with one or more antibodies targeting one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; (b) measuring the concentrations of the one or more biomarkers in the one or more biological samples; and (c) comparing the concentrations of the one or more biomarkers in the one or more biological samples with the concentrations of the one or more biomarkers in one or more control samples; wherein the patient is likely to benefit from treatment for epilepsy, ES, NES, NS, PNES, or NEE when the concentrations of the one or more biomarkers are altered in the one or more biological samples relative to the one or more control samples. In some embodiments, an altered biomarker concentration is independently selected for each biomarker from an increased concentration and a decreased concentration. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1B and osteoactivin. In some embodiments, the one or more biomarkers are IL-16, ICAM-1, and TRAIL. In some embodiments, the one or more biomarkers are IL-16, ICAM-1, TRAIL, and MIP-1β. In some embodiments, the one or more biomarkers are TRAIL, ICAM-1, MCP-2, and TNF-R1. In some embodiments, the one or more biomarkers are IL-10, MCP-4, MMP-3, and TNF-α. In some embodiments, the patient has suffered one or more seizures. In some embodiments, the patient has suffered one seizure, two seizures, or more than two seizures. In some embodiments, the patient has not suffered any seizures. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with likelihood to respond to epilepsy, ES, NES, NS, PNES, or NEE treatment. In some embodiments, a trained model output value allows classification of the patient with likelihood not to respond to epilepsy, ES, NES, NS, PNES, or NEE treatment.

The disclosure also provides a method of treating epilepsy, ES, NES, NS, PNES, or NEE in a patient having an altered blood level of one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A, the method comprising administering to the patient one or more therapeutic agents selected from parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, this may be for drugs and therapeutic agents and methods currently in development and or in clinical trials. The disclosure also provides a method of treating epilepsy, ES, NES, NS, PNES, or NEE in a patient having an altered blood level of one or more biomarkers selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12XIL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, VEGF-A, the method comprising administering to the patient one or more of psychotherapy, cognitive therapy, behavioral therapy, and standard medical care. In some embodiments, the altered blood level of the one or more biomarkers is determined by a serum based analytical method comprising: contacting one or more biological samples obtained from the patient with one or more antibodies targeting the one or more biomarkers; measuring the concentrations of the one or more biomarkers in the one or more biological samples; and comparing the concentrations of the one or more biomarkers in the one or more biological samples to the concentration of the one or more biomarkers in one or more controls. In some embodiments, an altered biomarker blood level is independently selected for each biomarker from an increased blood level and a decreased blood level. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1B and osteoactivin. In some embodiments, the one or more biomarkers are IL-16, ICAM-1, and TRAIL. In some embodiments, the one or more biomarkers are IL-16, ICAM-1, TRAIL, and MIP-1β. In some embodiments, the one or more biomarkers are TRAIL, ICAM-1, MCP-2, and TNF-R1. In some embodiments, the one or more biomarkers are IL-10, MCP-4, MMP-3, and TNF-α. In some embodiments, the patient has suffered one or more seizures. In some embodiments, the patient has suffered one seizure, two seizures, or more than two seizures. In some embodiments, the patient has not suffered any seizures. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient with having an altered blood level of one or more biomarkers correlated with a likelihood to respond to epilepsy, ES, NES, NS, PNES, or NEE treatment. In some embodiments, a trained model output value allows classification of the patient with having an altered blood level of one or more biomarkers correlated with a likelihood not to respond to epilepsy, ES, NES, NS, PNES, or NEE treatment.

In some embodiments of a method described herein, the patient has been identified as having one or more of a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma.

The disclosure also provides a system for one or more of: diagnosing epilepsy, ES, NES, NS, PNES, or NEE in a patient; differentially and/or comparatively diagnosing between epilepsy, ES, NES, NS, PNES, or NEE in a patient; evaluating patient epileptic seizure burden and/or frequency in a patient; and determining the likelihood of a patient to respond to epilepsy, ES, NES, NS, PNES, or NEE treatment; the system comprising: memory; one or more processors; and one or more modules stored in memory and configured for execution by the one or more processors, the modules comprising instructions for carrying out one or more methods described herein.

The disclosure also provides a non-transitory computer readable storage medium for one or more of: diagnosing epilepsy, ES, NES, NS, PNES, or NEE in a patient; differentially and/or comparatively diagnosing between epilepsy, ES, NES, NS, PNES, or NEE in a patient; evaluating, monitoring, and/or predicting patient epileptic seizure burden and/or frequency in a patient; and determining the likelihood of a patient to respond to epilepsy, ES, NES, NS, PNES, or NEE treatment; the non-transitory computer readable storage medium storing one or more programs for execution by one or more processors of a computer system, the one or more computer programs comprising instructions for carrying out one or more methods described herein.

The disclosure also provides a system for one or more of: diagnosing epilepsy, ES, NES, NS, PNES, or NEE in a patient; differentially and/or comparatively diagnosing between epilepsy, ES, NES, NS, PNES, or NEE in a patient; evaluating, monitoring, and/or predicting patient epileptic seizure burden and/or frequency in a patient; and determining the likelihood of a patient to respond to epilepsy, ES, NES, NS, PNES, or NEE treatment; the system comprising: memory; one or more processors; and one or more modules stored in memory and configured for execution by the one or more processors, the modules comprising instructions for: (a) obtaining the concentration of one or more biomarkers in one or more biological samples obtained from the patient by contacting the one or more biological samples with one or more antibodies targeting the one or more biomarkers, wherein the one or more biomarkers are selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, VEGF-A; and (b) comparing the concentrations of the one or more biomarkers in the one or more biological samples to the concentration of the one or more biomarkers in one or more controls and determining whether the concentrations of the one or more biomarkers are altered in the one or more biological samples relative to the one or more control samples. In some embodiments, the modules further comprise instructions for: (c) providing instructions for treating the subject for epilepsy, ES, NES, NS, PNES, or NEE to the subject or to a practitioner charged with caring for the subject. In some embodiments, altered concentrations of the one or more biomarkers in the one or more biological samples compared to the concentration of the one or more biomarkers in the one or more controls indicate a positive diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a negative diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a differential and/or comparative diagnostic of one of epilepsy, ES, NES, NS, PNES, or NEE in the patient. In some embodiments, altered concentrations of the one or more biomarkers in the one or more biological samples compared to the concentration of the one or more biomarkers in the one or more controls predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, altered concentrations of the one or more biomarkers in the one or more biological samples compared to the concentration of the one or more biomarkers in the one or more controls indicate a likelihood of the patient to respond to epilepsy, ES, NES, NS, PNES, or NEE treatment. In some embodiments, an altered biomarker concentration is independently selected for each biomarker from an increased concentration and a decreased concentration. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1b and osteoactivin. In some embodiments, the one or more biomarkers are IL-16, ICAM-1, and TRAIL. In some embodiments, the one or more biomarkers are IL-16, ICAM-1, TRAIL, and MIP-1B. In some embodiments, the one or more biomarkers are TRAIL, ICAM-1, MCP-2, and TNF-R1. In some embodiments, the one or more biomarkers are IL-10, MCP-4, MMP-3, and TNF-a. In some embodiments, the patient has suffered one or more seizures. In some embodiments, the patient has suffered one seizure, two seizures, or more than two seizures. In some embodiments, the patient has not suffered any seizures. In some embodiments, the treatment regimen comprises administering to the patient one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, the treatment regimen comprises administering to the patient one or more of psychotherapy, cognitive therapy, behavioral therapy, and standard medical care. In some embodiments, this may be for drugs and therapeutic agents and methods currently in development and or in clinical trials. In some embodiments, the patient has been identified as having one or more of a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient into a diagnosis class for epilepsy, ES, NES, NS, PNES, or NEE. In some embodiments, a trained model output value allows classification of the patient into a differential and/or comparative diagnosis class for epilepsy, ES, NES, NS, PNES, or NEE. In some embodiments, a trained model output value allows classification of the patient into a diagnosis class for evaluating, monitoring, and/or predicting patient epileptic seizure burden and/or frequency. In some embodiments, a trained model output value allows classification of the patient into a diagnosis class for likelihood to respond to epilepsy, ES, NES, NS, PNES, or NEE treatment.

The disclosure also provides a non-transitory computer readable storage medium for one or more of: diagnosing epilepsy, ES, NES, NS, PNES, or NEE in a patient; differentially and/or comparatively diagnosing between epilepsy, ES, NES, NS, PNES, or NEE in a patient; evaluating, monitoring, and/or predicting patient epileptic seizure burden and/or frequency in a patient; and determining the likelihood of a patient to respond to epilepsy, ES, NES, NS, PNES, or NEE treatment; the non-transitory computer readable storage medium storing one or more programs for execution by one or more processors of a computer system, the one or more computer programs comprising instructions for: (a) obtaining the concentration of one or more biomarkers in one or more biological samples obtained from the patient by contacting the one or more biological samples with one or more antibodies targeting the one or more biomarkers, wherein the one or more biomarkers are selected from calbindin, CRP, cytokeratin-8, eotaxin, eotaxin-2, eotaxin-3, GM-CSF, ICAM-1, IFN-a, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; and (b) comparing the concentrations of the one or more biomarkers in the one or more biological samples to the concentration of the one or more biomarkers in one or more controls and determining whether the concentrations of the one or more biomarkers are altered in the one or more biological samples relative to the one or more control samples. In some embodiments, the one or more computer programs further comprise instructions for: (c) providing instructions for treating the subject for epilepsy, ES, NES, NS, PNES, or NEE to the subject or to a practitioner charged with caring for the subject. In some embodiments, altered concentrations of the one or more biomarkers in the one or more biological samples compared to the concentration of the one or more biomarkers in the one or more controls indicate a positive diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a negative diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a differential and/or comparative diagnostic of one of epilepsy, ES, NES, NS, PNES, or NEE in the patient. In some embodiments, altered concentrations of the one or more biomarkers in the one or more biological samples compared to the concentration of the one or more biomarkers in the one or more controls predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, altered concentrations of the one or more biomarkers in the one or more biological samples compared to the concentration of the one or more biomarkers in the one or more controls indicate a likelihood of the patient to respond to epilepsy, ES, NES, NS, PNES, or NEE treatment. In some embodiments, an altered biomarker concentration is independently selected for each biomarker from an increased concentration and a decreased concentration. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1B and osteoactivin. In some embodiments, the one or more biomarkers are IL-16, ICAM-1, and TRAIL. In some embodiments, the one or more biomarkers are IL-16, ICAM-1, TRAIL, and MIP-1B. In some embodiments, the one or more biomarkers are TRAIL, ICAM-1, MCP-2, and TNF-R1. In some embodiments, the one or more biomarkers are IL-10, MCP-4, MMP-3, and TNF-a. In some embodiments, the patient has suffered one or more seizures. In some embodiments, the patient has suffered one seizure, two seizures, or more than two seizures. In some embodiments, the patient has not suffered any seizures. In some embodiments, the treatment regimen comprises administering to the patient one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, the treatment regimen comprises administering to the patient one or more of psychotherapy, cognitive therapy, behavioral therapy, and standard medical care. In some embodiments, the patient has been identified as having one or more of a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient into a diagnosis class for epilepsy, ES, NES, NS, PNES, or NEE. In some embodiments, a trained model output value allows classification of the patient into a differential and/or comparative diagnosis class for epilepsy, ES, NES, NS, PNES, or NEE. In some embodiments, a trained model output value allows classification of the patient into a diagnosis class for evaluating, monitoring, and/or predicting patient epileptic seizure burden and/or frequency. In some embodiments, a trained model output value allows classification of the patient into a diagnosis class for likelihood to respond to epilepsy, ES, NES, NS, PNES, or NEE treatment.

The disclosure also provides a system for one or more of: diagnosing epilepsy, ES, NES, NS, PNES, or NEE in a patient; differentially and/or comparatively diagnosing between epilepsy, ES, NES, NS, PNES, or NEE in a patient; evaluating, monitoring, and/or predicting patient epileptic seizure burden and/or frequency in a patient; and determining the likelihood of a patient to respond to epilepsy, ES, NES, NS, PNES, or NEE treatment; the system comprising:

memory; one or more processors; and one or more modules stored in memory and configured for execution by the one or more processors, the modules comprising instructions for: (a) obtaining one or more input values relating to the patient having a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma; and (b) comparing the one or more input values to one or more reference values and determining whether the input values are altered relative to the one or more reference values. In some embodiments, the modules further comprise instructions for: (c) providing instructions for treating the subject for epilepsy, ES, NES, NS, PNES, or NEE to the subject or to a practitioner charged with caring for the subject. In some embodiments, a difference between the one or more input values and the one or more reference values indicate a positive diagnostic of epilepsy, ES, NES, NS, PNES, or NEE in the patient. In some embodiments, a difference between the one or more input values and the one or more reference values indicate a negative diagnostic of epilepsy, ES, NES, NS, PNES, or NEE in the patient. In some embodiments, a difference between the one or more input values and the one or more reference values indicate a differential and/or comparative diagnostic of one of epilepsy, ES, NES, NS, PNES, or NEE in the patient. In some embodiments, a difference between the one or more input values and the one or more reference values predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, a difference between the one or more input values and the one or more reference values indicate a likelihood of the patient to respond to epilepsy, ES, NES, NS, PNES, or NEE treatment. In some embodiments, a difference between the one or more input values and the one or more reference values is independently selected for each value from having a risk factor, and not having a risk factor. In some embodiments, the modules further comprise instructions for: (d) obtaining the concentration of one or more biomarkers in one or more biological samples obtained from the patient by contacting the one or more biological samples with one or more antibodies targeting the one or more biomarkers, wherein the one or more biomarkers are selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A; and (e) comparing the concentrations of the one or more biomarkers in the one or more biological samples to the concentration of the one or more biomarkers in one or more controls and determining whether the concentrations of the one or more biomarkers are altered in the one or more biological samples relative to the one or more control samples. In some embodiments, altered concentrations of the one or more biomarkers in the one or more biological samples compared to the concentration of the one or more biomarkers in the one or more controls indicate a positive diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a negative diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a differential and/or comparative diagnostic of one of epilepsy, ES, NES, NS, PNES, or NEE in the patient. In some embodiments, altered concentrations of the one or more biomarkers in the one or more biological samples compared to the concentration of the one or more biomarkers in the one or more controls predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, altered concentrations of the one or more biomarkers in the one or more biological samples compared to the concentration of the one or more biomarkers in the one or more controls indicate a likelihood of the patient to respond to epilepsy, ES, NES, NS, PNES, or NEE treatment. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1β, MIP-1B and SCF, MCP-4 and MMP-3, IL-10 and MMP-3, IL-16 and MIP-1B, MIP-1B and Nectin-4, and MIP-1B and osteoactivin. In some embodiments, the one or more biomarkers are IL-16, ICAM-1, and TRAIL. In some embodiments, the one or more biomarkers are IL-16, ICAM-1, TRAIL, and MIP-1β. In some embodiments, the one or more biomarkers are TRAIL, ICAM-1, MCP-2, and TNF-R1. In some embodiments, the one or more biomarkers are IL-10, MCP-4, MMP-3, and TNF-α. In some embodiments, the patient has suffered one or more seizures. In some embodiments, the patient has suffered one seizure, two seizures, or more than two seizures. In some embodiments, the patient has not suffered any seizures. In some embodiments, the treatment regimen comprises administering to the patient one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, this may be for drugs and therapeutic agents and methods currently in development and or in clinical trials. In some embodiments, the treatment regimen comprises administering to the patient one or more of psychotherapy, cognitive therapy, behavioral therapy, and standard medical care. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient into a diagnosis class for epilepsy, ES, NES, NS, PNES, or NEE. In some embodiments, a trained model output value allows classification of the patient into a differential and/or comparative diagnosis class for epilepsy, ES, NES, NS, PNES, or NEE. In some embodiments, a trained model output value allows classification of the patient into a diagnosis class for evaluating, monitoring, and/or predicting patient epileptic seizure burden and/or frequency. In some embodiments, a trained model output value allows classification of the patient into a diagnosis class for likelihood to respond to epilepsy, ES, NES, NS, PNES, or NEE treatment.

The disclosure also provides a non-transitory computer readable storage medium for one or more of: diagnosing epilepsy, ES, NES, NS, PNES, or NEE in a patient; differentially and/or comparatively diagnosing between epilepsy, ES, NES, NS, PNES, or NEE in a patient; evaluating, monitoring, and/or predicting patient epileptic seizure burden and/or frequency in a patient; and determining the likelihood of a patient to respond to epilepsy, ES, NES, NS, PNES, or NEE treatment; the non-transitory computer readable storage medium storing one or more programs for execution by one or more processors of a computer system, the one or more computer programs comprising instructions for: (a) obtaining one or more input values relating to the patient having a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma; and (b) comparing the one or more input values to one or more reference values and determining whether the input values are altered relative to the one or more reference values. In some embodiments, the one or more computer programs further comprise instructions for: (c) providing instructions for treating the subject for epilepsy, ES, NES, NS, PNES, or NEE to the subject or to a practitioner charged with caring for the subject. In some embodiments, a difference between the one or more input values and the one or more reference values indicate a positive diagnostic of epilepsy, ES, NES, NS, PNES, or NEE in the patient. In some embodiments, a difference between the one or more input values and the one or more reference values indicate a negative diagnostic of epilepsy, ES, NES, NS, PNES, or NEE in the patient. In some embodiments, a difference between the one or more input values and the one or more reference values indicate a differential and/or comparative diagnostic of one of epilepsy, ES, NES, NS, PNES, or NEE in the patient. In some embodiments, a difference between the one or more input values and the one or more reference values predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, a difference between the one or more input values and the one or more reference values indicate a likelihood of the patient to respond to epilepsy, ES, NES, NS, PNES, or NEE treatment. In some embodiments, a difference between the one or more input values and the one or more reference values is independently selected for each value from having a risk factor, and not having a risk factor. In some embodiments, the one or more computer programs further comprise instructions for: (d) obtaining the concentration of one or more biomarkers in one or more biological samples obtained from the patient by contacting the one or more biological samples with one or more antibodies targeting the one or more biomarkers, wherein the one or more biomarkers are selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1B, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, VEGF-A; and (e) comparing the concentrations of the one or more biomarkers in the one or more biological samples to the concentration of the one or more biomarkers in one or more controls and determining whether the concentrations of the one or more biomarkers are altered in the one or more biological samples relative to the one or more control samples. In some embodiments, altered concentrations of the one or more biomarkers in the one or more biological samples compared to the concentration of the one or more biomarkers in the one or more controls indicate a positive diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a negative diagnostic of epilepsy, ES, NES, NS, PNES, or NEE in the patient. In some embodiments, altered concentrations of the one or more biomarkers in the one or more biological samples compared to the concentration of the one or more biomarkers in the one or more controls indicate a differential and/or comparative diagnostic of one of epilepsy, ES, NES, NS, PNES, or NEE in the patient. In some embodiments, altered concentrations of the one or more biomarkers in the one or more biological samples compared to the concentration of the one or more biomarkers in the one or more controls predict a change in epileptic seizure burden and/or frequency in the patient. In some embodiments, the seizure burden and/or frequency of the patient is predicted to increase or decrease by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99%, or by about 100%. In some embodiments, altered concentrations of the one or more biomarkers in the one or more biological samples compared to the concentration of the one or more biomarkers in the one or more controls indicate a likelihood of the patient to respond to epilepsy, ES, NES, NS, PNES, or NEE treatment. In some embodiments, a biological sample is independently for each biomarker a blood sample. In some embodiments, the one or more biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1B and osteoactivin. In some embodiments, the one or more biomarkers are IL-16, ICAM-1, and TRAIL. In some embodiments, the one or more biomarkers are IL-16, ICAM-1, TRAIL, and MIP-1B. In some embodiments, the one or more biomarkers are TRAIL, ICAM-1, MCP-2, and TNF-R1. In some embodiments, the one or more biomarkers are IL-10, MCP-4, MMP-3, and TNF-$\alpha$. In some embodiments, the patient has suffered one or more seizures. In some embodiments, the patient has suffered one seizure, two seizures, or more than two seizures. In some embodiments, the patient has not suffered any seizures. In some embodiments, the treatment regimen comprises administering to the patient one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and any pharmaceutically acceptable salts, prodrugs, and derivatives thereof. In some embodiments, the treatment regimen comprises administering to the patient one or more of psychotherapy, cognitive therapy, behavioral therapy, and standard medical care. In some embodiments, this may be for drugs and therapeutic agents and methods currently in development and or in clinical trials. In some embodiments, a control sample is a sample obtained from a healthy patient. In some embodiments, a control sample is a sample obtained from a patient previously diagnosed with epilepsy, ES, NES, NS, PNES, or NEE. In some embodiments, a biomarker concentration is computer readable. In some embodiments, the method further comprises inputting a computer readable biomarker concentration into a trained model panel and obtaining a trained model output value for the patient. A trained model panel can be a first tier trained model panel, a second tier trained model panel, a third tier trained model panel, etc., and/or a $n^{th}$ trained model panel. In some embodiments, a trained model output value allows classification of the patient into a diagnosis class for epilepsy, ES, NES, NS, PNES, or NEE. In some embodiments, a trained model output value allows classification of the patient into a differential and/or comparative diagnosis class for epilepsy, ES, NES, NS, PNES, or NEE. In some embodiments, a trained model output value allows classification of the patient into a diagnosis class for evaluating, monitoring, and/or predicting patient epileptic seizure burden and/or frequency. In some embodiments, a trained model output value allows classification of the patient into a diagnosis class for likelihood to respond to epilepsy, ES, NES, NS, PNES, or NEE treatment.

BRIEF DESCRIPTION OF THE DRAWINGS

The foregoing summary, as well as the following detailed description of the invention, will be better understood when read in conjunction with the appended drawings.

FIG. 1 illustrates criteria for different types of seizures.

comparative respective biomarker concentrations/levels in NES vs. Seizure vs. Control; protein concentration distributions were compared for 9 NES/NS/PNES samples, 29 normal healthy controls, and 32 epileptic seizures. Concentration mean is indicated with the red horizontal line, boxes extend from 25-75 interquartile ranges and whiskers extend 1.5× of the interquartile range.

Figure 7:
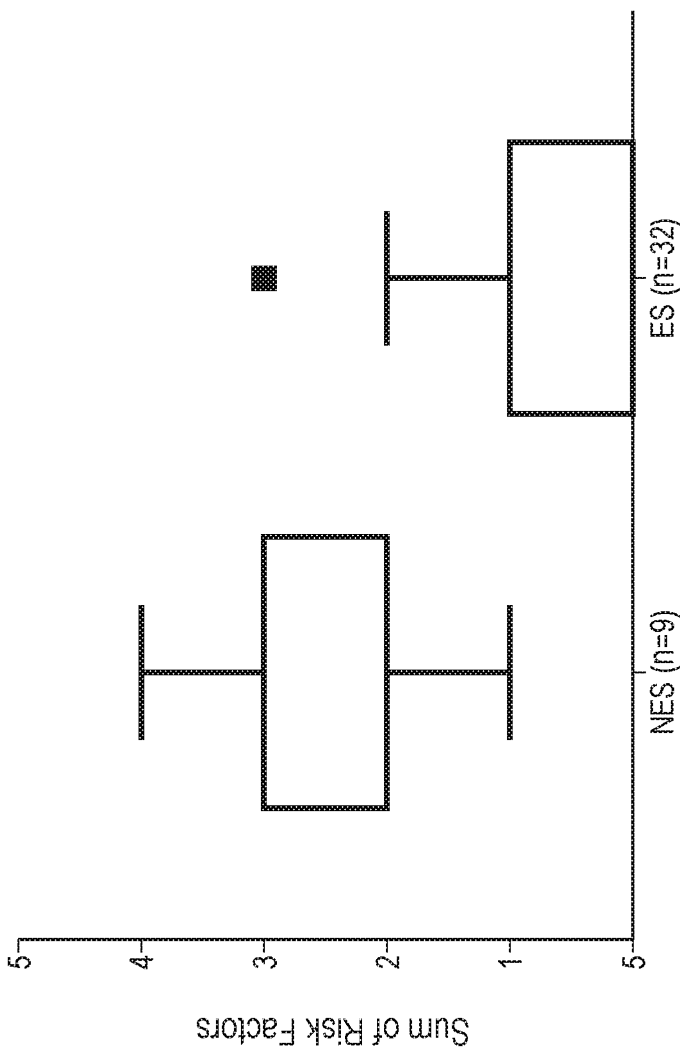

FIG. 7 illustrates Prevalence of NES/NS/PNES Risk Factors (Sum of Risk Factors) in NES vs. ES.

Figure 8B:
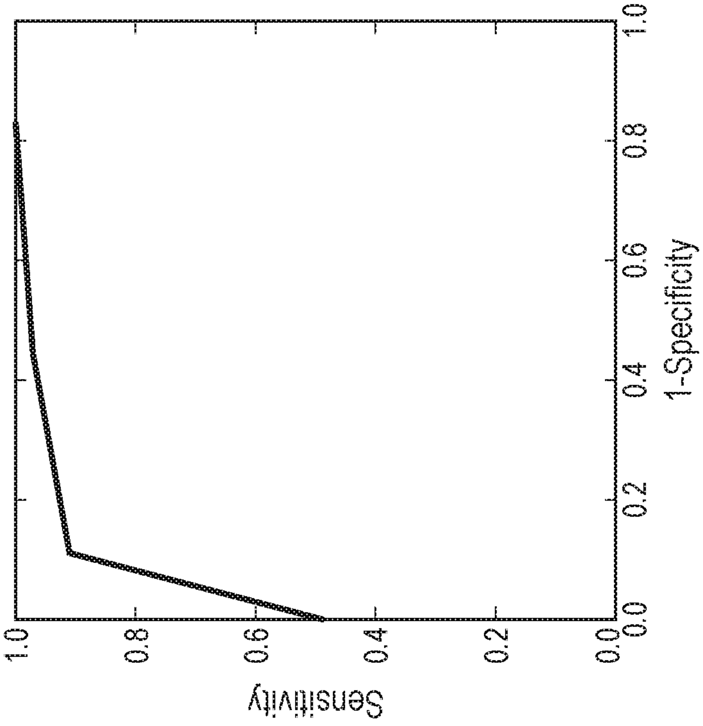
Figure 8A:
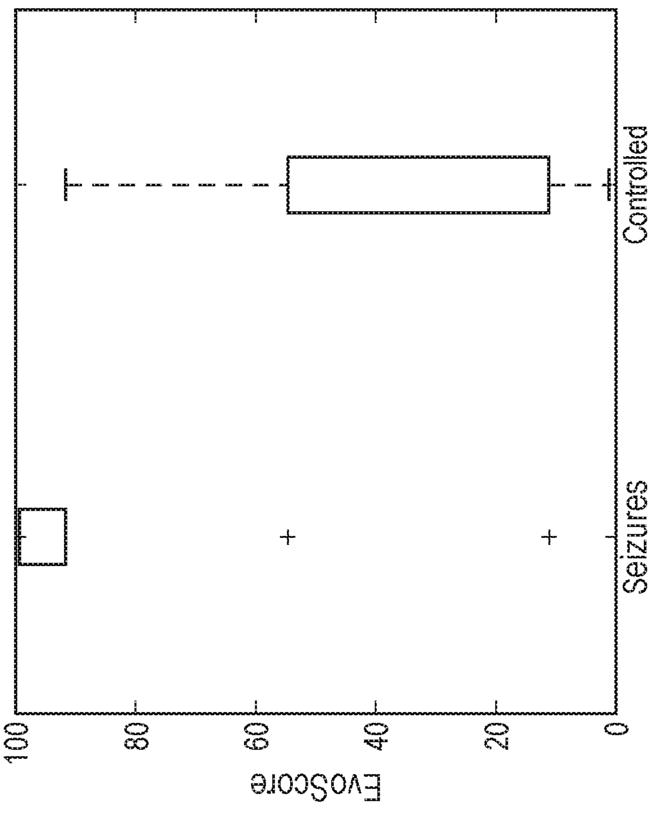

FIGS. 8A-8C illustrate the sum of NES/NS/PNES risk factors; the number of risk factors confirmed for each patient was summed and used to create a diagnostic algorithm using a logistical regression. FIG. 8A: EvoScore in Seizures vs. Controlled; FIG. 8B Sensitivity; FIG. 8C: performance matrix.

Figure 9A:
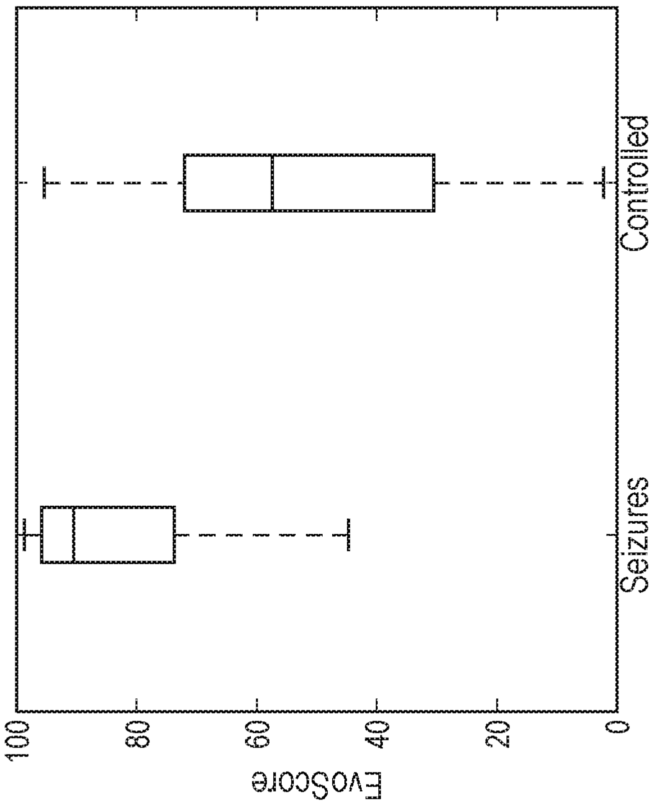
Figure 9B:
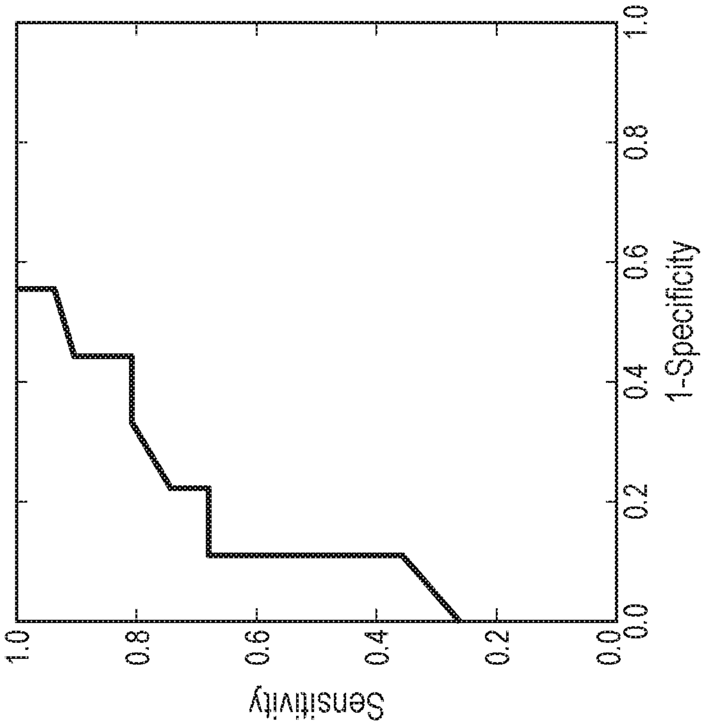

FIGS. 9A-9C illustrate a diagnostic algorithm for biomarkers IL-16, ICAM-1, and TRAIL; plasma protein concentrations were determined for IL-16, ICAM-1, and TRAIL using a multiplexed ELISA and combined into a diagnostic algorithm using a logistical regression; FIG. 9A: EvoScore Seizure vs. Controlled, threshold=85; FIG. 9B: Sensitivity, AUC=83; FIG. 9C: Performance Matrix (9C); 31 of 32 ES samples used to refine the algorithm. Insufficient sample was available to test TRAIL for one sample.

Figure 10B:
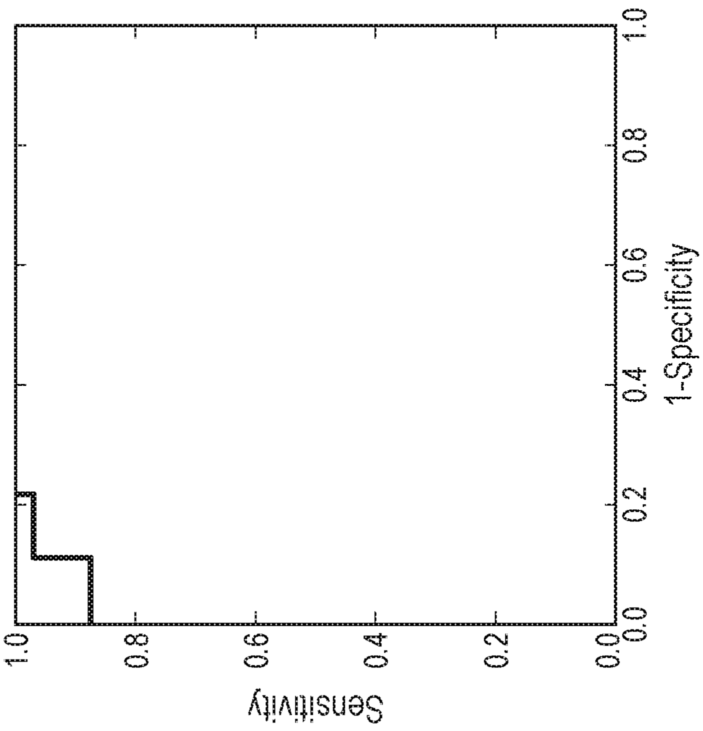
Figure 10A:
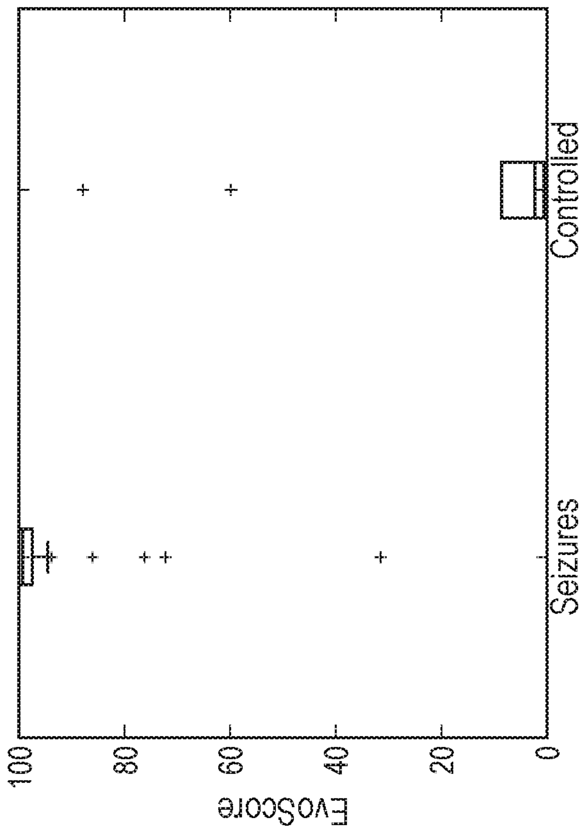

FIGS. 10A-10C illustrate a diagnostic algorithm for biomarkers IL-16, ICAM-1, and TRAIL; protein concentrations of IL-16, ICAM-1 and TRAIL and the sum of a patients NES/NS/PNES risk factors were combined using a logistical regression to generate a diagnostic algorithm; AUC 93.2; 31 of 32 ES samples used to refine the algorithm. Insufficient sample was available to test TRAIL for one sample; FIG. 10C: performance matrix.

Figure 11B:
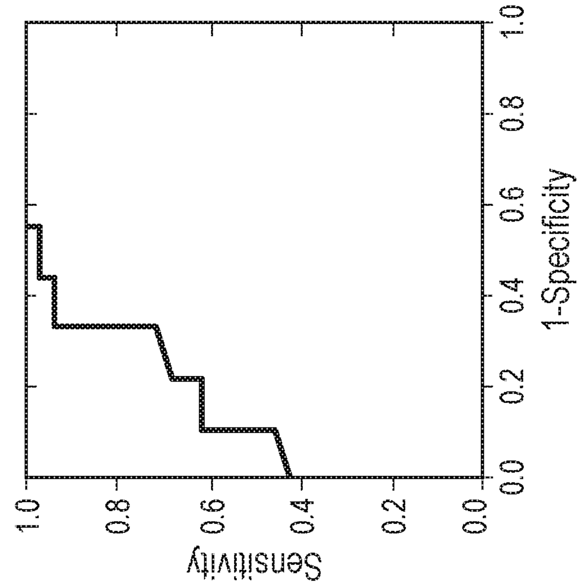
Figure 11A:
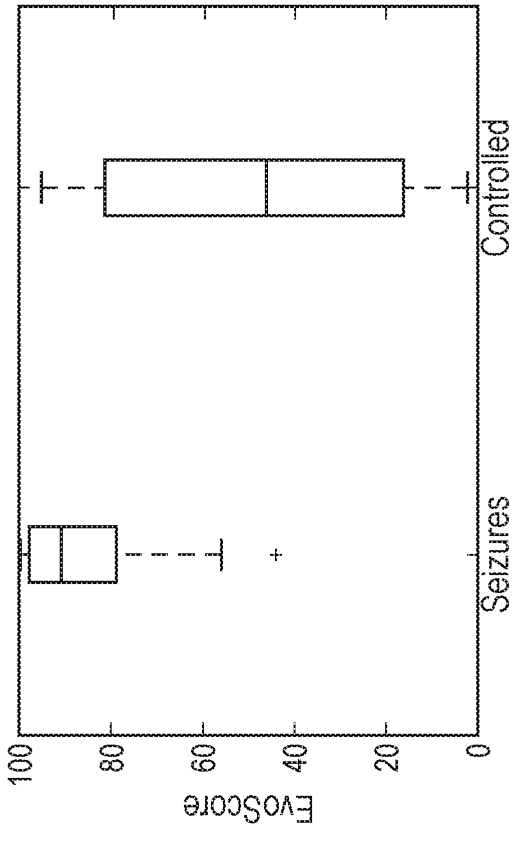

FIGS. 11A-11C illustrate a diagnostic algorithm for biomarkers IL-16, ICAM-1, TRAIL, MIP-1β; protein concentrations of concentrations of IL-16, ICAM-1, TRAIL and MIP-1β were combined using a logistical regression to generate a diagnostic algorithm; threshold 60.0; AUC 0.8495; 31 of 32 ES samples used to refine the algorithm. Insufficient sample was available to test TRAIL for one sample; FIG. 11C: performance matrix.

Figure 12B:
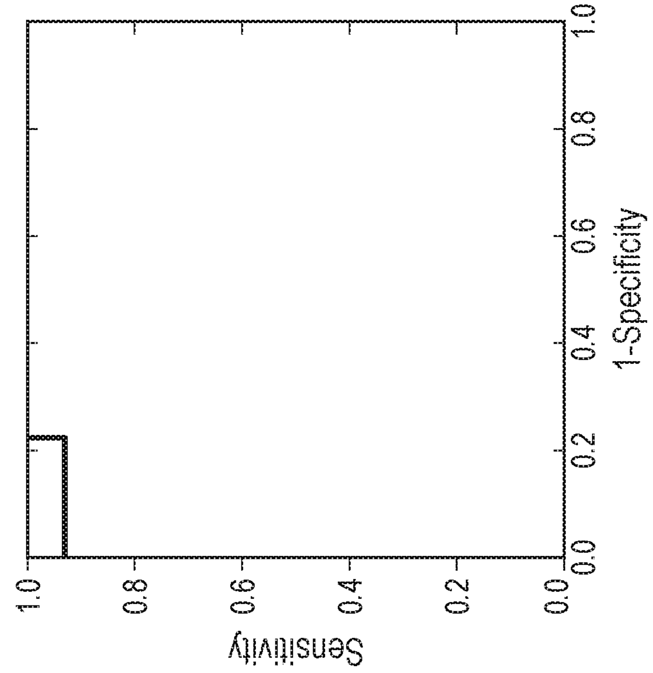
Figure 12A:
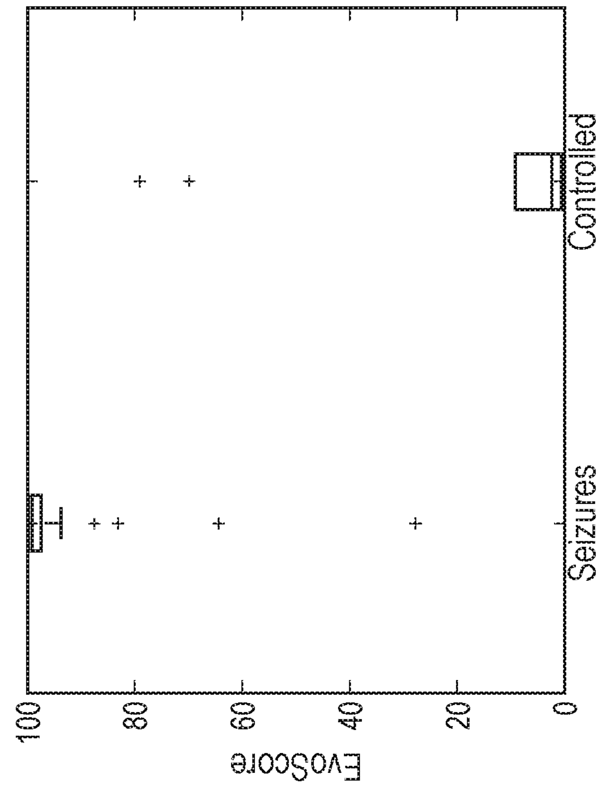

FIGS. 12A-12C illustrate a diagnostic algorithm for biomarkers IL-16, ICAM-1, TRAIL, MIP-1β, Sum of risks; protein concentrations of IL-16, ICAM-1, TRAIL and MIP-1β and the sum of a patients NES/NS/PNES risk factors were combined using a logistical regression to generate a diagnostic algorithm; 31 of 32 ES samples used to refine the algorithm. Insufficient sample was available to test TRAIL for one sample; threshold 83.0; AUC 98.5; FIG. 12C: performance matrix.

Figure 13:
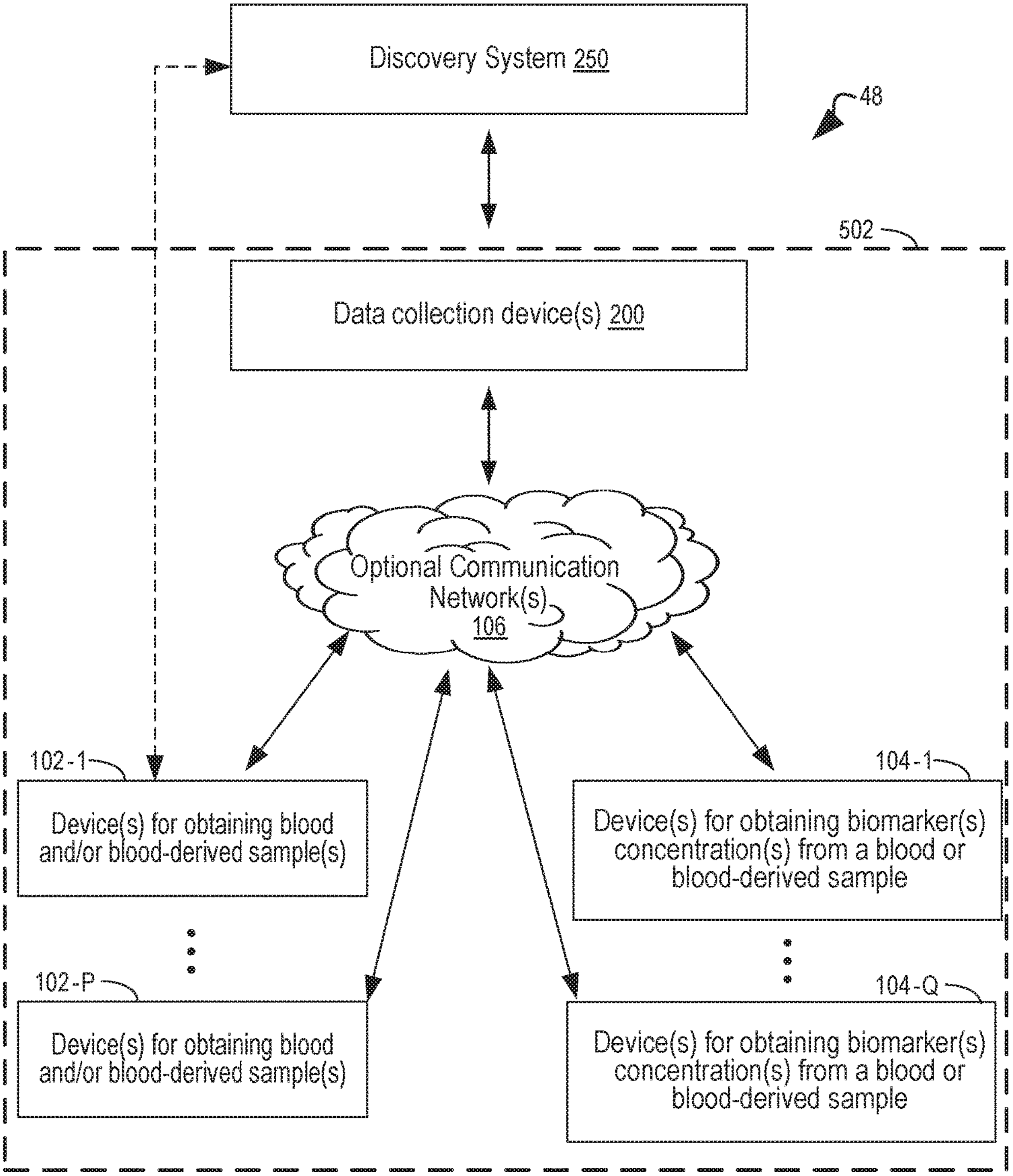

FIG. 13 illustrates an exemplary system topology for a system for screening a subject to determine the likelihood that the subject will be responsive to a treatment regimen that comprises administering to the subject an epilepsy, ES, NES, NS, PNES or NEE therapeutic agent, in accordance with an embodiment of the present disclosure.

Figure 14A:
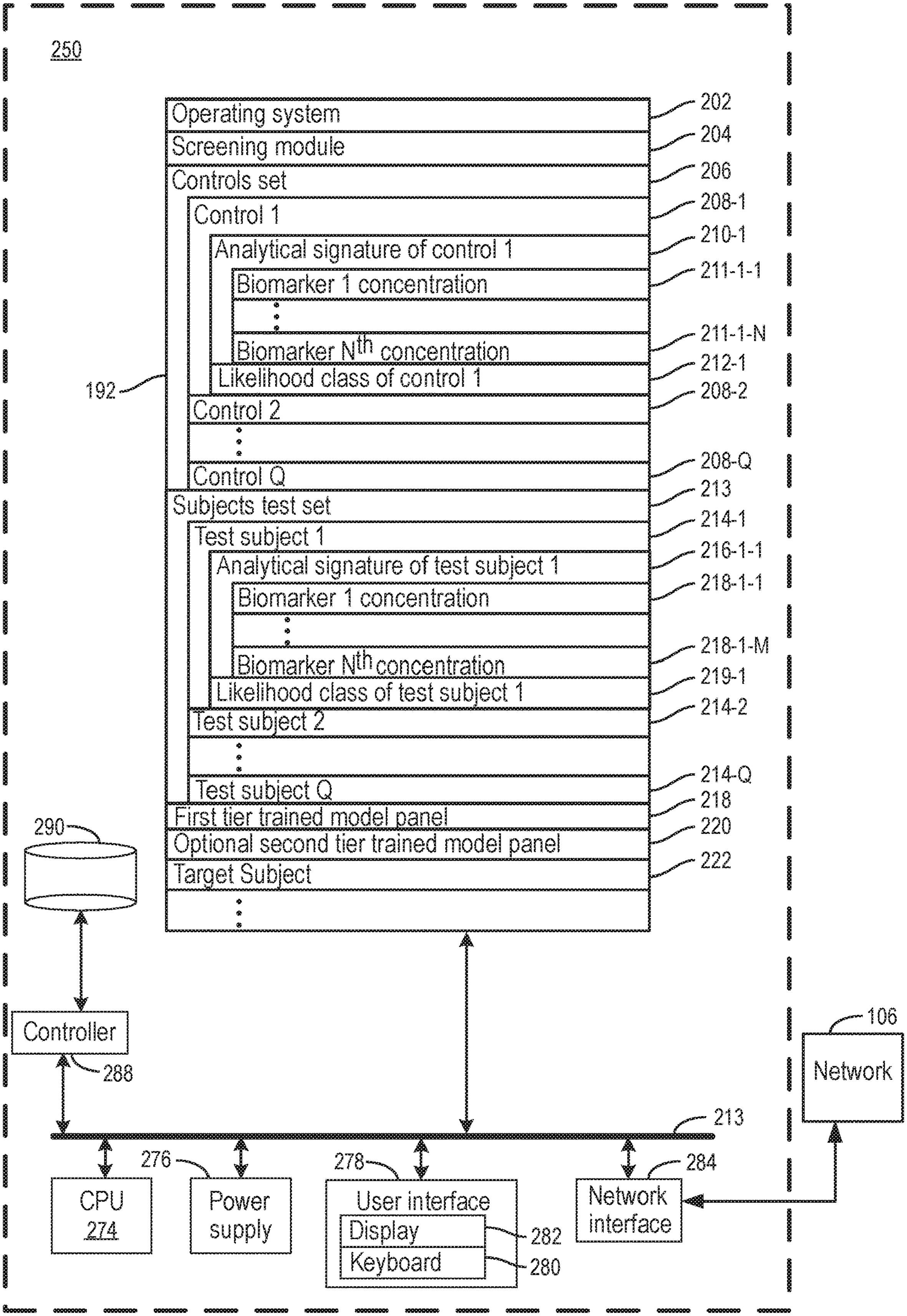
Figure 14B:
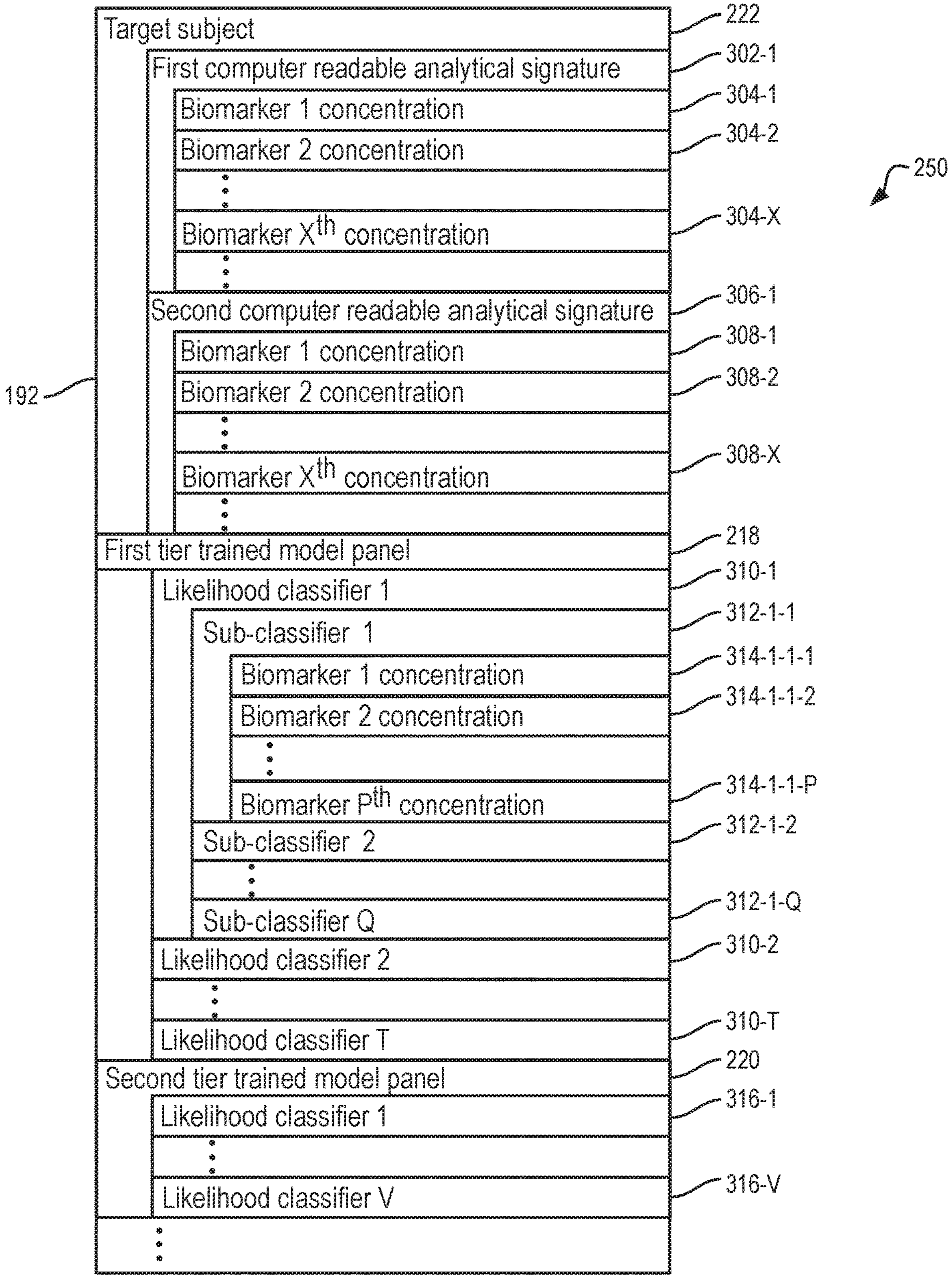

FIGS. 14A and 14B illustrate an exemplary system for screening a subject to determine the likelihood that the subject will be responsive to a treatment regimen that comprises administering to the subject an epilepsy, ES, NES, NS, PNES or NEE therapeutic agent, in accordance with an embodiment of the present disclosure; FIG. 14B illustrates exemplary data structures, in accordance with an embodiment of the present disclosure.

Figure 15:
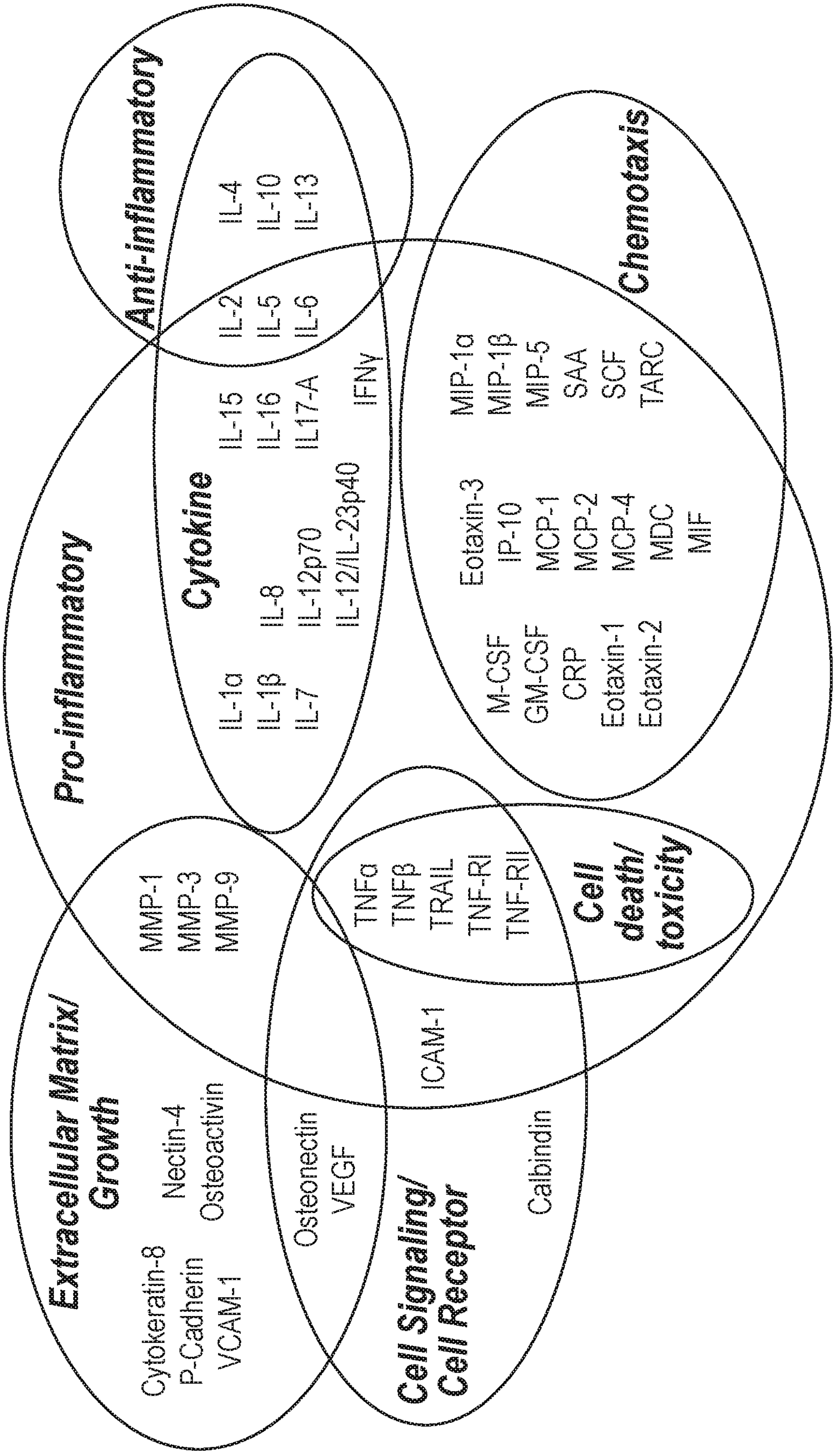

FIG. 15 illustrates biomarkers identified for a targeted proteomic screen, including 51 proteins spanning the realm of adaptive and innate immunity.

Figure 16:
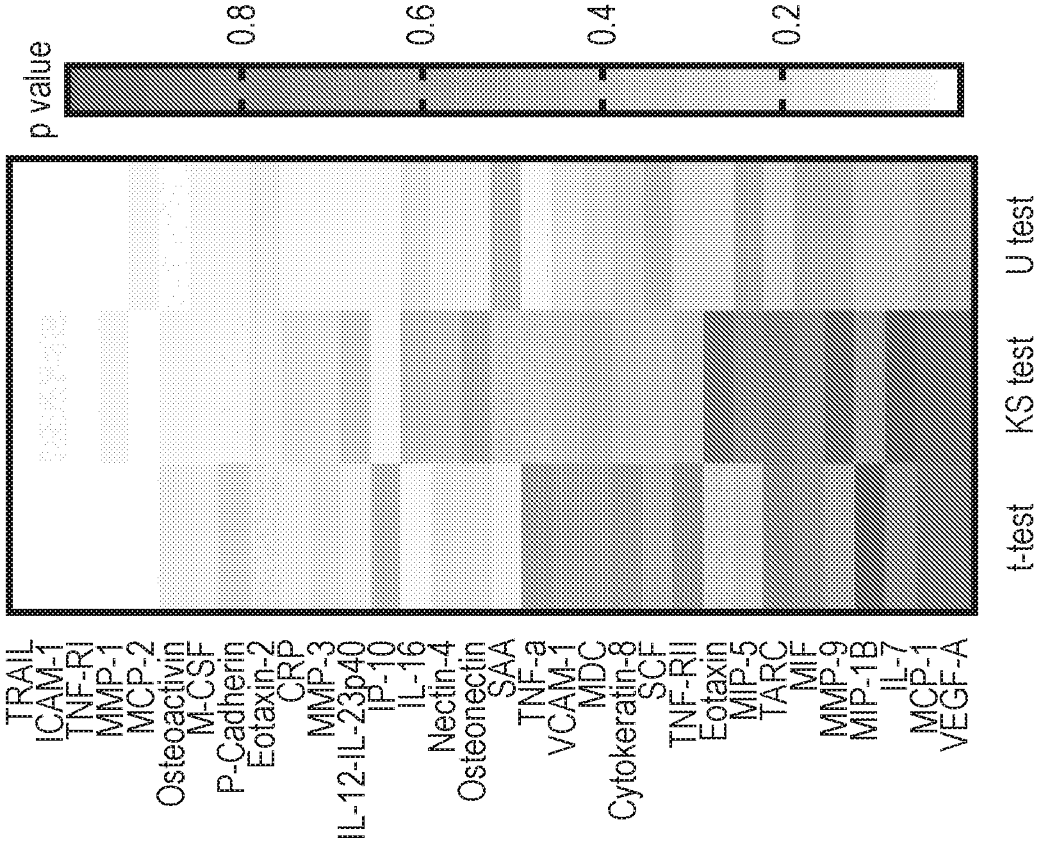

FIG. 16 illustrates a comparison of protein concentrations; the protein concentrations of the ES and PNES cohorts were compared for each protein tested using the Student's t-test, Kolmogorov-Smirnov test, and the Mann-Whitney U test.

Figure 17B:
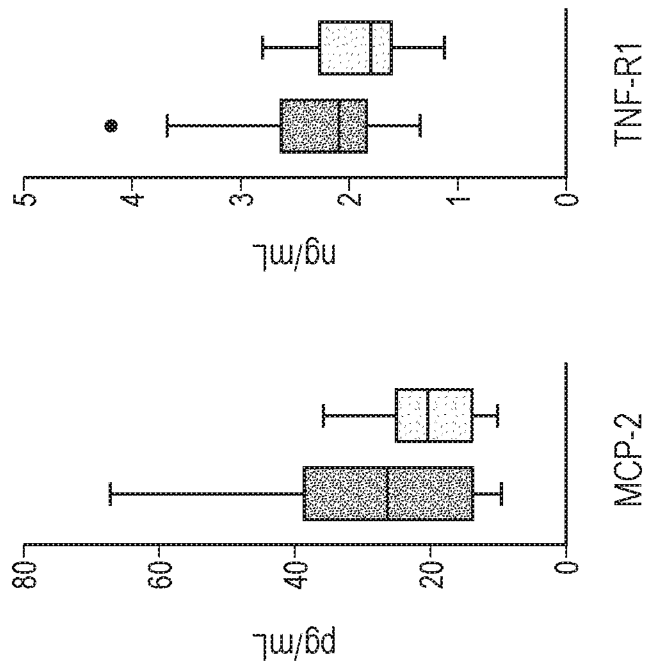
Figure 17A:
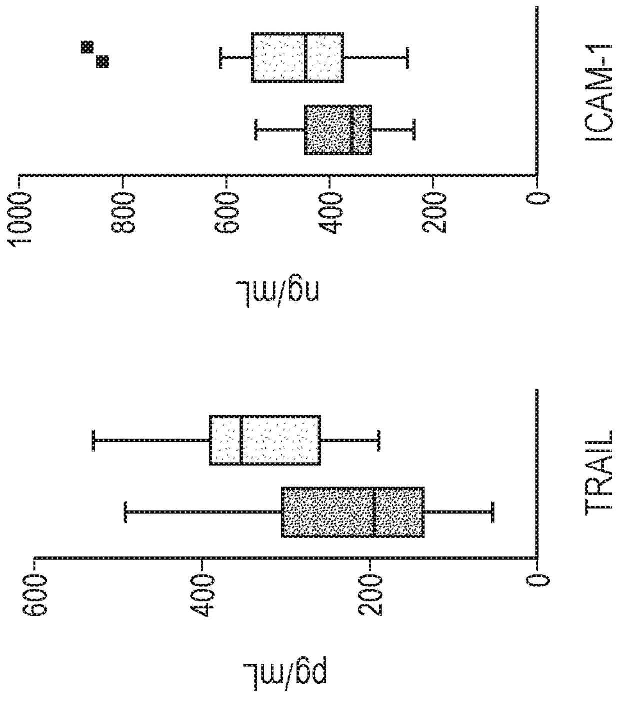

FIGS. 17A and 17B illustrate a comparison of protein concentrations protein response fingerprint; the observed protein responses are specific to epilepsy. In the case of generalized inflammation or co-occurring diseases it could be expected that protein concentrations increase while in the context of seizure both increases and decreases are observed.

Figure 18A:
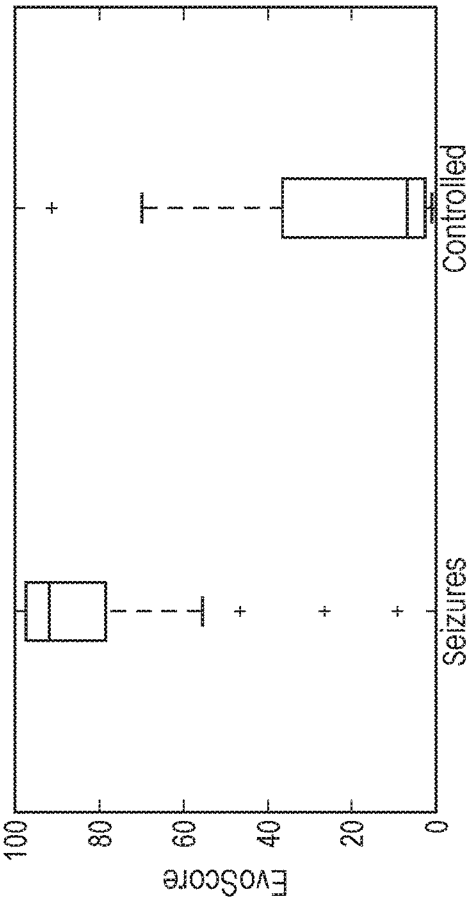
Figure 18B:
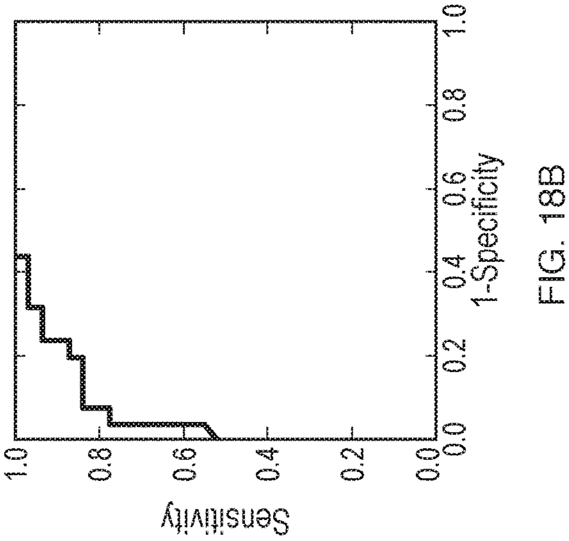
Figure 18C:
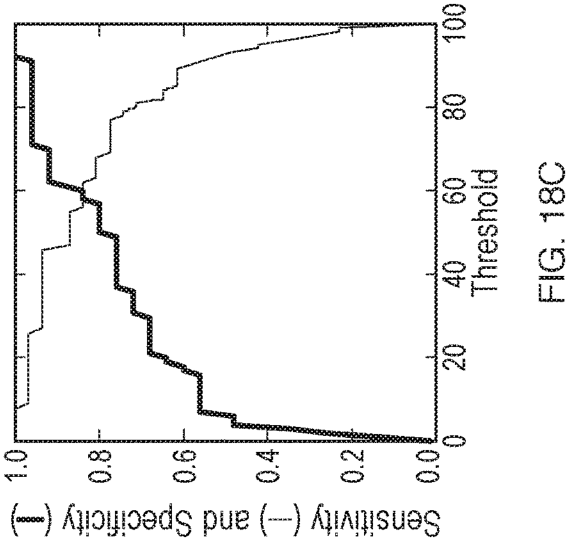

FIGS. 18A-18C illustrate a diagnostic algorithm development in presence of generalized inflammation or co-occurring diseases; Exhaustive Search Results-4 protein algorithm for 'TRAIL', 'MCP-2', 'ICAM-1', 'TNF-RI'; threshold 62.0; AUC 0.9387; 26 2 5 23; sensitivity 0.838709677419; specificity 0.92; LOO % Correct 82.1; Confidence range-Se-0.27, .213.

Figure 19A:
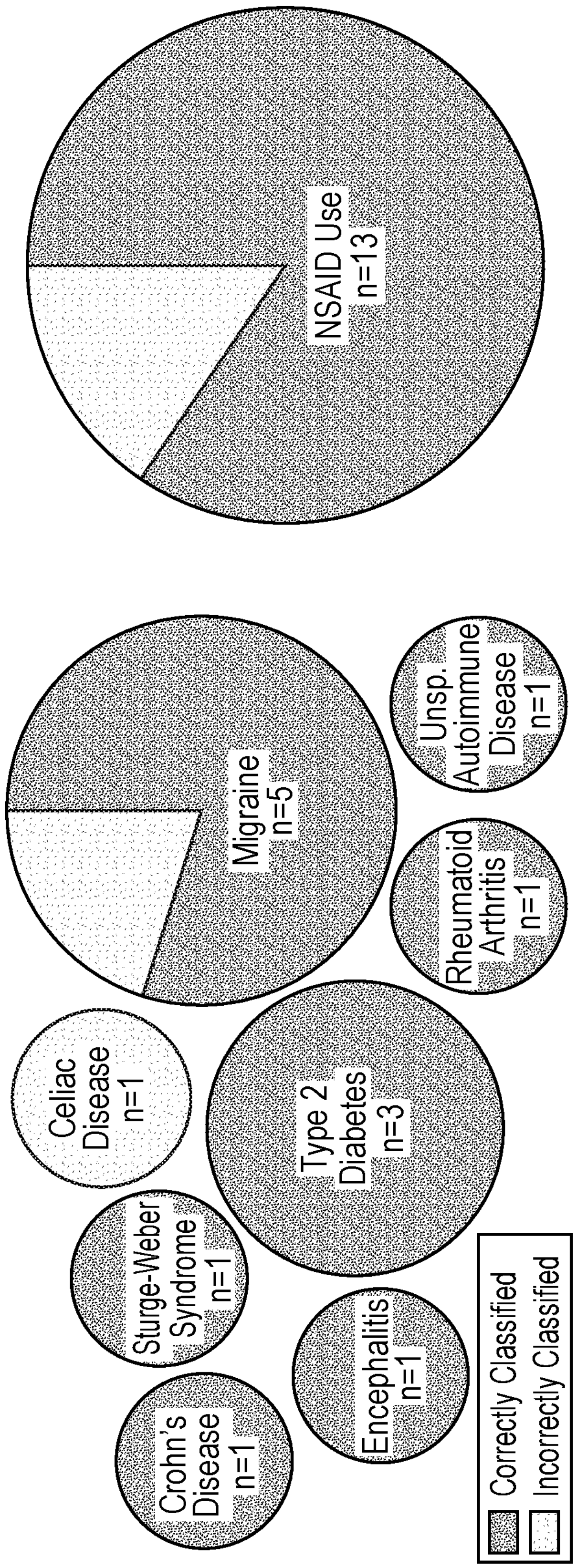
Figure 19B:
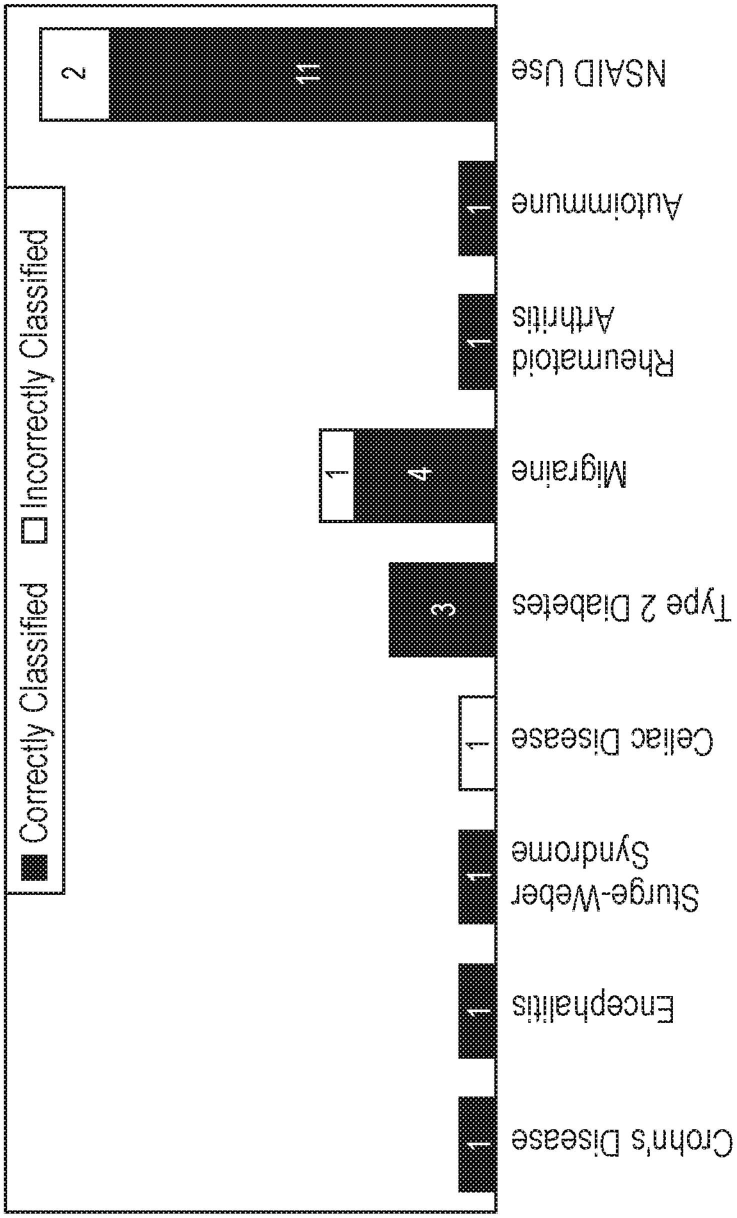

FIGS. 19A and 19B illustrate the influence of co-occurring inflammation associated disease in both the ES and PNES cohorts which was investigated by analyzing medical records from the patients who were included into both the ES and PNES cohorts; comorbid inflammation or NSAID use does not affect the classification efficiency of the diagnostic algorithm; EvoScoreDX successfully identifies epileptic seizures in challenging patients with confounding indication; a retrospective analysis of patient medical records identified 48 patients with co-occurring inflammation related disease (23 suffering epileptic seizure and 25 suffering psychogenic seizures); correct classification includes patients who were having seizures, and those who were not having seizures.

Figure 20:
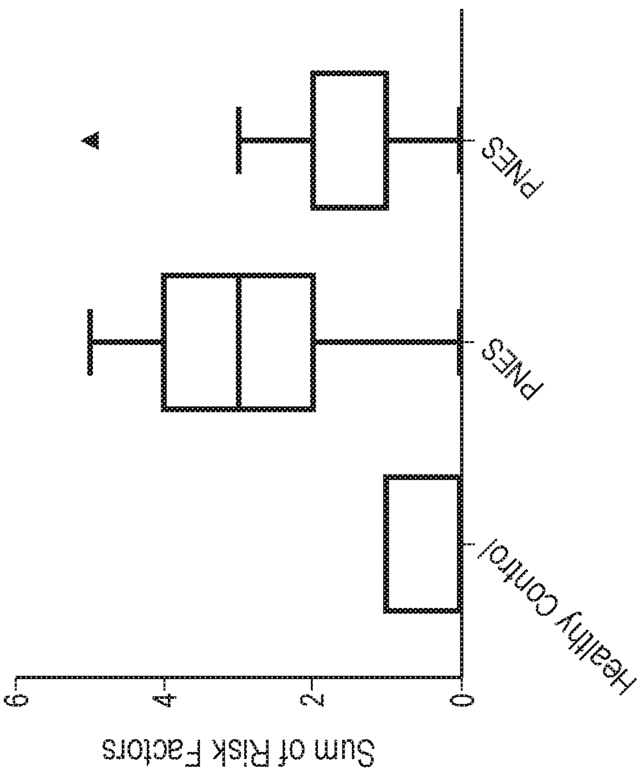

FIG. 20 illustrates the sum of risk factors in Healthy Control vs. PNES vs. ES.

Figure 21A:
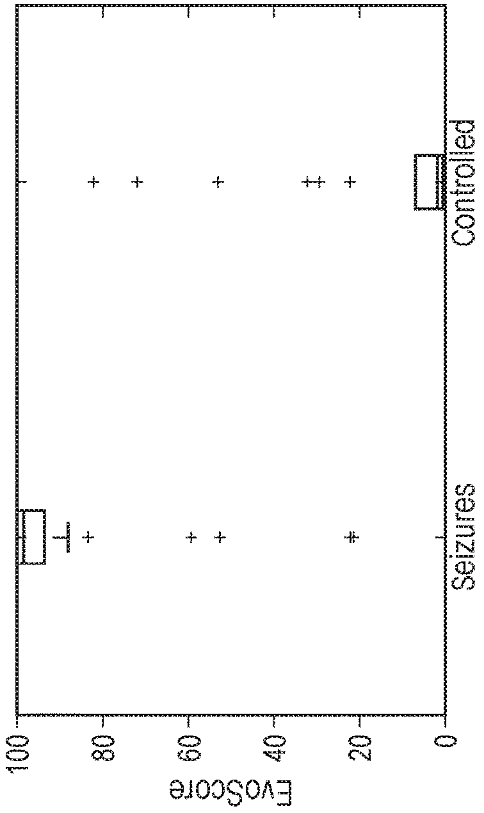
Figure 21B:
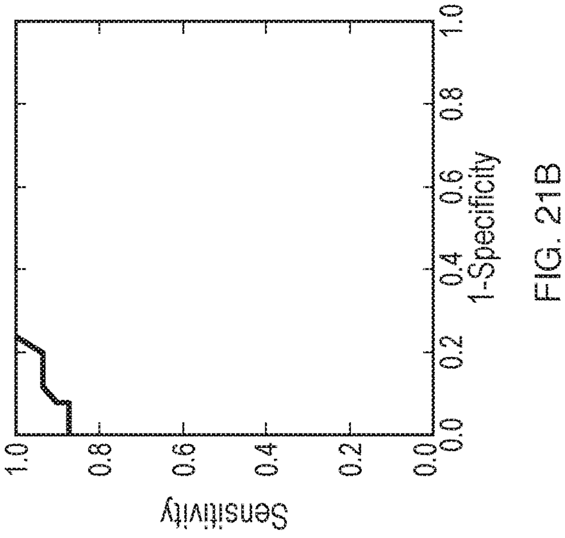
Figure 21C:
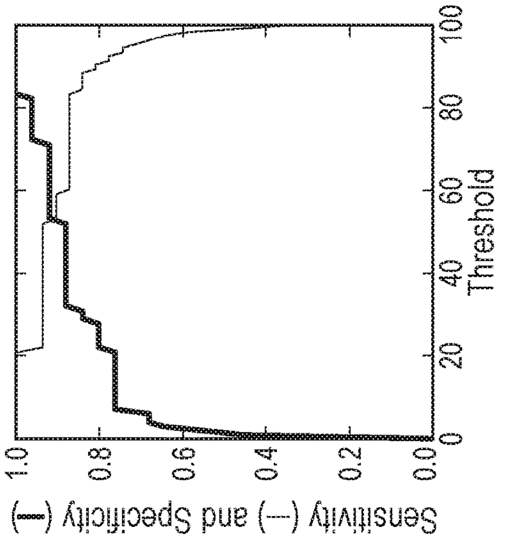

FIGS. 21A-21C illustrate the prevalence of PNES Risk Factors with biomarker algorithms; includes patients who had confirmed ES and PNES events during EMU admission.

Figure 22A:
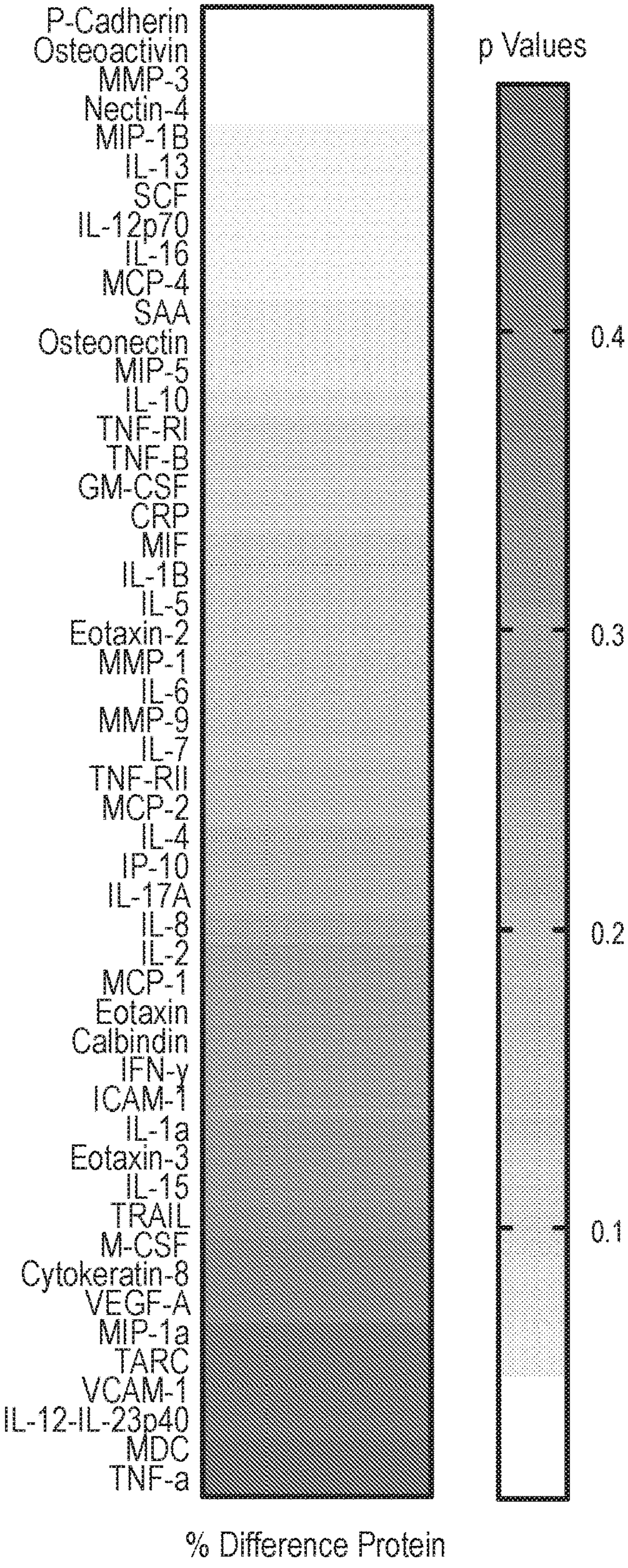
Figure 22B:
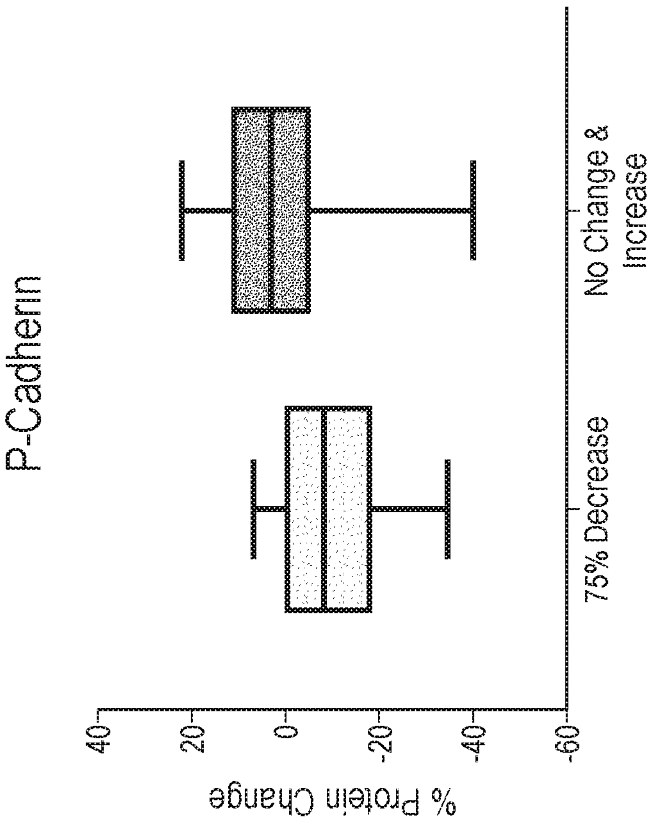
Figure 22C:
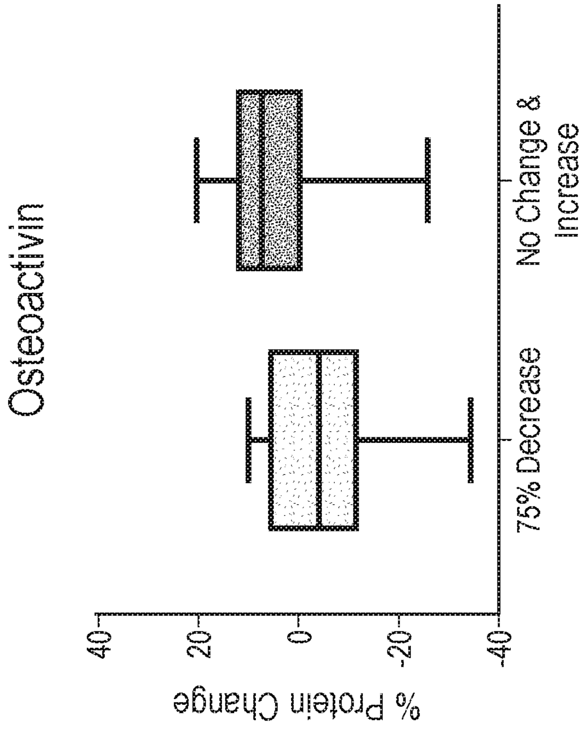

FIGS. 22A-22C illustrate the difference in proteins as a function of 75% seizure reduction; samples were stratified by 75% seizure reduction, and changes between proteins were evaluated; the Mann-Whitney test was used to assess differences for each protein, showing 10 proteins with p values <0.05 (two protein examples included).

Figure 23B:
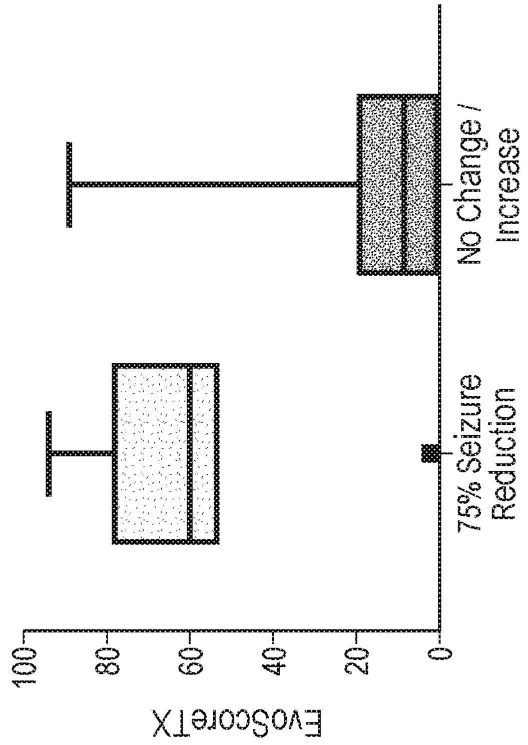
Figure 23A:
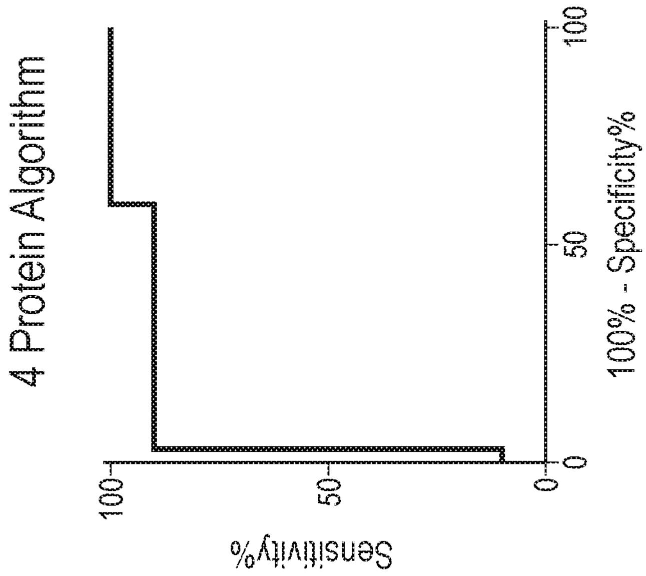

FIGS. 23A and 23B illustrate a 4 biomarker algorithm: 'IL-10', 'MCP-4', 'MMP-3', 'TNF-α'; 75% reduction in seizure burden or frequency (monitoring algorithms). The concentration differences of IL-10, MCP-4, MMP-3 and TNF-α were refined into an algorithm to stratify patients by 75% seizure reduction, (left). The AUC of the algorithm is 0.92, left, and the sensitivity and specificity are 90% and 97%, respectively (right).

Figure 24A:
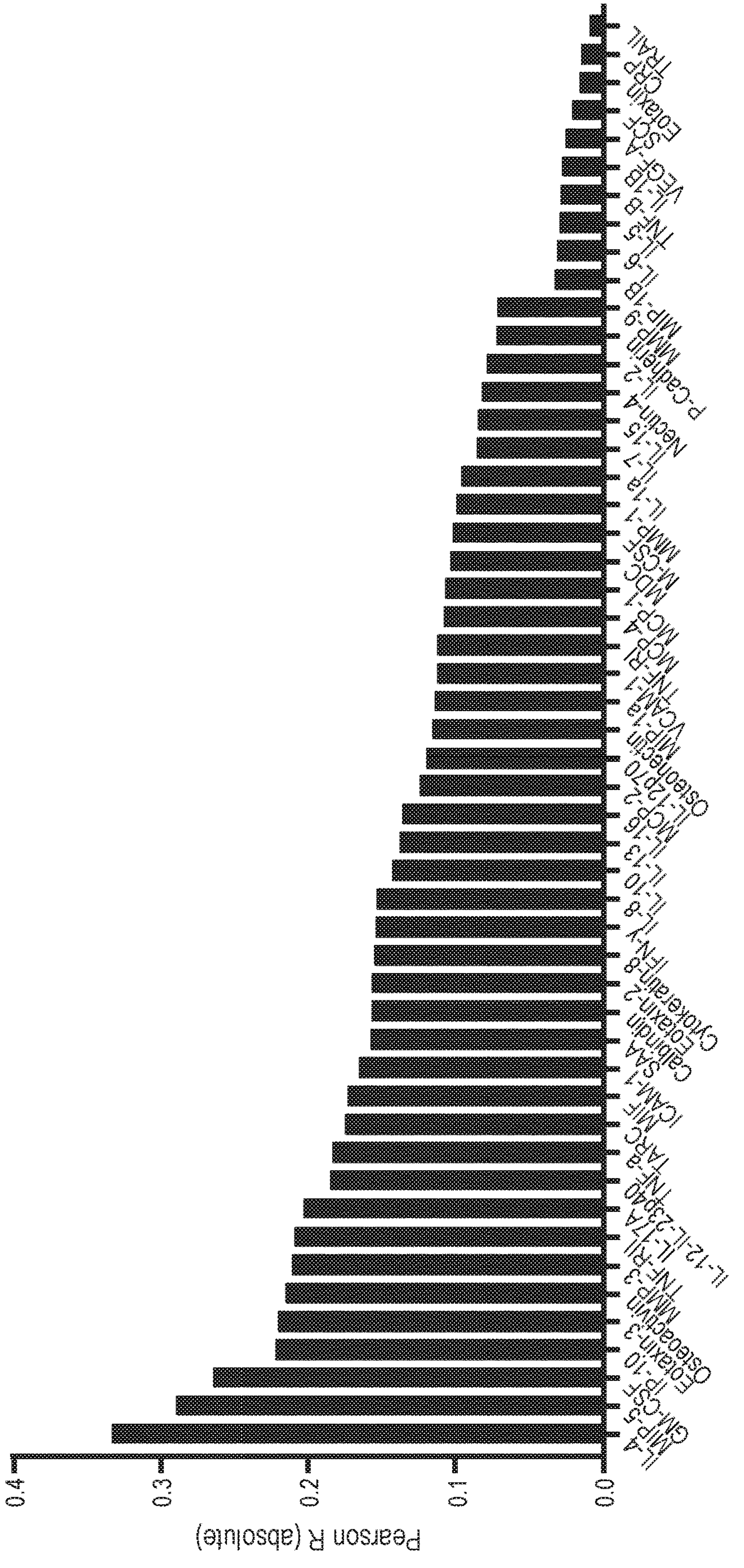
Figure 24B:
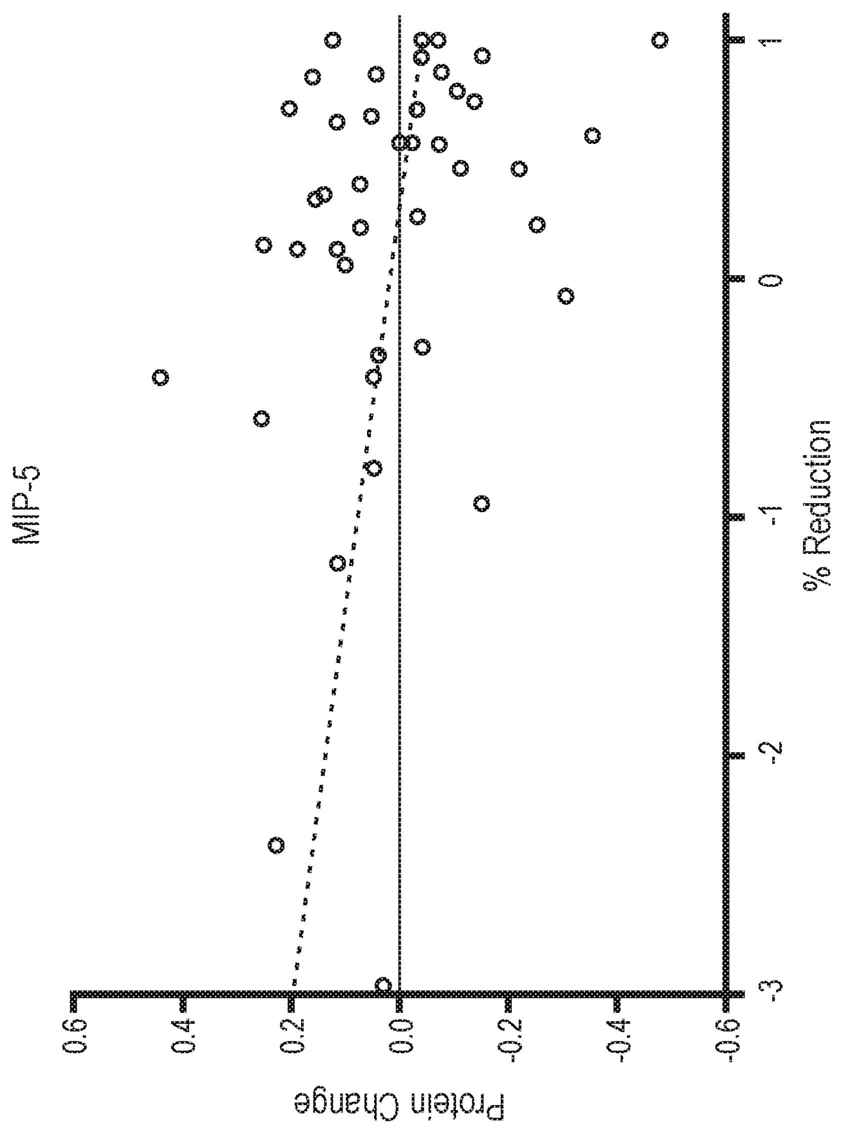

FIGS. 24A and 24B illustrate correlation of protein change with seizure frequency used to monitor change in seizure burden.

Figure 25A:
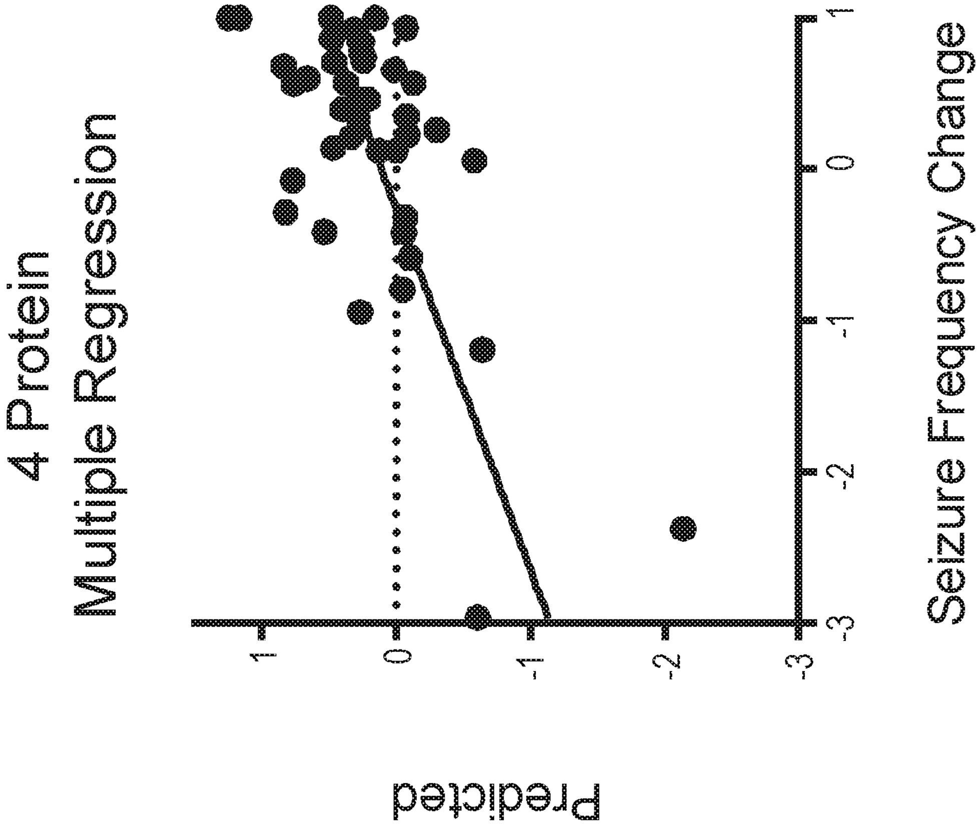

FIGS. 25A and 25B illustrate the correlation of multiple protein changes with seizure burden or frequency using a multiple regression (monitoring algorithms).

Figure 26:
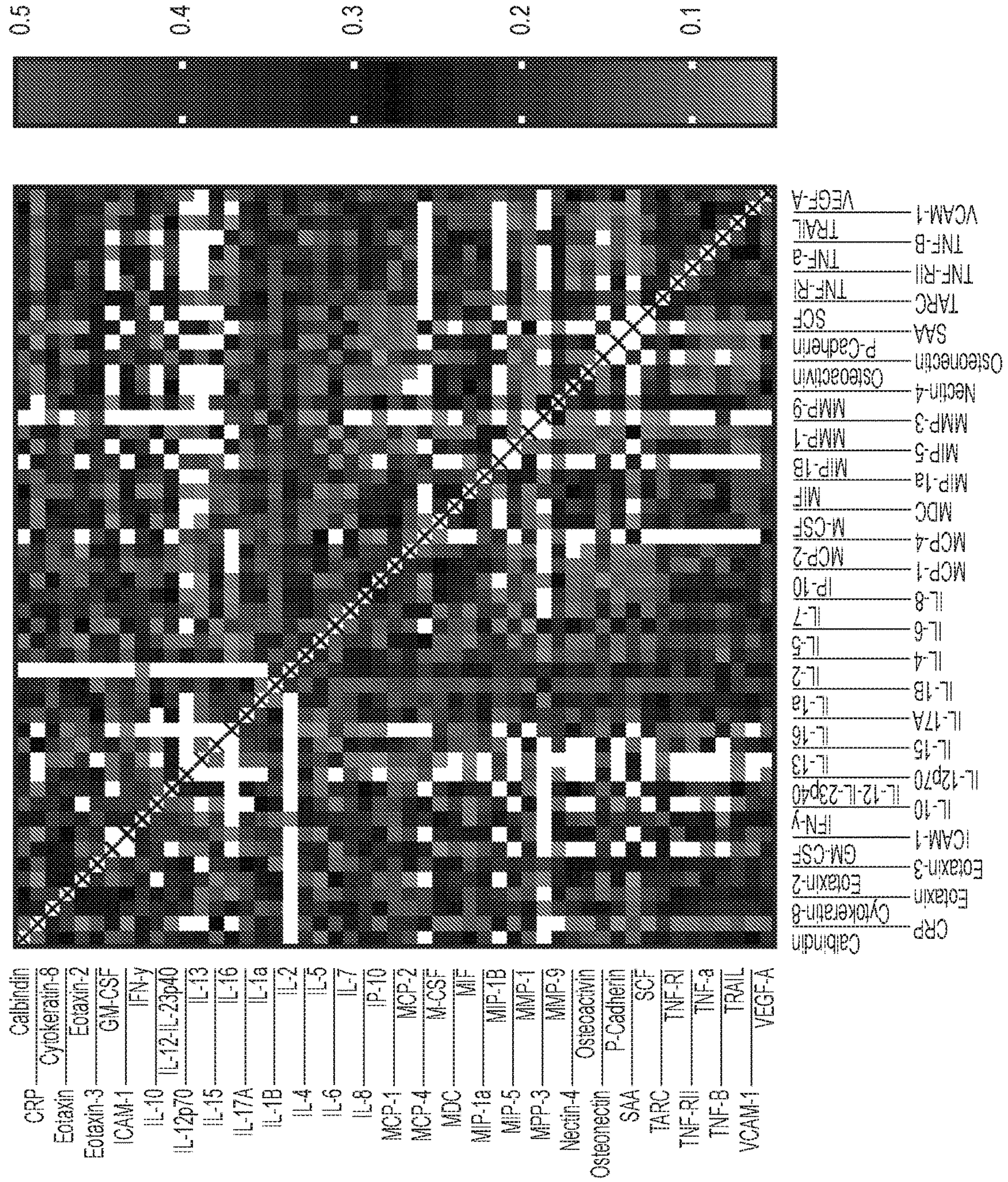

FIG. 26 illustrates the p value of changes in various protein ratios (interaction of protein changes). Relative concentration could serve to normalize noise in the data and enhance differences between cohorts (monitoring algorithms).

Figure 27:
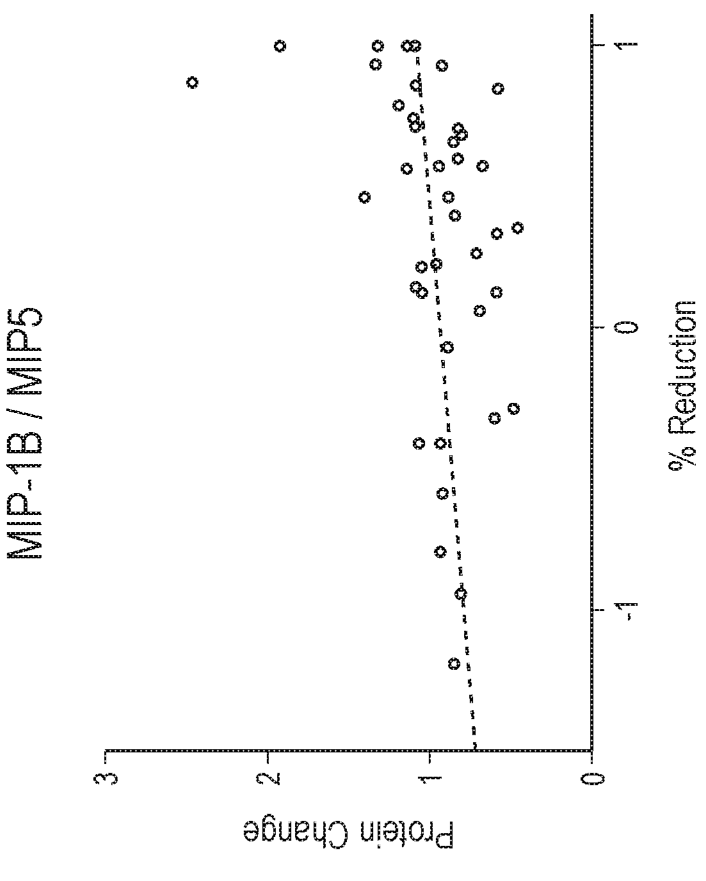

FIG. 27 illustrates that relative concentration could serve to normalize noise in the data and enhance differences between cohorts (monitoring algorithms).

Figure 28A:
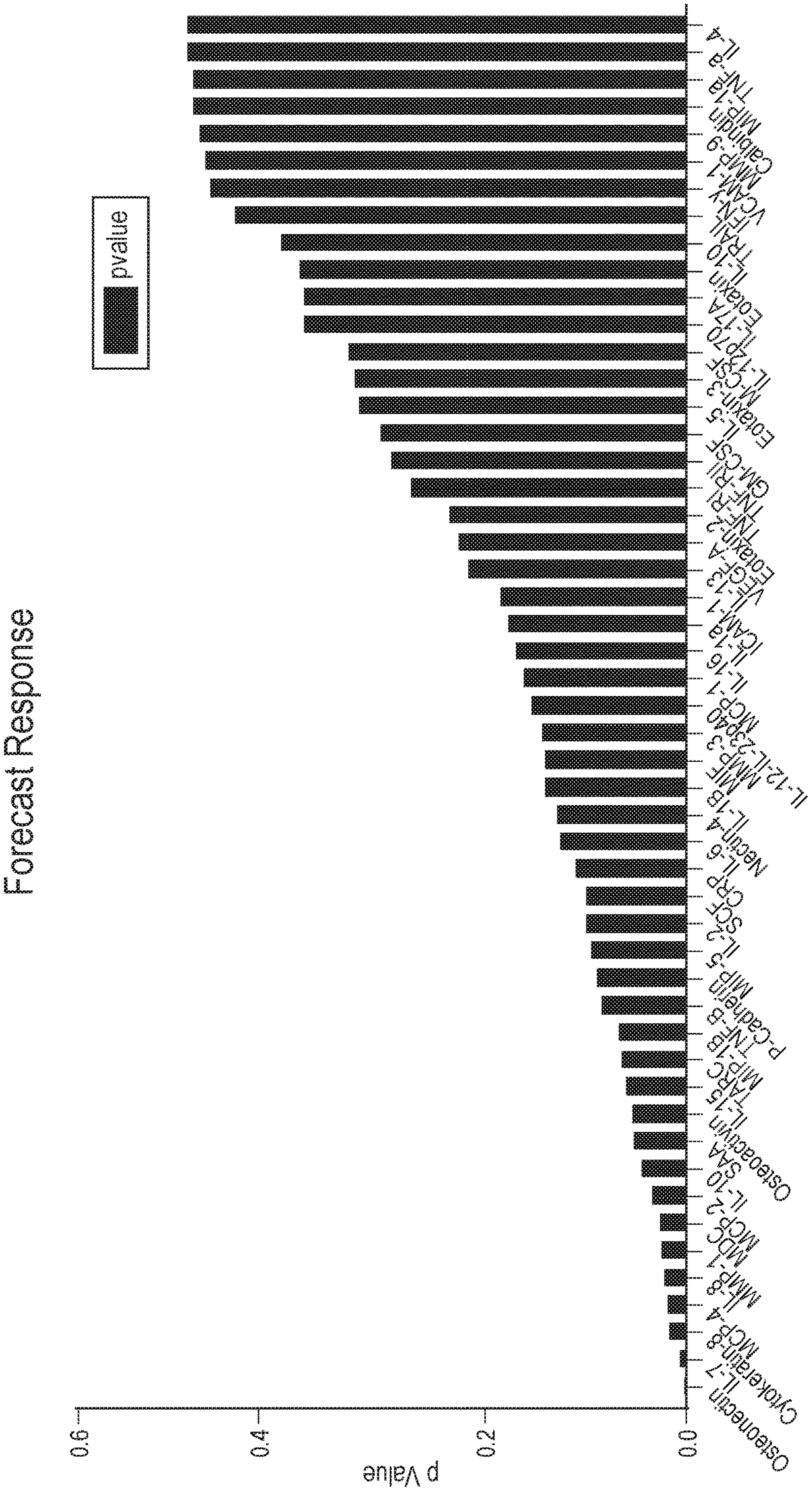
Figure 28C:
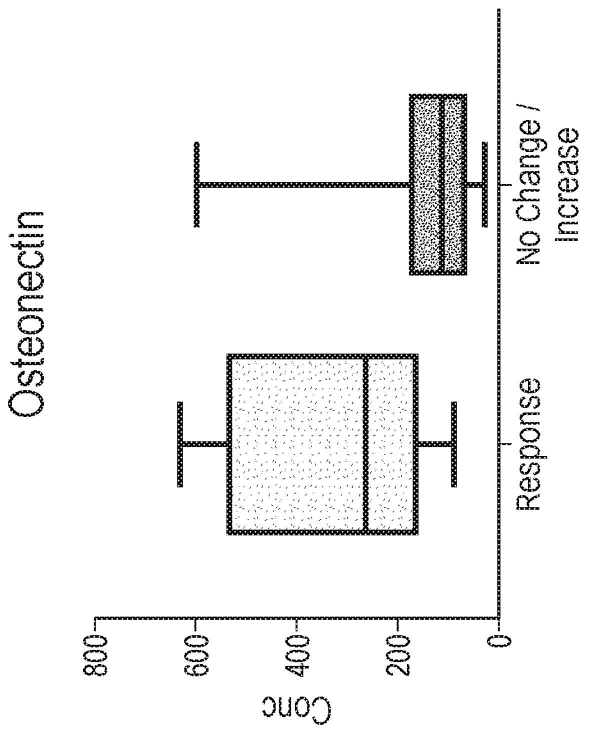
Figure 28B:
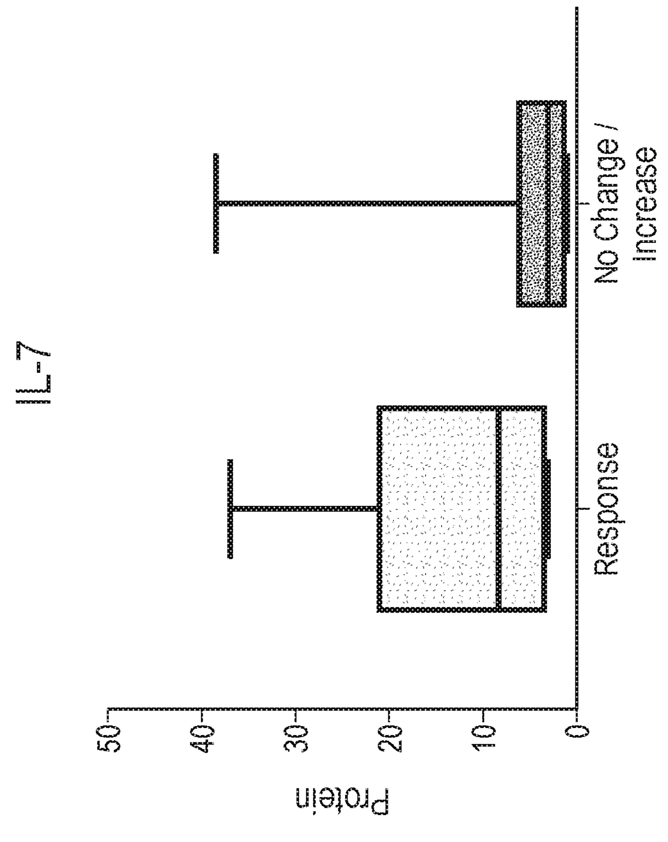

FIGS. 28A-28C illustrate the forecast drug response by looking at the baseline samples for drug treated patients and seeing whether there are differences in concentrations as a function of 75% seizure reduction (predictive algorithms).

Figure 29A:
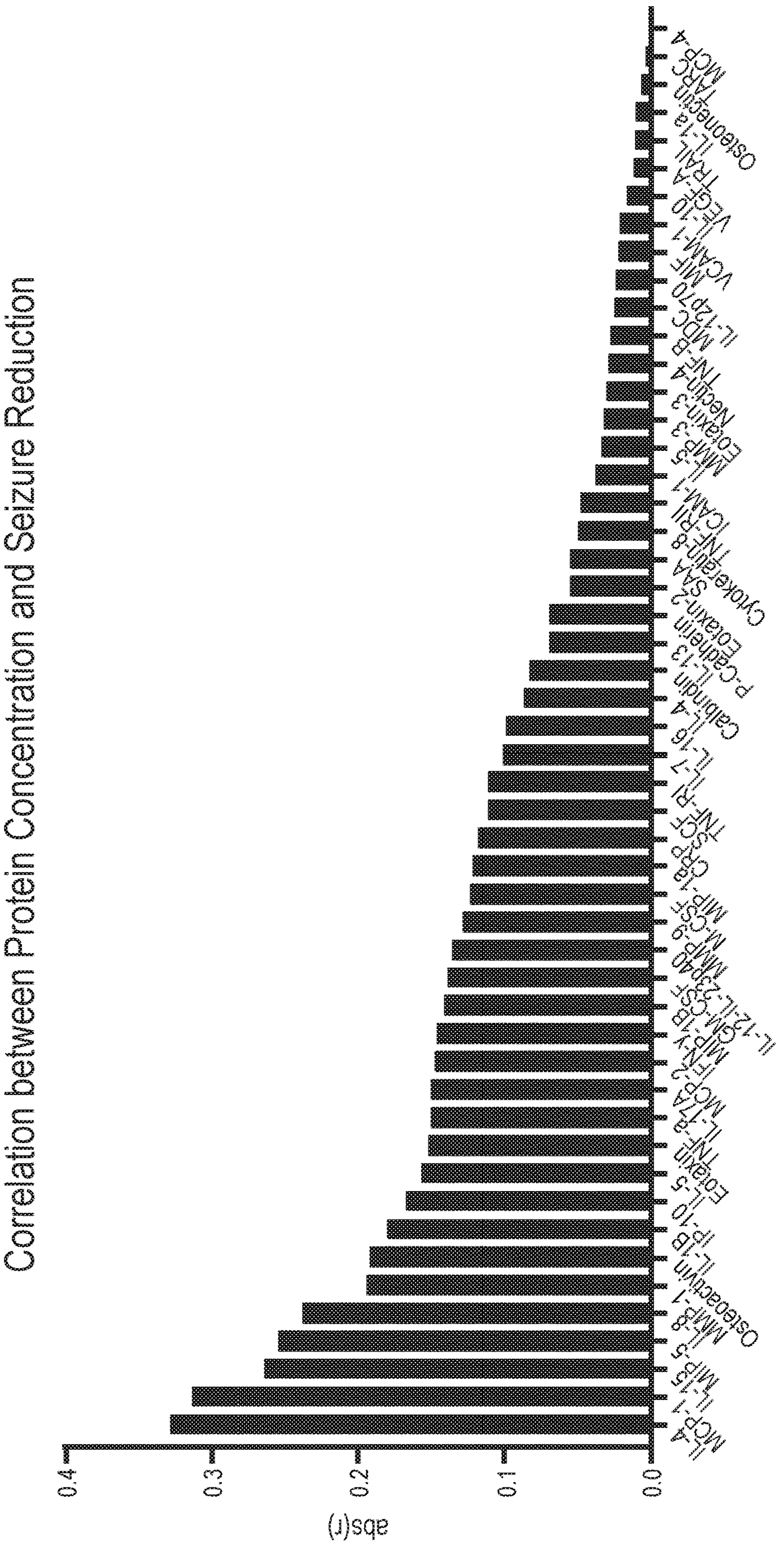
Figure 29B:
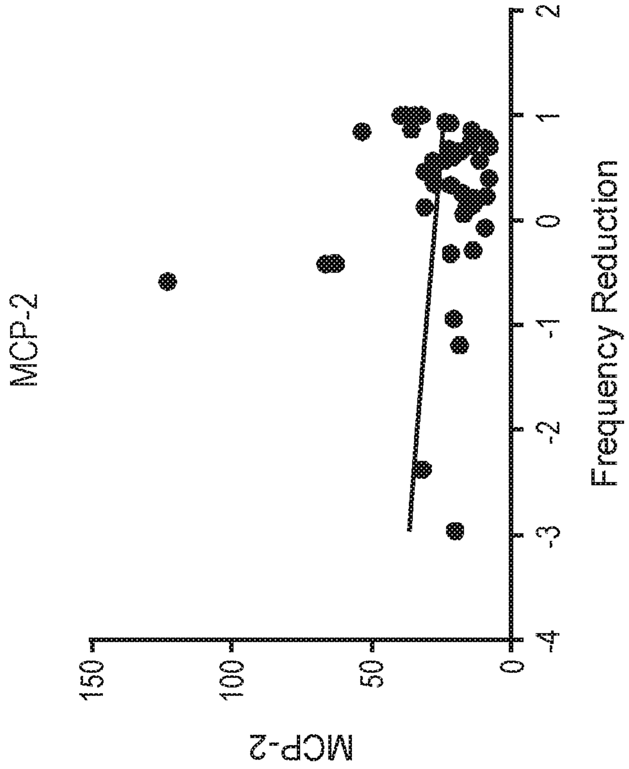

FIGS. 29A and 29B illustrate the correlation of protein concentration with seizure reduction (predictive algorithms).

DETAILED DESCRIPTION OF THE INVENTION

Epileptic seizures, NES, NS, PNES and NEE are difficult to diagnose and are often difficult to distinguish from several conditions with similar presentations, and therefore, diagnosis of seizures is often a long, expensive, and unreliable process. Predictive Models (EvoScore™) give clinicians the ability to quickly triage patients by ruling out epilepsy, ES, NES, NS, PNES or NEE. Predictive Models will allow patients to proceed immediately to diagnostic protocols that are most likely to result in effective treatment, saving significant time and money and sparing patients from unnecessary tests.

Figure 2:
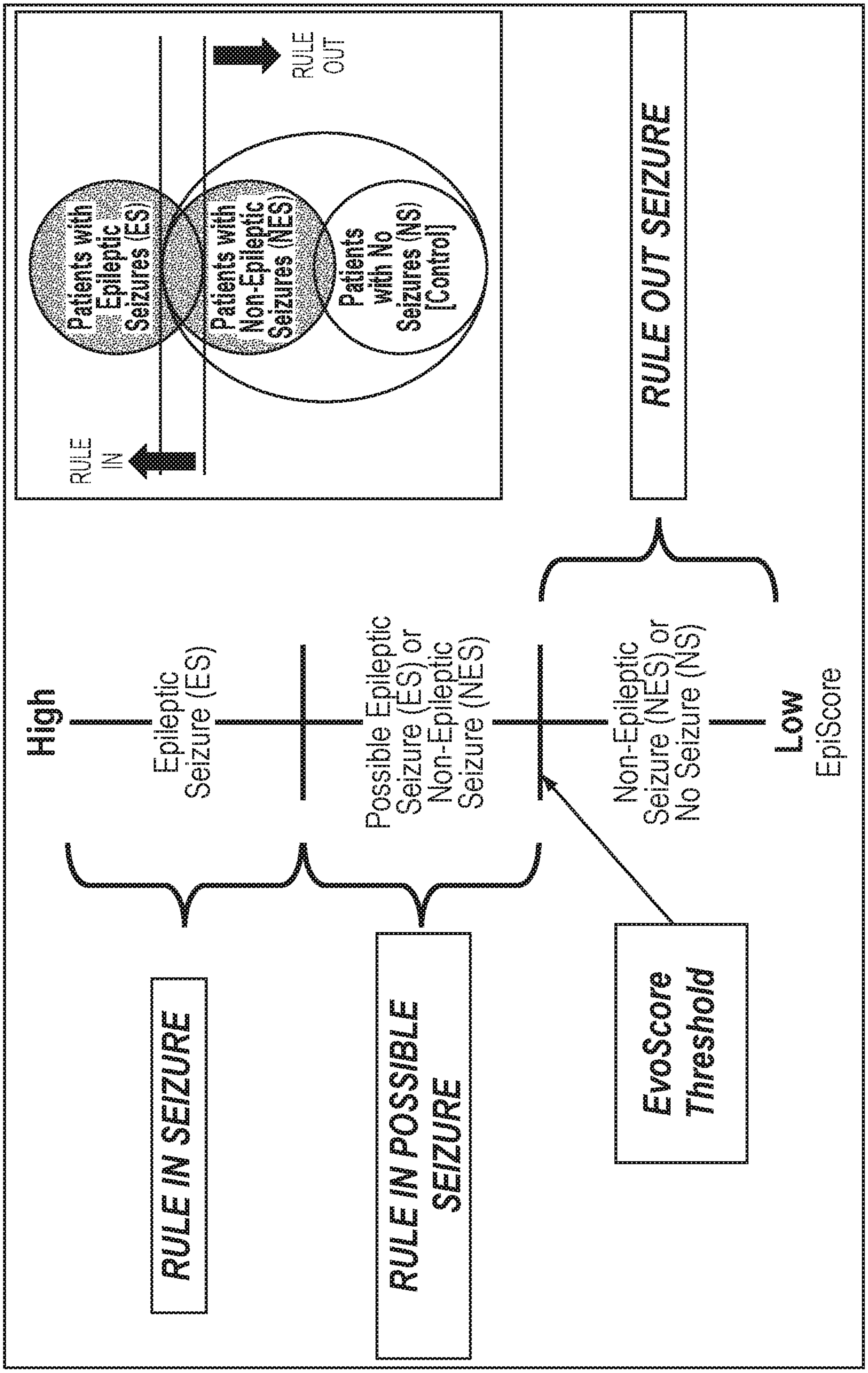
FIG. 2 illustrates the objectives of the algorithm and ultimate actionable results.

This application is directed towards a blood test for seizure and epilepsy, ES, NES, NS, PNES or NEE diagnosis and etiology classification in all clinical settings. In some embodiments, individual and panels/arrays of biomarkers indicative of seizure or a tendency to have seizure are provided, including methods for detecting seizure, methods for assessing the effectiveness of a treatment of seizure, a tendency to have seizure or treatment of any underlying disorder resulting in seizure, and diagnostic kits. In other embodiments, Predictive Models are provided, providing both quantitative and qualitative scores predicting phasic and tonic changes associated with seizures and epilepsy, ES, NES, NS, PNES or NEE. The score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative." (FIG. 1 illustrates criteria for different types of seizures, and FIG. 2 illustrates the objectives of algorithms described herein and ultimate actionable results).

Psychogenic non-epileptic seizures (PNES)*(taken and abridged from References: Epilepsy foundation, including epilepsy.com/article/2014/3/truth-about-psychogenic-non-epileptic-seizures, epilepsy.com/article/2014/3/truth-about-psychogenic-nonepileptic-seizures and epilepsy.com/learn/types-seizures/nonepileptic-seizures-or-events) are commonly misdiagnosed as epilepsy, leading to treatment that does not treat the events and may have many side effects. PNES are attacks that may look like epileptic seizures, but are not caused by abnormal brain electrical discharges. It is estimated that PNES are diagnosed in 20-30% of patients seen at epilepsy centers for seizures. Psychogenic seizures or events are caused by subconscious thoughts, emotions, or stress, not abnormal electrical activity in the brain. In addition to being common, psychogenic symptoms pose an uncomfortable and often frustrating challenge, both in diagnosis and management. Frequently, People with PNES may look like they are experiencing generalized convulsions similar to tonic-clonic seizures with falling and shaking. Less frequently, PNES may mimic absence seizures or complex partial seizures with temporary loss of attention or staring. A physician may suspect PNES when the seizures have unusual features, such as type of movements, duration, triggers and frequency. PNES are a physical manifestation of a psychological disturbance and are a type of somatoform disorder called a conversion disorder.

Differentiating between epileptic seizures (ES) and Non-epileptic seizures (NES)/No Seizures (NS) is an unmet medical need. The most reliable method for diagnosing NES/NS is video EEG, but is not generally available, requires long inpatient hospital stays, is expensive and does not always provide a definitive diagnosis. See following figure. Given the shortcoming of diagnosing NES/NS, Evogen has developed a novel diagnosis technology that allows physicians to retrospectively differentiate ES and NES/NS events. The test is based on determining protein concentrations derived from patient blood samples, collected within 24 hours of an event, coupling the concentrations with documented NES risk factors using a diagnostic algorithm that generates an NES/NS probability score.

Events (taken and abridged from References: Epilepsy foundation, including epilepsy.com/article/2014/3/truth-about-psychogenic-nonepileptic-seizures, epilepsy.com/article/2014/3/truth-about-psychogenic-nonepileptic-seizures and epilepsy.com/learn/types-seizures/nonepileptic-seizures-or-events) that look like seizures but are not due to epilepsy are called "non-epileptic seizures" or "non-epileptic events" (NEE) Some people prefer to use the term "events" rather than seizures. You will see the terms used interchangeably here.

In this document, NES, NS, NES/NS, PNES, NES/NS/PNES, and/or NEE may be used interchangeably, all referring to seizures that are not directly caused by epilepsy, epileptic seizures.

While much research has been devoted to developing new anti-epileptic drugs (AEDs), the "gold standard" diagnostic protocol—which often hinges on EEGs—has remained constant and inadequate. When patients present with a suspected seizure, the process to diagnose whether the event was caused by epilepsy, ES, NES, NS, PNES or NEE or another disorder is most often long and expensive. Patients undergo a lengthy work-up that regularly includes blood tests, imaging studies, EEGs, and video EEGs where available. Other methods for evaluating whether a person has suffered an ES, NES, NS or PNES include evaluation of the autonomic nervous system, prolactin levels, cortisol levels, creatinine kinase, neuron-specific emolase, neuropeptides, brain derived neurotrophic factor, leukocytosis and platelet membrane serotonin transporter have all been tried, but lack diagnostic accuracy sufficient for consistent, reliable and objective results (Reference: Epilepsy Foundation, epilepsy-.com/article/2016/5/helpful-tools-diagnosis-and-study-psychogenic-nonepileptic-seizures and ncbi.nlm.nih.gov/pubmed/26774202). Often the diagnosis is one of exclusion where other medical conditions are "ruled-out;" and definitive diagnosis of epilepsy is typically made if an EEG records an epileptic seizure "event" while it is occurring, usually during a lengthy and expensive stay in an in-patient epilepsy monitoring unit.

In addition to the high cost associated with a long engagement with the health system, the current state of epilepsy, ES, NES, NS, PNES or NEE diagnosis presents another critical issue: in the absence of a good triage tool for early diagnosis, patients who experience suspected seizures because of other underlying conditions may be either over- or under-treated erroneously with AEDs, during which time their underlying conditions remain untreated, while patients experience undesirable side-effects from unnecessary medications. Thus, timely diagnosis of the patient's condition (whether epilepsy, ES, NES, NS, PNES or NEE or not) remains a significant unmet medical need.

Epilepsy, ES, NES, NS, PNES or NEE Diagnostic Methodologies

Accurately diagnosing epilepsy, ES, NES, NS, PNES or NEE is very challenging and time consuming because clinicians rarely observe the actual seizure, plus there are many different types of seizures and epilepsy, ES, NES, NS, PNES or NEE syndromes with differing presentations. Furthermore, other NES, NS, PNES or NEE neurological disorders can be mimics for seizures leading to erroneous diagnosis, inappropriate treatments with significant potential adverse events, incorrect prognosis, and significant waste of health care resources. NES, NS, PNES or NEE clinical events such as movement disorders e.g., tremors, tics, dyskinesias, fainting spells/syncope, transient ischemic attacks (TIA), sleep disorders/parasomnias, and somatiform psychiatric disorders can be mistaken for seizures even by seasoned clinicians. Rendering a definitive diagnosis of seizures NES, NS, PNES or NEE is critical to long-term patient health and outcome that will lead to early treatment, subsequent follow up and surveillance, counseling, and support. Currently, obtaining a definitive diagnosis of seizures or epilepsy, ES, NES, NS, PNES or NEE is expensive and inconvenient for patients as it may require inpatient evaluation and a battery of costly tests.

The diagnosis of epilepsy, ES, NES, NS, PNES or NEE has for years relied on broad, costly, and often cumbersome medical-neurological evaluation. The "gold standard" test is electroencephalography (EEG). If a seizure is captured during the recording, seizure activity will appear as rapid spiking waves on the EEG. Brain lesions, i.e., tumors, strokes, may cause slowing of normal electrical brain rhythms. The challenge with EEG is that it is typically performed as a post hoc assay, that is, after the clinical event is finished, and may in fact be normal. A continuous EEG is a 24 hour EEG done in the hospital to get a prolonged pattern and try to "catch" the seizure when occurring. This requires a costly inpatient hospital stay, and there is no way to know for certain that a clinical event will occur during the stay. Obviously, this provides a significant logistical challenge to caregivers in the outpatient and emergency department (ED) settings since most patients come to the ED after the event has ended and only historical information is gathered; definitive diagnosis of a single seizure is essentially impossible and empiric at best. EEG is only about at best 30 to 50% sensitive (measures proportion of positives that are correctly identified).

Medical History to determine circumstances surrounding first seizure like event, the duration and frequency of the event, and age of onset can also be used. Often the patients or caregivers cannot give the level of detail needed for accurate diagnosis. Missing information regularly includes time of onset and duration of event due to the fact that a caregiver was either not present or failed to keep accurate records. Seizure-like events are traumatic events for patients, caregivers, and responders where the first reaction is to care for the patient and not to keep track of timing or other information necessary for diagnosis.

Laboratory studies including complete blood count (CBC), chemistry metabolic panel (CMP), and toxicology screen tests. These do not diagnose the "seizure" itself, but instead may provide clues to explain neurological dysfunction. Measurement of prolactin levels is unreliable. EEG is used to evaluate several types of brain disorders.

MRI is a technique used to create an image or scan of the brain. MRI scans can be used examine a person's brain structure. An MRI scan cannot, by itself, determine whether the person has epilepsy, ES, NES, NS, PNES or NEE, but when considered with other information, may help the clinician decide if epilepsy, ES, NES, NS, PNES or NEE is a likely cause of the seizure like events.

PET scan may be used to locate the part of the brain causing seizure like events as it gives clinicians additional information about how the cells in the body are functioning. While PET scans are helpful in some cases, they often show abnormalities that are not related to epilepsy, ES, NES, NS, PNES or NEE and are less often part of the diagnostic process.

Lumbar puncture is a procedure in which fluid surrounding the spinal cord is withdrawn through needle aspiration and analyzed in the lab. It is performed to rule out infections, such as meningitis or encephalitis, as the cause of seizure like events.

Other methods for evaluating whether a person has suffered an ES, NES, NS or PNES include evaluation of the autonomic nervous system, prolactin levels, cortisol levels, creatinine kinase, neuron-specific emolase, neuropeptides, brain derived neurotrophic factor, leukocytosis and platelet membrane serotonin transporter have all been tried, but lack diagnostic accuracy sufficient for consistent, reliable and objective results (Reference: Epilepsy Foundation, epilepsy-.com/article/2016/5/helpful-tools-diagnosis-and-study-psychogenic-nonepileptic-seizures and ncbi.nlm.nih.gov/pubmed/26774202). Timely Diagnosis:

The diagnostic process can take several months before clinical events are pinpointed as epileptic seizures, and often clinical care is largely empiric, based on supporting but not definitive evidence-often resulting in either under- or over-diagnosis and treatment. Thus, timely and accurate seizure diagnosis remains an unmet medical need. Not only is the diagnostic process long, there is a significant burden on the healthcare system with annual figures for epilepsy, ES, NES, NS, PNES or NEE diagnostic methodologies totaling greater than $15 billion in the US alone. Thus, a critical gap in our clinical assessment of seizures in virtually every clinical setting is an accurate diagnostic blood test for seizures that can be used for either single or recurrent events to identify both phasic and tonic changes in brain activity. Numerous clinical scenarios can be envisioned in which a clinical diagnostic test for seizures would be invaluable to explain a patient's clinical condition: 1) an individual is brought to the ED after collapsing at home; 2) an individual is found confused and wandering in the street; 3) a hospitalized patient has a brief episode of unresponsiveness or change in mental status; 4) patients in third world countries where EEG, CT, or MRI are not readily available. A simple blood test that could provide immediate and definitive explanation of the clinical event with actionable results would be an enormous diagnostic advance and could direct further studies towards ("rule in") or away ("rule out") from epilepsy, ES, NES, NS, PNES or NEE, saving resources, time, and expense. In short, a simple blood test for seizures would be a major innovation.

Accurately diagnosing epilepsy, ES, NES, NS, PNES or NEE is very challenging and time consuming because clinicians rarely observe seizures and there are many different types of seizures and epilepsy, ES, NES, NS, PNES or NEE syndromes with differing presentations. The diagnosis of epilepsy, ES, NES, NS, PNES or NEE has for years relied on a "gold standard" to include patient medical history (inclusive of complete blood count and chemistry metabolic profile) and electroencephalograph (EEG). Once these are analyzed, the clinician may also perform magnetic resonance imaging (MRI) and continuous video EEG (vEEG) where available. Additional diagnostic techniques may include positron emission tomography (PET) scan and lumbar puncture (spinal tap). A major challenge in the diagnosis of epilepsy, ES, NES, NS, PNES or NEE using the gold standard EEG is the fact that EEG has a low sensitivity for epilepsy, ES, NES, NS, PNES or NEE, ranging between 25-56%. Specificity is better, but also variable at 78-98%—as specificity is dependent on the skill of the physician reading the EEG. Additionally, while often adequate for the appropriate diagnosis of a seizure disorder, EEGs can appear persistently normal for patients with epilepsy, ES, NES, NS, PNES or NEE. In fact, in our studies, EEG was demonstrated to have a Sensitivity of 37-55%, Specificity of 98-99%, PPV of 98%, and NPV of 64-66%, which validates the need for a test that maximizes sensitivity when diagnosing a seizure.

Importantly, while patients are undergoing months of diagnostic work-up for epilepsy, ES, NES, NS, PNES or NEE, as described above, they are typically subjected to a period of AED medication trial and error to determine which-if any-medications control their seizures. Especially when considering the side-effect-laden and in some cases teratogenic consequences of AEDs, this unnecessary medication cost is huge and when combined with the long diagnostic process, there is a significant burden on the health care system with annual figures for epilepsy, ES, NES, NS, PNES or NEE diagnostic methodologies totaling greater than $15 billion in the US alone.

In an effort to streamline epilepsy, ES, NES, NS, PNES or NEE diagnosis, it has been observed that prolactin levels were altered subsequent to a seizure. Further clinical evaluation of application of prolactin for seizure diagnosis indicated that prolactin is only a viable biomarker for seizure if a sample is collected within 10 and 20 minutes of a seizure. Additionally, Prolactin is only applicable to a subset of seizures including primary or secondarily generalized tonic-clonic seizures and partial complex seizures of temporal lobe origin. Accordingly, the short window of viability (minutes after), coupled with inadequate diagnostic sensitivity, specificity, and accuracy, preclude prolactin from being a practical seizure biomarker, and is rarely, if ever used today in clinical settings.

Link Between Inflammation and Seizures

Seizures induce an inflammatory response in brain tissue where the seizure starts. For example, there may be a robust inflammatory response in the resected brain specimens of intractable epilepsy patients including expression of critical proinflammatory cytokines and chemokines such as tumor necrosis factor alpha (TNF$\alpha$, interleukin-8 (IL-8), interleukin-6 (IL-6), and interferon gamma (IFN$\gamma$). Increased levels of TNF$\alpha$, IL-8, IL-6, and IFN$\gamma$ have also been detected in mouse seizure models highlighting the idea that inflammatory processes in the brain contribute to the pathogenesis of seizures and to the establishment of a chronic epileptic focus. Many of these cytokines have been detected in the cerebrospinal fluid of seizure patients immediately following seizures as well. Expression of several cytokine receptor subtypes is also upregulated on neurons and astrocytes, suggesting a mechanism for activated intracellular signaling, highlighting autocrine and paracrine actions of cytokines in the brain. Functional interactions between cytokines and classical neurotransmitters such as glutamate and GABA suggest the possibility that these interactions underlie established cytokine-mediated changes in neuronal excitability, thus promoting seizures. There is also clear evidence that acute seizures can induce increased blood-brain barrier permeability. The effect has been shown to facilitate passage of activated T-cells and macrophages into brain tissue, facilitating an inflammatory response in the brain, and fostering the leakage of brain specific inflammatory cytokines and chemokines into peripheral blood.

TARC (Thymus and activation-regulated chemokine; CCL17) is a chemokine (i.e., cytokine that is responsible for the movement of T and B lymphocytes, monocytes, neutrophils, eosinophils and basophils, in allergic and other inflammatory conditions) that principally expressed in the thymus and blood mononuclear cells. TARC functions as a proinflammatory cytokine and lymphocyte chemoattractor that binds specifically to CCR4 receptors on T-cells and induces chemotaxis in T-cell lines. Since TARC binds to CCR4, it is considered a Th2 type chemokine. TARC is produced by multiple cell types including dendritic cells, endothelial cells, keratinocytes and fibroblasts. Serum TARC levels have been shown to be a useful assay for disease activity in atopic dermatitis, an inflammatory disorder of the skin affecting children and adults. Indeed, TARC is an established systemic rheostat for inflammation. TARC exhibits low-level expression in the choroid plexus in the brain but has minimal expression by neurons or astrocytes.

However, little is known about changes in plasma TARC expression as a consequence of seizures.

TNF-α is a secreted cytokine that has been implicated in a range of neurological disorders including stroke, Alzheimer's disease, cancer, and autism. A number of studies have examined TNFα levels in both experimental epilepsy model systems as well as human samples including CSF and serum. Kainate induced seizures in the rat induce TNF-α expression in hippocampus. In dogs with spontaneous seizures, TNF-α levels are altered in CSF and manipulation of TNF-α signaling cascades in mouse seizure models can attenuate seizure. TNF-α levels are robustly altered in patients with temporal lobe epilepsy suggesting it is a broad marker of inflammation in the brain, especially in the setting of seizures.

Interleukin (IL)-16, also known as lymphocyte chemoattractant factor, is a pro-inflammatory cytokine produced by a variety of immune (T cells, eosinophils, and dendritic cells) and non-immune (fibroblasts, epithelial, and neuronal) cells. IL-16 can be produced in a precursor (pro) form that is cleaved by caspase-3 and then secreted as IL-16 and interacts with its receptor, CD4. IL-16 acts as an immunomodulator, contributing to CD4+ cell recruitment and activation at sites of inflammation. IL-16 has been associated with asthma, inflammatory bowel disease, cancer, and autoimmune diseases, including multiple sclerosis. In the brain, IL-16 can be produced in neurons as a different pro-form, NIL-16, or by microglia, and can interact with CD4 expressed on neurons or microglia. IL-16 levels are reported to correlate with seizure time during electroconvulsive therapy for depression, and IL-16 positive microglia have also been shown to accumulate in the brain after focal cerebral infarctions. Prior to the current work, IL-16 had not been directly investigated in relationship to epilepsy.

Serum amyloid A (SAA) is a family of homologous apolipoproteins that respond to acute inflammation and bind to high-density lipoprotein (HDL). SAA is produced predominantly in the liver in response to inflammatory cytokines, such as IL-1β, IL-6, and TNF-α. SAA has been implicated in several pathological conditions including atherosclerosis, rheumatoid arthritis, Alzheimer's disease, and cancer. Increases in SAA levels have been previously noted after brain injury and epilepsy.

Tumor necrosis factor-related apoptosis-inducing ligand (TRAIL), also known as Apo2L and TNFSF10 (tumor necrosis factor ligand superfamily 10), is a cytokine that produces apoptotic cell death through binding to death receptors and activating caspase-8, NF-κB, and BID. The major known function of TRAIL is in tumor defense and protection against malignancies. TRAIL may also mediate cell death in a variety of other cell types and has been implicated in cell death associated with Alzheimer's disease and Multiple Sclerosis. Increased TRAIL expression has been identified in brain tissue of patients with epilepsy.

Monocyte chemotactic protein (MCP)-4, also known as chemokine (C-C motif) ligand (CCL)-13, is a potent chemoattractant for eosinophils, monocytes, lymphocytes, and basophils. MCP-4 binds to chemokine receptors, through which it recruits leukocytes to inflamed tissues. MCP-4 has been mainly implicated in inflammatory diseases such as asthma, rheumatoid arthritis, and chronic obstructive pulmonary disease. No association with epilepsy or neuronal injury has previously been identified.

Intercellular adhesion molecule (ICAM)-1 is a cell surface glycoprotein structurally related to immunoglobulins. ICAM-1 expression is upregulated in response to inflammation, resulting in T-cell proliferation and cytokine release. ICAM-1 is also involved in angiogenesis, wound healing, and bone metabolism. Soluble forms of ICAM-1 (sICAM-1) can be generated through proteolytic cleavage. Altered levels of SICAM-1 are associated with cardiovascular disease, type 2 diabetes, rheumatoid arthritis, and certain cancers. Reduced sICAM-1 has been previously observed in schizophrenic patients. In a separate study, sICAM levels were noted to be higher in epileptic patients than neurotic controls.

Matrix Metalloproteinase (MMP)-3 is a proteolytic enzyme involved in remodeling of the extracellular matrix. MMP-3's major function is in tissue injury and repair. MMP-3 has been implicated in arthritis, arthrosclerosis, fibrosis, neurodegeneration, and cancer. A previous study found MMP-3 levels decreased in epilepsy patients versus controls.

Macrophage inflammatory protein (MIP)-13, also known as CCL4, is a chemoattractant for natural killer cells, monocytes and a variety of other immune cells. MIP-1β is one of the major HIV suppressive factors produced by CD8+ T cells. MIP-1β has been additionally implicated in diabetes, arthritis, and arthrosclerosis. Increased expression of MIP-1β has been found in the brain of patients with epilepsy.

P-Cadherin is a classical cellular adhesion molecule, localized to isolated tissues. The designation "P" indicates its expression in the placenta, but P-cadherin is additionally found in tissues such as hair follicles, keratinocytes, mammary myoepithelium, melanocytes, prostate, retina, serum, and skin. Due to a relative lack of characterization compared to other cadherins, expression and functional data are limited. P-Cadherin has been implicated in breast cancer and other malignancies. P-Cadherin has yet to be linked to epilepsy.

Osteoactivin, also known as glycoprotein nonmetastatic melanoma protein B (GPNMB), is a transmembrane glycoprotein involved in regulation of the extracellular matrix of several cell types. Functions include regulation of cell proliferation, adhesion, differentiation, and synthesis of extracellular matrix proteins. Osteoactivin is crucial for the differentiation and function of osteoclasts and osteoblasts. Altered expression of osteoactivin has been reported in osteoarthritis, breast cancer, melanoma, and glioblastoma. Neuroprotective effects of osteoactivin have been noted in ALS and ischemic injury. Osteoactivin has not been directly linked to epilepsy.

Macrophage colony-stimulating factor (M-CSF), also known as colony stimulating factor (CSF)-1, is a cytokine that stimulates macrophage proliferation, differentiation, and survival. Increased serum M-CSF have been noted during pregnancy and immune thrombocytopenia purpura. Abnormal levels of M-CSF have also been associated with neurological diseases, brain tumors, and other malignancies. M-CSF has not been linked to epilepsy.

IL-7 is a cytokine secreted mainly by stromal cells, but can also be produced by keratinocytes, dendritic cells, hepatocytes, neurons, and epithelial cells. Its main function is for the differentiation, growth, and survival of lymphocytes. IL-7 plays a fundamental role in T-cell development, peripheral T-cell homeostasis, and immune tolerance. IL-7 has been implicated in autoimmune diseases, muscle hypertrophy, and cancer. Increased IL-7 expression has been found in brain tissue of patients with epilepsy.

MCP-2, also known as CCL8, is a chemokine that attracts monocytes, lymphocytes, basophils and eosinophils, recruiting T-cells to sites of inflammation. Increases in MCP-2 has been noted in tuberculosis, arthritis, multiple sclerosis, allograft rejection, and arthrosclerosis. MCP-2 has not previously been investigated in relationship to epilepsy.

The abbreviation "IP-10" refers to interferon gamma-induced protein 10, small-inducible cytokine B10, C-X-C motif chemokine 10 (CXCL10), or variants thereof. IP-10 is a chemoattractant for monocytes, T-cells, NK cells, and dendritic cells.

Eotaxin, also known as eotaxin-1, refers to chemokine (C-C motif) ligand 11 (CCL11), or variants thereof. Eotaxin is a potent chemoattractant for eosinophils.

Eotaxin-2 refers to chemokine (C-C motif) ligand 24 (CCL24), or variants thereof. Eotaxin-2 is chemoattractant for eosinophils.

Eotaxin-3 refers to chemokine (C-C motif) ligand 26 (CCL26), or variants thereof.

The abbreviation "VCAM-1" refers to vascular cell adhesion molecule 1 or cluster of differentiation 106 (CD106). VCAM-1 mediates cellular adhesion molecule of lymphocytes, monocytes, eosinophils, and basophils to the vascular endothelium. VCAM-1 may be detected in soluble form (sVCAM1)

The abbreviation "VEGF-A" refers to vascular endothelial growth factor A. VEGF-A is a growth factor for endothelial cells.

Interleukin 5 (IL5) is an interleukin produced by type-2 T helper cells and mast cells.MIP-5 refers to macrophage inflammatory protein 5, also known as CCL15 or hemofiltrate CC chemokine-2. MIP-5 is a chemokine primarily expressed in heart and skeletal muscle.

TNF-β refers to tumor necrosis factor β, also known as Lymphotoxin-alpha. TNF-β is a cytokine involved in proliferation, cell survival, differentiation, and apoptosis.

MIF refers to macrophage migration inhibitory factor, also known as glycosylation-inhibiting factor (GIF), L-dopachrome isomerase, or phenylpyruvate tautomerase. MIF is an important regulator of innate immunity.

Nectin-4 is a cellular adhesion molecule.

TNF-RI refers to tumor necrosis factor receptor 1, also known as tumor necrosis factor receptor superfamily member 1A (TNFRSF1A) or CD120a. TNF-RI is a ubiquitous receptor that binds TNF-α.

TNF-RII refers to tumor necrosis factor receptor 2, also known as tumor necrosis factor receptor superfamily member 1B (TNFRSF1B) or CD120b. TNF-RII is a membrane receptor that binds TNF-α.

IL-8 refers to interleukin 8, also known as chemokine (C-X-C motif) ligand 8 (CXCL8). IL-8 is a chemokine produced by macrophages and other cell types.

MCP-1 refers to monocyte chemoattractant protein-1, also known as chemokine C-C motif) ligand 2 (CCL2) and small inducible ligand A2. MCP-1 recruits monocytes, memory T-cells, and dendritic cells to sites of inflammation.

CRP refers to C-reactive protein, an acute phase inflammatory protein produced by the liver.

Calbindin refers to calcium binding proteins.

MMP-1 refers to matrix metalloproteinase-1, also known as interstitial collagenase and fibroblast collagenase. MMP-1 is involved in the breakdown of the extracellular matrix.

MMP-9 refers to matrix metalloproteinase-9, also known as 92 kDa type IV collagenase, 92 kDa gelatinase, or gelatinase B. MMP-9 is involved in the breakdown of the extracellular matrix.

Osteonectin refers to a glycoprotein in the bone that binds calcium, also known as secreted protein acidic and rich in cysteine (SPARC) or basement-membrane protein 40.

IL-12/IL-23p40 refers to the p40 subunit of interleukin-12 and interleukin-23, which are heterodimers that share the p40 subunit.

IL-1a refers to interleukin-1alpha, also known as hematopoietin 1. IL-1a is a cytokine that produces inflammation and promotes fever and sepsis.

SCF refers to stem cell factor, also known as KIT-ligand or steel factor. SCF is a cytokine that binds to the c-KIT receptor.

Cytokeratin-8 refers to keratin type II cytoskeletal 8, also known as keratin-8. IL-17A refers to interleukin-17A, a pro-inflammatory cytokine produced by activated T-cells.

IL-15 refers to interleukin-15, a cytokine that induced proliferation of natural killer cells.

MDC refers to macrophage derived chemokine, also known as chemokine (C-C motif) ligand 22 (CCL22). MDC is a chemokine secreted by dendritic cells and macrophages.

IL-10 refers to interleukin 10, also known as human cytokine synthesis inhibitory factor (CSIF). IL-10 is an anti-inflammatory cytokine produced by monocytes and lymphocytes.

MIP-1alpha or MIP-1a refers to macrophage inflammatory protein-1, also known as chemokine (C-C motif) ligand 3. MIP-1a is involved in acute inflammatory response, recruiting leukocytes.

GM-CSF refers to granulocyte macrophage colony stimulating factor, also known as colony stimulating factor 2 (CSF2). GM-CSF is a monomeric glycoprotein that functions as a cytokine.

IFN-γ refers to interferon-gamma, a cytokine that is critical for innate and adaptive immunity.

IL-13 refers to interleukin-13, a mediator of allergic inflammation.

IL-1B refers to interleukin-1beta or IL-1β, also known as leukocytic pyrogen, leukocytic endogenous mediator, mononuclear cell factor, and lymphocyte activating factor. IL-1B is an important cytokine mediating inflammatory responses. IL-12p70 refers to the heterodimer of interleukin-12, also known as IL-12, cytotoxic lymphocyte maturation factor, natural kill stimulatory factor. IL-12p70 is a cytokine composed of protein products from two separate genes, IL12A and IL12B. IL-12 is involved in the differentiation of T-cells into Th1 cells.

IL-2 refers to interleukin-2, a cytokine that regulates the activities of leukocytes.

IL-4 refers to interleukin-4, a cytokine that induces differentiation of Th0 cells to Th2 cells.

IL-6 refers to interleukin-6, a cytokine with both pro-inflammatory and anti-inflammatory functions.

As indicated in the description of some of the proteins, some markers had not previously been investigated in regards to epilepsy, ES, NES, NS, PNES or NEE, and others may have been investigated in animal models or in dissected or post-mortem brain tissue. This work provides therefore several novel biomarkers that can be detected in patient plasma that relates to a patient with epilepsy, ES, NES, NS, PNES or NEE. In addition, the combination of biomarkers provides a novel mechanism for identifying patients with epilepsy, ES, NES, NS, PNES or NEE.

As shown herein, the described invention ameliorates the deficiencies in the field. Indeed, based on a link between inflammation and seizures both in experimental models and in humans with epilepsy, an initial proteomics screen in patient plasma was used to probe a panel of biomarkers linked to inflammatory cytokines, chemokines, enzymes, and cellular adhesion molecules that were hypothesized to exhibit phasic or tonic changes in response to seizures in our studies. It was speculated that measurable changes in levels of specific plasma proteins could yield a diagnostic blood test for seizures.

In epilepsy, an immune response is generated within the region of seizure onset. In several distinct tissue lesion types such as tuberous sclerosis (TSC) and mesial temporal sclerosis (MTS), pro-inflammatory cytokines such as IL-1β, IL-6, TNF-α, Fas, and Fas-ligand are activated. In addition, there is complement fixation and deposition, altered blood-brain barrier permeability, and macrophage infiltration. Inflammation may generate a wide variety of downstream effects including upregulation of IL-1β production, activation of TLR4, NFκB, mTOR, and MAPK cascades, attraction of activated lymphocytes, microglia, and macrophages, and alteration of astrocyte physiology. Additionally, the relative balance with anti-inflammatory cytokines can also be modulated, demonstrating a change in levels of cytokines like IL-4, IL-10 and IL-13. Without being bound by theory, these changes may be a result of a disease process leading to seizures, caused by seizures, and/or be the result of seizures (see FIG. 1). Diagnostic tests and algorithms developed are able to distinguish seizures from a lack of seizure, and epilepsy, ES, NES, NS, PNES or NEE from normal (see FIG. 2). The present application addresses a need in the art for markers associated with seizures.

Definitions

The terms "comprising" and "including" are used interchangeably, unless otherwise noted. The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

The term "cryptogenic" is used herein to refer to a seizure or epilepsy, ES, NES, NS, PNES or NEE of unknown origin.

The term "phasic" is used herein to refer to a change in blood biomarkers directly related to an immediate or sudden event or seizure. The change in the blood is short-lived and resolves within a specific period of time after the event.

The term "tonic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The term "acute" is used herein to refer to a change in blood biomarkers directly related to an immediate or sudden event or seizure, ES, NES, NS, PNES or NEE. The change in the blood is short-lived and resolves within a specific period of time after the event.

The term "chronic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The terms "disease", "disorder", or "condition" are used herein to refer to any manifestations, symptoms, or combination of manifestations or symptoms, recognized or diagnosed as leading to, causing, or influencing seizure, ES, NES, NS, PNES or NEE. The terms include, but are not limited to, traumas, inflammatory and autoimmune responses, physiological malformations, and genetic defects.

The term "ictal" refers to a physiologic state or event such as a seizure.

The term "indicative" "indicative of") encompasses both prediction/forecasting (including tendency), and detection (proximate to the occurrence of a seizure), and unless otherwise noted, embodiments encompassing the term are intended to define and encompass embodiments specific to prediction, specific to detection, and for prediction as well as for detection of a past or current event. Use of the term indicative in conjunction with the term "tendency" is intended solely for emphasis of evidence of a past event versus a tendency, predicting or forecasting toward a future event, but the use solely of indicative is intended to encompass tendency unless otherwise indicated.

The term "monitoring" is used herein, but not limited, to refer to: monitoring if a patient experienced an ES, NES, NS, PNES, or NEE, monitoring the seizure frequency of a patient as a function of treatment, and to monitor the progression of epilepsy and/or epileptogenesis.

The terms "predictive," "prediction," and/or "predict" are used herein, but not limited, to refer to the ability to identify patients who are most likely to respond to treatment; response could include, without limitation, both symptomatic benefit or adverse effect.

The terms "monitoring biomarker" and/or "monitoring algorithm" are used herein, but not limited, to refer to a monitoring biomarker approach and algorithm, that reports on changes in seizure burden.

The terms "predictive biomarker" and/or "predictive algorithm are used herein, but not limited, to refer to predictive biomarker approach and algorithm that identifies patients with probability of responding as measured by seizure burden.

The terms "seizure burden" or "seizure frequency" are used herein, but not limited to refer to a patient's current status of having an ES, NES, NS, PNES or NEE, including how often or how frequently or how severe. Time frames for measurement of seizure burden or frequency can be measured in seconds, minutes, hours, days, weeks, months, years or other measure. Seizure burden or frequency can be measured in patients, healthy controls, drug controlled patients, and/or non-drug controlled patients. Seizure burden severity can be measured by the Chalfont Seizure Severity Scale (J Neurol Neurosurg Psychiatry, 1991 October; 54 (10): 873-876), or National Hospital Seizure Severity Scale (Epilepsia, 1996 June; 37 (6): 563-71), type of seizure manifestation, loss of awareness, seizure duration, region of brain affected, seizure foci, if secondarily generalized or other measures.

The term "sample" is used herein to refer to a blood plasma or blood serum sample, unless otherwise noted. In each embodiment described herein, the use of blood plasma is contemplated as an independent embodiment from the alternative of blood plasma or blood serum. In each embodiment described herein, the use of blood serum is contemplated as an independent embodiment from the alternative of blood plasma or blood serum. In each embodiment described herein, the use of another biological sample, including but not limited to cerebrospinal fluid (CSF), a tissue sample obtained by resection, saliva, and urine is contemplated according to conventional techniques in the art for obtaining the sample and for analysis of same. The sample can be treated prior to use, such as preparing plasma from blood, diluting viscous fluids, and the like. Methods of treatment can involve filtration, distillation, extraction, concentration, inactivation of interfering components, the addition of reagents, and the like.

The terms “seizure” and “epilepsy,” are used interchangeably, two unprovoked seizures being required for a clinical diagnosis of epilepsy, unless otherwise noted. The term epilepsy may also be defined by the understanding of, or theories of, seizure as understood as of the time of filing of the application. Epilepsy includes and is not limited to all forms of epilepsy. An epileptic seizure is an abnormal electrical discharge in the brain.

The terms “subject”, “individual”, and “patient” are used interchangeably herein to refer to a mammal from which a sample is taken, unless otherwise noted. The terms are intended to encompass embodiments specific to humans. A subject, individual or patient may be afflicted with, at risk for, or suspected of having a tendency to have seizure or a disorder for which seizure is symptomatic. The term also includes domestic animals bred for food or as pets, including horses, cows, sheep, pigs, cats, dogs, and zoo animals. Typical subjects for treatment include persons susceptible to, suffering from or that have suffered one or more seizures. In particular, suitable subjects for treatment in accordance with the invention are persons that are susceptible to or that have suffered one or more seizures.

The term “tendency”, e.g., “tendency to have seizure”, is intended to refer to a reasonable medical probability of an event, e.g., seizure to occur or recur. The term also encompasses the frequency with which such events may occur before, after, or during ongoing treatment.

As used herein, the term “treat” or “treating” refers to any method used to partially or completely alleviate, ameliorate, relieve, inhibit, prevent, delay onset of, reduce severity of and/or reduce incidence of one or more symptoms or features of a particular condition, in any clinical setting e.g., seizure or a seizure-related disorder. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, frequency thereof, or of one or more symptoms associated with such condition. The terms “treatment” and “therapeutically” refer to the act of treating, as “treating” is defined above. The purpose of intervention is to combat the condition and includes the administration of therapy to prevent or delay the onset of the symptoms or complications, or alleviate the symptoms or complications, or eliminate the condition. For example, a treatment may be used to ameliorate symptoms or frequency thereof (e.g., frequency of seizure) associated with a disorder. Treatment can be a therapeutic or other therapy options that may or may not include a therapeutic agent, an external device or internal or implantable device that helps to control and minimize seizures and epilepsy, ES, NES, NS, PNES or NEE. Treatment for NES, NS, PNES or NEE can be a therapeutic, including with one or more therapeutic agents or other treatment options, including, but not limited to psychotherapy, cognitive therapy, behavioral therapy, standard medical care or other therapeutic agents not listed herein.

In this document, NES, NS, NES/NS, PNES, NES/NS/PNES, and/or NEE may be used interchangeably, all referring to seizures or events that are not directly caused by epilepsy or epileptic seizures.

The terms “tuberous sclerosis”, “tuberous sclerosis complex”, and the abbreviation/acronyms “TS” and “TSC”, are used interchangeably herein. IL-16

IL-16 is also an effective marker, differentially distributed in the blood plasma or blood serum of epilepsy, ES, NES, NS, PNES or NEE patients relative to healthy patients and it is shown to be reduced in seizure patients.

In another embodiment, a polypeptide expression panel or array is provided, the panel or array comprising a probe capable of binding IL-16 in blood plasma or blood serum of a mammalian subject, wherein an altered plasma or serum concentration of IL-16 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used. MMP-3

MMP-3 is also an effective marker, differentially distributed in the blood plasma or blood serum of epilepsy, ES, NES, NS, PNES or NEE patients relative to healthy patients and it is shown to be reduced in seizure patients.

In another embodiment, a polypeptide expression panel or array is provided, the panel or array comprising a probe capable of binding MMP-3 in blood plasma or blood serum of a mammalian subject, wherein an altered plasma or serum concentration of MMP-3 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Trail

TRAIL is also an effective marker, differentially distributed in the blood plasma or blood serum of epilepsy, ES, NES, NS, PNES or NEE patients relative to healthy patients and it is shown to be reduced in seizure patients.

In another embodiment, a polypeptide expression panel or array is provided, the panel or array comprising a probe capable of binding TRAIL in blood plasma or blood serum of a mammalian subject, wherein an altered plasma or serum concentration of TRAIL relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Tarc

TARC is also an effective marker, differentially distributed in the blood plasma or blood serum of epilepsy, ES, NES, NS, PNES or NEE patients relative to healthy patients and it is shown to be altered in seizure patients.

In another embodiment, a polypeptide expression panel or array is provided, the panel or array comprising a probe capable of binding TARC in blood plasma or blood serum of a mammalian subject, wherein an altered plasma or serum concentration of TARC relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used. TNF-α

TNF-α is also an effective marker, differentially distributed in the blood plasma or blood serum of epilepsy, ES, NES, NS, PNES or NEE patients relative to healthy patients and it is shown to be reduced in seizure patients In another embodiment, a polypeptide expression panel or array is provided, the panel or array comprising a probe capable of binding TNF-α in blood plasma or blood serum of a mammalian subject, wherein an altered plasma or serum concentration of TNF-α relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used. MIP-1β

MIP-1β is also an effective marker, differentially distributed in the blood plasma or blood serum of epilepsy, ES, NES, NS, PNES or NEE patients relative to healthy patients and it is shown to be reduced in seizure patients In another embodiment, a polypeptide expression panel or array is provided, the panel or array comprising a probe capable of binding MIP-1β in blood plasma or blood serum of a mammalian subject, wherein an altered plasma or serum concentration of T MIP-1β relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

MCP-1 or CCL2

MCP-1 is also an effective marker, differentially distributed in the blood plasma or blood serum of epilepsy, ES, NES, NS, PNES or NEE patients relative to healthy patients and it is shown to be reduced in seizure patients In another embodiment, a polypeptide expression panel or array is provided, the panel or array comprising a probe capable of binding MCP-1 in blood plasma or blood serum of a mammalian subject, wherein an altered plasma or serum concentration of T MCP-1 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

VCAM-1 or sVCAM1

VCAM-1 is also an effective marker, differentially distributed in the blood plasma or blood serum of epilepsy, ES, NES, NS, PNES or NEE patients relative to healthy patients and it is shown to be reduced in seizure patients In another embodiment, a polypeptide expression panel or array is provided, the panel or array comprising a probe capable of binding VCAM-1 in blood plasma or blood serum of a mammalian subject, wherein an altered plasma or serum concentration of VCAM-1 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Other Markers Contained Herein

Other markers contained herein can also an effective marker(s), differentially distributed in the blood plasma or blood serum of epilepsy, ES, NES, NS, PNES or NEE patients relative to healthy patients and it is shown to be reduced in seizure patients In another embodiment, a polypeptide expression panel or array is provided, the panel or array comprising a probe capable of other markers contained herein in blood plasma or blood serum of a mammalian subject, wherein an altered plasma or serum concentration of other markers contained herein relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Biomarker Ratios

In further embodiments, a polypeptide or array comprising a probe capable of binding one, two or more biomarkers in blood plasma or blood serum of a mammalian subject, wherein a change in plasma or serum concentration ratio in tested subjects relative to control (healthy, non-epileptic/non-seizure) is altered relative to healthy controls and is indicative of a seizure or a tendency to have seizure. In some embodiments, the biomarkers can be any combination of those biomarkers described herein, including but not limited to TARC, TNF-α, IL-16, MMP-3, TRAIL, MIP-1β and VCAM-1.

Individual measurements may be taken and analyzed individually or in any combination using linear or logarithmic units, or by using ratios of linear or logarithmic units. The reciprocals of ratios of linear or logarithmic units may also be used.

Combination of Individual Measures and Ratios

In further embodiments, a polypeptide or array comprising a probe capable of binding one, two or more biomarkers in blood plasma or blood serum wherein a change in plasma or serum concentration of two or more biomarkers and the change of the ratio of two or more biomarkers in tested subjects relative to control (healthy, non-epileptic/non-seizure) is altered relative to healthy controls and is indicative of a seizure or a tendency to have seizure. Any combinations of individual concentrations and ratios may be used.

Individual measurements may be taken and analyzed individually or in any combination using linear or logarithmic units, or by using ratios of linear or logarithmic units. The reciprocals of ratios of linear or logarithmic units may also be used.

Patient Demographic Characteristics

In another embodiment, when combined any biomarkers concentrations for one or more biomarkers measured in blood plasma or serum, combined with patient demographics or other characteristics associated with the patient, including but not limited to age, sex and/or race may indicate a seizure having occurred or a tendency to have a seizure in comparison to relative normal or healthy controls.

When combined with patient demographic characteristics, the individual measurements may be taken and analyzed individually or in any combination using linear or logarithmic units, or by using ratios of linear or logarithmic units. The reciprocals of ratios of linear or logarithmic units may also be used.

Other BioMarkers

Figure 3:
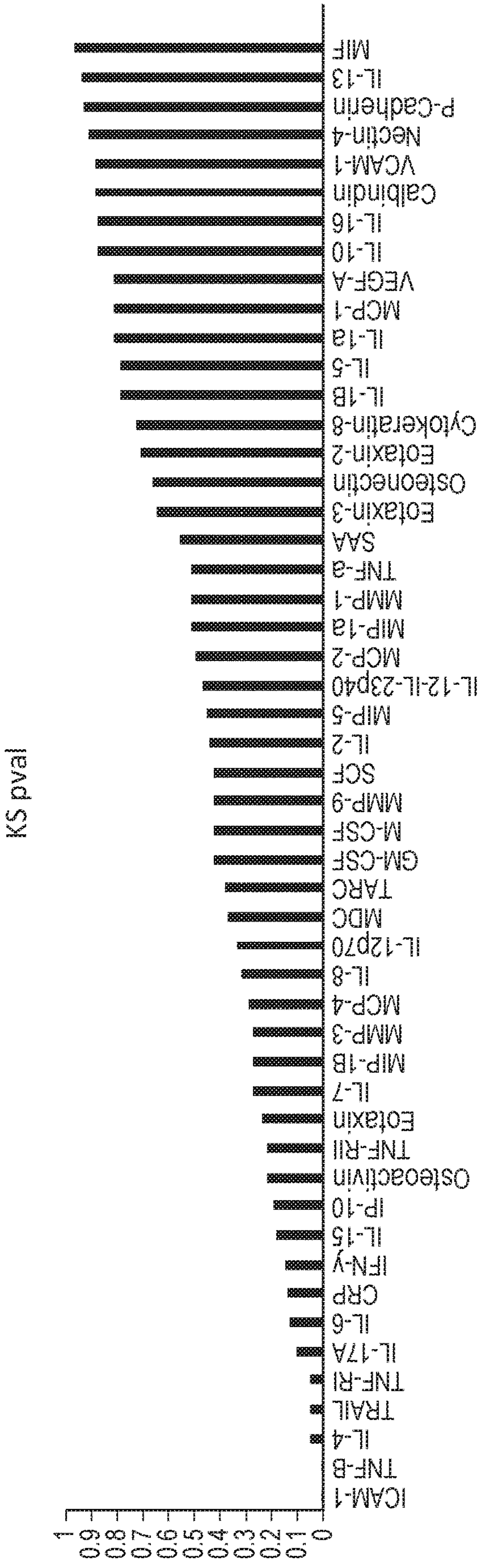
FIG. 3 illustrates descriptive statistics (KS: Kolmogorov-Smirnov) of all biomarkers considered-51 protein screen: 9 NES/NS/PNES Samples compared to 32 ES Seizure Samples.

Additional markers that are useful include, alone or in combination, include IL-1B, IL-2, IL-6, IL-8, IL-10, IL-12p70, IFN-γ, IL-13, IL-4, TNF-α, IL-17A, GM-CSF, IL-12/IL-23p40, IL-15, IL-16, IL-1a, IL-5, IL-7, TNF-β, VEGF-A, MCP-1/CCL2, Eotaxin, Eotaxin-3, IP-10, MCP-4, MDC, MIP-1a, MIP-1β, TARC, SICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL (FIG. 3 illustrates descriptive statistics (KS: Kolmogorov-Smirnov) of all biomarkers considered-51 protein screen: 9 NES/NS/PNES Samples compared to 32 ES Seizure Samples.)

Still additional markers that are useful include, alone or in combination, IL-1alpha, IL-3, IL-9, IL-22, IFN-alpha, CCL11, CX3CL1, HMGB1, bFGF, PDGFbeta, Fas, Fas-ligand, BDNF, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

Figure 4:
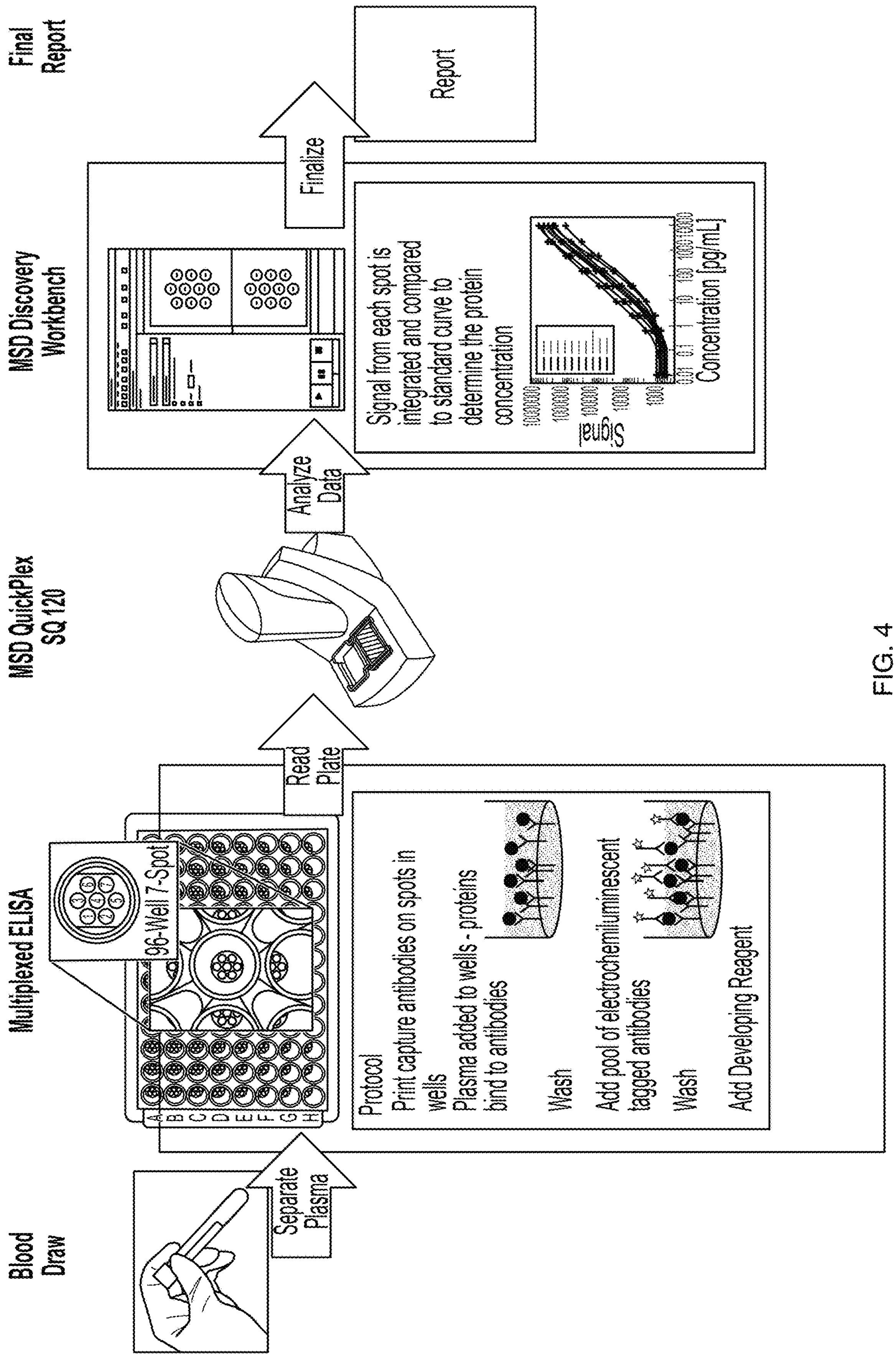
FIG. 4 illustrates a sample Protein Concentration workflow—from blood draw, to plated assay, to result/report.

The panels or arrays of the invention may also include one or more probes capable of binding one or more of the biomarkers listed herein, wherein an altered plasma or serum concentration of one or more relative to a healthy control is indicative of seizure or a tendency to have seizure (FIG. 4 illustrates a sample Protein Concentration workflow—from blood draw, to plated assay, to result/report). Still additional markers that are useful include, alone or in combination, IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In another embodiment, a method for predicting or detecting a seizure, epilepsy, ES, NES, NS, PNES or NEE is provided, comprising contacting a blood plasma or blood serum sample obtained from a mammalian subject with a diagnostic reagent that can measure or detect the expression level of one or more biomarkers, wherein a change in plasma or serum concentration of one or more biomarkers relative to a healthy control indicates a seizure having occurred or a tendency to have seizure. Individual measurements may be taken and analyzed individually or in any combination using linear or logarithmic units, or by using ratios of linear or logarithmic units. The reciprocals of ratios of linear or logarithmic units may also be used.

In another embodiment, a method for predicting or detecting seizure, epilepsy, ES, NES, NS, PNES or NEE is provided, comprising contacting a blood plasma or blood serum sample obtained from a mammalian subject with a diagnostic reagent that can measure or detect the expression level of one or more biomarkers, wherein a change in plasma or serum concentration of one or more biomarkers relative to a healthy control indicates seizure, epilepsy, ES, NES, NS, PNES or NEE. Individual measurements may be taken and analyzed individually or in any combination using linear or logarithmic units, or by using ratios of linear or logarithmic units. The reciprocals of ratios of linear or logarithmic units may also be used. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet another embodiment, a method for assessing the effectiveness of a treatment of seizure, epilepsy, ES, NES, NS, PNES or NEE or a disorder for which said seizure, epilepsy, ES, NES, NS, PNES or NEE is symptomatic, the method including contacting a first blood plasma or blood serum sample obtained from a mammalian subject prior to treatment with one or more diagnostic reagents that can measure or detect the expression level of one or more biomarkers and contacting a second blood plasma or blood serum sample obtained from a mammalian subject subsequent to treatment with a diagnostic reagent that can measure or detect the expression level of one or more biomarkers, wherein an altered plasma or serum concentration of one or more biomarkers relative to the first blood plasma or blood serum sample indicates effectiveness in treatment of seizure or a disorder for which seizure, epilepsy, ES, NES, NS, PNES or NEE is symptomatic. The method may further include contacting the first blood plasma or blood serum sample and the second blood plasma or blood serum sample with one or more diagnostic reagents that can measure or detect the expression of Fas, Fas-ligand, IL-1alpha, IL-3, IL-9, IL-22, IFN-alpha, CCL11, CX3CL1, HMGB1, bFGF, PDGFbeta, Eotaxin-3, Eotaxin, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In still further embodiments, a method for determining whether or not one or more seizures, epilepsy, ES, NES, NS, PNES or NEE are resultant from inflammation, comprising contacting a blood plasma or blood serum sample obtained from a mammalian subject with a diagnostic reagent that can measure or detect the expression level of one or more biomarkers and/or contacting a blood plasma or blood serum sample obtained from a mammalian subject with a diagnostic reagent that can measure or detect the expression level of one or more biomarkers, wherein an altered plasma or serum concentration of one or more biomarkers relative to a healthy control indicates an inflammatory basis or component of seizure, epilepsy, ES, NES, NS, PNES or NEE. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet other embodiments, a method for determining whether or not seizure, epilepsy, ES, NES, NS, PNES or NEE is likely to occur in a subject is provided, comprising contacting a blood plasma or blood serum sample obtained from a mammalian subject with a diagnostic reagent that can measure or detect the expression level of one or more biomarkers and/or contacting a blood plasma or blood serum sample obtained from a mammalian subject with a diagnostic reagent that can measure or detect the expression level of one or more biomarkers, wherein an altered plasma or serum concentration of one or more biomarkers relative to a healthy control indicates a tendency to have seizure. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin $E_2$, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

For any biomarker selected, individual measurements may be taken and analyzed individually or in any combination using linear or logarithmic units, or by using ratios of linear or logarithmic units. The reciprocals of ratios of linear or logarithmic units may also be used.

In further embodiments of the above, the seizure may be associated with temporal lobe epilepsy. In a further embodiment, the temporal lobe epilepsy may be mesial temporal sclerosis (MTS). In other embodiments, the seizure may be associated with tuberous sclerosis complex (TSC).

In further embodiments, the seizure may be classified according to the: Operational Classification of Seizure Types, including seizures, NES, and NS by the International League Against Epilepsy which is located at the following web address: ilae.org/visitors/centre/documents/ClassificationSeizureILAE-2016.pdf.

In still other specific further embodiments of the above, the seizure, NES, NS, PNES or NEE may be cryptogenic. In further embodiments, the seizure, NES, NS, PNES or NEE is not associated with immune response to a pathogen.

The embodiments, including the probes and panels/arrays of probes, described herein may be used to detect whether or not a seizure has (or is likely to have) occurred. They may also be used to predict the likelihood of further seizure. Additionally, they may be used to predict whether or not seizure is likely following a brain injury or head trauma. They are also useful in identifying whether or not a seizure is the result of an inflammatory process. Further, they may be used in assessing whether or not a treatment is effective.

By way of non-limiting example, the following polypeptide panels or arrays are embodiments of the application (the terms “altered,” “modified,” and/or “changed” refer to the expression level in the epileptic, ES, NES, NS, PNES or NEE patient versus that in a healthy subject):

TARC;
TNF-α;
IL-16;
MMP-3;
TRAIL;
ICAM-1
MCP-2
TNF-R1
P-Cadherin
Osteoactivin
MIP-1β
MIP-5
M-CSF
MCP-1
VCAM-1.
IL-7

IL-10
MCP-4
GM-CSF.
IL-17a
VEGF-A.

Plus any combination of one or more of TARC, TNF-α, IL-16, MMP-3, TRAIL, P-Cadherin, MIP-1β, MCP-1, VCAM-1, IL-16, ICAM-1, MCP-2, TNF-R1, Osteoactivin, MIP-5, M-CSF, MCP-1, IL-7, IL-10, MCP-4, GM-CSF, IL-17a, and/or VEGF-A.

Other polypeptide panels or arrays are embodiments of the application, and may include the above and additionally one or more of the following:

IL-1B, IL-2, IL-6, IL-8, IL-10, IL-12p70, IFN-γ, IL-13, IL-4, IL-17A, GM-CSF, IL-12/IL-23p40, IL-15, IL-16, IL-1α, IL-5, IL-7, TNF-β, VEGF-A, MCP-1/CCL2, Eotaxin, Eotaxin-3, IP-10, MCP-4, MDC, MIP-1α, MIP-1β, sICAM1, sVCAM1, CRP, SAA, MMP-9, Calbindin, Eotaxin-2, MIP-5, MMP-1, Osteoactivin, TNF-RI, TNF-RII, MIF, Cytokeratin-8, MCP-2, M-CSF, Nectin-4, Osteonectin, SCF.

IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin $E_2$, nerve growth factor (NGF), CCL-5 (RANTES), α1AT, and HGF one or more components of the complement cascade, e.g., C1q, C3c and C3d.

Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5).

Samples may be obtained from patients by conventional techniques. These techniques may include those covered by an institutional review board (IRB) approved protocol, including blood, urine, saliva and CSF. In one embodiment, the samples are anticoagulated using sodium citrate. In a further embodiment, plasma is prepared by centrifuging samples, e.g., at 5,000 g (g=gravity) for 15 minutes at 4° C. Control samples may also be purchased from commercial vendors.

Levels (concentrations) of the polypeptide to be quantified in plasma may be obtained by any of a number of methods known in the art, the particular procedure not being a limitation of the embodiments herein. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art. A variety of capture and detect antibodies may be used to detect biomarkers by those skilled in the art. Single- and multi-probe kits are available from commercial suppliers, e.g., Meso Scale Discovery. These kits include the kits referenced in the Examples hereto. Individual measurements may be taken and analyzed individually or in any combination using linear or logarithmic units, or by using ratios of linear or logarithmic units. The reciprocals of ratios of linear or logarithmic units may also be used.

Also described herein are methods of treating or preventing seizure, epilepsy, ES, NES, NS, PNES or NEE or a disorder for which seizure is symptomatic in a mammalian subject or patient, comprising delivery of anti-inflammatoires or other therapeutic agents targeting one or more of the biomarkers included herein. In a further embodiment, the mammal is a human. Treating patients with seizures and epilepsy, ES, NES, NS, PNES or NEE with anti-inflammatory or other therapeutic agents targeting one or more of the biomarkers included herein in order to reduce seizures or epilepsy, ES, NES, NS, PNES or NEE symptoms.

Anti-inflammatory or other therapeutic agent treatment or prevention targeting one or more of the biomarkers included herein may be made intravenous or via intra-cerebrospinal fluid (intra-CSF) by techniques known to one of skill in the art. Delivery of anti-inflammatory or other therapeutic agent treatment or prevention targeting one or more biomarkers included herein may also be made by any other suitable means, including but not limited to orally, orally with suitable carrier or excipient, extended or controlled release dosing, skin patches or other external extended release mechanism, absorption through the skin, nasal delivery, drug delivery mechanisms, intravenously, targeted delivery systems, delivery systems designed to cross the blood brain barrier, intravenously via pump or similar mechanism for on-demand or automated delivery, inhaled, injected, emergency injections (such as epi-pens) and intranasal delivery to the CSF with a suitable carrier or excipient.

Anti-inflammatory other therapeutic agent treatment targeting one or more of the biomarkers included herein may be administered by a device that determines the levels of concentration of the biomarkers defined herein, makes an assessment of the markers relative to normal controls or previously measured levels of a patient, and makes determinations to either increase, decrease or remain the same with respect to current therapeutic dosage and or protocols.

ES, Epilepsy, NES, NS, PNES or NEE therapeutic agent as used herein is used interchangeably with one or more therapeutic agents or other treatment options, including, but not limited to psychotherapy, cognitive therapy, behavioral therapy, standard medical care or other therapeutic agents not listed herein. NES, NS, PNES or NEE patients can be considered “drug controlled,” “therapeutic controlled” and/or treatment controlled as responsive to therapeutic agents and or other treatment options. Therapeutic agents can currently be in the market, in development, yet to be identified, in clinical trials, branded therapeutics and/or generic therapeutics. Treatment options include options currently used, and or developed in the future, but not limited to psychotherapy, cognitive therapy, behavioral therapy, standard medical care or other therapeutic agents not listed herein or in development, or yet to be identified.

Other Applications

In some embodiments of the invention, biomarkers and algorithms that form a blood-based diagnostic test, such as EvoScore, as described herein, can be leveraged for seizure prediction; anti-epileptic drug (AED) clinical trial eligibility, endpoints, and effectiveness; multiple diagnostic combinations including EEG, MRI, Genomics, Genetics and proteomics, companion diagnostics; and potential identification of inflammation based therapeutics and response. In some embodiments, the blood-based diagnostic test described herein may be used to determine absolute changes in biomarker levels in an event as well as relative changes in biomarkers in a patient over time. In some embodiments, the biomarkers and algorithms in the blood-based diagnostic test described herein in known epilepsy, ES, NES, NS, PNES or NEE patients who are well-controlled or not well-controlled with medications or other therapeutic intervention, may be used to prepare a corresponding score and a user may determine if the score correlates with AED or other therapeutic intervention responsiveness and, by extension, predict subsequent breakthrough seizures and medical intractability. Similarly, the blood-based diagnostic test described herein may be used to predict AED response in newly identified epilepsy patients to quickly assess therapeutic response. In medically refractory patients after epilepsy, surgery, the blood-based diagnostic test described herein may, in some embodiments, be provided that is predictive of surgical success. In some embodiments, the blood-based diagnostic test described herein, can be used to assess patients at risk for seizures following, for example, head injury or stroke to determine if their risk of seizures is increased. Furthermore, there is an important potential use in AED clinical trials to ensure more robust enrollment criteria resulting in faster, smaller trials allowing new medicines to reach patients earlier. In some embodiments, the blood-based diagnostic test described herein can be used as a personalized medicine diagnostic, to allow treatment and tracking of seizures and epilepsy, ES, NES, NS, PNES or NEE over time, at defined intervals, to establish individualized response to therapies, effectiveness, control, and prediction of future events in order to improve patient quality of life and reduce burden on the healthcare system. In certain embodiments, the foregoing blood-based diagnostic test of the invention is EvoScore.

Test Methods

Blood was collected from human neurology patients or normal controls into lavender-topped vacutainer blood collection tubes containing $K_2$EDTA as an anticoagulant (BD Biosciences). The blood collection tubes were inverted eight times, and then placed on wet ice at 4° C. for 10-15 minutes before centrifuging. The blood was centrifuged at 1000 RCF for 10 minutes at 4° C. Plasma supernatant was aliquotted into sterile 2 ml microtubes (Sarstedt, Type I) and frozen at −70° C. to −80° C.

Protein levels in human plasma were measured by sandwich ELISA with electrochemiluminescent detection using multiplexed assay plates from Meso Scale Discovery (MSD) (Gaithersburg, MD) and analyzed on the MSD Sector Imager 2400. The following assay plates were used: Proinflammatory Panel 1, Cytokine Panel 1, Chemokine Panel 1, Vascular Injury Panel 2, Screen Panel A, and Screen Panel B. Together, the panels assessed the levels of the following proteins: IL-1B, IL-2, IL-6, IL-8, IL-10, IL-12p70, IFN-γ, IL-13, IL-4, TNF-α, IL-17A, GM-CSF, IL-12/IL-23p40, IL-15, IL-16, IL-1α, IL-5, IL-7, TNF-β, VEGF-A, MCP-1/CCL2, Eotaxin, Eotaxin-3, IP-10, MCP-4, MDC, MIP-1α, MIP-1β, TARC, SICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL.

Each plate was coated with specific capture antibodies with up to 10 distinct spots per well in a 96-well format. MSD provided the antibodies and coated the plates, accordingly.

For all incubation steps, plates were sealed with adhesive plate seals and incubations were performed at room temperature (RT) with rotation (705 pm) on a microtiter plate shaker (Denville 210A #C0210). In all wash steps, wells were emptied and then washed three times with 300 μL of Phosphate Buffered Saline (PBS) with 0.05% Tween-20 (Wash Buffer, MSD). Reverse pipetting was employed to avoid the production of bubbles throughout the assay.

To run samples, coated plates were removed from 4° C. and allowed to equilibrate to room temperature for 30 to 60 minutes, after which each plate was washed three times with wash buffer prior to adding protein standard and sample for the assay.

Protein standards for each of the markers were provided by MSD and prepared per MSD assay guidelines. Protein standards and human plasma samples were diluted in the same diluent, but varied per assay panel. The following dilution of sample and diluent was used for each assay panel: 2-fold dilution in diluent 2 for Proinflammatory Panel 1, 2-fold dilution in diluent 43 for Cytokine Panel 1, 4-fold dilution in diluent 43 for Chemokine Panel 1, 1000-fold dilution in diluent 101 for Vascular Injury Panel 2, 10-fold dilution and diluent 7 for Screen Panel A, and 2-fold dilution and diluent 2 for Screen Panel B. Fifty μL of protein standard or diluted sample was plated in duplicate on each plate, according to MSD assay guidelines. Standards and samples were incubated for two hours at room temperature.

After incubation, plates were washed three times with wash buffer. SULFO-TAG labeled detection antibodies for each target protein were provided by MSD. Antibodies were combined as per MSD assay protocol in diluent 3 for all assay panels except the Vascular Injury Panel 2, where diluent 101 was used. 100 μl of diluted detection antibodies were added to each well in a multiplexed fashion (separately for each target assay plate). Antibodies were incubated for two hours at room temperature.

Plates were then washed with wash buffer prior to developing and reading the assay.

4X MSD Read Buffer T was diluted to 2× with sterilized reverse-osmosis $H_2O$. Plates were developed by adding 150 μL of RT 2X Read Buffer T to each well, and then read immediately on the MSD Sector Imager 2400 coupled with the MSD Discovery Workbench 4.0 software. MSD Discovery Workbench 4.0 software was used to determine the protein concentrations of the plasma samples, final concentrations of protein values were determined by multiplying by the dilution factor for each assay.

Patient Enrollment

A clinical trial was performed to determine whether EvoScore can be used effectively and accurately to diagnose patients with seizures, and to establish the threshold for diagnosis. All inpatient and outpatient subjects were 18 years of age or older and cognitively able to give informed consent. Subjects aged 18-20 provided assent, and a legally authorized representative gave consent on their behalf. There were no ethnic or gender limitations for these studies, and all eligible patients were recruited to ensure that there was no selection bias.

Inpatients admitted to an epilepsy monitoring unit (EMU) were invited to give a single sample of 15 ml of blood each morning and an additional 15 ml sample of blood following a seizure or seizure-like event. Inpatient subjects' EvoScore results were compared with all of their individual event diagnoses during their EMU stay, and their ultimate patient diagnosis at the conclusion of their EMU stay.

Outpatients were eligible to join the study only if they were attending their first visit at the outpatient neurology clinic for evaluation of their suspected seizures; these patients did not yet have a diagnosis of their events as either epileptic or non-epileptic. Outpatient subjects gave a single 15 mL sample of blood for research, and the study team collected all available clinical information relevant to their diagnostic workup for approximately 6 months after they joined the study. After six months, a team of independent neurologists evaluated their relevant medical history and "diagnosed" the subjects, and this diagnosis was compared to the EvoScore results to determine diagnostic accuracy (agreement among two epileptologists was sufficient).

Subjects 21 years of age and older who accompanied patients to epilepsy center appointments were considered to be normal controls and were eligible to join the study if they were cognitively able to provide informed consent, had not been diagnosed with epilepsy, and were not taking any anti-epileptic drugs for any reason. A total of 401 study subjects were enrolled overall. 240 outpatients, 131 inpatients, and an additional 30 controls were enrolled from both the inpatient EMU and the outpatient neurology clinic. For the inpatient and outpatient subjects, the average age was 36.5 (range 18-82) and 52% were female (n=209).

Explanation of Individual Event Diagnosis (IED) and Patient Diagnosis (PD)

Inpatients initiated and ended their stays in the EMU. Outpatients were recruited from a neurology outpatient clinic, but some returned for a stay in the EMU. For all patients that stayed in the EMU, EMU reports were examined and the time was recorded of any observed neurological event immediately prior to the blood draw. The description of the event was also recorded, and neurologists independently diagnosed each individual event (Individual Event Diagnosis). Events were characterized as Non-Epileptic events (IED0), Epileptic events (with a positive EEG) (IED1), Unclear diagnosis event (IED2), or no event recorded (when there was no record of any event in the EMU report during that EMU stay) (IED3). When there was not agreement on the event diagnosis, the EMU reports were consulted and a consensus was reached. If no consensus could be reached, the event was rated with an unclear diagnosis (IED2). Individual event diagnosis is considered evaluation of phasic changes. Individual event diagnosis can also be called event diagnosis.

The final overall patient diagnosis recorded in the "Epilepsy Diagnosis" section of the EMU report was used for each patient for the Patient Diagnosis (PD). Patients either received a diagnosis of Non-Epilepsy (PD0), Epilepsy (PD1), Epilepsy+Other Non-Epileptic condition PD2), or an Unclear diagnosis (PD3). Patient diagnosis is considered evaluation of tonic changes.

EMU reports were thoroughly reviewed to identify risk factors that have previously been reported to correlate with NES, NS, PNES or NEE. The factors include, but are not limited to status as unemployed or disabled, history of physical, sexual, or psychological trauma, sex, poly allergies, post-traumatic stress disorder, previous diagnosis of major depressive disorder, cluster B personality disorders, dependent personality disorder, conversion disorder and fibromyalgia. (FIG. 7 illustrates Prevalence of NES/NS/PNES Risk Factors (Sum of Risk Factors) in NES vs. ES; FIGS. 8A-8C illustrate the sum of NES/NS/PNES risk factors; the number of risk factors confirmed for each patient was summed and used to create a diagnostic algorithm using a logistical regression. FIG. 8A: EvoScore in Seizures vs. Controlled; FIG. 8B Sensitivity; FIG. 8C: performance matrix.)

Predictive Models and Score

As used herein, a "predictive model," which term may be used synonymously herein with "multivariate model" or simply a "model," is a mathematical construct developed using a statistical algorithm or algorithms for classifying sets of data. Predictive models can provide an interpretation function; e.g., a predictive model can be created by utilizing one or more statistical algorithms or methods to transform a dataset of observed data into a meaningful determination of disease activity or the disease state of a subject. Algorithms developed herein, based upon concentrations and ratios of biomarkers, and or combined with patient demographic characteristics, identify the phasic and tonic changes (acute and chronic) associated with a seizure event. Individual measurements may be taken and analyzed individually or in any combination using linear or logarithmic units, or by using ratios of linear or logarithmic units. The reciprocals of ratios of linear or logarithmic units may also be used.

The predictive model can be used in all clinical settings for one or more of following purposes (a) ruling in or ruling out seizure; (c) assessing the patient quality of life by predicting when and if seizures will continue to occur; and (c) the ability of a therapeutic or therapeutic protocol to control the seizures over time.

As used herein, a "score" is a value or set of values selected so as to provide a quantitative measure of a variable or characteristic of a subject's condition, and/or discriminate, differentiate or otherwise characterize a subject's condition. The values(s) comprising the score can be based on, for example, a measured amount of one or more sample constituents obtained from the subject or from clinical parameters or from clinical assessments or any combination thereof. In certain embodiments the score can be derived from a single constituent parameter or assessment, while in other embodiments the score is derived from multiple constituents, parameters and/or assessments. The score can be based upon or derived from an interpretation function, e.g., an interpretation function derived from a particular predictive model using any of carious statistical algorithms known in the art. A "change in score" can refer to the absolute change in score, e.g., from one time point to the next, or the percent change in score, or the change in the score per unit of time. For example, a score referred to herein may be provided by a blood-based diagnostic test of the invention (e.g., EvoScore).

The score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative" or other form to convey results of phasic and/or tonic changes in the identification of seizure and epilepsy, ES, NES, NS, PNES or NEE.

The predictive models and scores can be used in combination with any of the current standard diagnostic techniques, including EEG and MRI to develop an ultimate patient diagnosis. The predictive score would add improved accuracy in terms of sensitivity, specificity, positive predictive value and negative predictive value when combined with other standard diagnostic techniques.

Algorithm Objectives, Thresholds and Actionable Results

Scoring algorithms included in the blood-based diagnostic tests described herein (e.g., EvoScore) were developed by the following methodologies: (a) For individual event diagnosis of seizure or not: Classification Tree and Regression analysis and/or Multiple Logistic Regression which may include risk groups defined by the classification tree analysis; and (b) For patient diagnosis of epilepsy, ES, NES, NS, PNES or NEE or not: Logistic regression and Multiple Logistic Regression including risk groups defined by classification tree analysis. Logistical regression techniques were applied to refine diagnostic algorithms that integrate both protein concentrations and NES, NS, PNES or NEE risk factor parameters. The factors include, but are not limited to status as unemployed or disabled, history of physical, sexual, or psychological trauma, sex, poly allergies, post-traumatic stress disorder, previous diagnosis of major depressive disorder, cluster B personality disorders, dependent personality disorder, conversion disorder and fibromyalgia.

EvoScore algorithms and methodologies for both individual event diagnosis of seizure or not and patient diagnosis of epilepsy, ES, NES, NS, PNES or NEE or not were determined to be a function of measurable changes of the concentration, natural logarithm scaled changes in the concentration, ratios of the biomarkers and ratios of the scaled concentrations of one or more biomarkers and can include patient physical characteristics, including age, sex and prescription information.

All of these methodologies and results yielded algorithms meeting diagnostic test clinical and market performance and accuracy objectives. The algorithms' predictive results are designed to maximize sensitivity and True Positives, and minimize False Negatives, and maximize accuracy and correctly classified. Specificity and True Negatives can also be maximized with minimal false positives.

Thresholds or quantitative boundaries can be set to both maximize individual diagnostic values and or optimize combinations of diagnostic values, including sensitivity, specificity, and positive and negative predicted value. Different embodiments of the algorithms can use different thresholds depending on the goals of the algorithm. Thresholds can ultimately determine how a score is interpreted as the individual test score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative." Ultimate selections of thresholds are driven by the maximization and/or optimization of one or more characteristics of diagnostic accuracy as desired for performance.

FIG. 1 defines diagnosis parameters between epileptic seizures, non-epileptic seizures, and no seizures.

FIG. 2 defines the objectives of the algorithm and ultimate actionable results.

The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy, ES, NES, NS, PNES or NEE patients, drug controlled epilepsy, ES, NES, NS, PNES or NEE patients and drug refractory patients. Diagnostic algorithms integrate both protein concentrations and may include NES, NS, PNES or NEE risk factor parameters. The factors include, but are not limited to status as unemployed or disabled, history of physical, sexual, or psychological trauma, sex, poly allergies, post-traumatic stress disorder, previous diagnosis of major depressive disorder, cluster B personality disorders, dependent personality disorder, conversion disorder and fibromyalgia.

The test score and biomarkers can be analyzed and compared across patients, patient groups, other indications and normal controls, and across an individual patient over time for personalized medicine.

Combination Diagnostic and Therapeutic Approaches

To achieve the maximum therapeutic benefits for individual subjects, it is important to be able to specifically quantify and assess the subject's disease burden at any particular time, determine the effects of treatment on disease activity, and predict future outcomes. The embodiments of the present teachings identify multiple serum biomarkers for accurate clinical assessment of disease activity in subjects with acute and chronic disease.

Current therapeutic approaches for epilepsy include and are not limited to therapeutically effective dose of an anti-epileptic compound selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. New therapeutic approaches are currently in development and are applicable to diagnostic evaluation and can be combination diagnostic and therapeutic approaches.

Treatment for ES, NES, NS, PNES or NEE can be a therapeutic, including with one or more therapeutic agents or other treatment options, including, but not limited to psychotherapy, cognitive therapy, behavioral therapy, standard medical care or other therapeutic agents not listed herein.

In some embodiments, a blood-based diagnostic test of the invention (e.g., EvoScore) can evaluate known epilepsy, ES, NES, NS, PNES or NEE patients who are well-controlled or not well-controlled with medications to determine if the score correlates with AED responsiveness and by extension, if changes in EvoScore predict subsequent breakthrough seizures and medical intractability. In some embodiments, a blood-based diagnostic test of the invention (e.g., EvoScore) can predict AED response in newly identified epilepsy, ES, NES, NS, PNES or NEE patients to quickly assess therapeutic response. In some embodiments, a blood-based diagnostic test of the invention (e.g., EvoScore) can be used to assess in medically refractory patients after epilepsy, ES, NES, NS, PNES or NEE surgery to determine if the score can predict surgical success. In some embodiments, a blood-based diagnostic test of the invention (e.g., EvoScore) can be used to assess patients at risk for seizures following for example, head injury or stroke to determine if their risk of seizures is increased. In some embodiments, a blood-based diagnostic test of the invention (e.g., EvoScore) can be used as a personalized medicine diagnostic, to allow for the treatment and tracking of seizures and epilepsy, ES, NES, NS, PNES or NEE over time, at defined intervals, to establish individualized response to therapies, effectiveness, control, and prediction of future events in order to improve patient quality of life and reduce burden on the healthcare system.

In some embodiments, a blood-based diagnostic test of the invention (e.g., EvoScore) can be used in combination with EEG, MRI and other diagnostic approaches described herein. EvoScore can be used in combination with EEG for patient diagnosis and treatment. Additionally, EvoScore can be used in combination with other diagnostic and test approaches as defined herein.

In other embodiments, EvoScore alone, or in combination with other biomarkers as described herein and/or other clinical tests, can be utilized in other neurological diseases/indications including migraine, Alzheimer's disease, Parkinson's disease, traumatic brain injury, stroke, infections and immune response to a pathogen, autoimmune response, immune response, tumors and other neurological diseases/indications with an inflammation component and/or effect.

Kits

In an embodiment, the invention provides a diagnostic kit comprising a polypeptide expression panel or array. The kit may also be predictive, useful in determining imminent risk of seizure or recurrence of seizure, or in assessing recurrence risk. The kit may also contain a syringe and/or vile for drawing blood. The kit may also contain a blood card or other repository to hold blood and lancet in order to draw blood for the patient to supply a drop or drops of blood on a card or other repository for analysis. The kit may contain one or more probes corresponding to the polypeptide markers of the panel or array. The kit may also contain an ELISA plate based on chemiluminescent, luminist or equivalent technology. A multiple and portable (M&P) ELISA may also be provided as part of a kit of an embodiment. Still other suitable components will be known to one of skill in the art, and are encompassed hereby. Kits may include software, computers and instruments for presenting the diagnostic result.

Other aspects of the present invention provide a kit for the kit comprising: (a) assay (b) instructions (c) computer or computer system to perform a method of the present invention, or, in (d) other embodiments, an algorithm that forms part of a method of the present invention.

Other embodiments comprise biomarker detection reagents packaged together in the form of a kit for conducting any of the assays of the present teachings. In certain embodiments, the kits comprise oligonucleotides that specifically identify one of more biomarker nucleic acids based on homology and/or complimentary with biomarker nucleic acids. The oligonucleotide sequences may correspond to fragments of the biomarker nucleic acids. For example, the oligonucleotides can be more than: 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody, control formulations (positive and/or negative), and/or a detectable label. Instructions for carrying out the assay, including optionally instructions for generating a score can be included in the kit. The assay can be in the form of ELISA as known in the art.

Additionally, biomarkers concentrations can be determined by other means as available by technical methods equivalent to ELISA. For means by which the biomarkers may be assessed known and emerging, biomarkers and algorithms additionally apply and can be leveraged for applications defined herein. For example, instantaneous measurements can be made to immediately assess a patient biomarker levels.

The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy, ES, NES, NS, PNES or NEE patients, drug or therapeutic controlled epilepsy, ES, NES, NS, PNES or NEE patients and drug or therapeutic refractory patients or not well-controlled patients. The test score and biomarkers can be analyzed and compared across patients, patient groups, other indications and normal controls, and across an individual patient over time for personalized medicine.

Systems, Software, Instruments, and Computers

The predictive models can be manually or automatically performed using software engineered for performing such a task. The analysis of concentrations of selected biomarkers may be performed manually or alternatively the analysis may be performed using software engineered for performing such a task. In preferred embodiments, an algorithm forms part of a predictive method of the present invention analyzes the concentrations of the selected biomarkers to present the diagnostic result or score. The algorithm may be performed manually or automatically via software engineered. The software engineered may be part of the instrument reading the concentrations of the selected biomarkers or may be part of an external computer. In other embodiments, the aforementioned software is loaded onto a computer. The computer also interfaces with the instrument inputs data directly from the instrument either manually or automatically. Individual measurements may be taken and analyzed individually or in any combination using linear or logarithmic units, or by using ratios of linear or logarithmic units, with and/or without patient demographic characteristics. The reciprocals of ratios of linear or logarithmic units may also be used. In some embodiments, the computer belongs to the end user, while in other embodiments, the computer or processor is provided as part of the kit. In preferred embodiments, the software engineered directs the computer to (a) access a file containing data from the instrument and (b) analyze these data using an algorithm of the invention. In other embodiments, the software engineered presents the results in a user-friendly format for interpreting the diagnostic results.

In some embodiments, methods and systems of the invention, can be embodied as a computer implemented process or processes for performing such computer-implemented process or processes, and can also be embodied in the form of a tangible storage medium (i.e., non-transitory computer readable medium) containing a computer program or other machine-readable instructions (herein "computer program"), wherein when the computer program is loaded into a computer or other processor (herein "computer") and/or is executed by the computer, the computer becomes an apparatus for practicing the process or processes. Storage media for containing such computer program include, for example, floppy disks and diskettes, compact disk (CD)-ROMs (whether or not writeable), DVD digital disks, RAM and ROM memories, computer hard drives and back-up drives, external hard drives, solid state drives, "thumb" drives, and any other storage medium readable by a computer. The process or processes can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the process or processes. The process or processes may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation.

A detailed description of a system 48 for screening a subject to determine the likelihood that the subject will be responsive to a treatment regimen including administering epilepsy, ES, NES, NS, PNES or NEE therapeutic agents is described in conjunction with FIGS. 13 and 14. As described herein, a system 48 can be used, without limitation, for diagnosing epilepsy, ES, NES, NS, PNES, or NEE in a patient; for differentially and/or comparatively diagnosing between epilepsy, ES, NES, NS, PNES, or NEE in a patient; for evaluating, monitoring, and/or predicting patient epileptic seizure burden and/or frequency in a patient; and/or for determining the likelihood of a patient to respond to epilepsy, ES, NES, NS, PNES, or NEE treatment. As such, FIGS. 13 and 14 collectively illustrate the topology of the system in accordance with the present disclosure. In the topology, there is a discovery system for screening a subject to diagnose any condition described herein, or to determine whether it has a likelihood to respond to treatment ("discovery system 250") (FIGS. 13 and 14), one or more data collection devices 200, devices for obtaining blood and/or blood-derived samples 102, and devices for obtaining computer readable analytical signatures, for example biomarkers concentrations, from such samples 104 (FIG. 13). Throughout the present disclosure, the data collection devices 200 and the discovery system 250 will be referenced as separate devices solely for purposes of clarity. That is, the disclosed functionality of the data collection device 200 and the disclosed functionality of the discovery system 250 are contained in separate devices as illustrated in FIG. 13. However, it will be appreciated that, in fact, in some embodiments, the disclosed functionality of the one or more data collection devices 200 and the disclosed functionality of the discovery system 250 are contained in a single device. Likewise, in some embodiments, the data collection device 200 and the devices for obtaining blood and/or blood-derived samples 102 (or any other biological sample as described herein) and/or the devices for obtaining computer readable analytical signatures from such samples 104 are the same devices. As described herein, the disclosed systems are equally applicable for i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

Referring to FIG. 13, the discovery system 250 screens a subject for a diagnosis described herein, or for the likelihood that the subject will be responsive to a treatment regimen including administering epilepsy, ES, NES, NS, PNES or NEE therapeutic agents. To do this, the data collection device 200, which is in electrical communication with the discovery system 250, A) acquires a first computer readable analytical signature from a sample of the subject, for example a biomarker concentration, B) inputs the first computer readable analytical signature of the subject into a trained model panel of controls thereby obtaining a first trained model output value for the subject, and C) classifies the subject based upon the first trained model output value with a likelihood class in an enumerated set of likelihood classes. Each respective likelihood class in the enumerated set of likelihood classes is associated with a different likelihood that the subject will respond to the treatment regimen. However, as described herein, any likelihood class can be determined and applied, including, without limitation, likelihood of having a diagnosis of epilepsy, ES, NES, NS, PNES, or NEE; likelihood of differentially and/or comparatively having a diagnosis between epilepsy, ES, NES, NS, PNES, or NEE; likelihood of having a given and/or future epileptic seizure burden and/or frequency; and likelihood of responding to any epilepsy, ES, NES, NS, PNES, or NEE treatment described herein. Moreover, the likelihood includes a discernable effect of providing an epilepsy, ES, NES, NS, PNES or NEE therapeutic agent to the subject classified with a likelihood class. In some embodiments, the subject has suffered one or more seizures. In some embodiments, the subject has suffered one seizure. In some embodiments, the subject has suffered two seizures. In some embodiments, the subject is a human subject.

In some embodiments, the data collection device 200 receives such data directly from the device(s) 102 and the device(s) 104. For instance, in some embodiments the data collection device 200 receives this data wirelessly through radio-frequency signals. In some embodiments such signals are in accordance with an 802.11 (WI-FI®), BLUETOOTH®, ZIGBEE®, or by RFID communication. In some embodiments, the data collection device 200 receives such data directly, analyzes the data, and passes the analyzed data to the discover system 250. In some embodiments, the data collection device 200 and/or the discovery system 250 is not proximate to the devices 102 and/or devices 104 and/or does not have direct wireless capabilities or such wireless capabilities are not used for the purpose of acquiring data. In such embodiments, a communication network 106 may be used to communicate measurements of the first computer readable analytical signature (and/or second computer readable analytical signatures) from the devices 102 and the devices 104 to the data collection device 200 and/or the discovery system 250. Examples of networks 106 include, but are not limited to, the World Wide Web (WWW), an intranet and/or a wireless network, such as a cellular telephone network, a local area network (LAN) and/or a metropolitan area network (MAN), and other devices by wireless communication. The wireless communication optionally uses any of a plurality of communications standards, protocols and technologies, including but not limited to Global System for Mobile Communications (GSM®), Enhanced Data GSM® Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC®), wideband code division multiple access (W-CDMA), code division multiple access (CDMA), time division multiple access (TDMA), Bluetooth, Wireless Fidelity (WI-FI®) (e.g., IEEE 802.11a, IEEE 802.11ac, IEEE 802.11ax, IEEE 802.11b, IEEE 802.11g and/or IEEE 802.11n), voice over Internet Protocol (VOIP), Wi-MAX™, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Other topologies of the system 48 are possible. For instance, rather than relying on a communications network 106, the one or more devices 102 and the one or more devices 104 may wirelessly transmit information directly to the data collection device 200 and/or discovery system 250. Further, the data collection device 200 and/or the discovery system 250 may constitute a portable electronic device, a server computer, or in fact constitute several computers that are linked together in a network or be a virtual machine in a cloud computing context. As such, the exemplary topology shown in FIG. 13 merely serves to describe the features of an embodiment of the present disclosure in a manner that will be readily understood to one of skill in the art.

Referring to FIG. 14A, in typical embodiments, the discovery system 250 comprises one or more computers. For purposes of illustration in FIG. 14A, the discovery system 250 is represented as a single computer that includes all of the functionality for screening a subject to determine its likelihood to respond to the treatment regimen. However, the disclosure is not so limited. In some embodiments, the functionality for screening a subject to determine whether it has a likelihood to a given diagnosis, a likelihood to respond to treatment, a likelihood to have a seizure, a likelihood to need treatment, a likelihood to respond to specific therapeutic agents, or a likelihood to adjust dosage pf a therapeutic agent, is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 14A with the foregoing in mind, an exemplary discovery system 250 for screening a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the discovery system 250 but that can be electronically accessed by the discovery system 250 over an Internet, intranet, or other form of network or electronic cable (illustrated as element 106 in FIG. 13) using network interface 284. As described herein, screening can be done as part of any number of methods, i.e.: i) methods of screening a subject to determine the likelihood of a diagnosis; ii) methods of screening a subject to determine the likelihood that the subject will have a seizure in the future; iii) methods of screening the likelihood that a subject needs to begin a treatment regimen; iv) methods of screening the likelihood that the subject needs an adjustment, for example an increase, in a treatment regimen or therapeutic agent dosage; and/or v) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, the memory 192 of the discovery system 250 for screening a subject, stores:

- an operating system 202 that includes procedures for handling various basic system services;
- a screening module 204 for screening a subject to determine whether it is likely to respond to epilepsy, ES, NES, NS, PNES or NEE treatment;
- a controls set 206 that comprises one or more controls 208, each control comprising one or more analytical signatures 210, for each respective analytical signature, (i) one or more biomarkers concentrations from a sample from a training control entity and (ii) a likelihood class 212 of the training control entity 208;
- a test set 213 that comprises an analytical signature 216 for each test subject 214 in a plurality of test subjects and, for each respective analytical signature 216, (i) one or more biomarker concentrations 218 obtained from a sample from the corresponding test subject and (ii) a likelihood class 219 of the test subject 214;
- a first tier trained model panel 218 for screening a subject to determine whether it is likely to respond to epilepsy, ES, NES, NS, PNES or NEE treatment (and/or any other likelihood described herein);
- an optional second tier trained model panel 220 for screening a subject to determine whether it is likely to respond to epilepsy, ES, NES, NS, PNES or NEE treatment (and/or any other likelihood described herein); and
- data for a target subject 222 including an analytical signature for the target subject.

In some embodiments, the screening module 204 is accessible within any browser (phone, tablet, laptop/desktop). In some embodiments, the screening module 204 runs on native device frameworks, and is available for download onto the discovery system 250 running an operating system 202 such as Android or iOS.

In some embodiments, the controls set 206 is referenced in FIG. 2. In some embodiments, the subjects test set 213 is referenced in FIG. 2.

In some embodiments, the first tier trained model panel consists of a single support vector machine. In some embodiments, the first tier trained model panel consists of a plurality of support vector machines.

In some embodiments, the biomarkers are selected from Table 2. In some embodiments, the biomarkers are selected from calbindin, CRP, cytokeratin-8, eotaxin, eotaxin-2, eotaxin-3, GM-CSF, ICAM-1, IFN-y, IL-1a, IL-1B, IL-2, IL-4, IL-5, IL-7, IL-6, IL-13, IL-12, IL-23p40, IL-12p70, IL-10, IL-8, IL-15, IL-16, IL-17A, IP-10, MCP-1, MCP-2, MCP-4, M-CSF, MDC, MIF, MIP-1a, MIP-1β, MIP-5, MMP-1, MMP-3, MMP-9, Nectin-4, osteoactivin, osteonectin, p-cadherin, SAA, SCF, TARC, TNF-R1, TNF-R2, TNF-a, TNF-B, TRAIL, VCAM-1, and VEGF-A. In some embodiments, the biomarkers are selected from the group consisting of one biomarker, two biomarkers, three biomarkers, four biomarkers, and the like. In some embodiments, the biomarkers are selected from the group consisting of IL-16, TARC, ICAM-1, MIP-1B, TRAIL and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the biomarkers are two biomarkers selected from MIP-1B and MIP-5, MIP-1B and MMP-3, MIP-1B and TNF-a, eotaxin-2 and MIP-1B, MIP-1B and SCF, MCP-4 and MMP-3, IL-10 and MMP-3, IL-16 and MIP-1B, MIP-1B and Nectin-4, and MIP-1B and osteoactivin. In some embodiments, the biomarkers are IL-16, ICAM-1, and TRAIL (FIGS. 9A-9C, and FIGS. 10A-10C). In some embodiments, the biomarkers are IL-16, ICAM-1, TRAIL, and MIP-1β (FIGS. 11A-11C, and FIG. 12C). In some embodiments, the biomarkers are TRAIL, ICAM-1, MCP-2, and TNF-R1 (FIGS. 18A-18C). In some embodiments, the biomarkers are IL-10, MCP-4, MMP-3, and TNF-α (FIGS. 23A and 23B).

In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one or more seizures. In some embodiments, the subject has suffered one seizure. In some embodiments, the subject has suffered two seizures. In some embodiments, the subject has never suffered seizures.

In some embodiments, a program described herein further comprises instructions for: training, prior to the comparing, one or more models to thereby form a first tier trained model. In some embodiments, the training comprises: obtaining a training set that represents a plurality of training subjects, wherein some training subjects in the plurality of training subjects have epilepsy, ES, NES, NS, PNES or NEE and, for each respective training subject, the training set comprises (i) a computer readable analytical signature from a sample of the respective training subject and (ii) an effect that providing an epilepsy, ES, NES, NS, PNES or NEE therapeutic agent had on epilepsy, ES, NES, NS, PNES or NEE, and using the training set to train the one or more models thereby forming the first tier trained model panel. In some embodiments, the enumerated set of classes comprises i) a diagnosis of epilepsy, ES, NES, NS, PNES, or NEE, and ii) a diagnosis of non-epilepsy, non-ES, non-NES, non-NS, non-PNES, or non-NEE. In some embodiments, the enumerated set of classes comprises i) a differential and/or comparative diagnosis of epilepsy, ES, NES, NS, PNES, or NEE, and ii) a differential and/or comparative diagnosis of non-epilepsy, non-ES, non-NES, non-NS, non-PNES, or non-NEE. In some embodiments, the enumerated set of classes comprises i) likelihood to respond to epilepsy, ES, NES, NS, PNES, or NEE treatment, and ii) likelihood to not respond to epilepsy, ES, NES, NS, PNES, or NEE treatment. In some embodiments, the enumerated set of classes comprises i) likely to respond to treatment, and ii) unlikely to respond to treatment. In some embodiments, the enumerated set of classes consists of i) likely to respond to treatment, and ii) unlikely to respond to treatment. In some embodiments, the enumerated set of classes comprises i) likely to have a seizure, and ii) unlikely to have a seizure. In some embodiments, the enumerated set of classes consists of i) likely to have a seizure, and ii) unlikely to have a seizure. In some embodiments, the enumerated set of classes comprises i) likely to need treatment, and ii) unlikely to need treatment. In some embodiments, the enumerated set of classes consists of i) likely to need treatment, and ii) unlikely to need treatment. In some embodiments, the enumerated set of classes comprises i) likely to need specific therapeutic agent, and ii) unlikely to need specific therapeutic agent. In some embodiments, the enumerated set of classes consists of i) likely to need specific therapeutic agent, and ii) unlikely to need specific therapeutic agent. In some embodiments, the enumerated set of classes comprises i) likely to need therapeutic agent dosage change, and ii) unlikely to need therapeutic agent dosage change. In some embodiments, the enumerated set of classes consists of i) likely to need therapeutic agent dosage change, and ii) unlikely to need therapeutic agent dosage change.

In some embodiments, the training set comprises a different plurality of training subjects for each class in the enumerated set of classes. In some embodiments, the training set comprises: a first subset of subjects that have been provided epilepsy, ES, NES, NS, PNES or NEE treatment and responded to treatment, and a second subset of subjects that have been provided epilepsy, ES, NES, NS, PNES or NEE treatment and did not respond to treatment. In some embodiments, the training set comprises: a first subset of subjects that had past seizures, and a second subset of subjects that did not have past seizures. In some embodiments, the training set comprises: a first subset of subjects that had past treatment, and a second subset of subjects that did not have past treatment.

In some embodiments, the training set comprises: a first subset of subjects that has altered concentrations of the one or more biomarkers in the one or more biological samples compared to the concentration of the one or more biomarkers in the one or more controls, and a second subset of subjects that does not have altered concentrations of the one or more biomarkers in the one or more biological samples compared to the concentration of the one or more biomarkers in the one or more controls.

In some embodiments, the training set comprises: a first subset of subjects that have one or more of a NES risk factor, an NS risk factor, a PNES risk factor, or a NEE risk factor, and a second subset of subjects that do not have one or more of a NES risk factor, an NS risk factor, a PNES risk factor, or a NEE risk factor, the risk factors being independently selected from being unemployed or having a history of being unemployed, being disabled or having a history of being disabled, having a history of physical trauma, having a history of emotional trauma, having a history of sexual trauma, having a history of psychological trauma, being a female, having poly-allergies or having a history of poly-allergies, having post-traumatic stress disorder or having a history of post-traumatic stress disorder, having been diagnosed with a major depressive disorder or having a history of major depressive disorder, having one or more cluster B personality disorder or having a history of cluster B personality disorder, having a dependent personality disorder or having a history of dependent personality disorder, having conversion disorder or having a history of conversion disorder, having fibromyalgia or having a history of fibromyalgia, having migraine or having a history of migraine, having pain or having a history of pain, and having asthma or having a history of asthma.

In some embodiments, the treatment regimen comprises administering to the subject one or more therapeutic agents or other treatment options (such as psychotherapy, cognitive therapy, behavioral therapy, standard medical care or other therapeutic agents not listed herein) selected from the following group including, but not limited to, the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof. In some embodiments, this may be for drugs and therapeutic agents and methods currently in development and or in clinical trials. In some embodiments, the subject has suffered one seizure. In some embodiments, the subject has suffered two seizures. In some embodiments, the subject is a human subject.

Referring to FIG. 14B, in some embodiments, the target subject 222 has a first computer readable analytical signature 302 that comprises one or more biomarkers concentrations 304. For instance, in some embodiments, the first computer readable analytical signature 302 comprises one or more biomarker concentrations for one or more biomarkers provided in Table 2. In some embodiments, the target entity 222 has a second computer readable analytical signature 306 that comprises a separate biomarker concentration 308. As used herein, analytical signature may refer, without limitation, to any of a patient biomarker concentration, a control biomarker concentration, and/or a ratio between a patient biomarker concentration and a control biomarker concentration.

As described herein in reference to Table 2, or ay other biomarker described herein, in some embodiments, a biomarker concentration can be in a range defined as (mean value−standard deviation) to (mean value+standard deviation). For example, in some embodiments, a biomarker concentration described in Table 2 as subject (or patient) biomarker concentration, can be in a range from (seizure patient mean−seizure standard deviation) to (seizure patient mean+seizure standard deviation). In some embodiments, a biomarker concentration described in Table 2 as control biomarker concentration, can be in a range from (control mean−control standard deviation) to (control mean+control standard deviation).

Referring to FIG. 14B, in some embodiments, the likelihood classifier 310 is a single classifier. In some alternative embodiments, the likelihood classifier 310 is a composite of a plurality of sub-classifiers 312. In such embodiments, each sub-classifier 312 comprises, as input, a select biomarker concentration 314 (subsets). For instance, in some embodiments each biomarker concentration 314 corresponds to one or two of the subset ranges 304 of the first computer readable analytical signature. In some embodiments each likelihood classifier is trained using a different subset of the training controls set 206. As described herein, likelihood refers to one or more of likely to have a given diagnosis, unlikely to have a given diagnosis, likely to respond to treatment, unlikely to respond to treatment, likely to have a seizure, unlikely to have a seizure, likely to need treatment, unlikely to need treatment, likely to need specific therapeutic agent, unlikely to need specific therapeutic agent, likely to need therapeutic agent dosage change, and unlikely to need therapeutic agent dosage change.

In some embodiments, each likelihood classifier 310 is a nearest neighbor analysis against the subjects test set 213. That is, select biomarker concentrations subset ranges in an analytical signature from a target subject 222 serve as input into the first tier trained model panel 218 and/or second tier trained model panel 220 and nearest neighbor analysis is used to determine the most similar subjects in the test set 212 to the target subject 222. Then, the likelihood class of these most similar test subjects are polled and combined to form the likelihood class called by the first tier trained model panel 218 and/or second tier trained model panel 220 for the target subject 222.

In some embodiments, each likelihood classifier 310 is panel of nearest neighbor analyses against the subjects test set 213. In such embodiments, each nearest neighbor analysis in the panel is a sub-classifier 312. In such embodiments, select biomarker concentrations ranges 314 in an analytical signature 302/306 from the target subject 222 serve as input into each sub-classifier 312 and nearest neighbor analysis is used by each sub-classifier 312 to determine the most similar entities in the subjects test set 213 to the target subject 222. Then, the likelihood class of these most similar test subjects are polled and combined to form the likelihood class called by each respective likelihood classifier 310 for the target entity 222.

In some embodiments, the first trained model panel 218 and/or second trained model panel 218 is an artificial neural network. In some embodiments, the first trained model panel 218 and/or second trained model panel 218 is linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, *The Elements of Statistical Learning*, Springer, New York; and Agresti 1996, *An Introduction to Categorical Data Analysis*, John Wiley & Sons, New York, each of which is hereby incorporated by reference herein for such purpose.

In some embodiments, the first trained model panel 218 and/or second trained model panel 218 comprises a plurality of sub-classifiers 312 and each respective sub-classifier is an artificial neural network. In some embodiments, the first trained model panel 218 and/or second trained model panel 218 comprises a plurality of sub-classifiers 312 and each respective sub-classifier is a linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, *The Elements of Statistical Learning*, Springer, New York; and Agresti 1996, An Introduction to Categorical Data Analysis, John Wiley & Sons, New York, each of which is hereby incorporated by reference herein for such purpose. In such embodiments, the sub-classifiers are combined to form a final value for the respective first trained model panel 218 and/or second trained model panel 218

In some implementations, one or more of the above identified data elements or modules of the discovery system 250 for screening a target subject to determine whether it is likely to have or not have a given diagnosis, and/or to respond or not respond to epilepsy, ES, NES, NS, PNES or NEE treatment, are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above. As described herein, screening a subject can be done as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, a discovery system 250 for screening a target subject to determine whether it is likely to respond to epilepsy, ES, NES, NS, PNES or NEE treatment is a smart phone (e.g., an iPhone), laptop, tablet computer, desktop computer, or other form of electronic device (e.g., a gaming console). In some embodiments, the discovery system 250 is not mobile. In some embodiments, the discovery system 250 is mobile.

In some embodiments the discovery system 250 is a tablet computer, desktop computer, or other form or wired or wireless networked device. In some embodiments, the discovery system 250 has any or all of the circuitry, hardware components, and software components found in the discovery system 250 depicted in FIG. 12 or 13. In the interest of brevity and clarity, only a few of the possible components of the discovery system 250 are shown in order to better emphasize the additional software modules that are installed on the discovery system 250.

Now that details of a system 48 for screening a target subject to determine its likelihood to respond to epilepsy, ES, NES, NS, PNES or NEE treatment have been disclosed, details regarding aspects of methods for screening a target subject to determine whether it is likely to respond to epilepsy, ES, NES, NS, PNES or NEE treatment are disclosed below. As described herein, screening a subject can be done as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; iv) methods of screening a subject to determine the likelihood that the subject has a given diagnostic; and/or v) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, device 104 obtains abundance, levels, or concentrations of biomarkers to be quantified in plasma by any of a number of methods known in the art, the particular procedure not being a limitation of the embodiments herein. In some embodiments the analytical signature 210 of a control 208, the analytical signature 216 of a test subject 214, and/or the analytical signature 302 or 306 of a target subject is acquired using any method known in the art. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art, and a variety of capture and detect antibodies may be used to detect biomarkers by those skilled in the art. Single- and multi-probe kits are available from commercial suppliers, e.g., Meso Scale Discovery. These kits include the kits referenced in the Examples hereto. Individual measurements may be taken and analyzed individually or in any combination using linear or logarithmic units, or by using ratios of linear or logarithmic units. The reciprocals of ratios of linear or logarithmic units may also be used.

EXAMPLES

Reference is now made to the following examples, which, together with the above descriptions, illustrate certain embodiments of the invention in a non-limiting fashion. These examples are provided for the purpose of illustration only and the disclosure encompassed herein should in no way be construed as being limited to these examples, but rather should be construed to encompass any and all variations which become evident as a result of the teachings provided herein.

Example 1 and 2: Patient Demographics and Biomarker Data: Epilepsy, ES, NES/NS/PNES and Controls (Healthy)

Retrospective analysis confirmed enrollment of 33 NES Patients. Video EEG confirmed no epileptiform discharge was correlated with seizure clinical manifestations; 75 samples collected; 9 samples, collected within 24 hours of an event were selected for detailed proteomic analysis.

Equivalent Analysis confirmed enrollment of 55 ES patients. Video EEG confirmed epileptiform discharge was correlated with seizure clinical manifestations; 159 samples collected; 32 samples, collected within 24 hours of an event were selected for detailed proteomic analysis.

Patient demographics are summarized in Table 1. The demographics indicate the total number of patients, the number of samples taken, and the average age for each group, and also indicate the fraction of patients in each category. Biomarkers analyzed with key diagnostic parameters are shown in Table 2. These biomarkers can be used alone or in combination for the determination of seizure or not and epilepsy, ES, NES, NS, PNES or NEE or not. Additionally, these biomarkers serve as the basis for the algorithm determination.

TABLE 1

| Patient Demographics | | | |
|---|---|---|---|
| | | NES/NS/PNES | ES |
| | Patients | 9 | 23 |
| | Samples | 9 | 31 |
| Age (%) | <18 | 0 | 0 |
| | 18-29 | 22.2 | 21.7 |
| | 30-44 | 22.2 | 34.8 |
| | 45-59 | 55.6 | 30.4 |
| | >59 | 0 | 13.0 |
| Gender (%) | male | 22.2 | 34.8 |
| | female | 77.8 | 65.2 |
| # of AEDs (%) | 0 | 44.4 | 8.7 |
| | 1 | 44.4 | 21.7 |
| | 2 | 11.1 | 34.8 |
| | 3+ | 0 | 34.8 |
| Seizure Classification (%) | Focal | 0 | 87.0 |
| | Generalized | 0 | 13.0 |

TABLE 2

| Biomarker Concentrations and P-Values | | | | | | |
|---|---|---|---|---|---|---|
| | NES n = 9 | | Seizure n = 32 | | Control n = 29 | |
| | Conc | Std | Conc | Std | Conc | Std |
| ICAM-1 | 512.8888889 | 144.8485373 | 377.1875 | 78.13067479 | 432.8448276 | 100.8297988 |
| TNF-B | 0.323444444 | 0.119624051 | 0.207028571 | 0.130815769 | 0.247636842 | 0.080503999 |
| IL-17A | 2.847111111 | 2.226233912 | 1.669322581 | 1.224309743 | 2.138982456 | 3.301190899 |
| MMP-9 | 81.86111111 | 52.96973076 | 54.8359375 | 34.12041804 | 59.46896552 | 26.77690208 |
| IL-12-IL-23p40 | 187.0833333 | 138.5024839 | 128.871875 | 72.80496521 | 145.6741379 | 52.41984212 |
| IL-12p70 | 0.30686 | 0.250830638 | 0.184393125 | 0.156949474 | 0.157988537 | 0.147938567 |
| IL-15 | 2.415 | 0.325 | 2.8503125 | 0.857975394 | 2.709310345 | 0.58448876 |
| MMP-3 | 6.376666667 | 2.806446943 | 9.41578125 | 6.005315823 | 13.0862069 | 5.586556162 |
| MIP-1B | 58.67777778 | 20.95379986 | 73.09375 | 28.50044887 | 57.28448276 | 37.64436488 |
| IL-16 | 234.5666667 | 249.9542469 | 165.9859375 | 64.83981432 | 274.9017241 | 136.1033285 |
| TRAIL | 271.5 | 61.20298649 | 222.5935484 | 106.7615973 | 308.9655172 | 103.5102803 |
| IP-10 | 580.3888889 | 722.8468517 | 345.0953125 | 415.1703428 | 345.0517241 | 175.7897865 |
| VCAM-1 | 666.3333333 | 172.4151965 | 590.546875 | 157.9395582 | 556.6896552 | 124.4818512 |
| Eotaxin | 103.1555556 | 50.78708522 | 128.6421875 | 56.31261183 | 149.087931 | 96.46218319 |
| MDC | 1246.444444 | 493.5728273 | 1038.96875 | 458.9307876 | 1072.741379 | 401.2643191 |
| TNF-RI | 2.002222222 | 0.404743479 | 2.25625 | 0.643572791 | 2.230172414 | 0.862227451 |
| SAA | 7.055 | 5.267554788 | 34.50640625 | 82.07072612 | 5.844862069 | 4.349356355 |
| CRP | 5.669388889 | 5.527365106 | 16.07654688 | 33.42981021 | 4.272275862 | 3.49214201 |
| MIP-5 | 8.055555556 | 3.646703568 | 7.40796875 | 1.827609589 | 6.872241379 | 2.16107815 |
| M-CSF | 30.46111111 | 13.96468319 | 25.52 | 19.41859003 | 15.22206897 | 12.95845733 |
| MCP-2 | 25.85 | 7.366383856 | 29.42725806 | 16.86841104 | 21.50172414 | 11.1993456 |
| GM-CSF | 0.188877778 | 0.153172189 | 0.159305 | 0.117471101 | 0.2724978 | 0.293855191 |
| IL-1a | 4.366666667 | 2.015002068 | 10.8140625 | 32.22914887 | 19.23775862 | 52.09316313 |
| Eotaxin-3 | 15.01611111 | 7.674103016 | 13.4857377 | 6.417113507 | 23.49436364 | 31.23797862 |
| IL-8 | 10.92055556 | 16.12419144 | 8.66890625 | 7.499072884 | 5.842068966 | 1.933364727 |
| Osteonectin | 106.8222222 | 114.0432206 | 129.2725806 | 109.8243776 | 83.80689655 | 64.65977768 |
| IFN-y | 3.747777778 | 1.755722566 | 14.05696667 | 60.01290435 | 6.514607143 | 12.95373416 |
| MMP-1 | 1.623277778 | 2.130670833 | 1.918210938 | 2.176432277 | 2.139413793 | 2.430527629 |
| IL-6 | 1.697722222 | 1.116263151 | 2.289693548 | 5.621527429 | 0.955189655 | 0.750000309 |
| Cytokeratin-8 | 9.192777778 | 8.355213147 | 10.48322581 | 13.06599845 | 8.425172414 | 9.705347307 |
| Eotaxin-2 | 1405.444444 | 851.1961011 | 1530.75 | 1295.222833 | 1302.948276 | 969.1746653 |
| IL-7 | 7.306444444 | 8.470273046 | 8.07946875 | 7.604452499 | 3.760896552 | 3.920955666 |
| MCP-1 | 94.13333333 | 28.32070307 | 97.2296875 | 34.23722243 | 101.5517241 | 21.99255549 |
| IL-1B | 0.14822 | 0.143756007 | 0.130296667 | 0.087495789 | 0.494385714 | 0.499077069 |
| VEGF-A | 62.43333333 | 50.32791362 | 66.9015625 | 48.26488919 | 77.82068966 | 86.03752341 |
| IL-2 | 0.214483333 | 0.09696794 | 0.230717857 | 0.207567254 | 0.299171154 | 0.286791147 |
| MCP-4 | 131.9388889 | 135.5062366 | 123.7 | 83.97058079 | 73.80344828 | 50.82669664 |
| IL-10 | 0.409444444 | 0.23798021 | 0.38768125 | 0.273146343 | 1.422448276 | 5.081355245 |
| TNF-RII | 3714.444444 | 780.7882216 | 3622.0625 | 1226.306636 | 3685.172414 | 1637.959108 |
| MIF | 72413.22222 | 77739.83923 | 78048.46774 | 71784.37016 | 49578.24138 | 63932.04151 |
| IL-5 | 0.48375 | 0.263757583 | 0.454628571 | 0.433548697 | 0.609594828 | 0.339318451 |
| SCF | 42.39444444 | 9.291481895 | 41.65483871 | 15.88536228 | 44.51896552 | 12.35606032 |
| Calbindin | 0.242111111 | 0.105491911 | 0.24845 | 0.151319513 | 0.279931034 | 0.136104405 |
| P-Cadherin | 17.565 | 7.216435139 | 17.275625 | 6.439310637 | 22.12534483 | 7.822342275 |
| IL-13 | 1.122444444 | 0.819107524 | 1.178666667 | 1.478645542 | 0.604437037 | 0.439294263 |
| TARC | 172.6277778 | 264.4870902 | 177.725625 | 184.0786178 | 64.12068966 | 50.29419915 |
| Nectin-4 | 1077.277778 | 276.6063801 | 1084.725806 | 331.5330066 | 979.8275862 | 327.6408956 |
| TNF-a | 2.3 | 0.530837912 | 2.275953125 | 1.293613585 | 2.895344828 | 1.098747273 |

TABLE 2-continued

Biomarker Concentrations and P-Values

| | | | | | | |
|---|---|---|---|---|---|---|
| MIP-1a | 16.19833333 | 5.688911485 | 16.30984127 | 6.463404551 | 86.78465517 | 378.0911674 |
| Osteoactivin | 19.92777778 | 2.971682194 | 19.859375 | 4.809259258 | 23.1862069 | 5.27716121 |
| IL-4 | 0.027863571 | 0.017298252 | 0.027929231 | 0.024495798 | 0.0266216 | 0.016783566 |

| | NES + Control combined | | Pvalues | |
|---|---|---|---|---|
| | Conc | Std | NES − Seizure | (nes, control) − seizure |
| ICAM-1 | 4.52E+02 | 1.18E+02 | 1.55753E−06 | 3.25435E−05 |
| TNF-B | 0.265830667 | 0.096995225 | 0.001241273 | 0.003168602 |
| IL-17A | 2.308933333 | 3.092459635 | 0.005151077 | 0.130573724 |
| MMP-9 | 64.77236842 | 36.08800865 | 0.012269503 | 0.100839989 |
| IL-12-IL-23p40 | 155.4815789 | 83.36843198 | 0.020777993 | 0.049888407 |
| IL-12p70 | 0.197864821 | 0.192931003 | 0.030316791 | 0.702740024 |
| IL-15 | 2.639605263 | 0.548988162 | 0.04030154 | 0.083454244 |
| MMP-3 | 11.49710526 | 5.815510299 | 0.042801669 | 0.040953728 |
| MIP-1B | 57.61447368 | 34.43557564 | 0.051734168 | 0.005144672 |
| IL-16 | 265.3486842 | 1.71E+02 | 0.054977172 | 2.52756E−05 |
| TRAIL | 300.0921053 | 9.65E+01 | 0.070530155 | 1.84585E−05 |
| IP-10 | 400.7894737 | 396.667875 | 0.08484264 | 0.422610069 |
| VCAM-1 | 582.6578947 | 145.048953 | 0.085663607 | 0.760383823 |
| Eotaxin | 138.2092105 | 89.96321789 | 0.090958514 | 0.465154862 |
| MDC | 1113.881579 | 431.3121036 | 0.103761182 | 0.325351403 |
| TNF-RI | 2.176184211 | 0.784569891 | 0.12056879 | 0.51832825 |
| SAA | 6.131473684 | 4.612262459 | 0.165118742 | 0.003336328 |
| CRP | 4.603171053 | 4.11041407 | 0.197470974 | 0.003799941 |
| MIP-5 | 7.1525 | 2.639482169 | 0.310864145 | 0.517515807 |
| M-CSF | 18.83131579 | 14.70757121 | 0.323315324 | 0.023910314 |
| MCP-2 | 22.53157895 | 10.58247323 | 0.389803218 | 0.004279013 |
| GM-CSF | 0.250363088 | 0.266579639 | 0.396578433 | 0.018339782 |
| IL-1a | 15.71565789 | 45.9555623 | 0.404605861 | 0.477431187 |
| Eotaxin-3 | 21.40383562 | 27.62381758 | 0.404806392 | 0.031527245 |
| IL-8 | 7.044868421 | 8.312084812 | 0.409223516 | 0.233998764 |
| Osteonectin | 89.25789474 | 79.7919437 | 0.457102114 | 0.015269963 |
| IFN-y | 5.841594595 | 11.36407397 | 0.474152189 | 0.25479178 |
| MMP-1 | 2.017171053 | 2.373117084 | 0.615648371 | 0.800328315 |
| IL-6 | 1.131052632 | 0.907771127 | 0.662131327 | 0.081357312 |
| Cytokeratin-8 | 8.606973684 | 9.408776001 | 0.696730829 | 0.33291283 |
| Eotaxin-2 | 1327.223684 | 943.5746086 | 0.702860659 | 0.288642095 |
| IL-7 | 4.600631579 | 5.567516072 | 0.714753068 | 0.0023822 |
| MCP-1 | 99.79473684 | 23.85429948 | 0.729455817 | 0.606358777 |
| IL-1B | 0.35015 | 0.427822063 | 0.734315658 | 0.035136782 |
| VEGF-A | 74.17631579 | 79.32171978 | 0.735123267 | 0.525825557 |
| IL-2 | 0.277394286 | 0.254729737 | 0.752609616 | 0.273759219 |
| MCP-4 | 87.57236842 | 83.2542248 | 0.755560881 | 0.012547055 |
| IL-10 | 1.182526316 | 4.461363044 | 0.762602026 | 0.159951244 |
| TNF-RII | 3692.105263 | 1480.548872 | 0.765639133 | 0.765274718 |
| MIF | 54986.52632 | 68153.20587 | 0.777127523 | 0.057413455 |
| IL-5 | 0.582385135 | 0.328584992 | 0.800476329 | 0.053919238 |
| SCF | 44.01578947 | 11.7377938 | 0.852905607 | 0.321236524 |
| Calbindin | 0.270973684 | 0.13050398 | 0.86963196 | 0.349475932 |
| P-Cadherin | 21.04526316 | 7.924006409 | 0.87180361 | 0.002929527 |
| IL-13 | 0.733938889 | 0.602313091 | 0.917290234 | 0.117800269 |
| TARC | 89.81973684 | 143.6189962 | 0.926683391 | 0.002008562 |
| Nectin-4 | 1002.907895 | 319.0006673 | 0.931814457 | 0.146118311 |
| TNF-a | 2.754342105 | 1.025729953 | 0.93951621 | 0.016736435 |
| MIP-1a | 70.06684211 | 331.6683381 | 0.948014169 | 0.203767602 |
| Osteoactivin | 22.41447368 | 5.026265328 | 0.954973462 | 0.002884056 |
| IL-4 | 0.027133 | 0.01700837 | 0.993120455 | 0.88447541 |

| | Pvalues | |
|---|---|---|
| | control − NES | control − seizure |
| ICAM-1 | 0.01140591 | 0.000925912 |
| TNF-B | 0.003426925 | 0.047178488 |
| IL-17A | 0.403877915 | 0.30234611 |
| MMP-9 | 0.021303537 | 0.412920889 |
| IL-12-IL-23p40 | 0.067080527 | 0.153090506 |
| IL-12p70 | 0.009950201 | 0.424120849 |
| IL-15 | 0.047685424 | 0.299755954 |
| MMP-3 | 6.85919E-06 | 0.000758819 |

TABLE 2-continued

| Biomarker Concentrations and P-Values | | |
|---|---|---|
| MIP-1B | 0.88274777 | 0.010267441 |
| IL-16 | 0.388623439 | 9.67002E−08 |
| TRAIL | 0.154305962 | 1.90618E−05 |
| IP-10 | 0.027939288 | 0.999414384 |
| VCAM-1 | 0.004644432 | 0.197763954 |
| Eotaxin | 0.059633424 | 0.154286034 |
| MDC | 0.139177453 | 0.669994267 |
| TNF-RI | 0.287749186 | 0.850537692 |
| SAA | 0.337395048 | 0.009539413 |
| CRP | 0.212971867 | 0.009033574 |
| MIP-5 | 0.099104208 | 0.144060468 |
| M-CSF | 6.82614E−05 | 0.001033529 |
| MCP-2 | 0.131222406 | 0.003440768 |
| GM-CSF | 0.260403702 | 0.008794478 |
| IL-1a | 0.235968364 | 0.284190848 |
| Eotaxin-3 | 0.26456568 | 0.016894205 |
| IL-8 | 0.023451787 | 0.006589427 |
| Osteonectin | 0.291274355 | 0.00758325 |
| IFN-y | 0.375768114 | 0.363316673 |
| MMP-1 | 0.426937275 | 0.599881269 |
| IL-6 | 0.002083148 | 0.077971349 |
| Cytokeratin-8 | 0.766119273 | 0.335985851 |
| Eotaxin-2 | 0.692001707 | 0.28142913 |
| IL-7 | 0.018003974 | 0.000190525 |
| MCP-1 | 0.254901428 | 0.417571393 |
| IL-1B | 0.198957033 | 0.004812623 |
| VEGF-A | 0.478777787 | 0.387391297 |
| IL-2 | 0.230060517 | 0.160025927 |
| MCP-4 | 0.00920934 | 0.000165763 |
| IL-10 | 0.406789815 | 0.109340563 |
| TNF-RII | 0.942550346 | 0.810514454 |
| MIF | 0.219631907 | 0.02506418 |
| IL-5 | 0.179730095 | 0.032884023 |
| SCF | 0.508803905 | 0.278771261 |
| Calbindin | 0.288992583 | 0.234989004 |
| P-Cadherin | 0.033157739 | 0.000303516 |
| IL-13 | 0.025305531 | 0.065159424 |
| TARC | 0.00466675 | 1.51204E−05 |
| Nectin-4 | 0.26347779 | 0.08672537 |
| TNF-a | 0.031643279 | 0.005749761 |
| MIP-1a | 0.43697532 | 0.145023596 |
| Osteoactivin | 0.015961736 | 0.000443092 |
| IL-4 | 0.840090831 | 0.842302177 |

Example 3: Descriptive Statistics: Kolmogorov-Smirnov

Descriptive statistics Kolmogorov-Smirnov of all biomarkers are shown in FIG. 3.

Example 4: Boxplots Comparing Sample Cohorts

Figure 5A:
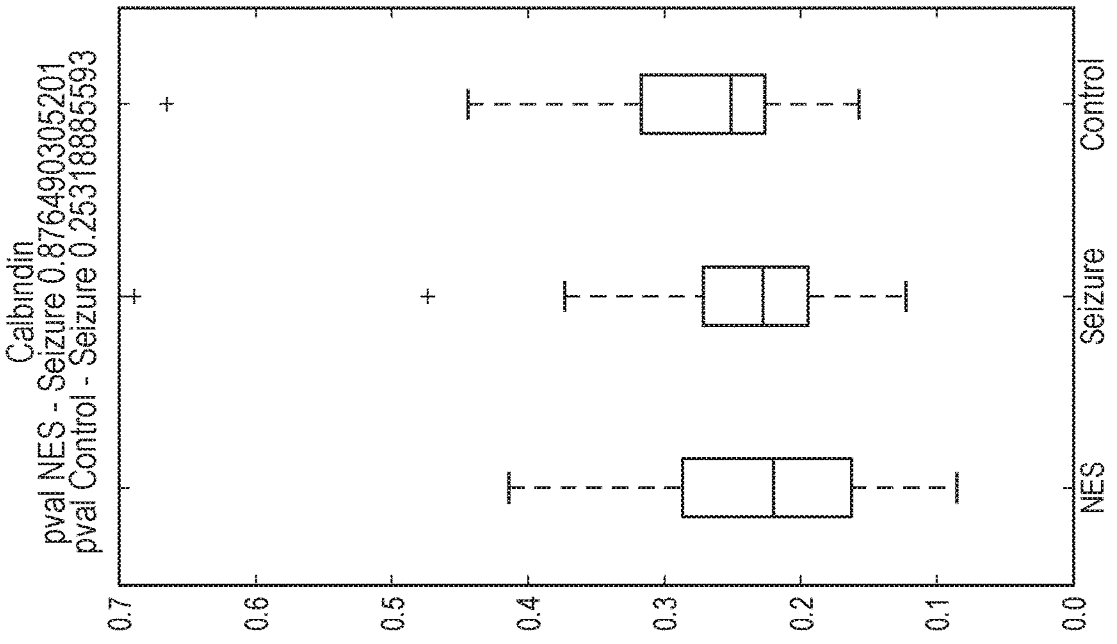
FIGS. 5A-6Y illustrate boxplots comparing various sample cohorts.
Figure 5B:
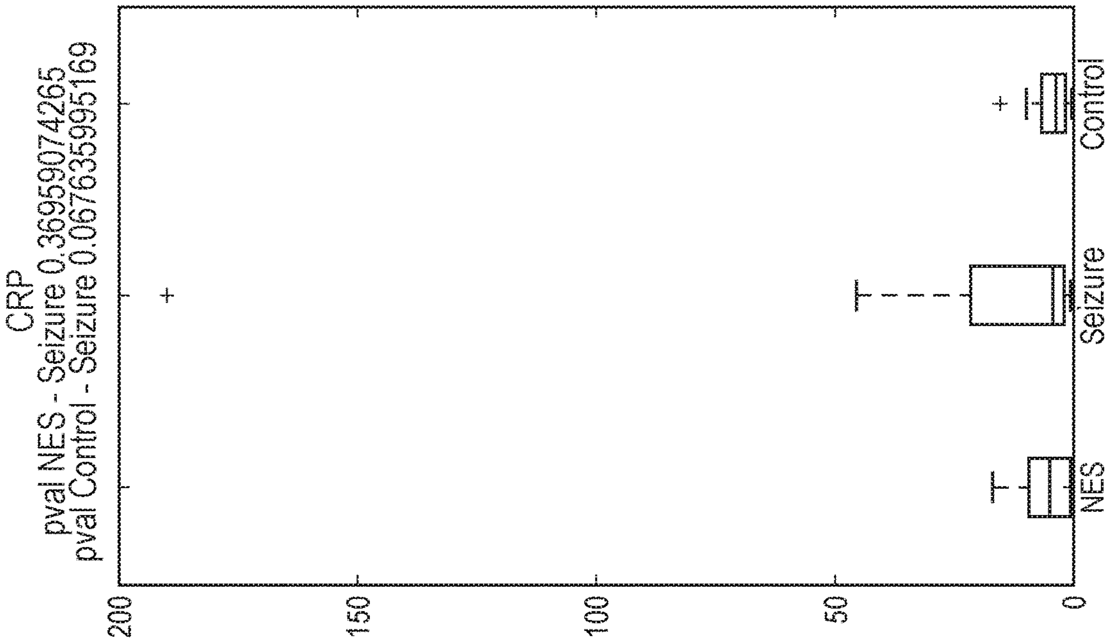
Figure 5D:
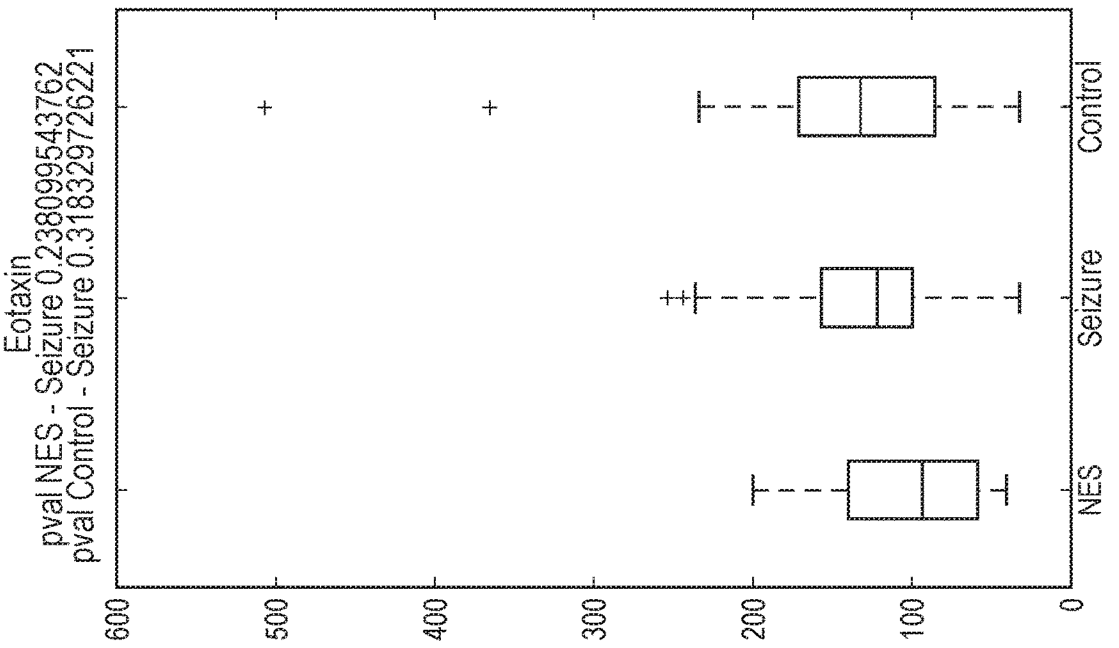
Figure 5C:
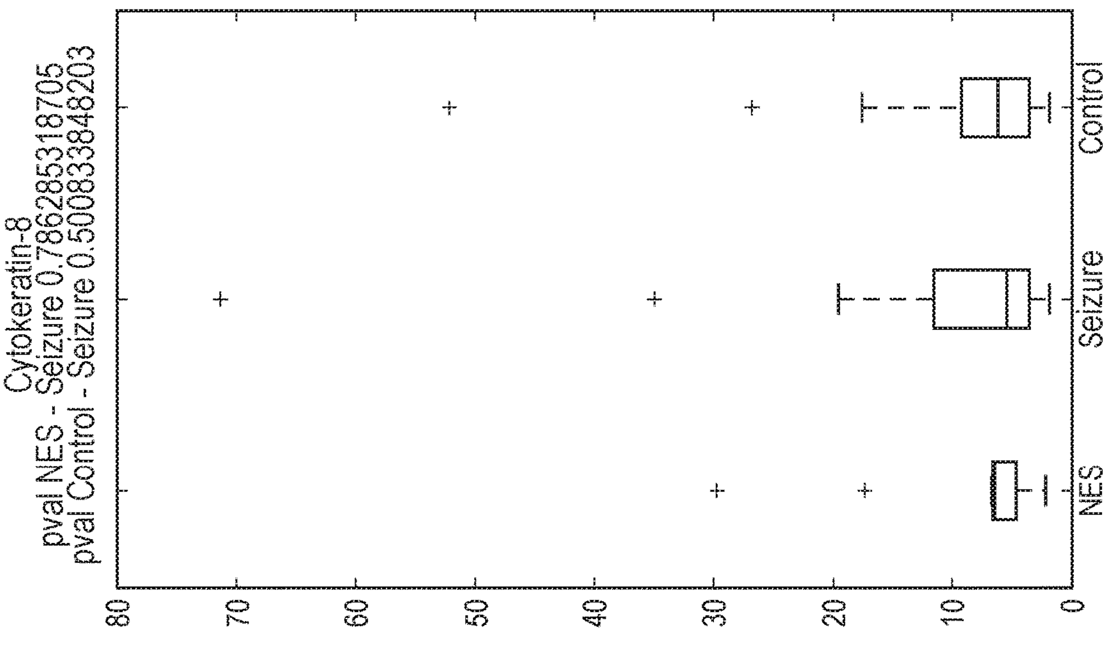
Figure 5F:
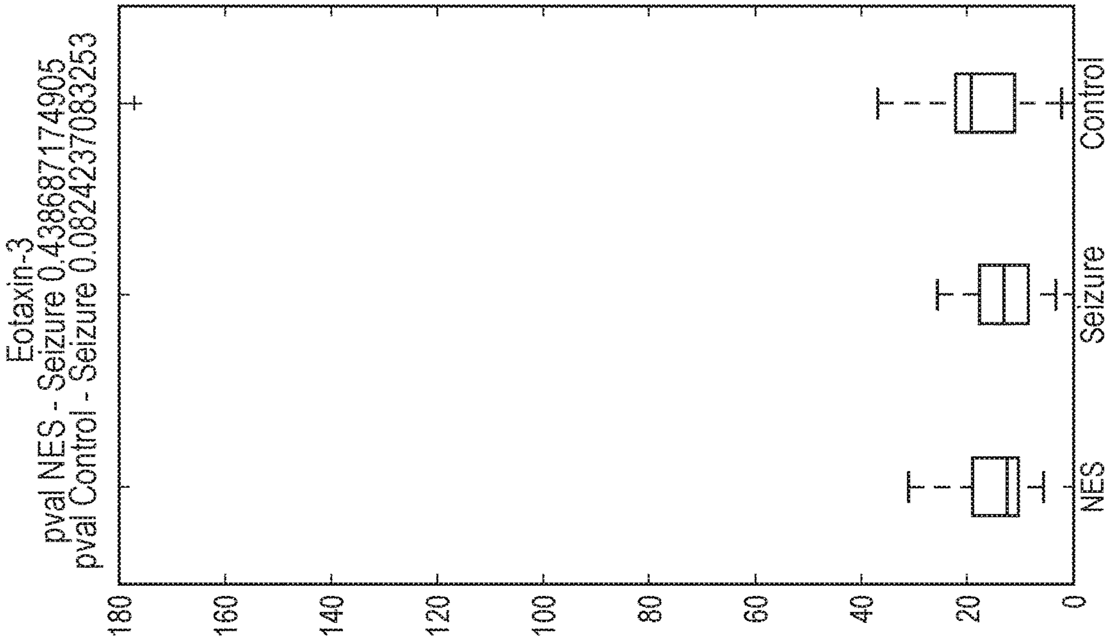
Figure 5E:
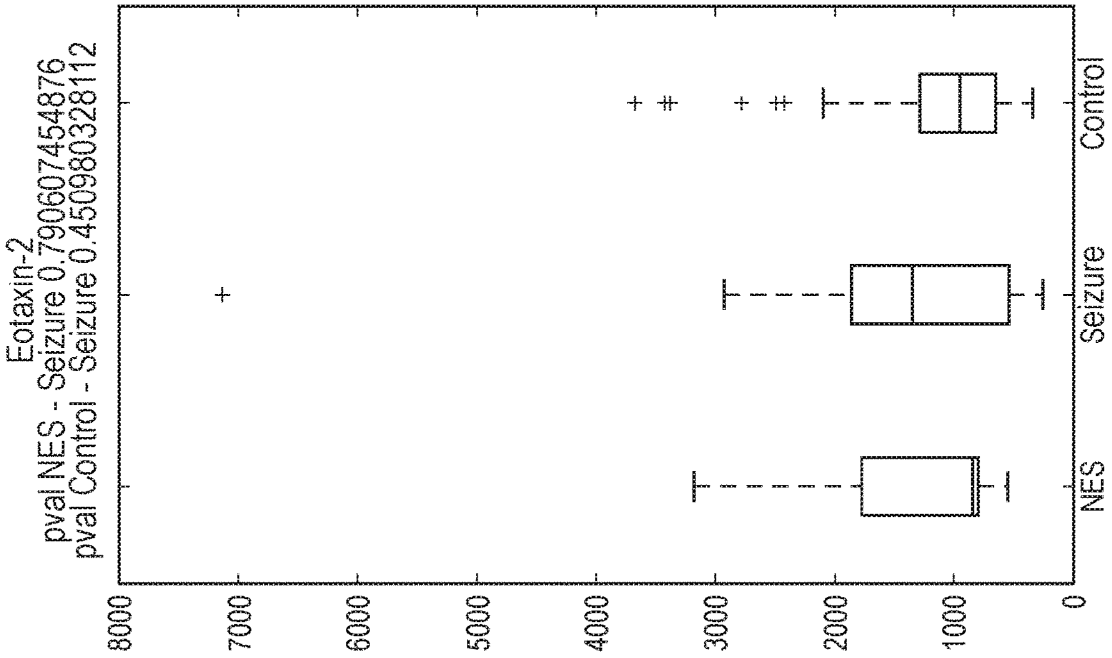
Figure 5G:
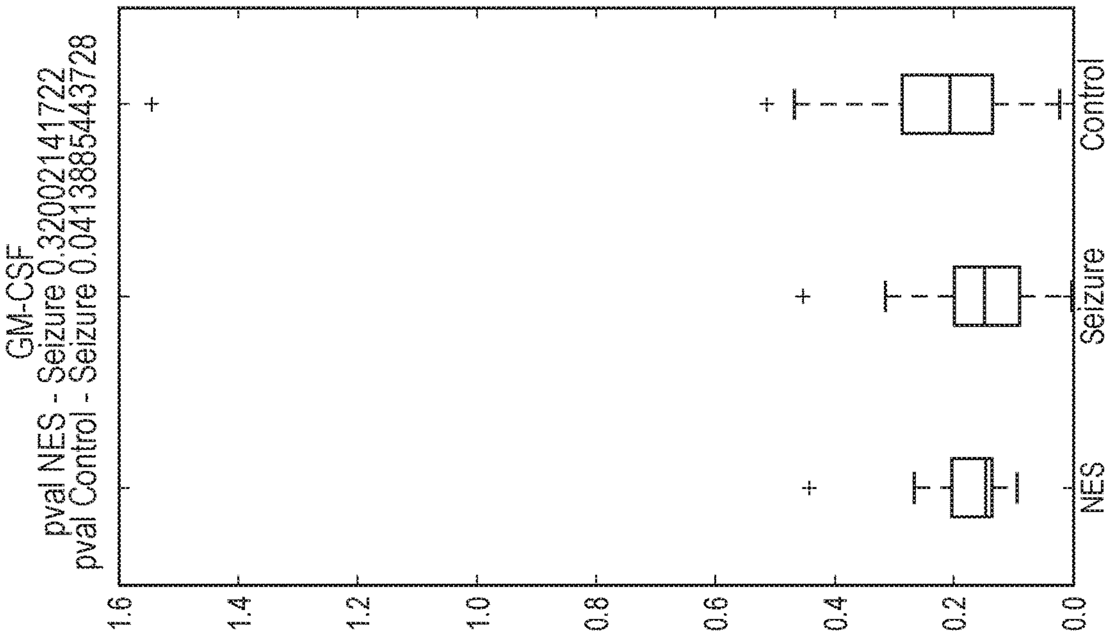
Figure 5H:
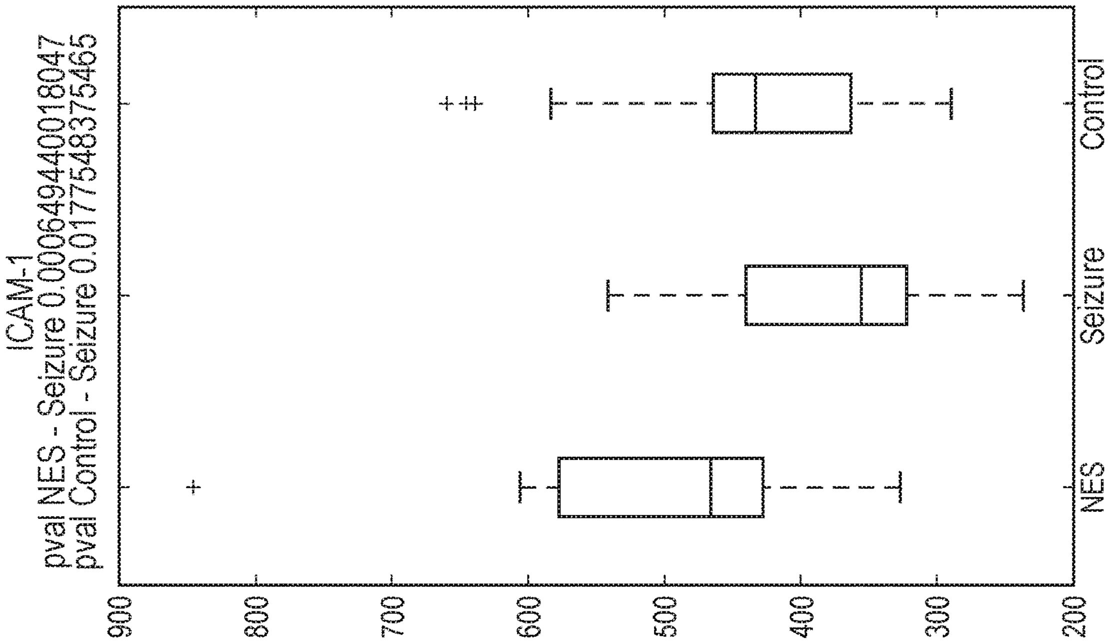
Figure 5I:
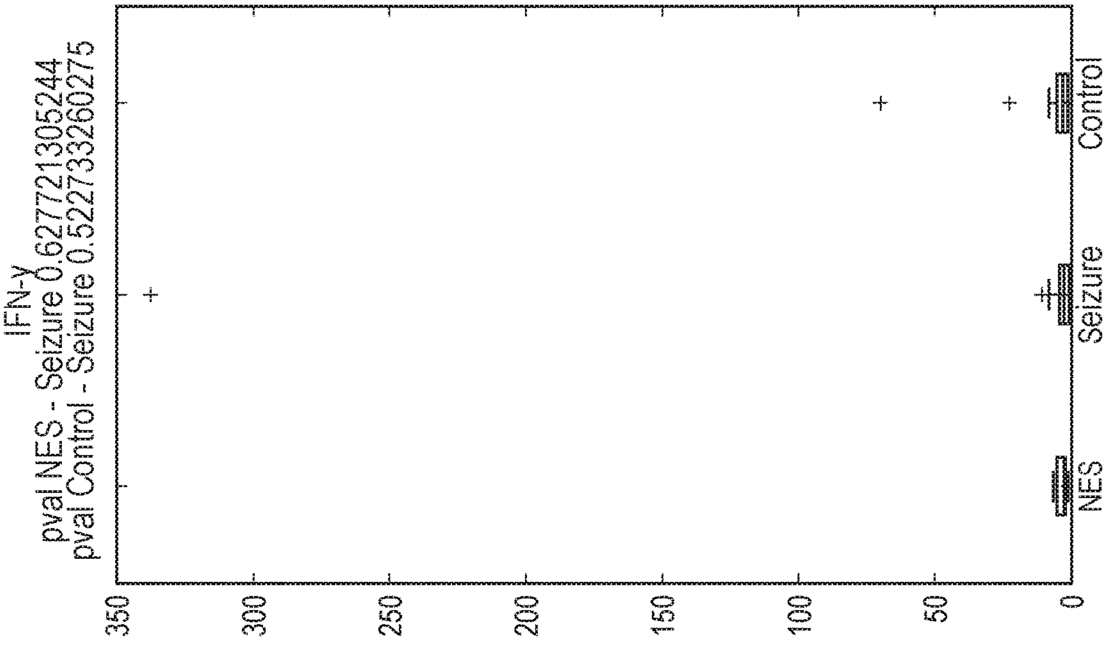
Figure 5J:
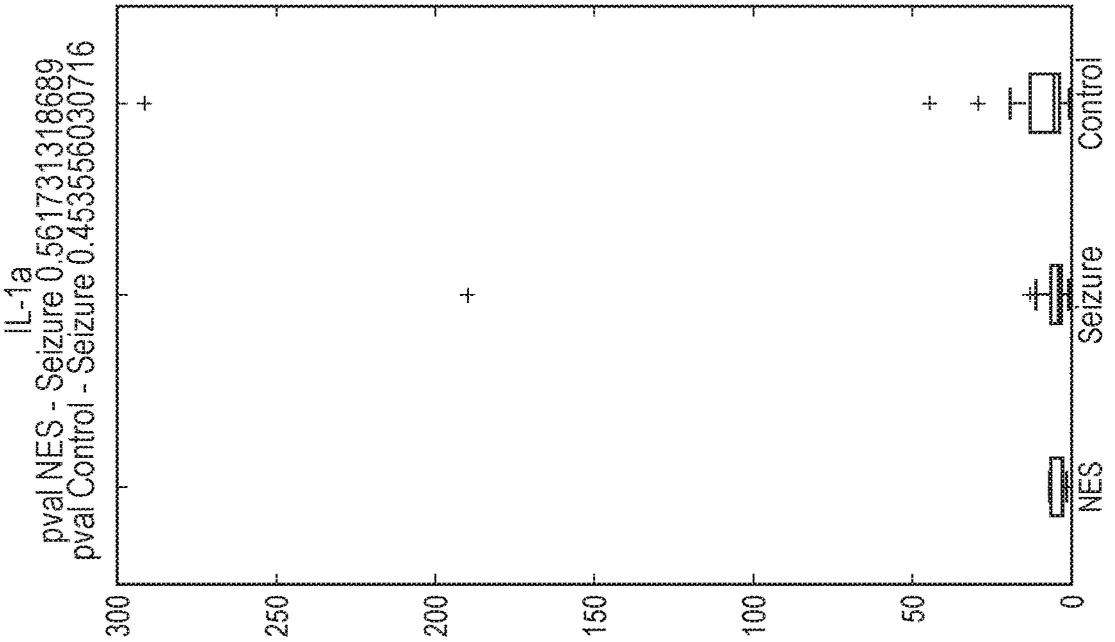
Figure 5K:
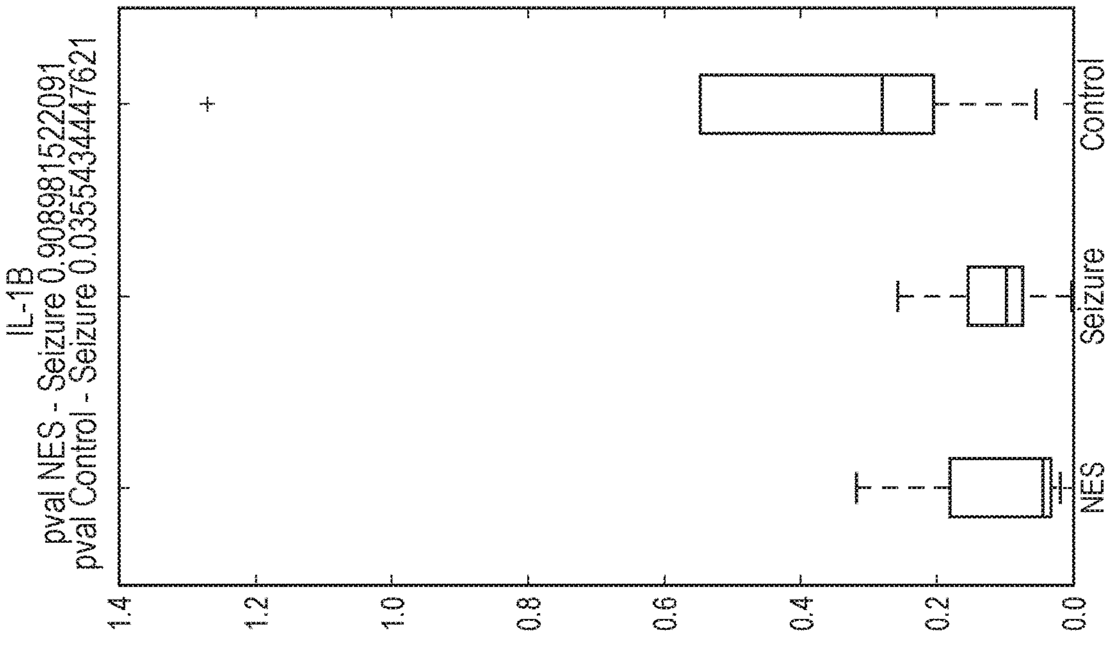
Figure 5L:
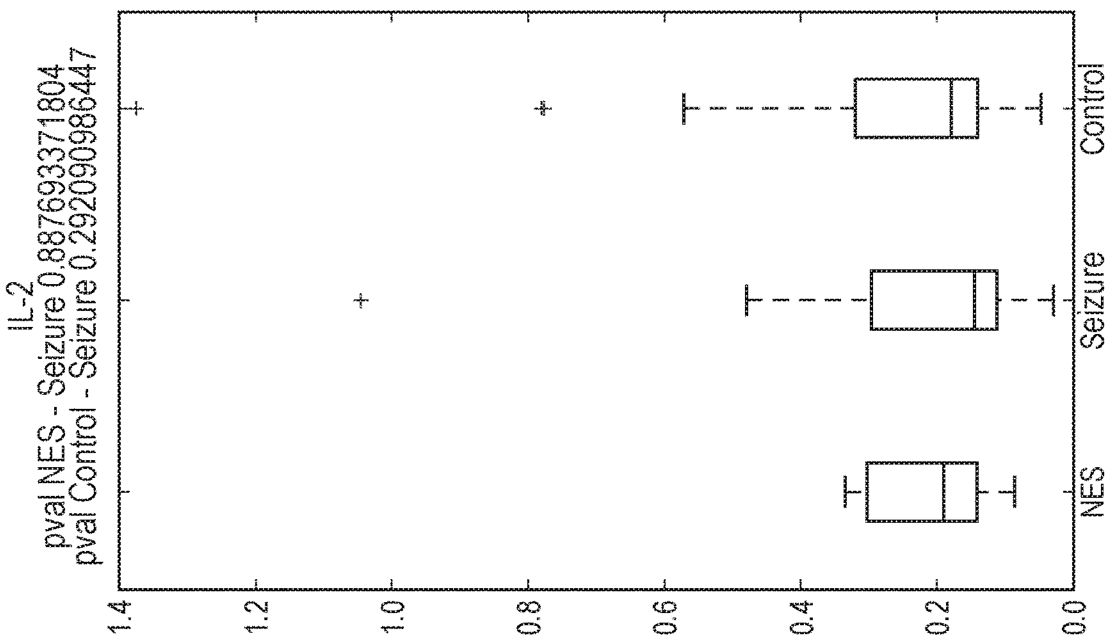
Figure 5N:
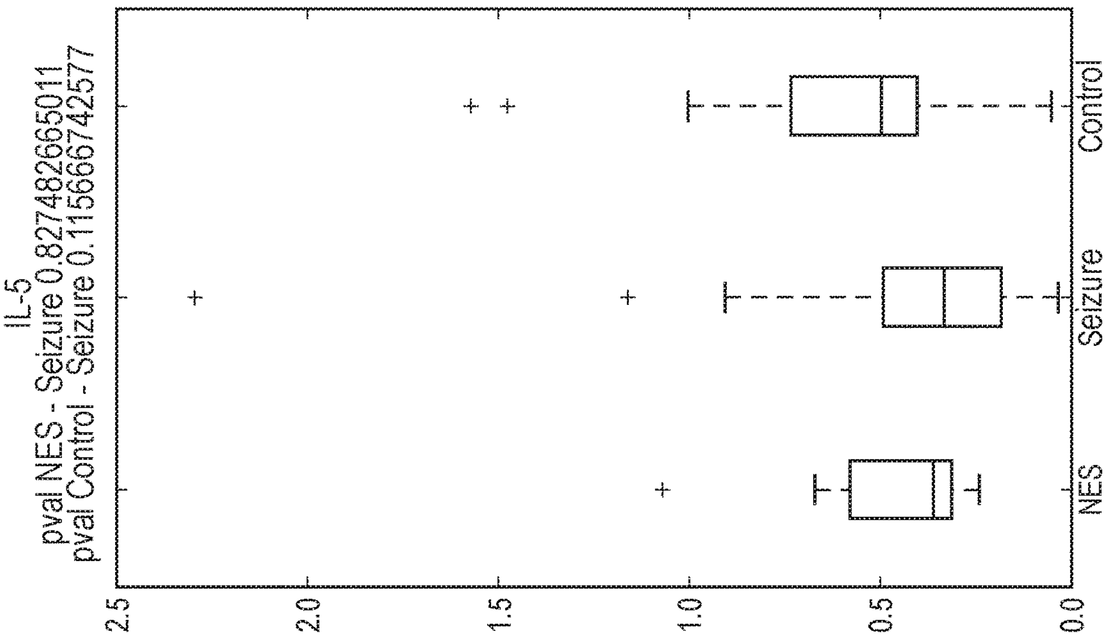
Figure 5M:
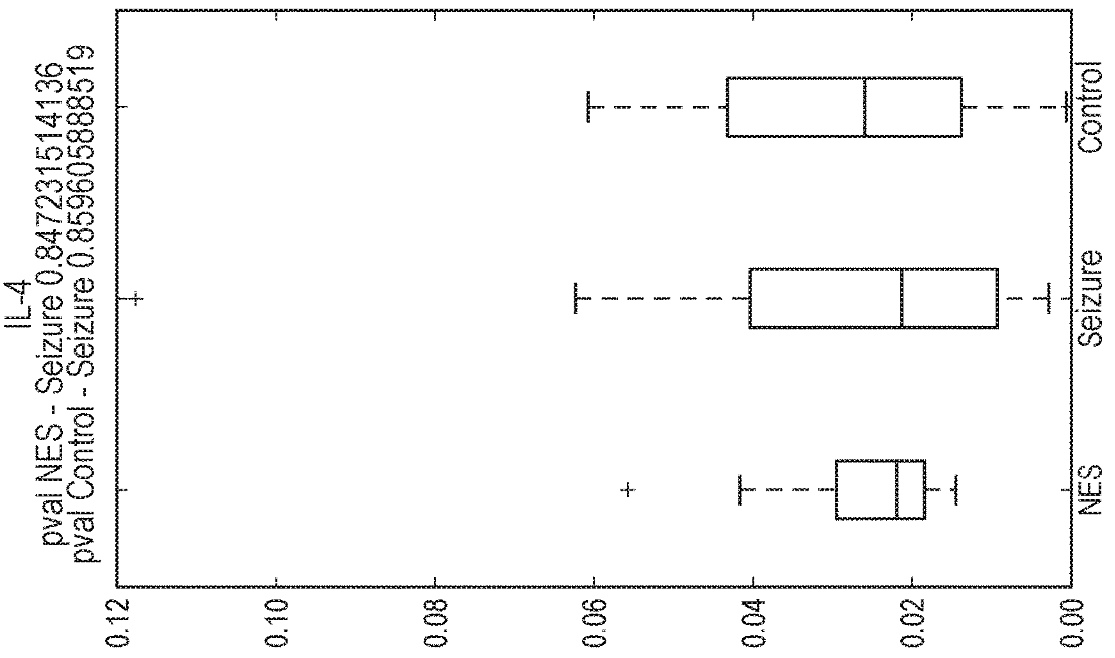
Figure 5O:
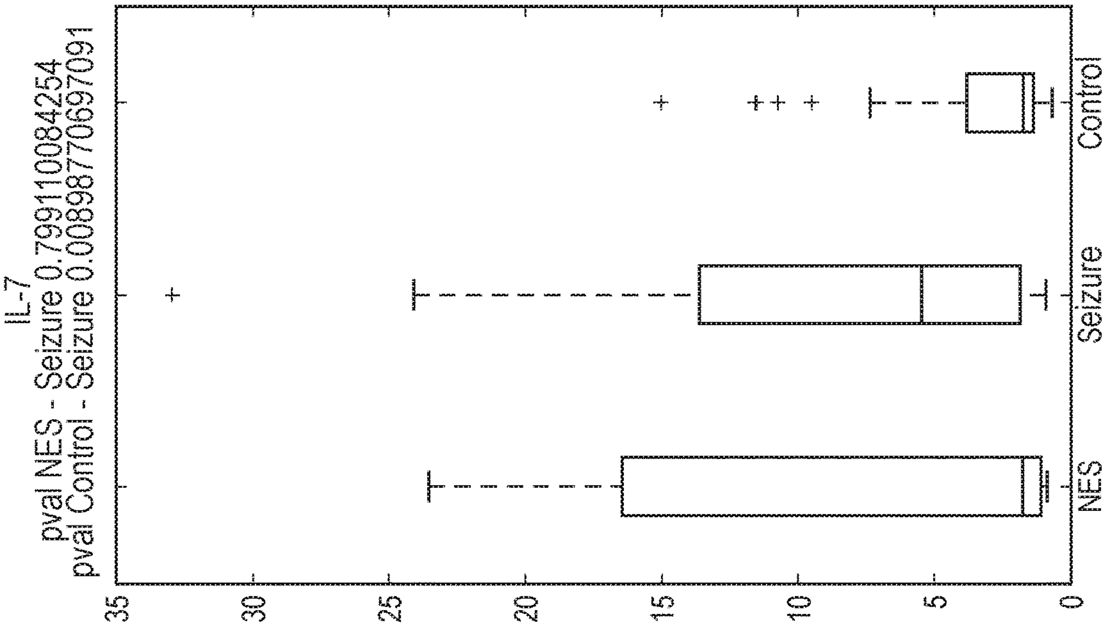
Figure 5P:
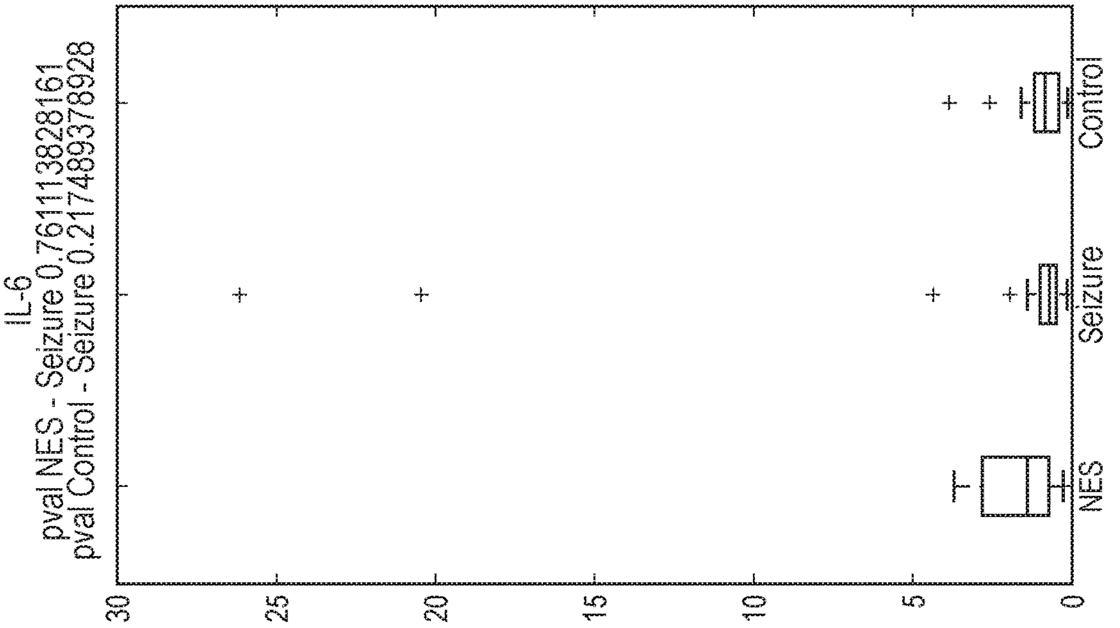
Figure 5R:
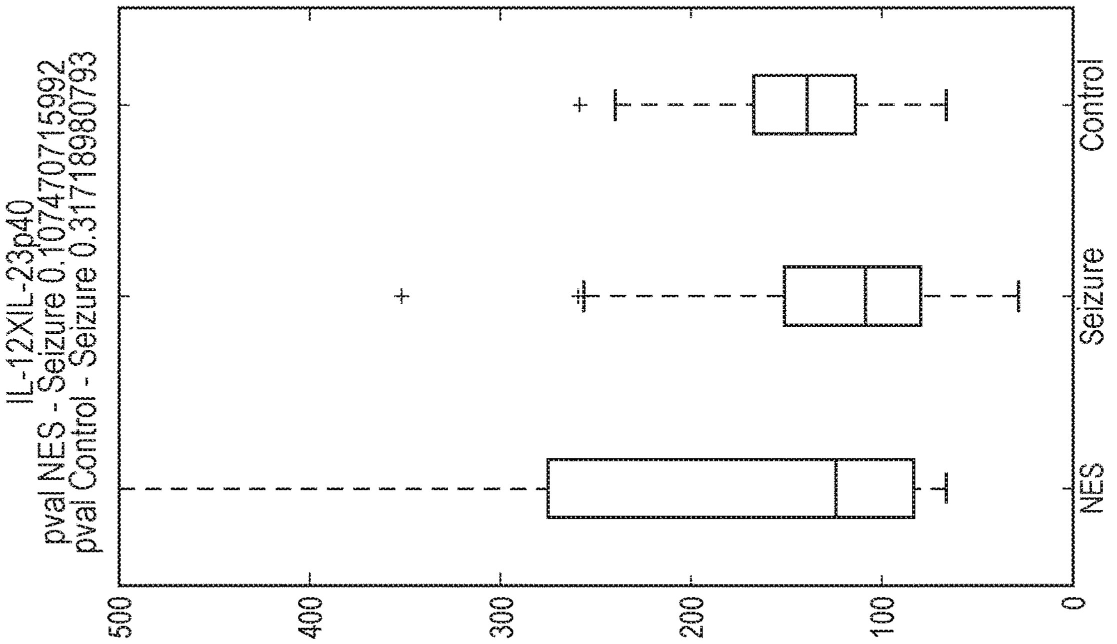
Figure 5Q:
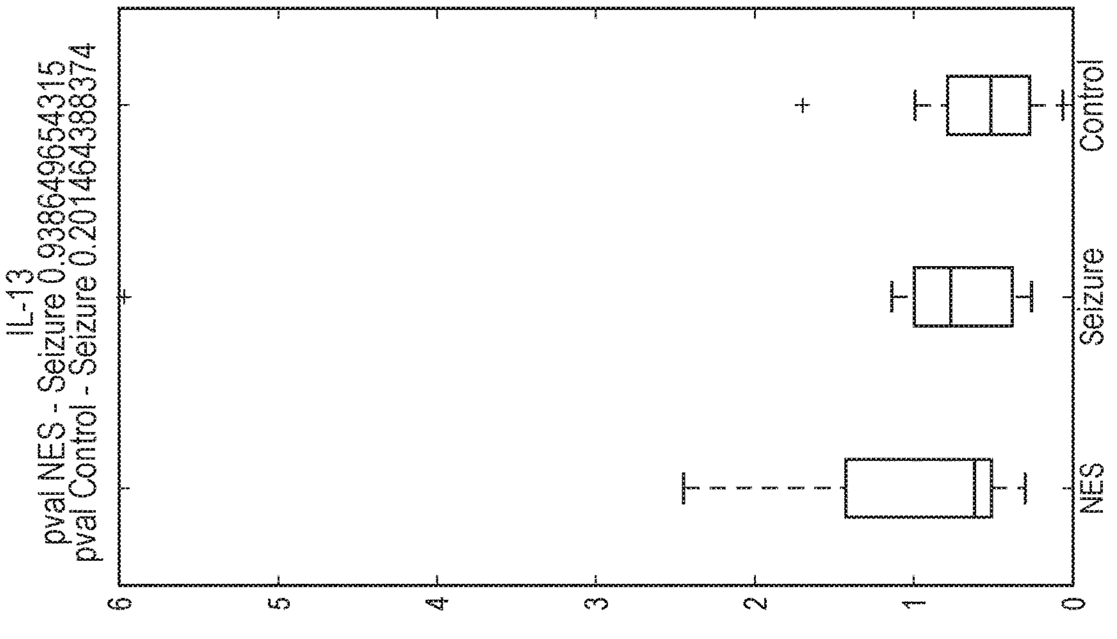
Figure 5S:
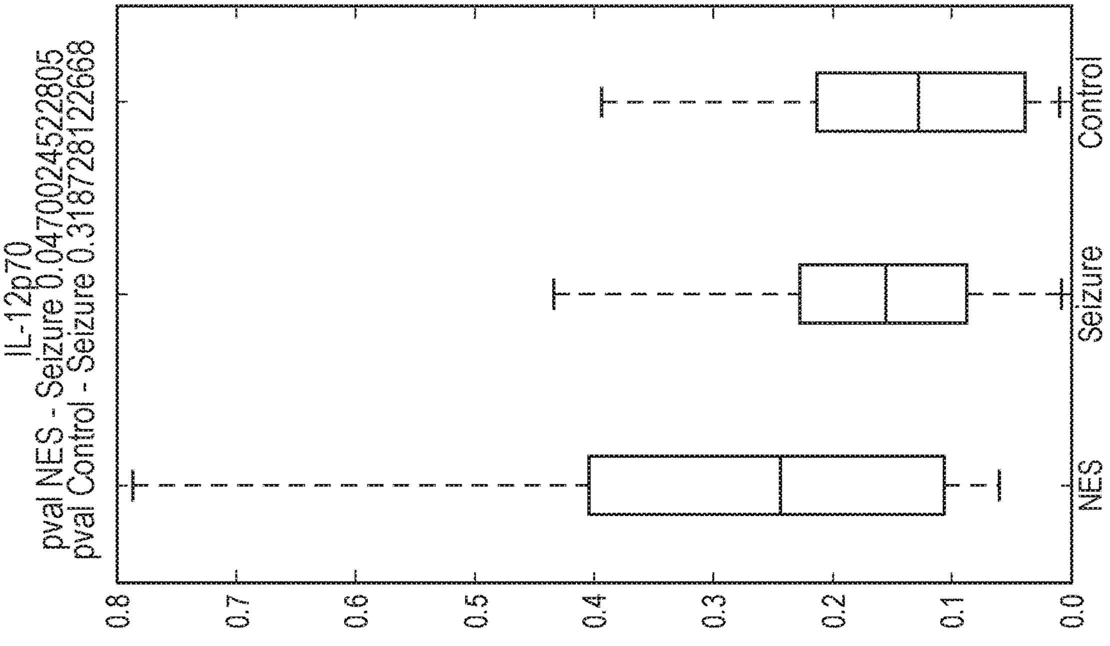
Figure 5T:
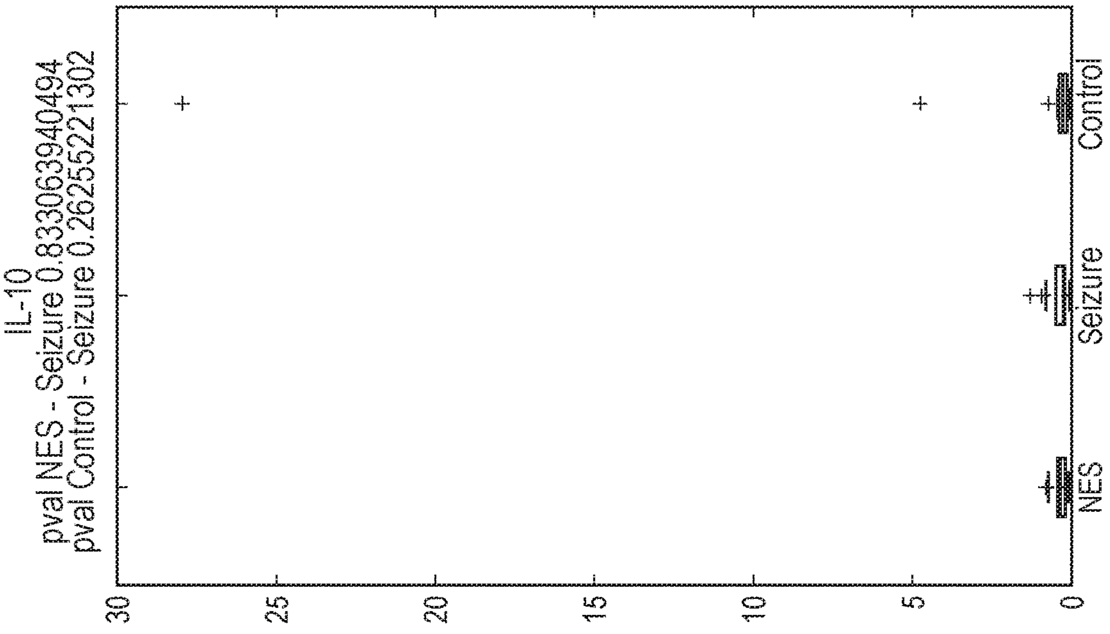
Figure 5U:
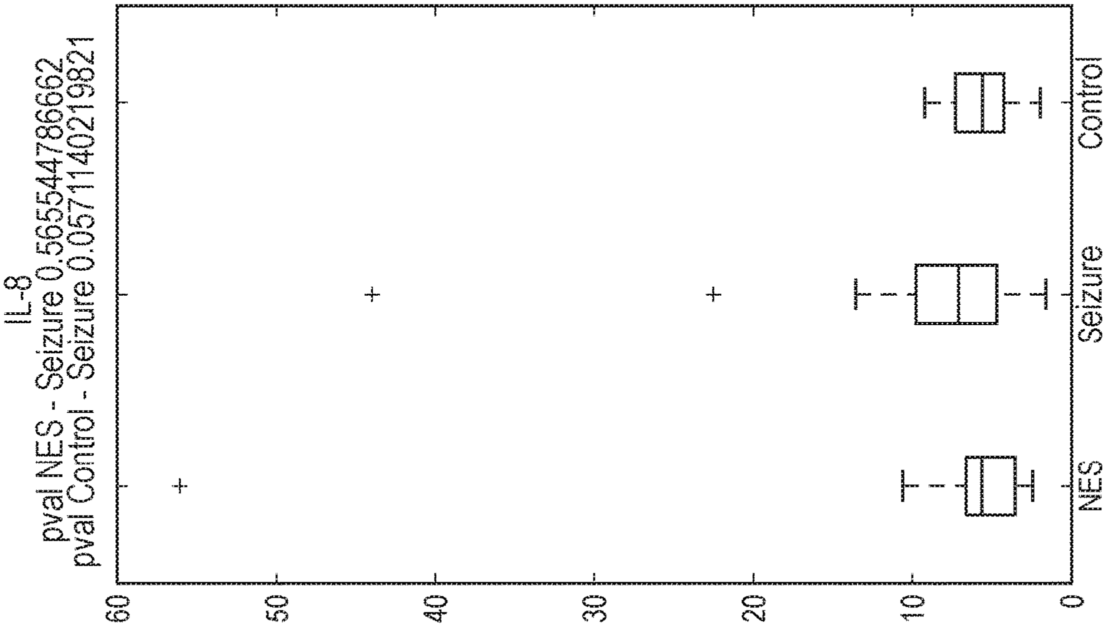
Figure 5V:
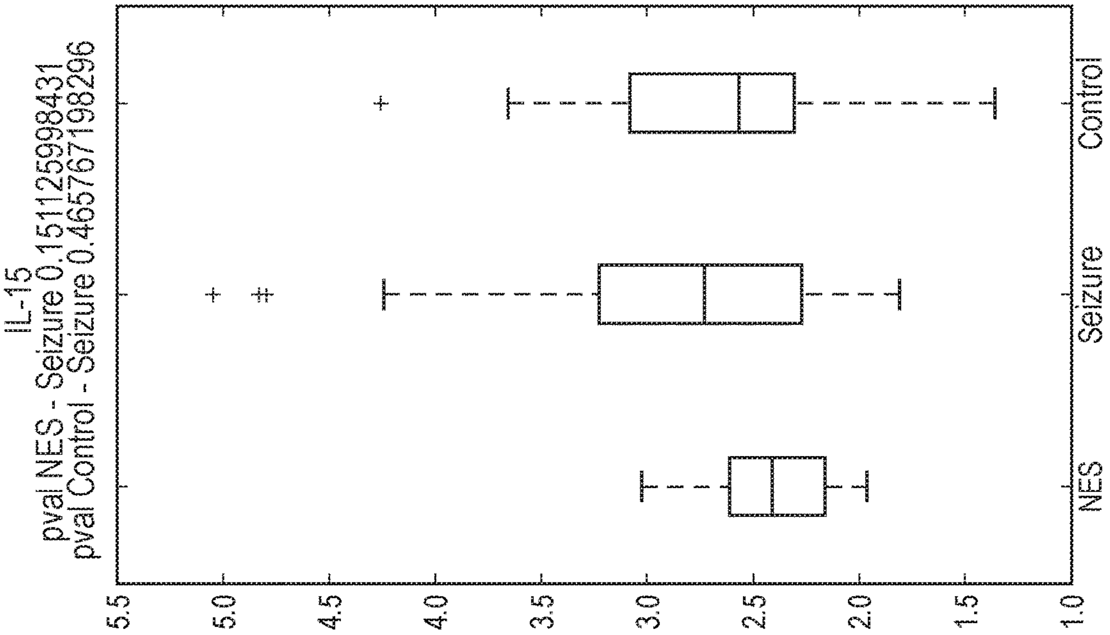
Figure 5X:
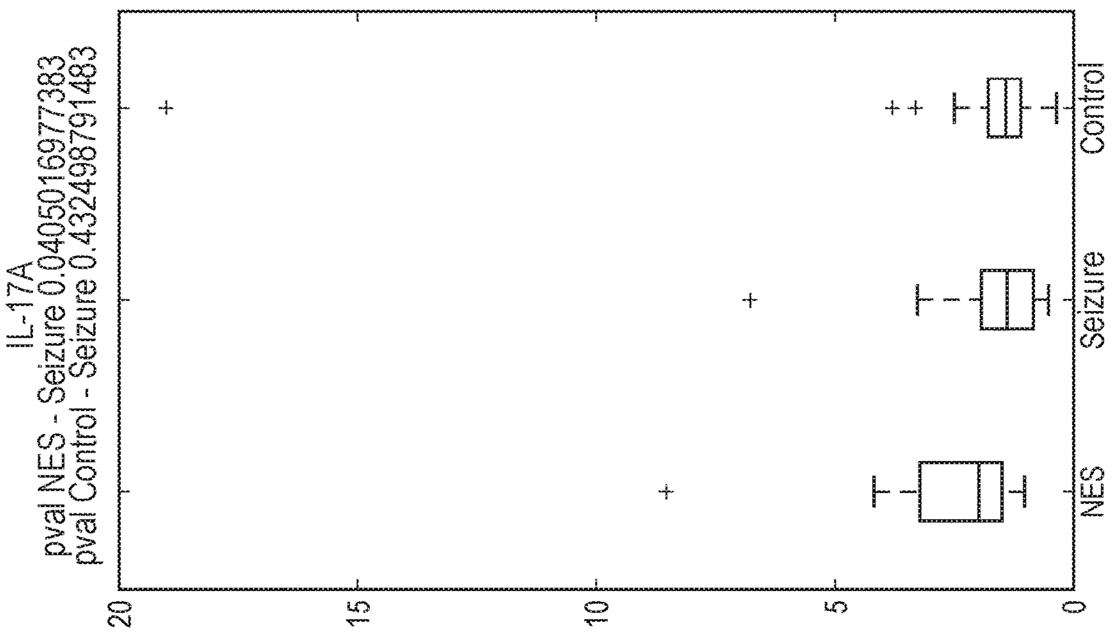
Figure 5W:
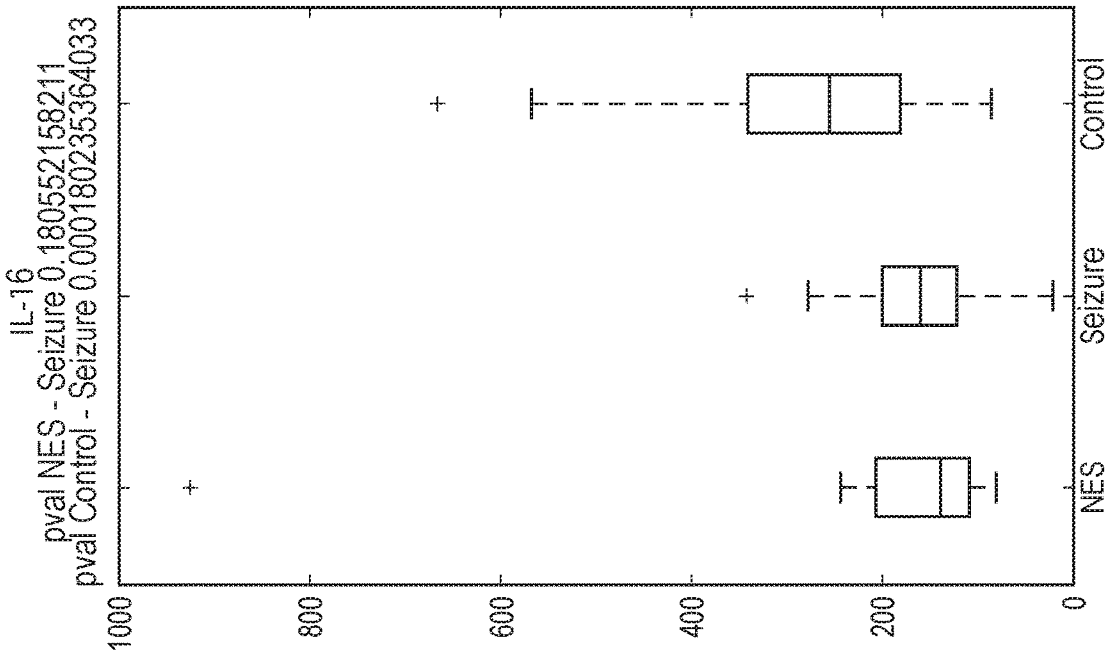
Figure 5Y:
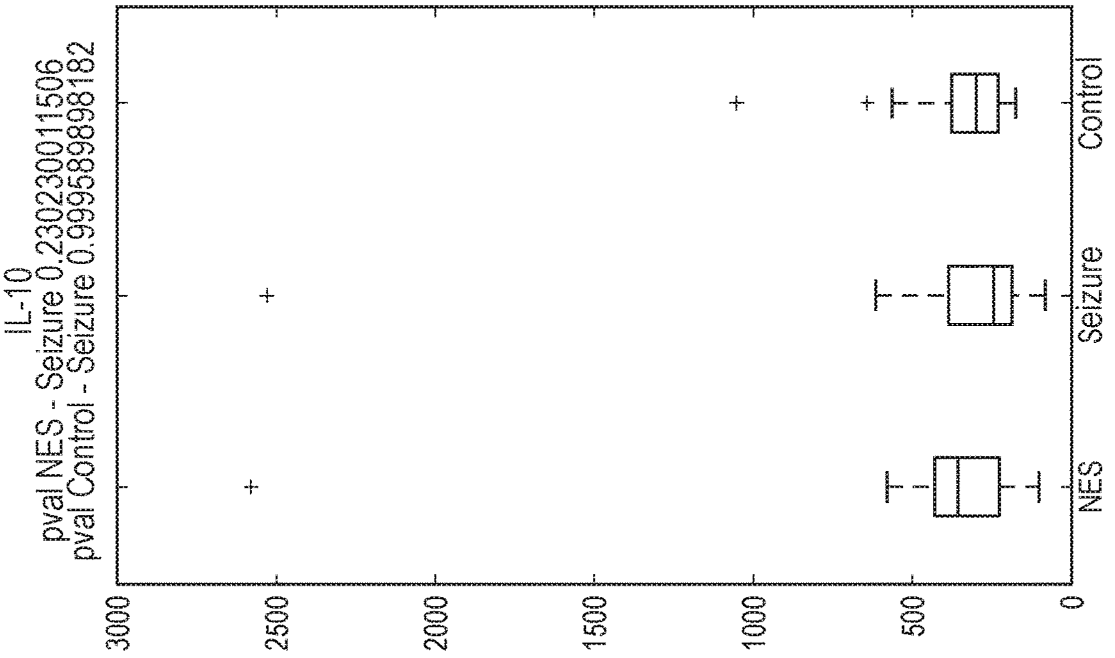
Figure 5Z:
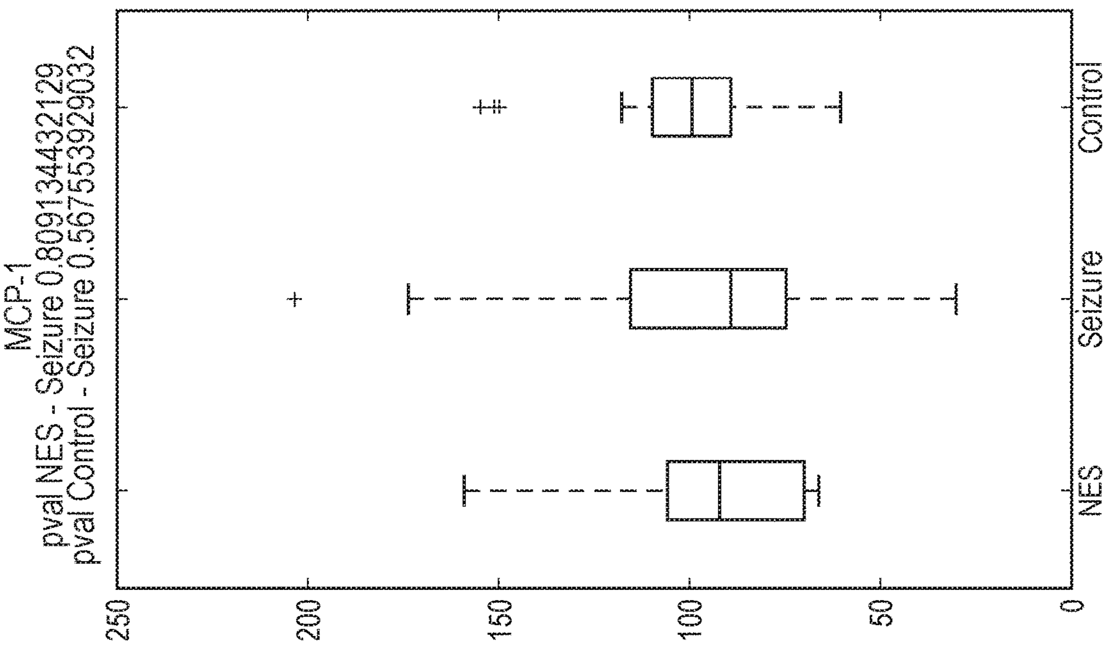
Figure 6A:
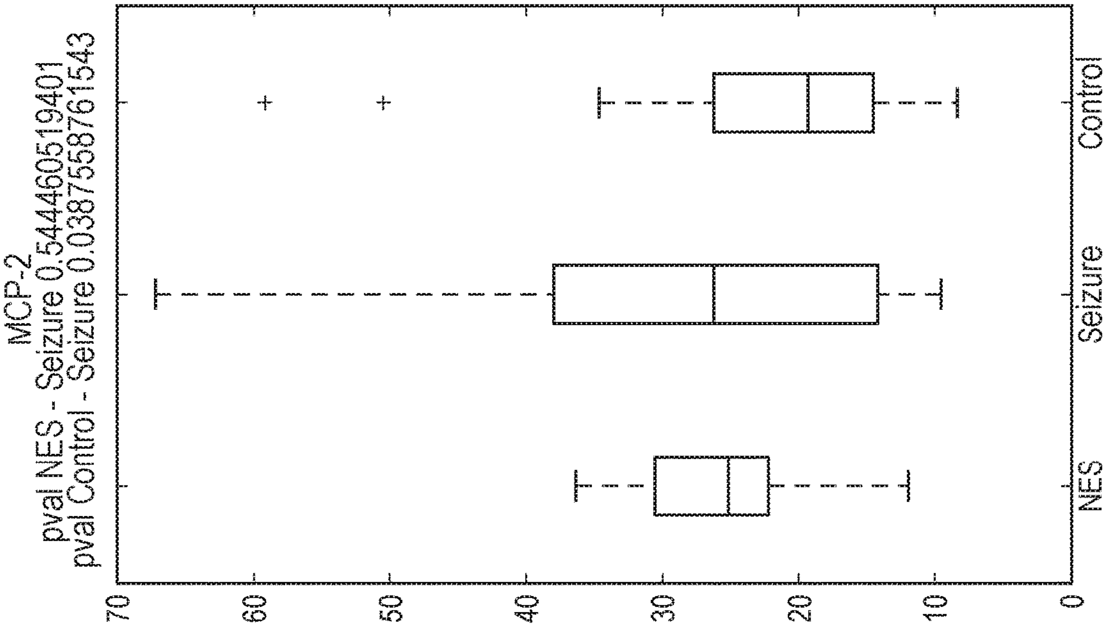
Figure 6B:
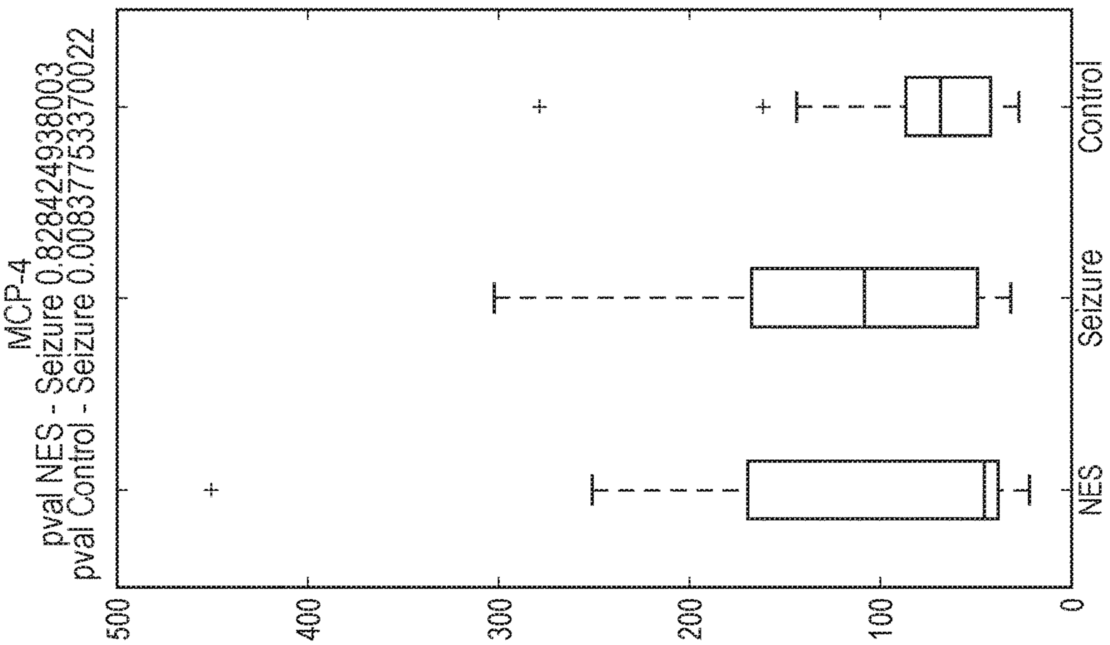
Figure 6C:
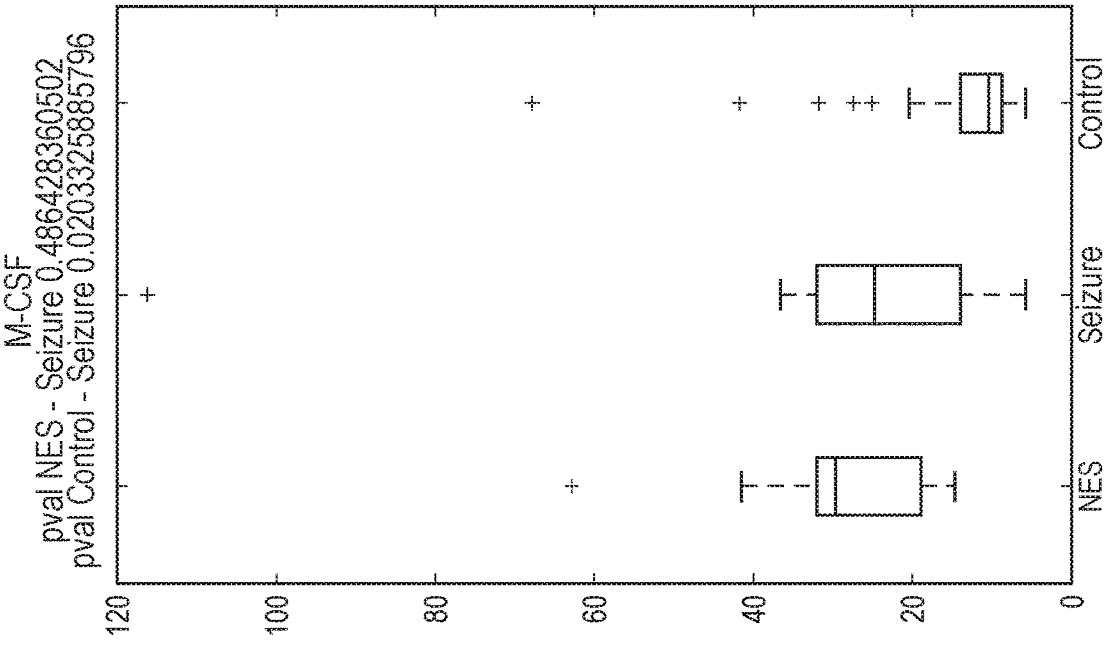
Figure 6D:
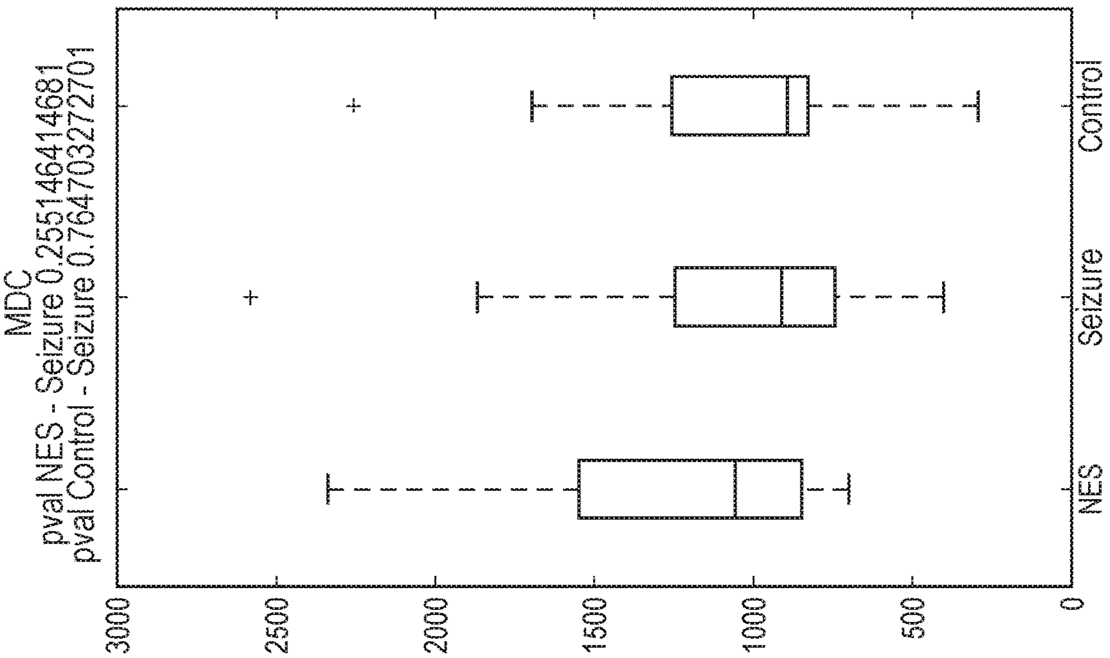
Figure 6E:
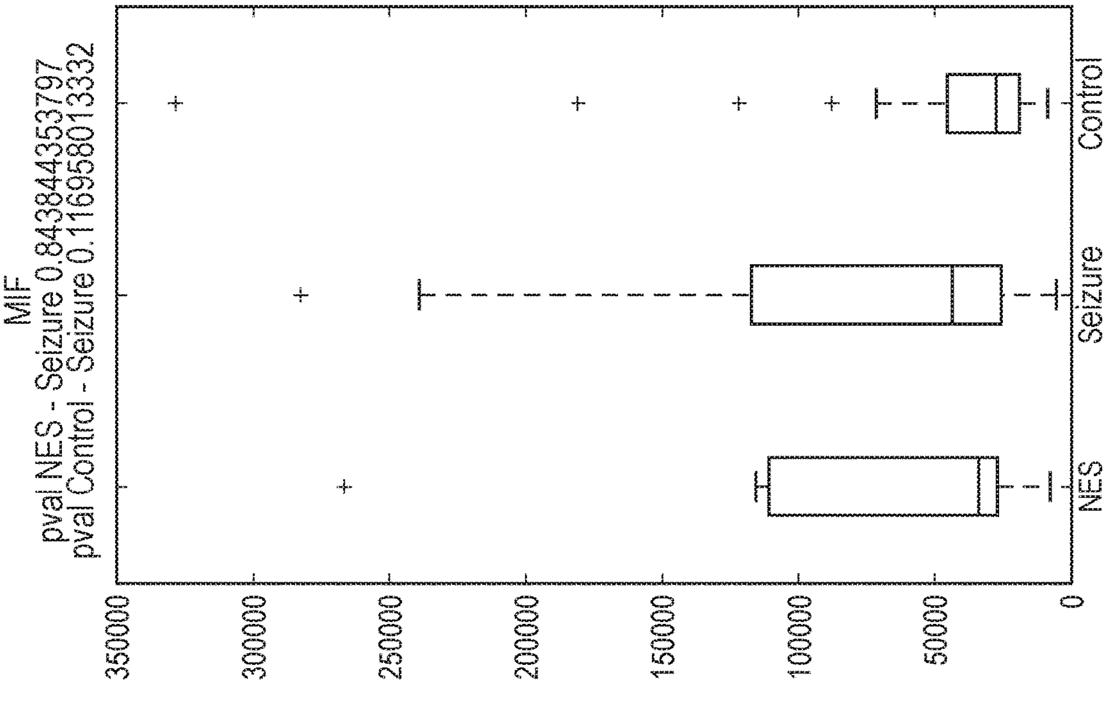
Figure 6F:
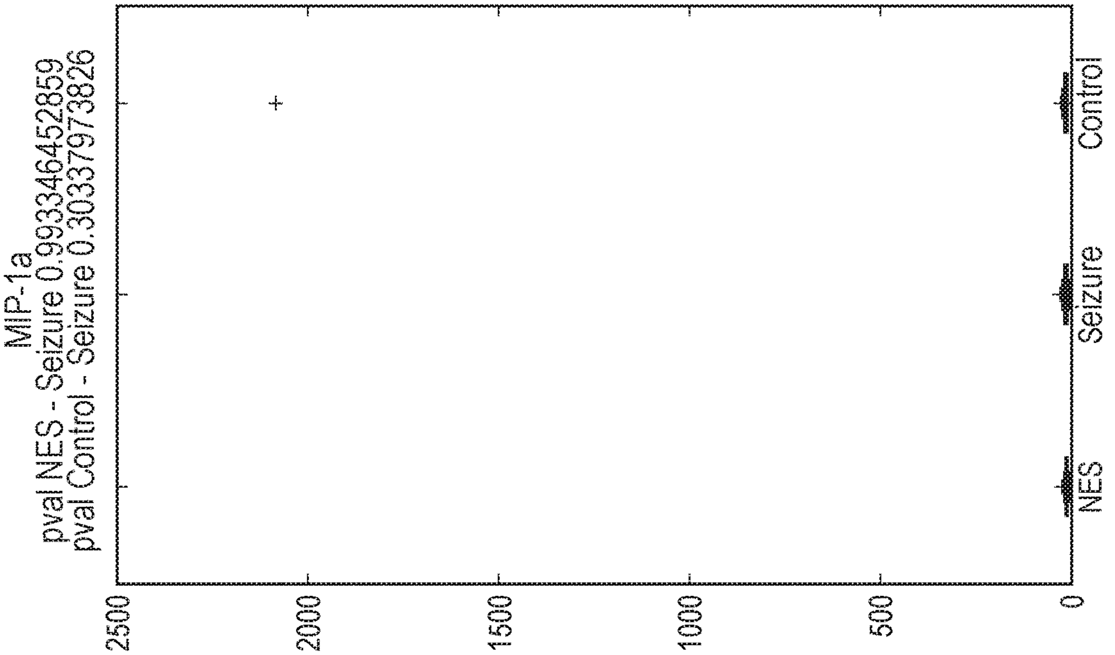
Figure 6H:
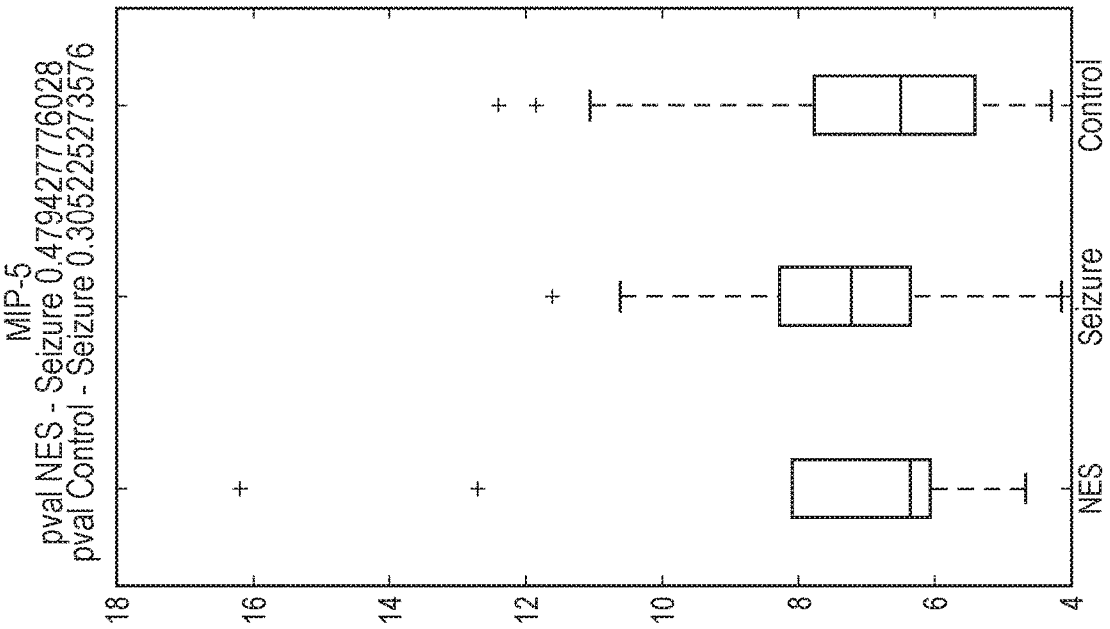
Figure 6G:
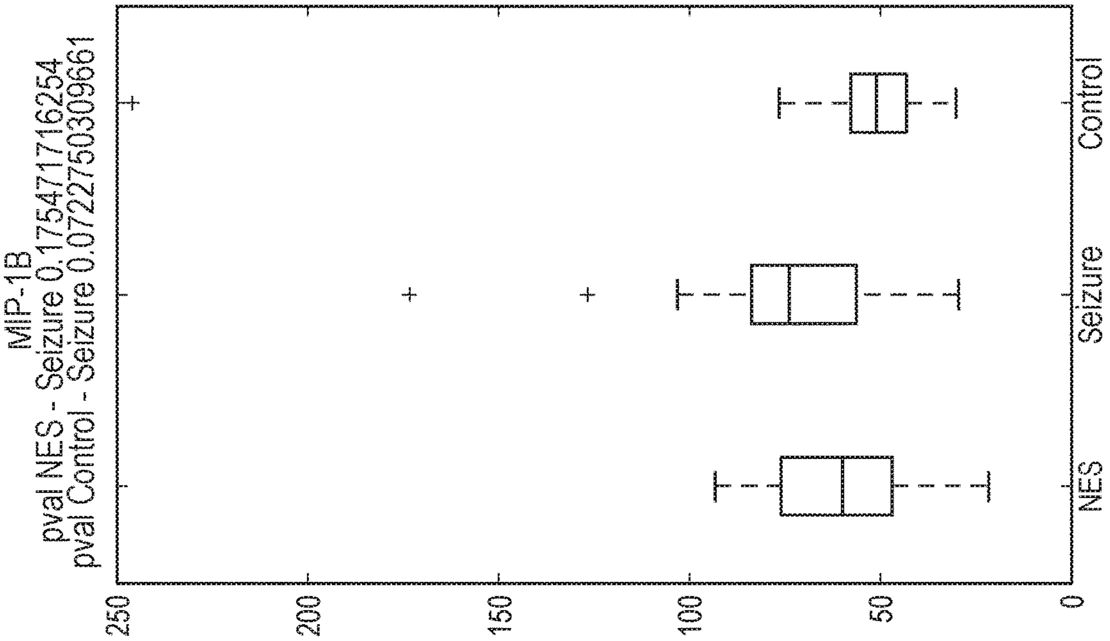
Figure 6I:
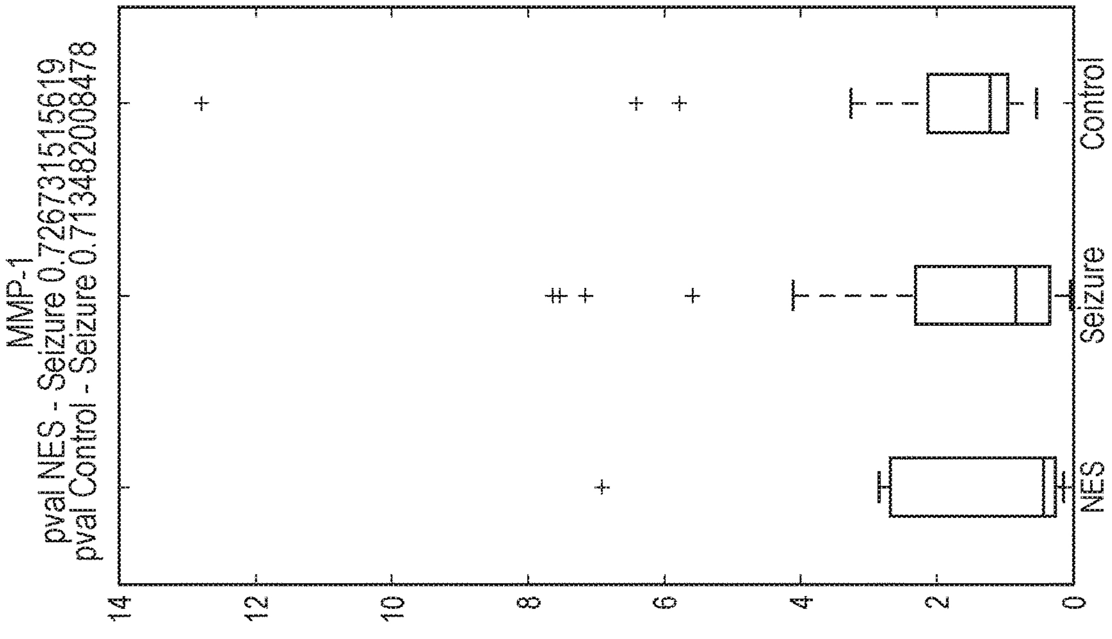
Figure 6J:
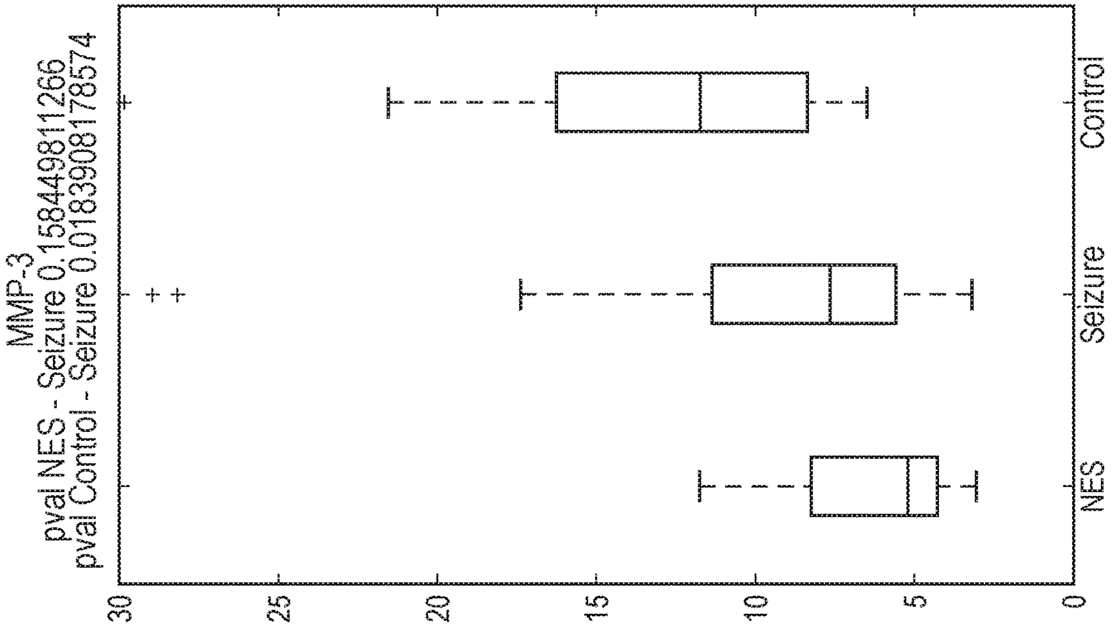
Figure 6L:
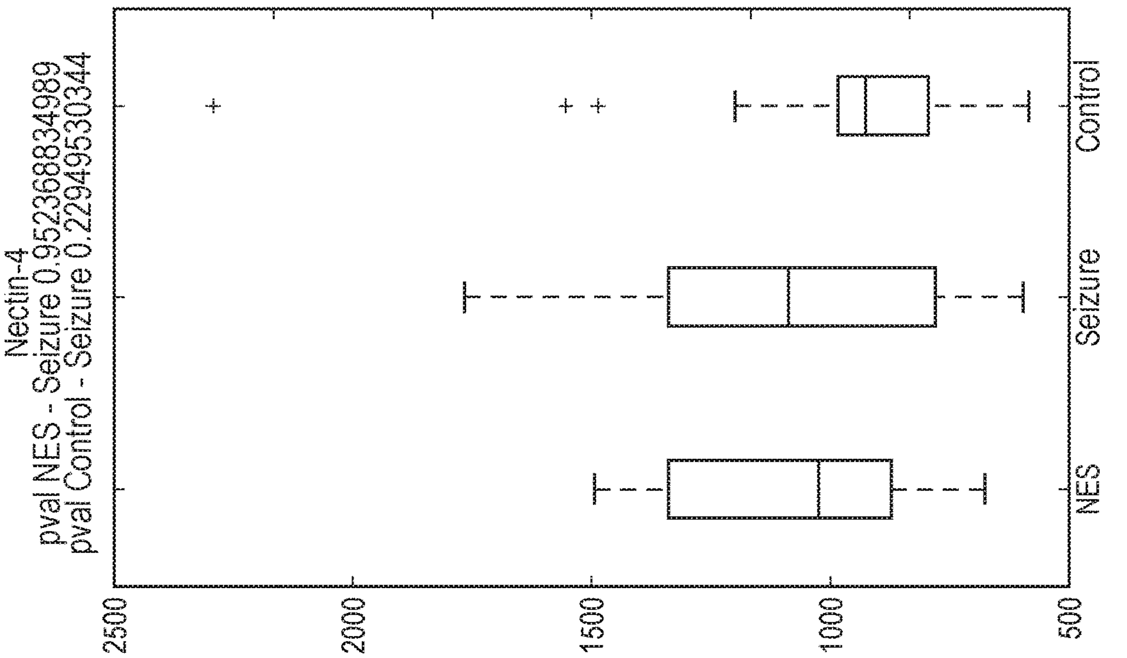
Figure 6K:
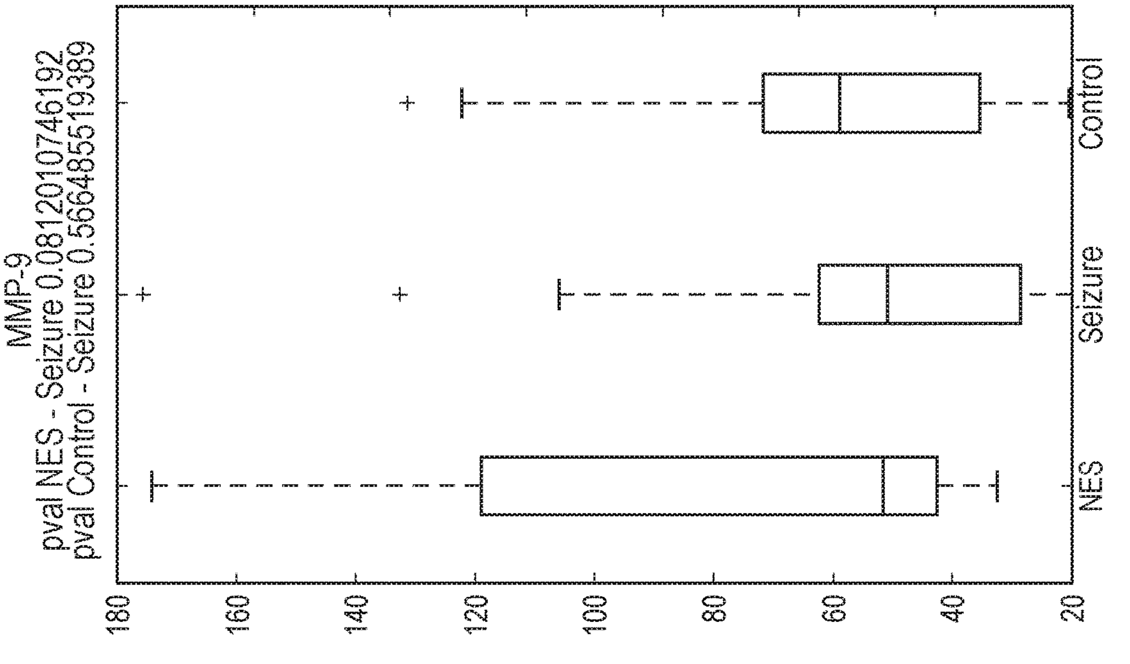
Figure 6N:
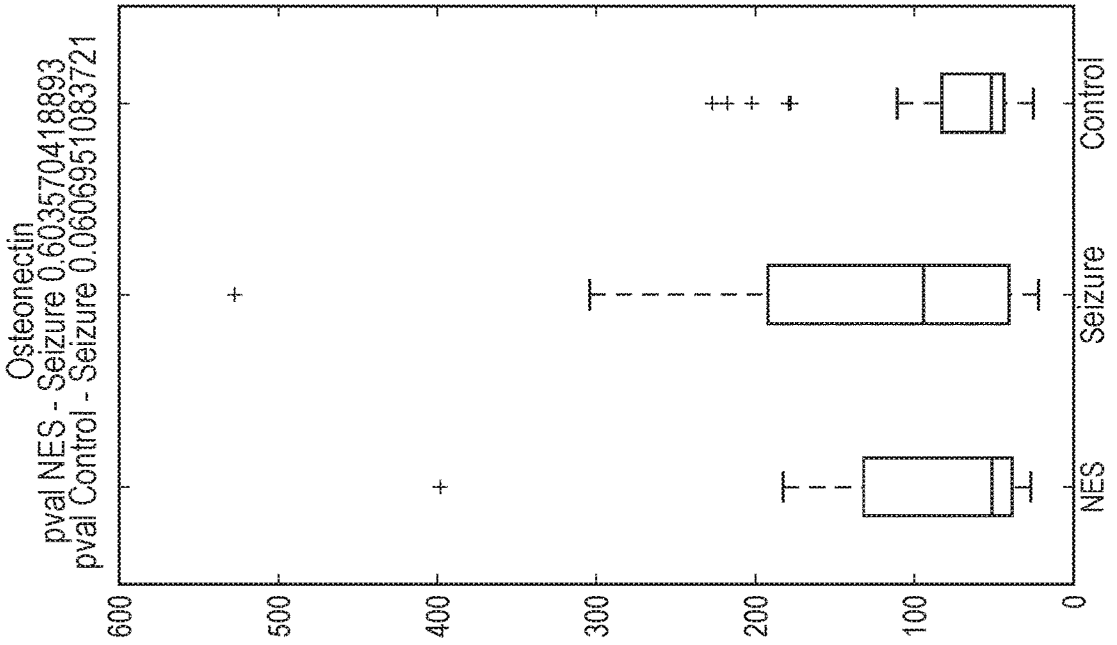
Figure 6M:
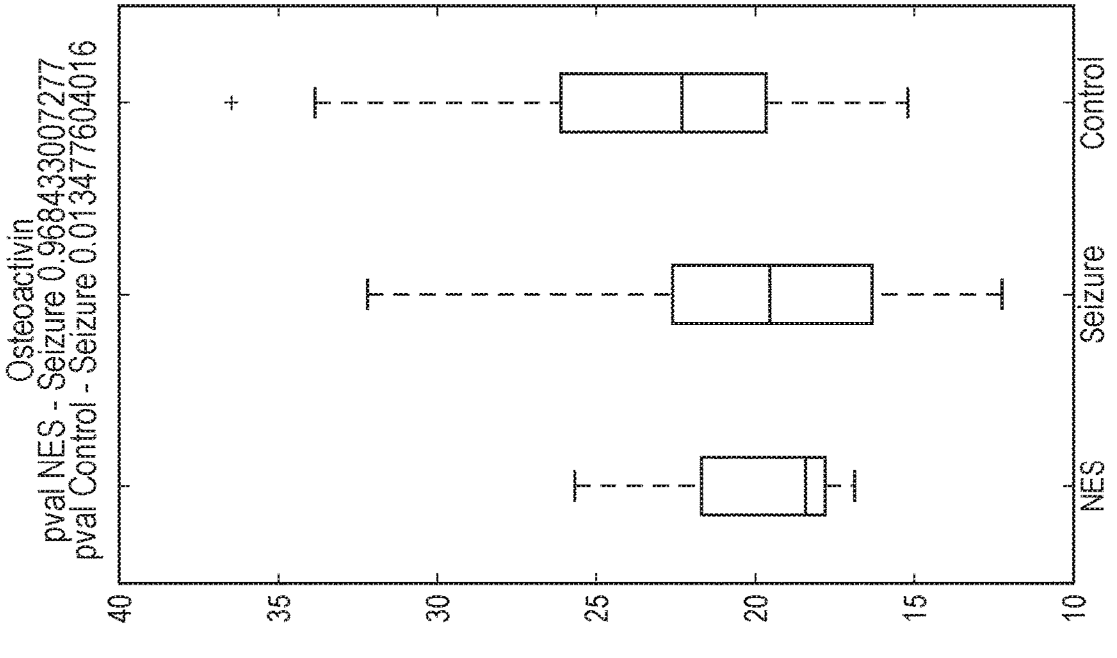
Figure 6O:
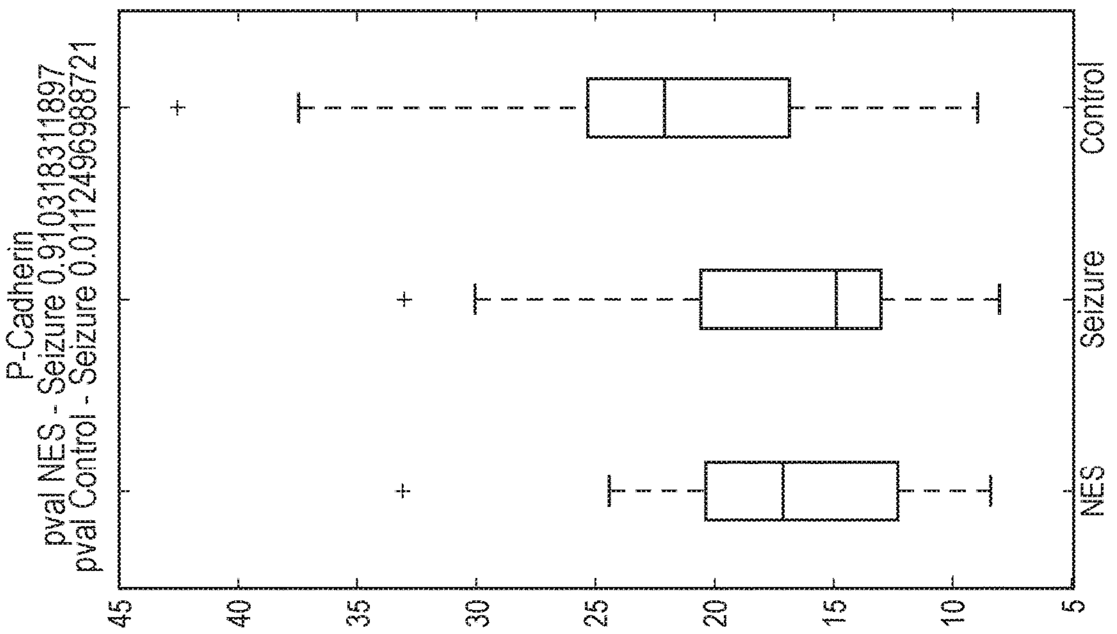
Figure 6P:
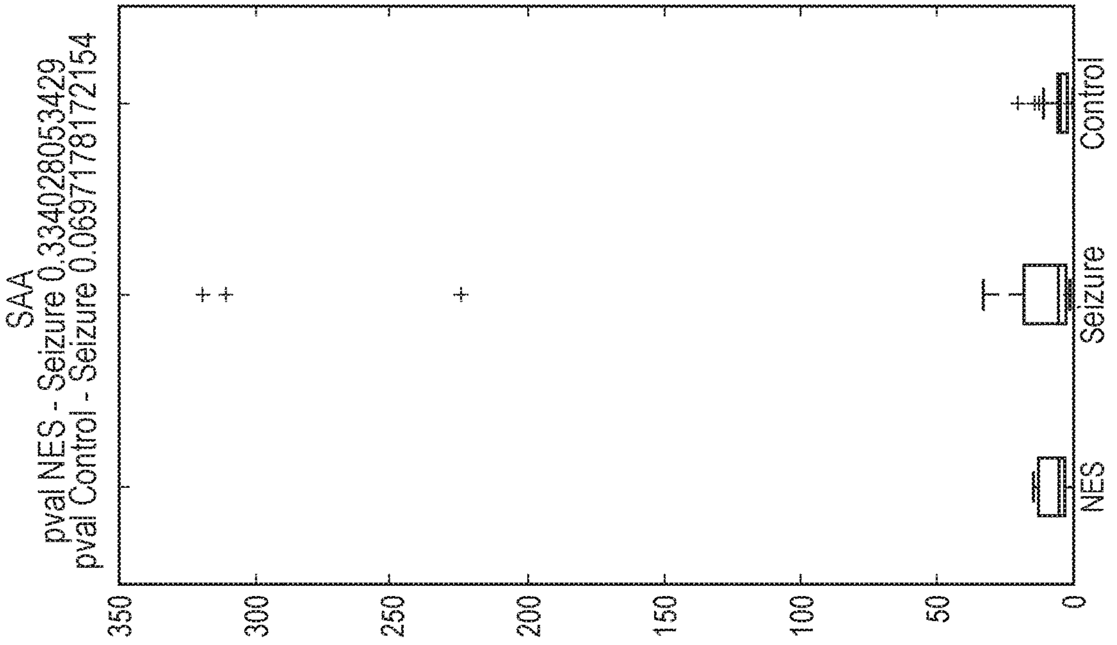
Figure 6Q:
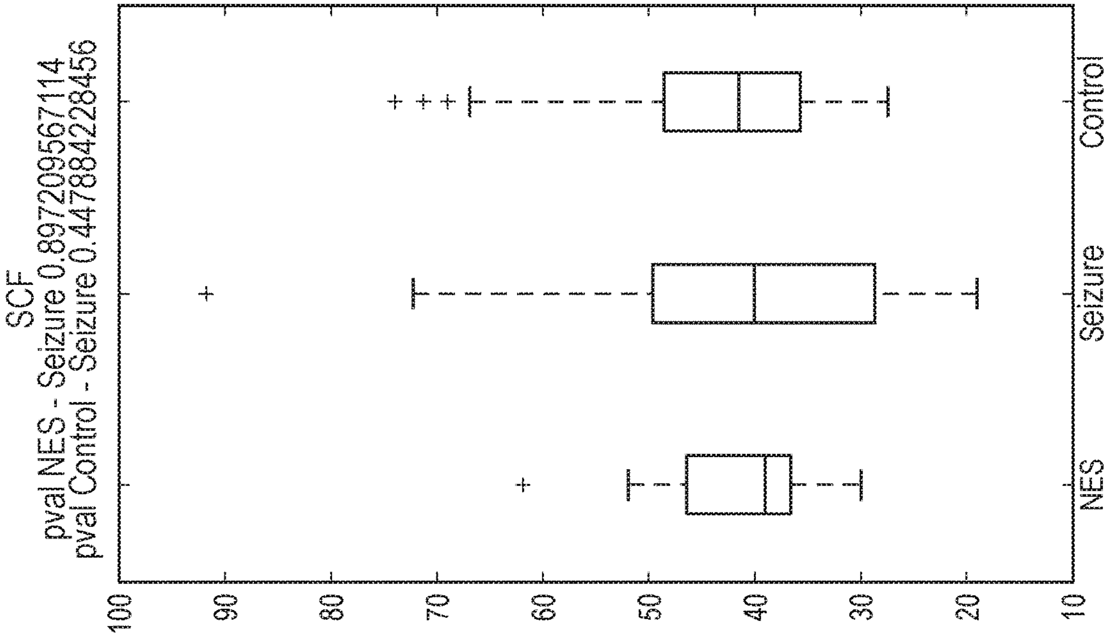
Figure 6R:
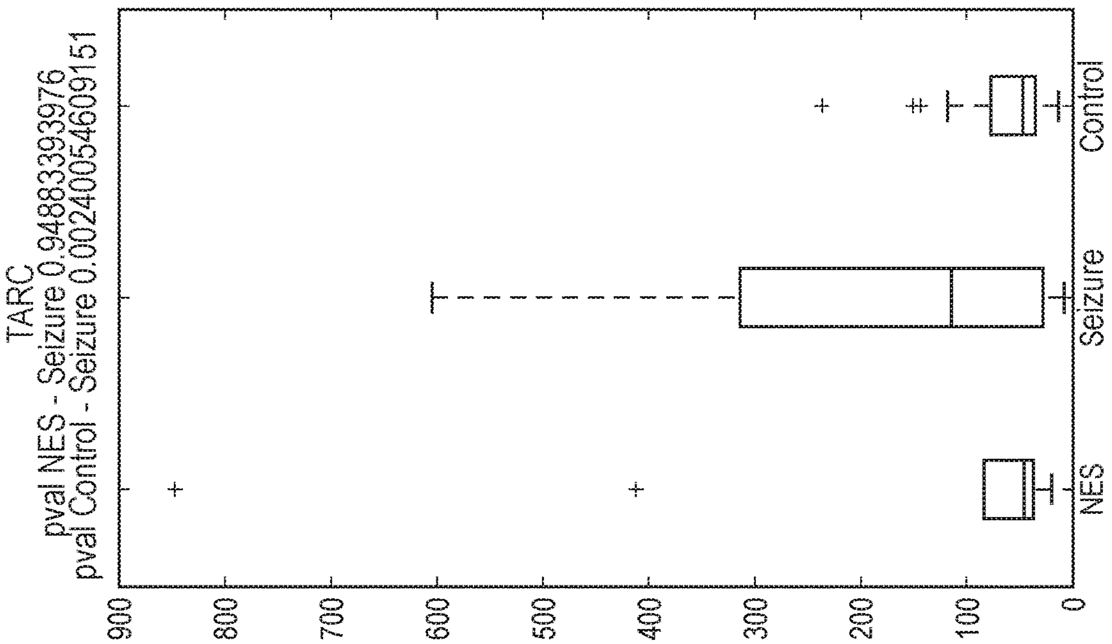
Figure 6S:
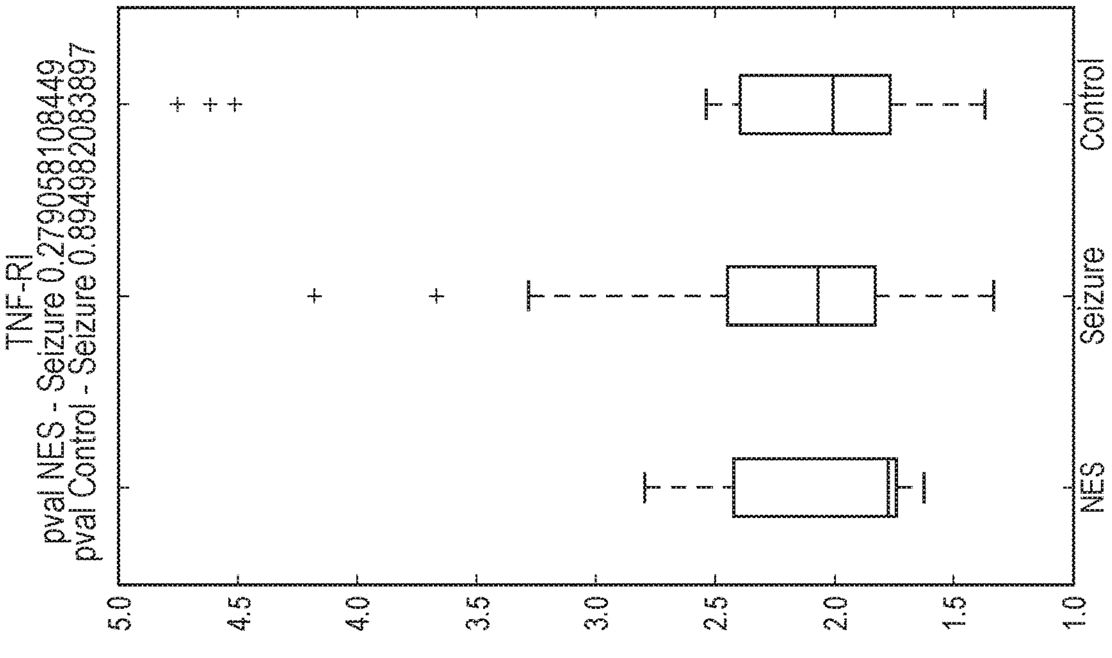
Figure 6T:
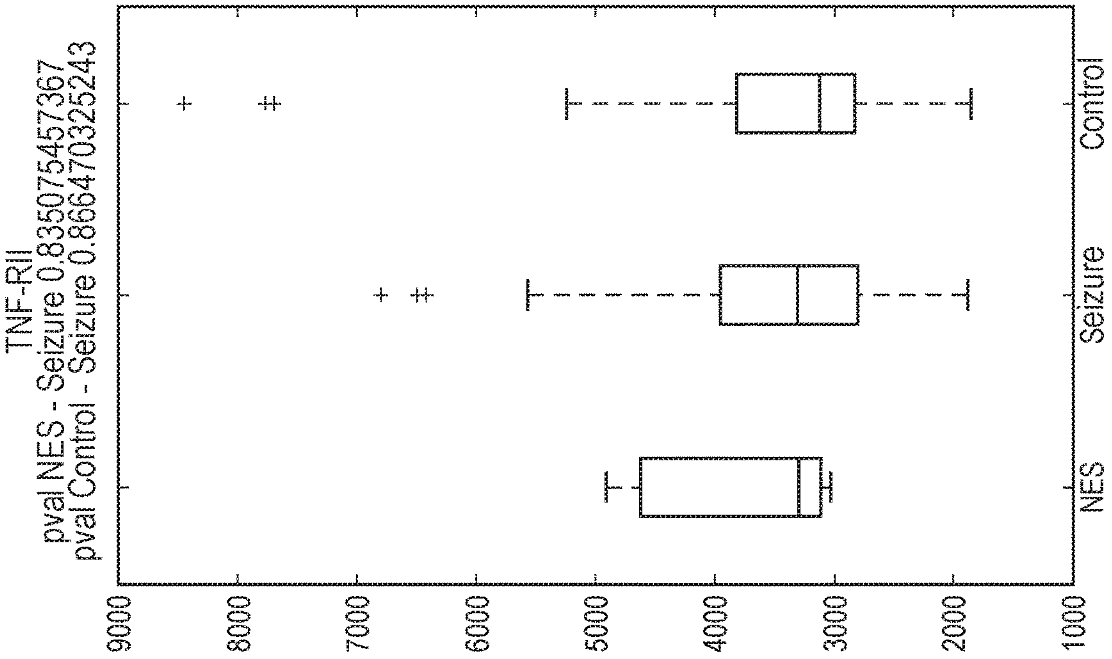
Figure 6U:
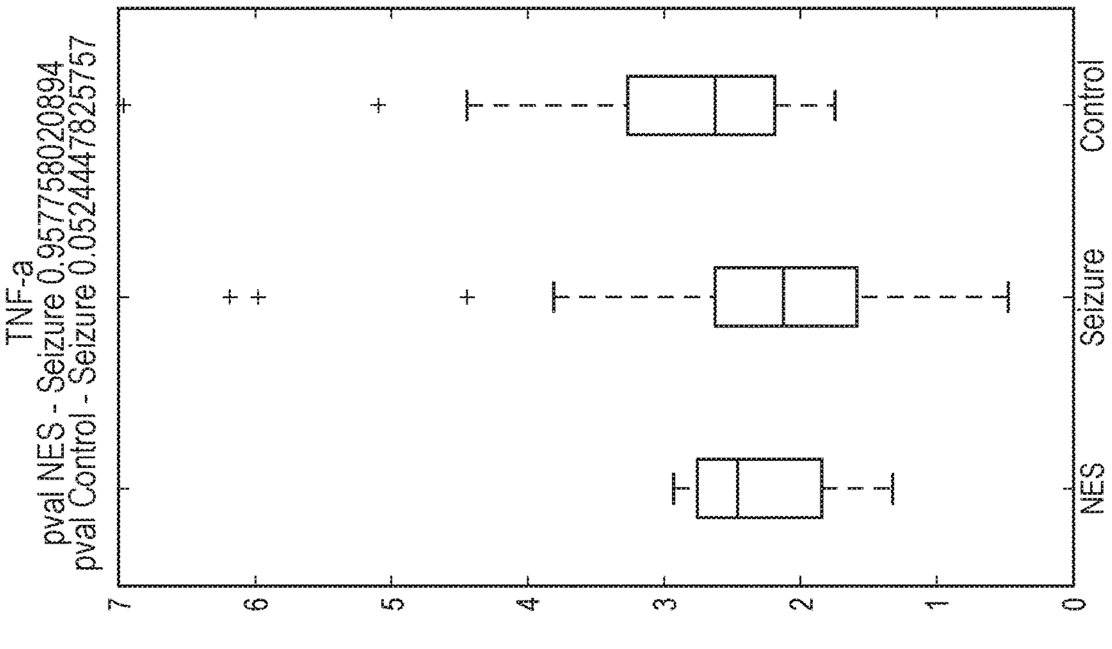
Figure 6V:
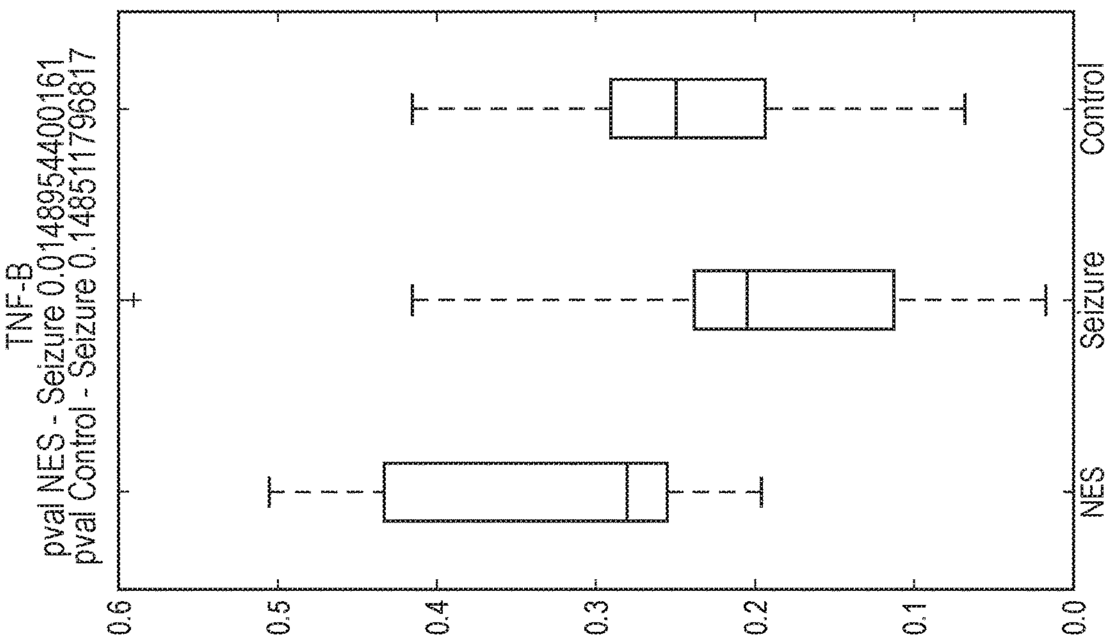
Figure 6X:
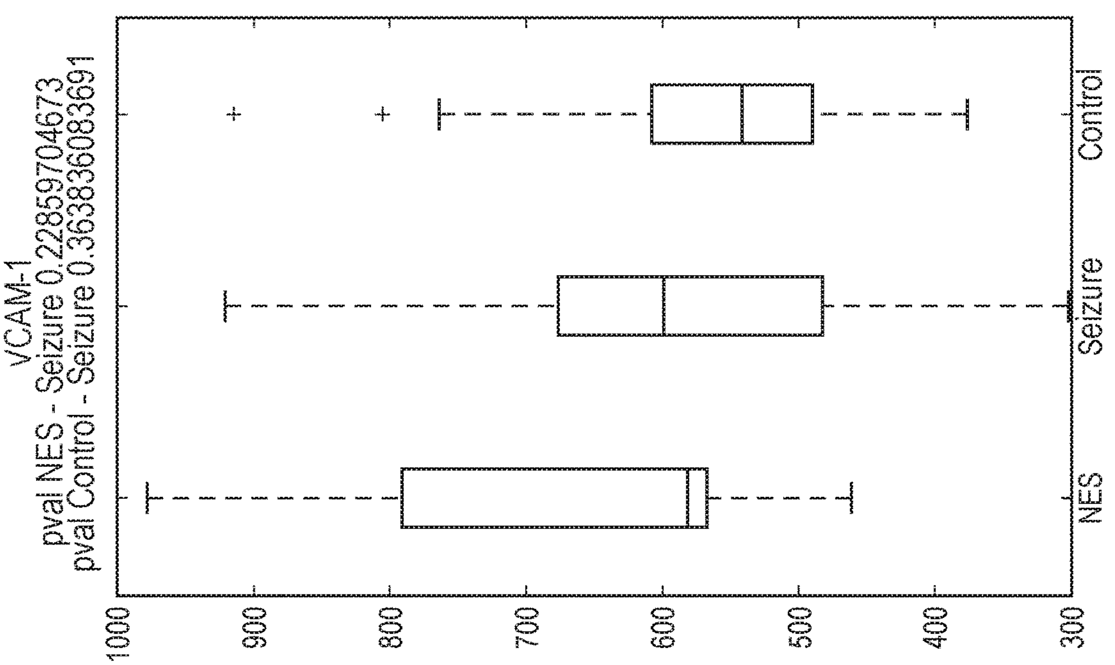
Figure 6W:
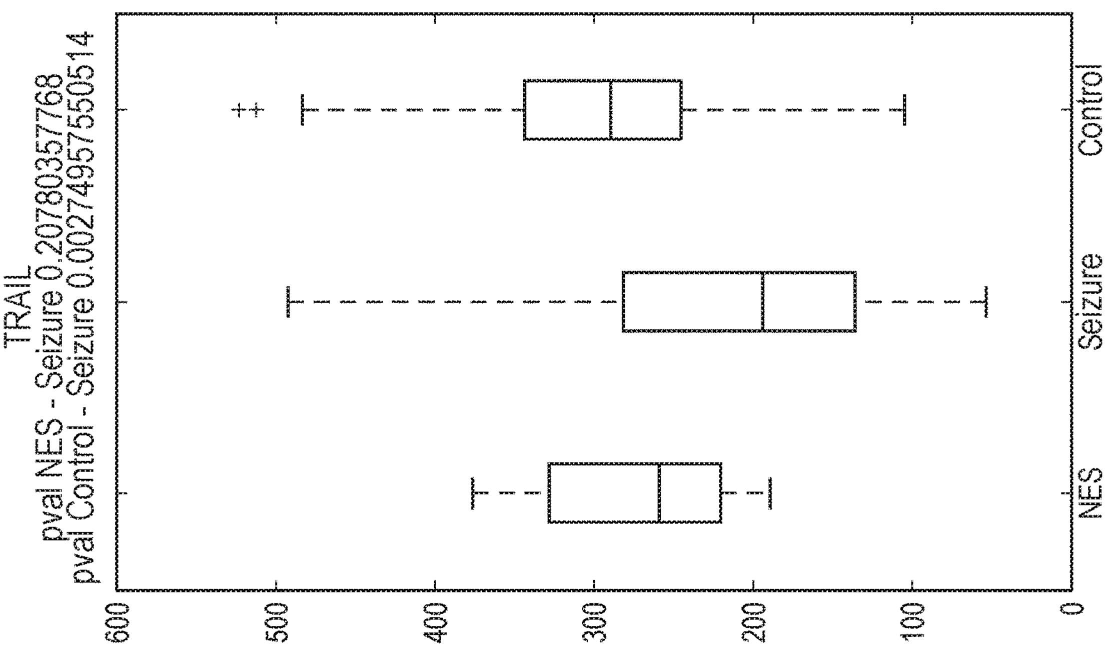
Figure 6Y:
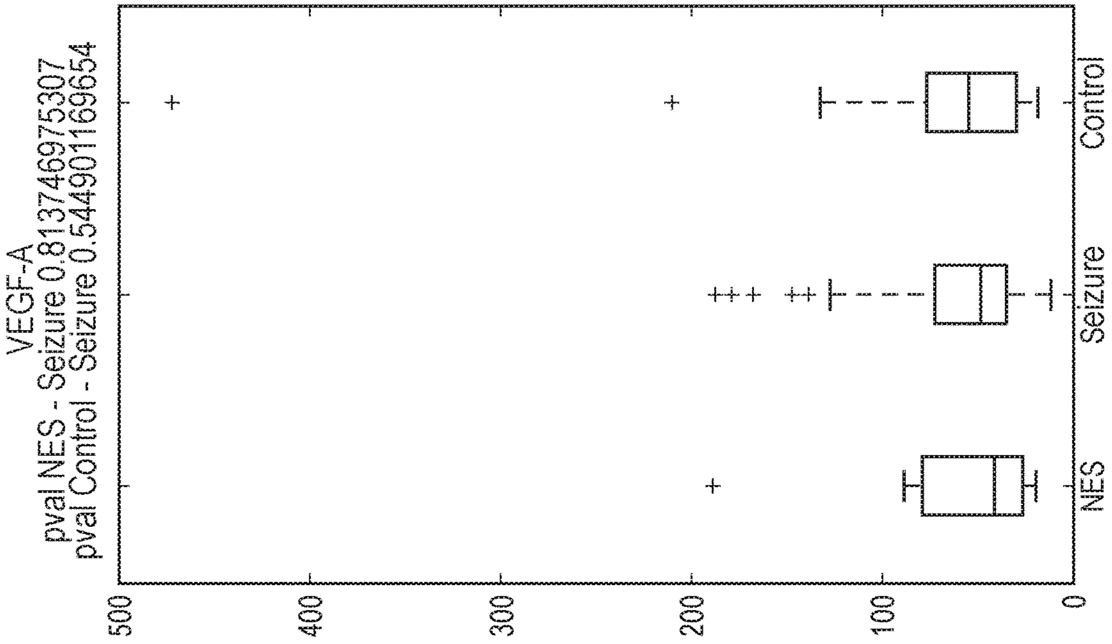

Boxplots comparing sample cohorts are shown in FIGS. 5A to 6Y (FIG. 5A: calbindin; FIG. 5B: CRP; FIG. 5C: cytokeratin-8; FIG. 5D: eotaxin; FIG. 5E: eotaxin-2; FIG. 5F: eotaxin-3; FIG. 5G: GM-CSF; FIG. 5H: ICAM-1; FIG. 5I: IFN-y; FIG. 5J: IL-1a; FIG. 5K: IL-1B; FIG. 5L: IL-2; FIG. 5M: IL-4; FIG. 5N: IL-5; FIG. 5O: IL-7; FIG. 5P: IL-6; FIG. 5Q: IL-13; FIG. 5R: IL-12XIL-23p40; FIG. 5S: IL-12p70; FIG. 5T: IL-10; FIG. 5U: IL-8; FIG. 5V: IL-15; FIG. 5W: IL-16; FIG. 5X: IL-17A; FIG. 5Y: IP-10; FIG. 5Z: MCP-1; FIG. 6A: MCP-2; FIG. 6B: MCP-4; FIG. 6C: M-CSF; FIG. 6D: MDC; FIG. 6E: MIF; FIG. 6F: MIP-1a; FIG. 6G: MIP-1B; FIG. 6H: MIP-5; FIG. 6I: MMP-1; FIG. 6J: MMP-3; FIG. 6K: MMP-9; FIG. 6L: Nectin-4; FIG. 6M: osteoactivin; FIG. 6N: osteonectin; FIG. 6O: p-cadherin; FIG. 6P: SAA; FIG. 6Q: SCF; FIG. 6R: TARC; FIG. 6S: TNF-RI; FIG. 6T: TNF-RII; FIG. 6U: TNF-a; FIG. 6V: TNF-B; FIG. 6W: TRAIL; FIG. 6X: VCAM-1; FIG. 6Y: VEGF-A).

Example 5: NES/NS/PNES Risk Factors

NES/NS/PNES risk factors prevalence in study are shown in Table 3. A literature survey was performed to identify reported NES/NS/PNES risk factors which include: demographics, comorbidities and employment status. Patient clinical records were retrospectively analyzed for confirmation of the above listed risk factors. Note, a standardized method was not used for recording the information and as a result may be underreported

TABLE 3

NES/NS/PNES risk factors in study

| | NES/NS/PNES (n = 9) | Epilepsy (n = 24) |
|---|---|---|
| Unemployment/disability | 11% (n = 1) | 17% (n = 4) |
| Major Depressive Disorder | 44% (n = 4) | 0% |
| Trauma (physical, emotional, sexual; w or w/o PTSD dx) | 67% (n = 2) | 4% (n = 1) |
| Cluster B Personality Disorder | 0% | 0% |
| Polyallergies | 44% (n = 4) | 13% (n = 3) |
| Conversion Disorder (previous dx) | 22% (n = 1) | 4% (n = 1) |
| Dependent Personality Disorder | 0% | 0% |
| Fibromyalgia | 0% | 0% |
| Female (sex) | 78% (n = 7) | 67% (n = 16) |

Example 6: Prevalence of NES/NS/PNES Risk Factors

Prevalence of NES/NS/PNES Risk Factors are shown in Table 4 and FIG. 7.

TABLE 4

| Prevalence of NES/NS/PNES Risk Factors | | |
|---|---|---|
| | NES/NS/PNES (n = 9) | Epilepsy (n = 24) |
| 1 + Risk Factors | 100% (n = 9) | 75% (n = 18) |
| 2 + Risk Factors | 89% (n = 8) | 25% (n = 6) |
| 3 + Risk Factors | 63% (n = 5) | 4% (n = 1) |
| 4 Risk Factors | 25% (n = 2) | 0% |

Example 7: Diagnostic Algorithm-Sum of NES/NS/PNES Risk Factors

Diagnostic Algorithm-Sum of NES/NS/PNES risk factors are shown in FIG. 6. The number of risk factors confirmed for each patient was summed and used to create a diagnostic algorithm using a logistical regression.

Example 8: Diagnostic Algorithm-IL-16, ICAM-1, TRAIL

Diagnostic Algorithm-IL-16, ICAM-1, TRAIL are shown in FIG. 7. Plasma protein concentrations were determined, for IL-16, ICAM-1 and TRAIL using a multiplexed ELISA and combined into a diagnostic algorithm using a logistical regression. Note, 31 of 32 ES samples used to refine the algorithm. Insufficient sample was available to test TRAIL for one sample.

Example 9: Diagnostic Algorithm-IL-16, ICAM-1, TRAIL, Sum of Risks

Diagnostic Algorithm-IL-16, ICAM-1, TRAIL, Sum of risks are shown in FIG. 8. Protein concentrations of IL-16, ICAM-1 and TRAIL and the sum of a patients NES/NS/PNES risk factors were combined using a logistical regression to generate a diagnostic algorithm. Note, 31 of 32 ES samples used to refine the algorithm. Insufficient sample was available to test TRAIL for one sample.

Example 10: Diagnostic Algorithm-IL-16, ICAM-1, TRAIL, MIP-1β

Diagnostic Algorithm-IL-16, ICAM-1, TRAIL, MIP-1β are shown in FIG. 9. Protein concentrations of concentrations of IL-16, ICAM-1, TRAIL and MIP-1β were combined using a logistical regression to generate a diagnostic algorithm. Note, 31 of 32 ES samples used to refine the algorithm. Insufficient sample was available to test TRAIL for one sample.

Example 11: Diagnostic Algorithm-IL-16, ICAM-1, TRAIL, MIP-1β, Sum of Risks

Diagnostic Algorithm-IL-16, ICAM-1, TRAIL, MIP-1β, Sum of risks are shown in FIG. 10. Protein concentrations of IL-16, ICAM-1, TRAIL and MIP-1β and the sum of a patients NES/NS/PNES risk factors were combined using a logistical regression to generate a diagnostic algorithm. Note, 31 of 32 ES samples used to refine the algorithm. Insufficient sample was available to test TRAIL for one sample.

Example 12: Differentiating Psychogenic Non-Epileptic Seizure and Epileptic Seizure in the Presence of Co-Occurring Inflammation Associated Disease A diagnostic algorithm that stratifies psychogenic non-epileptic seizures (PNES) from epileptic seizures (ES) was identified. Samples were collected from patient suffering EEG confirmed ES (n=31) and PNES (n=25) events. Samples were analyzed using a 51-protein panel multiplexed ELISA run on the MSD platform. Proteins were selected from immune response associated markers. Difference in protein concentrations between cohorts were analyzed using standard descriptive statistic methods. An exhaustive search (i.e. all combinations) of 2 through 6 protein combinations were used to refine a diagnostic algorithm and the top performing algorithm was selected. The performance of the algorithm in the context of co-occurring inflammation associated disease or NSAID use was analyzed by reviewing the medical records of the patients used to refine the algorithm Example 13: Biomarker Identification A total of 615 samples was collected from 240 outpatients and 131 inpatients. Subjects were males and females, 18-82 years of age, representing multiple races and ethnicities (e.g., African American, Hispanic), and cognitively able to give informed consent. Inpatients undergoing continuous video EEG monitoring; some had a longstanding history of undiagnosed events, often presumed to be seizures though never proven, while others had very recent onset events. Many (100/131) were being treated with anti-epileptic drugs. Asked to give a single sample of blood each morning during their admission. Blood samples from one minute to over 72 hours post-event were collected for analysis and spun to isolate plasma Outpatients did not yet have a diagnosis of their events as either epileptic or non-epileptic. Consisted of a heterogeneous group, with some patients having prior brain trauma, others with hippocampal sclerosis, others with normal brain imaging, and one with idiopathic generalized epilepsy. Gave a single sample of blood at their first visit. To test the hypothesis that seizure and/or epilepsy potentiates a measurable change in peripheral circulating biomarkers sample that were drawn within 24 hours of from patients with EEG confirmed epileptic seizure (n=31) or psychogenic non-epileptic seizure (n=25) were selected for testing.

TABLE 5

| Cohort Demographics | | | |
|---|---|---|---|
| | | ES | PNES |
| | Patients | 23 | 24 |
| | Samples | 31 | 25 |
| age | <18 | 0 | 0 |
| | 18-29 | 0.217391 | 0.25 |
| | 30-44 | 0.347826 | 0.291667 |
| | 45-59 | 0.304348 | 0.333333 |
| | >59 | 0.130435 | 0.125 |
| Gender | Male | 0.347826 | 0.208333 |
| | Female | 0.652174 | 0.791667 |

TABLE 5-continued

| Cohort Demographics | | | |
|---|---|---|---|
| | | ES | PNES |
| | Patients | 23 | 24 |
| | Samples | 31 | 25 |
| Race | White | 0.608696 | 0.541667 |
| | Black | 0.26087 | 0.333333 |
| | Asian | 0 | 0 |
| | Unknown | 0.130435 | 0.125 |
| # of AEDs | 0 | 0.043478 | 0.291667 |
| | 1 | 0.26087 | 0.5 |
| | 2 | 0.347826 | 0.083333 |
| | 3+ | 0.347826 | 0.125 |
| Seizure Classification | Focal | 87 | |
| | Generalized | 13 | |
| Seizure Frequency (/week) | | 5.62 | |

51 proteins were identified that span the realm of adaptive and innate immunity and act to modulate inflammation were identified for a targeted proteomic screen. (FIG. 15). As shown in FIG. 16, the protein concentrations of the ES and PNES cohorts were compared for each protein tested using the Student's t-test, Kolmogorov-Smirnov test and the Mann-Whitney U test.

An exhaustive search was performed to identify the combination of proteins, that when integrated into a diagnostic algorithm, most efficiently stratifies ES and PNES Optimization criteria include: leave one out (LOO) cross validation, average AUC for LOO algorithms, Wald Test P values. All proteins should have a significant contribution. Log likelihood ratio p value and pseudo R^2 were considered in the case that multiple algorithms satisfy the above. All combinations of 2 through 6 proteins were tested, total of 1.15 million combinations were tested. The search identified a combination of 4 proteins: TRAIL, ICAM-1, MCP-2, TNF-R1 (See Table 6). FIG. 17A and. 17B illustrate a comparison of protein concentrations/protein response fingerprint. FIGS. 18A-18C: threshold 62.0, AUC 0.9387, 26 2, 5 23, sensitivity 0.838709677419, specificity 0.92, LOO % Correct 82.1.

The observed protein responses are specific to epilepsy. In the case of generalized inflammation one would expect protein concentrations to increase while in the context of seizure both increases and decreases are observed.

TABLE 6

| Logit Regression Results | | | |
|---|---|---|---|
| Dep. Variable: | diagnosis | No. Observations: | 56 |
| Model: | Logit | Df Residuals: | 51 |
| Method: | MLE | Df Model: | 4 |
| Date: | Wed, 11 Jul. 2018 | Pseudo R-squ.: | 0.5476 |
| Time: | 17:17:12 | Log-Likelihood: | −17.417 |
| converged: | True | LL-Null: | −38.494 |
| | | LLR p-value: | 1.549e−08 |

| | coef | std err | z | P > \|z\| | [95.0% Conf. Int.] | |
|---|---|---|---|---|---|---|
| TRAIL | −0.0161 | 0.006 | −2.923 | 0.003 | −0.027 | −0.005 |
| MCP-2 | 0.1320 | 0.055 | 2.407 | 0.016 | 0.025 | 0.241 |
| ICAM-1 | −0.0121 | 0.005 | −2.339 | 0.019 | −0.022 | −0.002 |
| TNF-RI | 2.5789 | 1.117 | 2.308 | 0.021 | 0.389 | 4.769 |
| intercept | 1.4077 | 2.433 | 0.578 | 0.563 | −3.362 | 6.177 |

Diagnostic Algorithm Development: Confidence intervals of 4 protein algorithm was determined by using binomial proportional confidence interval—Wald test for AUC and the Wilson score interval for the sensitivity and specificity. Training Set: AUC 0.939±0.063; sensitivity 0.839 (95% Cl: 0.674-0.929); specificity 0.92 (95% Cl: 0.75-0.978). LOO cross validation: percent correct 0.821428571429; AUC 0.939±0.0632; Se 0.813 (95% Cl: 0.643 0.913); Sp 0.937 (95% Cl: 0.771 0.984). Confidence range −Se −0.27, .213.

A literature survey was performed to identify reported NES/NS/PNES risk factors which include: demographics, comorbidities and employment status. Patient clinical records were retrospectively analyzed for confirmation of the above listed risk factors. Note, a standardized method was not used for recording the information and as a result may be underreported.

TABLE 7

| PNES Risk Factor | PNES (n = 24) | Epilepsy (n = 23) |
|---|---|---|
| Major Depressive Disorder | 16% (n = 4) | 0% |
| Trauma (physical, emotional, sexual; w or w/o PTSD dx) | 46% (n = 11) | 4% (n = 1) |
| Cluster B Personality Disorder | 0% | 0% |
| Polyallergies | 42% (n = 10) | 13% (n = 3) |
| Conversion Disorder (previous dx) | 17% (n = 4) | 4% (n = 1) |
| Dependent Personality Disorder | 0% | 0% |
| Fibromyalgia | 8% (n = 2) | 0% |
| Female (sex) | 79% (n = 19) | 65% (n = 15) |
| Migraine | 25% (n = 6) | 4% (n = 1) |
| Pain | 29% (n = 7) | 13% (n = 3) |
| Asthma | 29% (n = 7) | 13% (n = 3) |

Prevalence of PNES Risk Factors *Includes on patient who had confirmed ES and PNES events during EMU admission.

TABLE 8

| | PNES (n = 24) | Epilepsy (n = 23) |
|---|---|---|
| 1 + Risk Factors | 96% (n = 23) | 74% (n = 17) |
| 2 + Risk Factors | 92% (n = 22) | 29% (n = 7)* |
| 3 + Risk Factors | 71% (n = 17) | 13% (n = 3) |
| 4 + Risk Factors | 25% (n = 6) | 4% (n = 1) |
| 5 Risk Factors | 8% (n = 2) | 4% (n = 1) |

Algorithm risk factor sum+4 protein ['Major depressive disorder', 'PTSD', 'Trauma', 'Cluster B', 'Polyallergies', 'Conversion Disorder', 'Sex', 'Fibromyalgia', 'Migraine', 'Pain', 'Asthma'] Ip=['TRAIL', 'MCP-2', 'ICAM-1', 'TNF-RI', 'risksum', 'diagnosis'].

TABLE 9

| Logit Regression Results | | | |
|---|---|---|---|
| Dep. Variable: | diagnosis | No. Observations: | 58 |
| Model: | Logit | Df Residuals: | 52 |
| Method: | MLE | Df Model: | 5 |
| Date: | Fri, 07 Sep. 2018 | Pseudo R-squ.: | 0.7487 |
| Time: | 15:27:48 | Log-Likelihood: | −10.070 |
| converged: | True | LL-Null: | −40.064 |
| | | LLR p-value: | 1.222e−11 |

| | coef | std err | z | P > \|z\| | [95.0% Conf. Int.] | |
|---|---|---|---|---|---|---|
| TRAIL | −0.0124 | 0.008 | −1.634 | 0.102 | −0.027 | 0.002 |
| MCP-2 | 0.2192 | 0.090 | 2.437 | 0.015 | 0.043 | 0.396 |
| ICAM-1 | −0.0146 | 0.007 | −1.972 | 0.049 | −0.029 | −8.9e−05 |
| TNF-RI | 3.8373 | 1.868 | 2.054 | 0.040 | 0.176 | 7.498 |
| risksum | −1.7309 | 0.728 | −2.378 | 0.017 | −3.158 | −0.304 |
| intercept | 0.5512 | 3.997 | 0.138 | 0.890 | −7.283 | 8.385 |

Threshold 83.0; AUC 0.9800+/−0.0367; 27 0; 4 25; sensitivity 0.870967741935 (0.71147593743693571, 0.9486571562537085); specificity 1.0 (0.86680774906095148, 0.999999 99999989).

Example 14: Co-occurring Inflammation Associated Disease and NSAID Use

Shown in FIGS. 19A and 19B is the influence of co-occurring inflammation associated disease and NSAID use in both the ES and PNES cohorts, which was investigated by analyzing medical records from the patients who were included into both the ES and PNES cohorts. A retrospective analysis of patient medical records identified 48 patients with co-occurring inflammation related disease (23 suffering epileptic seizure and 25 suffering psychogenic seizures). Correct classification includes patients who were having seizures, and those who were not having seizures. An exhaustive search (i.e. all combinations) of 1 through 6 protein combinations were used to refine a diagnostic algorithm and the top performing algorithm was selected. The performance of the algorithm in the context of co-occurring inflammation associated disease or NSAID use was analyzed by reviewing the medical records of the patients used to refine the algorithm. Co-occurring inflammation or NSAID use does not affect the classification efficiency of the diagnostic algorithm. EvoScoreDX successfully identifies epileptic seizures in challenging patients with confounding or co-occurring indication.

Example 15: Methods of Evaluating Patient Epileptic Seizure Burden and Frequency, Including Monitoring and Predicting Algorithms and Diagnostics Overview. Diagnostic algorithms that stratify patients experiencing a defined or desired seizure reduction over a defined period of time are developed. A method that can measure a desired seizure reduction over a defined period of time could be a result of a defined intervention (i.e., therapeutic, device, etc.) or protocol. Current methods are subjective, and rely on patient self-reporting seizures or activity, which are known to be inherently inaccurate due to missing seizures or misreporting seizures as epileptic. Biomarkers can be measured at defined periods of time, and leveraged into multi-protein algorithms to monitor a change in seizure burden over one or more time points. Biomarkers can be measured at defined periods of time, and leveraged into multi-protein algorithms to forecast a change in seizure burden over one or more time points. Additionally, biomarkers can be measured at defined periods of time, and leveraged into multi-protein algorithms to monitor a change in seizure burden over one or more time points, in order to assess the patient's individual disease state, and if intervention is needed. Finally, Biomarkers can be measured at defined periods of time, and leveraged into multi-protein algorithms monitor a change in seizure burden over one or more time points, based on any desired reduction threshold i.e., a reduction of greater than 1%, 10%, 20% or more) in order to assess the patients individual disease state, and if intervention is needed and/or intervention working. Where intervention is defined as any activity undertaken to improve the patient disease state including but not limited to, drug treatment, surgery, implantable devices, changes in diet, behavioral medications, and psychological counseling.

Further, biomarkers can be measured at defined periods of time, and leveraged into predictive algorithms to determine intervention effectiveness. Biomarkers can be measured at defined periods of time, and leveraged into predictive algorithms to forecast a change in seizure burden over one or more time points, in order to determine intervention effectiveness. Biomarkers can be measured at defined periods of time, and leveraged into predictive multi-protein algorithms to determine or a change in seizure burden over one or more time points, in order to determine intervention effectiveness. Biomarkers can be measured at defined periods of time, and leveraged into predictive multi-protein algorithms to determine a change in seizure burden over one or more time points, in order to determine or forecast intervention effectiveness. Predictive algorithms to determine a change in seizure burden over one or more time points, in order to determine or forecast intervention effectiveness for current or future therapeutic drugs.

Methodology. Monitoring algorithms are developed that stratify patients by a 75% reduction (seminal illustrative) in seizure frequency (or other selected reduction threshold) as well as a continuous algorithm that correlates protein concentration with seizure frequency. In both cases the relative changes in protein concentrations were calculated between time points to maximize the information to include in the algorithm. The statistical methods focused on repeated measures techniques including MANOVA or mixed models to account for the multiple measurements from subjects over time. Machine learning and artificial intelligence approaches to refine the classification algorithms, using logistical regression or similar methods, that stratify patients with a 75% seizure frequency reduction (or other selected reduction threshold) were leveraged. In brief, an exhaustive search to find an optimal multiple protein algorithm by considering all combinations from 1, 2 or more proteins is used. The performance of each algorithm was evaluated based on ROC AUC, accuracy, fit statistics, confusion matrix diagnostic statistics and a k-fold cross validation approach.

Monitoring algorithms can also be developed that evaluate the correlation between protein concentration and seizure frequency or burden as a continuous function. Here, a multiple regression analysis is used to refine all combinations of algorithms with 1-6 proteins. All of the algorithms are evaluated based on bias/variance tradeoff, confidence intervals and fit statistics to select the top performing algorithm.

A similar procedure was used to create predictive algorithms that evaluate the correlation between protein concentration or protein concentration changes and treatment efficacy as measured by seizure frequency or burden. A logistical regression analysis is used to refine all combinations of algorithms with 1-6 proteins to stratify treatment responders versus treatment non-responders. Where treatment response is defined as a reduction in seizure frequency or burden. All of the algorithms are evaluated based on bias/variance tradeoff, confidence intervals and fit statistics to select the top performing algorithm. Algorithm performance is evaluated using reserved data or cross validation methods to evaluate the algorithm performance.

Patient Samples and Biomarker Concentrations. Blood samples were collected from patients (n=43) at day zero and again on day 14. Plasma was isolated from samples subsequent to blood draws. The seizure frequency for the preceding 2-week period (as a seminal and illustrative example for time period) was recorded and the percent change in seizure frequency was calculated. Samples were analyzed using a 51-protein panel multiplexed ELISA run on the MSD platform. Proteins were selected from immune response associated markers as defined herein. Difference in protein concentrations between cohorts of patients with a reported seizure burden or frequency at time point one and decreased change at time point two versus a cohort of patients with no, minimal change, small change, etc., in seizure burden or frequency between the two time points. An exhaustive search (i.e. all combinations) of 1 through 6 protein combinations from the 51 Biomarkers Tested (and defined herein) were used to refine a diagnostic algorithm and the top performing algorithm was selected. The change in protein concentrations were calculated and diagnostic algorithms developed that demonstrated changes in seizure burden and frequency between patients who had a defined change in seizure burden or frequency from patients who did not. Diagnostic algorithms were developed based on protein changes between the two cohorts that accurately predicted the change in seizure burden across the two cohorts A group of epilepsy patients, who have an active seizure burden or frequency of > or =4 per week were admitted into a clinical trial. Patients were experiencing 4 or more focal seizures with or without secondary generalization were included. At time point 1, blood was taken as a baseline. At time point 2, blood was taken to determine the change in biomarkers as a change in seizure burden or frequency. Patients were maintained on their current AED medicines or therapeutic protocols throughout the period. Approximately one half of the patients received a new intervention and the other half a placebo intervention. Blood samples were taken 2 weeks apart.

Biomarker Identification and Diagnostic Algorithm Development—Exhaustive Search. Biomarker concentrations were compared between patient cohorts that experienced a decrease in seizure burden or frequency versus patient cohorts that did not experience a decrease in seizure burden or frequency. Any criteria can be selected for the changes in seizure burden or frequency (i.e., a reduction of greater than 1%, 10%, 20% or more). An exhaustive search was performed to identify the combination of proteins, that when integrated into a diagnostic algorithm, most efficiently stratifies between cohorts.

Optimization criteria. Accuracy and AUC; Wald Test P values; All proteins should have a significant contribution; Log likelihood ratio p value and pseudo R^2 considered in the case that multiple algorithms satisfy the above. All combinations of 1 through 6 proteins were tested (from the 51 Biomarkers Tested and defined herein)-total of 1.15 million combinations were tested for initial studies. In one embodiment, the search identified a combination of 4 proteins: IL-10, MCP-4, MMP-3, TNF-α to serve as an example of accuracy.

Monitoring and Drug Response. Drug Response was assessed for samples that were stratified by 75% seizure reduction. Baseline samples for drug treated patients were compared to see if there are differences in concentrations as a function of 75% seizure reduction over time. The changes between proteins were evaluated, using the Mann-Whitney test, to assess differences for each protein which included 10 proteins with p values <0.05. An algorithm and associated biomarkers was selected for illustrative purposes for monitoring to stratify 75% reduction in seizure burden or frequency which included 'IL-10', 'MCP-4', 'MMP-3', and 'TNF-α'. Tables 10-12 and FIGS. 23 through 17 illustrate Monitoring Biomarkers and Algorithms.

TABLE 10

Algorithm to Stratify 75% Reduction in Seizure Burden or Frequency:
Monitoring Algorithm
Logit Regression Results

| | | | |
|---|---|---|---|
| Dep. Variable: | response | No. Observations: | 43 |
| Model: | Logit | Df Residuals: | 38 |
| Method: | MLE | Df Model: | 4 |
| Date: | Tue, 19 Mar. 2019 | Pseudo R-squ.: | 0.4093 |
| Time: | 11:42:48 | Log-Likelihood: | −14.442 |
| converged: | True | LL-Null: | −24.451 |
| | | LLR p-value: | 0.0004953 |

| | coef | std err | z | P > \|z\| | [95.0% Conf. Int.] | |
|---|---|---|---|---|---|---|
| const | −1.5477 | 0.638 | −2.427 | 0.015 | −2.798 | −0.298 |
| IL-10 | 5.1309 | 2.193 | 2.339 | 0.019 | 0.832 | 9.430 |
| MCP-4 | 4.3271 | 1.959 | 2.209 | 0.027 | 0.489 | 8.166 |

TABLE 10-continued

| Algorithm to Stratify 75% Reduction in Seizure Burden or Frequency: Monitoring Algorithm Logit Regression Results | | | | | | |
|---|---|---|---|---|---|---|
| MMP-3 | −5.4512 | 2.302 | −2.368 | 0.018 | −9.964 | −0.939 |
| TNF-a | −8.6794 | 3.866 | −2.245 | 0.025 | −16.256 | −1.102 |

TABLE 11

| Results for Algorithm to Stratify 75% Reduction in Seizure Burden or Frequency: Monitoring Algorithm | |
|---|---|
| Accuracy | 95.2% |
| Sensitivity | 90% |
| Specificity | 96.8% |
| AUC | 0.92 |

TABLE 12

| AUC for Algorithm to Stratify 75% Reduction in Seizure Burden or Frequency: Monitoring Algorithm | |
|---|---|
| Area | 0.9156 |
| Std. Error | 0.06093 |
| 95% confidence interval | 0.7962 to 1.035 |
| P value | <0.0001 |

Predicting and Forecasting Drug Response. For seminal illustrative or methodology confirmation purposes, a decrease in seizure burden or frequency of 75% or more was compared to the group that had a smaller change. Other thresholds could be selected per above. Correlation of protein change with seizure burden or frequency was assessed. Correlation between protein ratio (time point 1 to time point 2) to percent change in seizure frequency was considered. Predicting and Forecasting Drug Response was assessed. Baseline samples for drug treated patients and see if there are differences in concentrations as a function of 75% seizure reduction. An algorithm and associated biomarkers was selected for illustrative purposes for predicting an illustrative 75% reduction in seizure burden or frequency which included ‘GM-CSF’, ‘IL-17a’, ‘VEGF-A’ and ‘TNF-α’. Tables 13 and 14 and FIGS. 28 and 29 illustrate Predictive Biomarkers and Algorithms.

TABLE 13

Correlation of multiple protein changes with seizure burden or frequency using Multiple regression: Prediction Algorithm (GM-CSF, IL-17a, TNF-alpha and VEGF-A)
OLS Regression Results

| | | | |
|---|---|---|---|
| Dep. Variable: | freq reduction | R-squared: | 0.418 |
| Model: | OLS | Adj. R-squared: | 0.355 |
| Method: | Least Squares | F-statistic: | 6.637 |
| Date: | Thu, 21 Mar. 2019 | Prob (F-statistic): | 0.000394 |
| Time: | 15:30:54 | Log-Likelihood: | −41.279 |
| No. Observations: | 42 | AIC: | 92.56 |
| Df Residuals: | 37 | BIC: | 101.2 |
| Df Model: | 4 | | |
| Covariance Type: | nonrobust | | |

| | coef | std err | z | P > \|z\| | [95.0% Conf. Int.] | |
|---|---|---|---|---|---|---|
| const | −0.0820 | 0.487 | −0.168 | 0.867 | −1.069 | 0.906 |
| GM-CSF | 0.5257 | 0.245 | 2.143 | 0.039 | 0.029 | 1.023 |
| IL-17A | 0.8183 | 0.219 | 3.737 | 0.001 | 0.375 | 1.262 |
| TNF-a | −1.7103 | 0.392 | −4.359 | 0.000 | −2.505 | −0.915 |
| VEGF-A | 0.4152 | 0.166 | 2.501 | 0.017 | 0.079 | 0.752 |

| | | | |
|---|---|---|---|
| Omnibus: | 16.686 | Durbin-Watson: | 1.837 |
| Prob(Omnibus): | 0.000 | Jerque-Bera (JB): | 21.088 |
| Skew: | −1.277 | Prob(JB): | 2.64e−05 |
| Kurtosis: | 5.352 | Cond. No. | 12.6 |

TABLE 14

Top Performing Combinations of 2 Biomarkers: Predictive Algorithm

| combination | p value |
|---|---|
| MIP-1B_MIP-5 | 0.002399 |
| MIP-1B_MMP-3 | 0.00263 |
| MIP-1B_TNF-a | 0.00263 |
| Eotaxin-2_MIP-1B | 0.003445 |
| MIP-1B_SCF | 0.003445 |
| MCP-4_MMP-3 | 0.004481 |
| IL-10_MMP-3 | 0.004883 |
| IL-16_MIP-1B | 0.005318 |
| MIP-1B_Nectin-4 | 0.006291 |
| MIP-1B_Osteoactivin | 0.006291 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The mathematical coefficients and algorithms provided herein are illustrative and exemplary and are provided for the purpose of illustration only, in order to demonstrate the effectiveness of leveraging one or more biomarkers in multiple potential diagnostic algorithms with performance to meet diagnostic needs. The disclosure encompassed herein should in no way be construed as being limited to these examples of coefficients and algorithms, but rather should be construed to encompass any and all variations which become evident as a result of the teachings provided herein. In particular, alternative coefficients and algorithms may become apparent as a result of the use of different clinical data.

Although the invention has been described in conjunction with specific embodiments thereof, it is evident that many alternatives, modification and variations will be apparent to those skilled in the art. Accordingly, it is intended to embrace all such alternatives, modification and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Any document (including but not limited to any patent, patent application, publication, and website) listed herein is hereby incorporated herein by reference in its entirety. While these developments have been disclosed with reference to specific embodiments, it is apparent that other embodiments and variations of this invention are devised by others skilled in the art without departing from the true spirit and scope of the developments. The appended claims include such embodiments and variations thereof.

The invention claimed is:

1. A method of diagnosing epilepsy or epileptic seizure (ES) in a patient, the method comprising:

(a) contacting one or more biological samples obtained from the patient, prior to treatment, with one or more antibodies targeting Interleukin-16 (IL-16);

(b) measuring the concentrations of IL-16 in the one or more biological samples;

(c) comparing the concentrations of IL-16 in the one or more biological samples with the concentrations of IL-16 in one or more control samples obtained from a healthy patient;

(d) determining the patient has epilepsy or ES when the concentrations of IL-16 are decreased in the one or more biological samples relative to the one or more control samples; and (e) administering, to the patient determined to have epilepsy or ES, one or more therapeutic agents selected from the group consisting of parsevenol, cenobamate, ganaxolone, phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, *cannabis*-based drugs, and pharmaceutically acceptable salts, prodrugs, and derivatives thereof.

2. The method of claim 1, wherein step (e) further comprises administering an external device or internal or implantable device that helps control and minimize seizures and epilepsy.

3. The method of claim 1, further comprising:

(a) contacting the one or more biological samples obtained from the patient with one or more antibodies targeting Intracellular Adhesion Molecule 1 (ICAM-1);

(b) measuring the concentrations of ICAM-1 in the one or more biological samples;

(c) comparing the concentrations of ICAM-1 in the one or more biological samples with the concentrations of ICAM-1 in one or more control samples obtained from a healthy patient; and (d) determining the patient has epilepsy or ES when the concentrations of ICAM-1 are decreased in the one or more biological samples relative to the one or more control samples.

4. The method of claim 1, further comprising:

(a) contacting the one or more biological samples obtained from the patient with one or more antibodies targeting Macrophage Inflammatory Protein-1B (MIP-1B);

(b) measuring the concentrations of MIP-1B in the one or more biological samples;

(c) comparing the concentrations of MIP-1B in the one or more biological samples with the concentrations of MIP-1B in one or more control samples obtained from a healthy patient; and (d) determining the patient has epilepsy or ES when the concentrations of MIP-1B are increased in the one or more biological samples relative to the one or more control samples.

5. The method of claim 1, further comprising:

(a) contacting the one or more biological samples obtained from the patient with one or more antibodies targeting Tumor Necrosis Factor-Related Apoptosis-Inducing Ligand (TRAIL);

(b) measuring the concentrations of TRAIL in the one or more biological samples;

(c) comparing the concentrations of TRAIL in the one or more biological samples with the concentrations of TRAIL in one or more control samples obtained from a healthy patient; and (d) determining the patient has epilepsy or ES when the concentrations of TRAIL are decreased in the one or more biological samples relative to the one or more control samples.

* * * * *